United States Patent
Rodgers et al.

(10) Patent No.: US 9,249,145 B2
(45) Date of Patent: Feb. 2, 2016

(54) HETEROCYCLIC DERIVATIVES OF PYRAZOL-4-YL-PYRROLO[2,3-D] PYRIMIDINES AS JANUS KINASE INHIBITORS

(75) Inventors: James D. Rodgers, Landenberg, PA (US); Yun-Long Li, Chadds Ford, PA (US); Stacey Shepard, Wilmington, DE (US); Haisheng Wang, Hockessin, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 395 days.

(21) Appl. No.: 12/872,925

(22) Filed: Aug. 31, 2010

(65) Prior Publication Data

US 2011/0059951 A1  Mar. 10, 2011

Related U.S. Application Data

(60) Provisional application No. 61/238,794, filed on Sep. 1, 2009.

(51) Int. Cl.
| | | |
|---|---|---|
| *C07D 487/04* | (2006.01) | |
| *A61K 31/519* | (2006.01) | |
| *A61P 35/00* | (2006.01) | |
| *A61P 35/02* | (2006.01) | |
| *A61P 35/04* | (2006.01) | |
| *A61K 31/551* | (2006.01) | |
| *A61P 37/06* | (2006.01) | |
| *A61P 29/00* | (2006.01) | |
| *A61P 17/00* | (2006.01) | |
| *A61P 19/00* | (2006.01) | |

(52) U.S. Cl.
CPC .................. *C07D 487/04* (2013.01)

(58) Field of Classification Search
CPC ............... C07D 487/04; A61K 31/519
USPC ........................ 544/280; 514/265.1
See application file for complete search history.

(56) References Cited

U.S. PATENT DOCUMENTS

| | | | |
|---|---|---|---|
| 2,985,589 A | 5/1961 | Broughton et al. |
| 3,832,460 A | 8/1974 | Kosti |
| 4,402,832 A | 9/1983 | Gerhold |
| 4,498,991 A | 2/1985 | Oroskar |
| 4,512,984 A | 4/1985 | Seufert et al. |
| 4,548,990 A | 10/1985 | Mueller et al. |
| 4,814,477 A | 3/1989 | Wijnberg et al. |
| 5,378,700 A | 1/1995 | Sakuma et al. |
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,060,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blumenkopf et al. |
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,167,750 B2 | 1/2007 | Knudson et al. |

(Continued)

FOREIGN PATENT DOCUMENTS

| | | |
|---|---|---|
| DE | 30 36 390 | 5/1982 |
| EP | 0223420 | 5/1987 |

(Continued)

OTHER PUBLICATIONS

26th Annual JPMorgan Healthcare Conference presentation dated Jan. 8, 2008 (28 pages).

(Continued)

*Primary Examiner* — Susanna Moore
(74) *Attorney, Agent, or Firm* — Fish & Richardson P.C.

(57) ABSTRACT

The present invention provides heterocyclic derivatives of pyrazol-4-yl-pyrrolo[2,3-d]pyrimidines of Formula I:

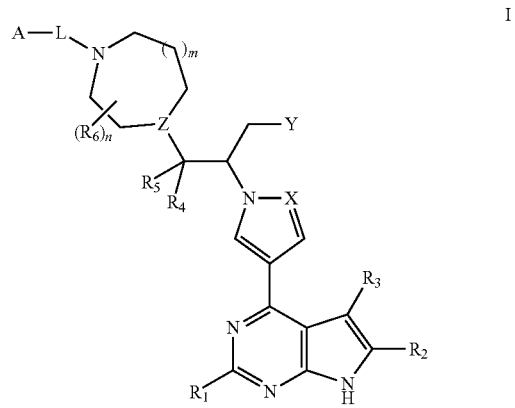

and pharmaceutically acceptable salts thereof, as well as their compositions and methods of use, that modulate the activity of Janus kinases (JAKs) and are useful in the treatment of diseases related to the activity of JAKs including, for example, inflammatory disorders, autoimmune disorders, cancer, and other diseases.

56 Claims, No Drawings

(56) References Cited

U.S. PATENT DOCUMENTS

| | | |
|---|---|---|
| 7,265,108 B2 | 9/2007 | Ozaki |
| 7,335,667 B2 | 2/2008 | Rodgers et al. |
| 7,358,255 B2 | 4/2008 | Nakamura |
| 7,517,870 B2 | 4/2009 | Auricchio |
| 7,598,257 B2 | 10/2009 | Rodgers et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda et al. |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2015/0087632 A1 | 3/2015 | Rodgers et al. |

FOREIGN PATENT DOCUMENTS

| | | |
|---|---|---|
| EP | 0587473 | 3/1994 |
| EP | 0727217 | 8/1996 |
| EP | 0795556 | 9/1997 |
| EP | 1104764 | 6/2001 |
| JP | 07-010876 | 1/1995 |

(56) References Cited

FOREIGN PATENT DOCUMENTS

| | | |
|---|---|---|
| JP | 2003/155285 | 5/2003 |
| JP | 2006/518341 | 8/2006 |
| WO | WO 96/30343 | 10/1996 |
| WO | WO 97/02262 | 1/1997 |
| WO | WO 97/02266 | 1/1997 |
| WO | WO 97/36587 | 10/1997 |
| WO | WO 97/38664 | 10/1997 |
| WO | WO 97/45412 | 12/1997 |
| WO | WO 98/44797 | 10/1998 |
| WO | WO 98/51391 | 11/1998 |
| WO | WO 99/00654 | 1/1999 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/51614 | 9/2000 |
| WO | WO 00/53595 | 9/2000 |
| WO | WO 00/63168 | 10/2000 |
| WO | WO 01/14402 | 3/2001 |
| WO | WO 01/27104 | 4/2001 |
| WO | WO 01/42246 | 6/2001 |
| WO | WO 01/64655 | 9/2001 |
| WO | WO 01/81345 | 11/2001 |
| WO | WO 01/98344 | 12/2001 |
| WO | WO 02/00196 | 1/2002 |
| WO | WO 02/00661 | 1/2002 |
| WO | WO 02/16370 | 2/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 2004/003026 | 1/2004 |
| WO | WO 2004/005281 | 1/2004 |
| WO | WO 2004/005282 | 1/2004 |
| WO | WO 2004/026406 | 4/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/092154 | 10/2004 |
| WO | WO 2004/099204 | 11/2004 |
| WO | WO 2004/099205 | 11/2004 |
| WO | WO 2005/005988 | 1/2005 |
| WO | WO 2005/013986 | 2/2005 |
| WO | WO 2005/020921 | 3/2005 |
| WO | WO 2005/026129 | 3/2005 |
| WO | WO 2005/028444 | 3/2005 |
| WO | WO 2005/049033 | 6/2005 |
| WO | WO 2005/051393 | 6/2005 |
| WO | WO 2005/060972 | 7/2005 |
| WO | WO 2005/061463 | 7/2005 |
| WO | WO 2005/062795 | 7/2005 |
| WO | WO 2005/089502 | 9/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/117909 | 12/2005 |
| WO | WO 2005/121130 | 12/2005 |
| WO | WO 2005/123719 | 12/2005 |
| WO | WO 2006/004984 | 1/2006 |
| WO | WO 2006/013114 | 2/2006 |
| WO | WO 2006/039718 | 4/2006 |
| WO | WO 2006/046023 | 5/2006 |
| WO | WO 2006/046024 | 5/2006 |
| WO | WO 2006/052913 | 5/2006 |
| WO | WO 2006/056399 | 6/2006 |
| WO | WO 2006/067445 | 6/2006 |
| WO | WO 2006/069080 | 6/2006 |
| WO | WO 2006/077499 | 7/2006 |
| WO | WO 2006/096270 | 9/2006 |
| WO | WO 2006/101783 | 9/2006 |
| WO | WO 2006/108103 | 10/2006 |
| WO | WO 2006/122806 | 11/2006 |
| WO | WO 2006/127587 | 11/2006 |
| WO | WO 2006/129199 | 12/2006 |
| WO | WO 2006/136823 | 12/2006 |
| WO | WO 2007/002433 | 1/2007 |
| WO | WO 2007/025090 | 3/2007 |
| WO | WO 2007/041130 | 4/2007 |
| WO | WO 2007/043677 | 4/2007 |
| WO | WO 2007/044894 | 4/2007 |
| WO | WO 2007/049041 | 5/2007 |
| WO | WO 2006/022459 | 6/2007 |
| WO | WO 2007/062459 | 6/2007 |
| WO | WO 2007/070514 | 6/2007 |
| WO | WO 2007/076423 | 7/2007 |
| WO | WO 2007/077949 | 7/2007 |
| WO | WO 2007/084557 | 7/2007 |
| WO | WO 2007/090141 | 8/2007 |
| WO | WO 2007/090748 | 8/2007 |
| WO | WO 2007/116313 | 10/2007 |
| WO | WO 2007/117494 | 10/2007 |
| WO | WO 2007/135461 | 11/2007 |
| WO | WO 2007129195 | 11/2007 |
| WO | WO 2007/140222 | 12/2007 |
| WO | WO 2008/013925 | 1/2008 |
| WO | WO 2008/028937 | 3/2008 |
| WO | WO 2008/035376 | 3/2008 |
| WO | WO 2008/043031 | 4/2008 |
| WO | WO 2008/058126 | 5/2008 |
| WO | WO 2008/064157 | 5/2008 |
| WO | WO 2008/067119 | 6/2008 |
| WO | WO 2008/077712 | 7/2008 |
| WO | WO 2008/079291 | 7/2008 |
| WO | WO 2008/079292 | 7/2008 |
| WO | WO 2008/082198 | 7/2008 |
| WO | WO 2008/082839 | 7/2008 |
| WO | WO 2008/082840 | 7/2008 |
| WO | WO 2008/106692 | 9/2008 |
| WO | WO 2008/124323 | 10/2008 |
| WO | WO 2008/139161 | 11/2008 |
| WO | WO 2008/145681 | 12/2008 |
| WO | WO 2008/145688 | 12/2008 |
| WO | WO 2008/157207 | 12/2008 |
| WO | WO 2008/157208 | 12/2008 |
| WO | WO 2009/016460 | 2/2009 |
| WO | WO 2009/049028 | 4/2009 |
| WO | WO 2009/064486 | 5/2009 |
| WO | WO 2009/064835 | 5/2009 |
| WO | WO 2009/071577 | 6/2009 |
| WO | WO 2009/100130 | 8/2009 |
| WO | WO 2009/109576 | 9/2009 |
| WO | WO 2009/114512 | 9/2009 |
| WO | WO 2009/115572 | 9/2009 |
| WO | WO 2009/155156 | 12/2009 |
| WO | WO 2009/158687 | 12/2009 |
| WO | WO 2010/000978 | 1/2010 |
| WO | WO 2010/001169 | 1/2010 |
| WO | WO 2010/020905 | 2/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/039939 | 4/2010 |
| WO | WO 2010/081692 | 7/2010 |
| WO | WO 2010/083283 | 7/2010 |
| WO | WO 2010/135621 | 11/2010 |
| WO | WO 2010/135650 | 11/2010 |

(56) References Cited

FOREIGN PATENT DOCUMENTS

| WO | WO 2011/003418 | 1/2011 |
|---|---|---|
| WO | WO 2011/025685 | 3/2011 |
| WO | WO 2011/028685 | 3/2011 |
| WO | WO 2011/029802 | 3/2011 |
| WO | WO 2011/031554 | 3/2011 |
| WO | WO 2011/035900 | 3/2011 |
| WO | WO 2011/044481 | 4/2011 |
| WO | WO 2011/057784 | 5/2011 |
| WO | WO 2011/069141 | 6/2011 |
| WO | WO 2011/112662 | 9/2011 |
| WO | WO 2011/130146 | 10/2011 |
| WO | WO 2011/144338 | 11/2011 |
| WO | WO 2011/146808 | 11/2011 |
| WO | WO 2012/003457 | 1/2012 |
| WO | WO 2012/068440 | 5/2012 |
| WO | WO 2012/068450 | 5/2012 |
| WO | WO 2012/177606 | 12/2012 |
| WO | WO 2013/007765 | 1/2013 |
| WO | WO 2013/007768 | 1/2013 |
| WO | WO 2013/023119 | 2/2013 |
| WO | WO 2013/026025 | 2/2013 |
| WO | WO 2013/036611 | 3/2013 |
| WO | WO 2013/173720 | 11/2013 |
| WO | WO 2014/071031 | 5/2014 |
| WO | WO 2014/138168 | 9/2014 |

OTHER PUBLICATIONS

Abe, et al., Heterocycles, "Effective Methods for Introducing Some Aryl and Heteroaryl Substituent Onto 1-Azaazulene Nuclei", 66, 229-240 (2005).
Abelson et al., "Alternate reference values for tear film break-up time in normal and dry eye populations, Lacrimal Gland, Tear Film, and Dry Eye Syndromes 3 Part B", Adv Exp Med Biol, 2002; 506:1121-1125.
Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002; 506:1079-86).
Abstract of Chilean patent application No. 3496-06 published in Official Gazette of the Republic of Chile (Jun. 1, 2007)* (I page + 1 page translation).
Aho, T. et al., Expression of human pim family genes is selectively up-regulated by cytokines promoting T helper type 1, but not T helper type 2, cell differentiation, Immunology 116: 82-88, 2005.
Albach et al., "Diagnosis of keratoconjunctivitis sicca in rheumatoid arthritis. The value of various tests", Ophthalmologe, Apr. 1994; 91(2):229-34—in German (with English abstract/summary contained therein).
Anderson et al., "Biochemical characterization of GSK1070916, a potent and selective inhibitor of Aurora B and Aurora C kinases with an extremely long residence time", Biochem. J., 420(2), 259-265 (2009).
Bachmann, et al., "The serine/threonine kineage Pim-1," The International Journal of Biochechemistry and Cell Biology 37: 726-730 (2005).
Banker, et al., "Modern Pharmaceuticals", p. 596 (1996).
Barabino et al., "Tear film and ocular surface tests in animal models of dry eye; uses and limitations", Experimental Eye Research, 2004, 79, 613-621.
Barr et al., "Corneal scarring in the Collaborative Longitudinal Evaluation of Keratoconus (CLEK) Study: baseline prevalence and repeatability of detection", Cornea, 1999; 18(1):34-46.
Baudouin et al., "Flow cytometry in impression cytology specimens. A new method for evaluation of conjunctival Inflammation", Invest Ophthalmol Vis Sci, 1997; 38:1458-1464.
Baytel et al., "The human Pim-2 proto-oncogene and its testicular expression" Biochimica et Biophysica Acta 1442: 274-285, (1998).
Begley, et al., "Use of the dry eye questionnaire to measure symptoms of ocular irritation in patients with aqueous tear deficient dry eye", Cornea, 2002:21:664-70.

Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.
Berge, et al., "Pharmaceutical salts", J. Pharma. Science (1977) vol. 66(1) pp. 1-19.
Beyer, "Uber die Synthese von 2-Methylmercapto-1.3.4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhovi, et al., "1,3-Dipolar Cycloaddition Reaction: Synthesis and Antimicrobial Activity of Some New 3-Ethoxycarbonyl-s-Methoxy-6-Bromo-2-Triazolylmethylindoles", Indian Journal of Heterocyclic Chemistry, vol. 14, (Jul.-Sep. 2004), pp. 15-18.
Bioreversible Carriers in Drug Design, ed. Edward B. Roche, American Pharmaceutical Association and Pergamon Press, 1987.
Blume-Jensen P. et al, "Oncogenic kinase signaling", Nature 2001, 411(6835):355-365.
Bolen JB. "Nonreceptor tyrosine protein kinases", Oncogene, 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).
Borie, D.C. et al., "Combined Use of the Jak3 Inhibitor CP-690, 550 with Mycophenolate Mofetil to Prevent Kidney Allograft Rejection in Nonhuman Primates", Transplantation, Dec. 27, 2005;80(12):1756-64.
Bosworth, "Hematologic Malignancies", Clinical Oncology, vol. 06:04 (Apr. 2011) 3 pages.
Boudny, V. et al., "JAK/STAT signaling pathways and cancer", Neoplasm, 49:349-355, 2002.
Bourcier et al., "Expression of CD40 and CD40 ligand in the human conjunctival epithelium", Invest Ophthalmol Vis Sci, 2000;41:120-126.
Bowman, T., et al. "STATs in oncogenesis", Oncogene, 19:2474-2488, 2000.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998;67:687-697.
Brignole et al., "Flow cytometric analysis of inflammatory markers in conjunctival epithelial cells of patients with dry eyes", Invest Ophthalmol Vis Sci, 2000; 41:1356-1363.
Brignole et al., "Flow cytometric analysis of inflammatory markers in KCS: 6-month treatment with topical cyclosporin A", Invest Ophthalmol Vis Sci, 2001; 42:90-95.
Brignole et al., "Flow cytometry in conjunctival impression cytology: a new tool for exploring ocular surface pathologies", Exp Eye Res, 2004;78:473-481.
Bromberg et al., "Inflammation and Cancer: IL-6 and STAT3 Complete the Link," Cancer Cell, 15:79-80 (2009).
Bron, et al., "Grading of corneal and conjunctival staining in the context of other dry eye tests", Cornea, 2003;22(7):640-50.
Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).
Burger et al., "Janus kinase inhibitor INCB20 has antiproliferative and apoptotic effects on human myeloma cells in vitro and in vivo", Mol Cancer Ther 2009;8(1), Jan. 2009 pp. 26-35.
Burger, R., et al., "Gp130 and ras mediated signaling in human plasma cell line IN/a-6: a cytokine-regulated tumor model for plasmacytoma", Hematol J., 2:42-53, 2001.
Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti, F., et al. (1997). "Structural and functional basis for JAK3-deficient severe combined immunodeficiency.", Blood, 90(10): 3996-4003.
Candotti, F., et al. (2002). "Molecular aspects of primary immunodeficiencies: lessons from cytokine and other signaling pathways.", J Clin Invest, 109(10): 1261-9.

(56) References Cited

OTHER PUBLICATIONS

Carey and Sundberg, Advanced Organic Chemistry, Part B: Reactions and Synthesis, 4th ed., Kluwer Academic/Plenum Publishers:New York, pp. 111-119 (2001).
Carey and Sundberg, Advanced Organic Chemistry, Part B: Reactions and Synthesis, Oxidations, 4th ed., Kluwer Academic/Plenum Publishers:New York, pp. 747-757 (2001).
Cermak et al, "Is complete androgen insensitivity syndrome associated with alterations in the meibomium gland and ocular surface", Cornea, 2003;22:516-521.
Cetkovic-Cvrlje, M., et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, P.S. et al., "Prevention of Organ Allograft Rejection by a Specific Janus Kinase 3 Inhibitor", Science, 2003, 302, 875-878.
Chauhan, et al, "Autoimmunity in Dry Eye due to resistance of Th17 to Treg Suppression", J. Immunology, 182(3):1247-52 (2009).
Chen, C.L. et al., "Stat3 Activation in Human Endometrial and Cervical Cancer", British Journal of Cancer, 96, 591-599, 2007.
Chew et al., "An instrument for quantifying meibomian lipid on the lid margin: the Meibometer", Curr Eye Res, 1993a;12:247-254.
Chew et al., "The casual level of meibomian lipids in humans", Current Eye Research, 1993b;12:255-259.
Cho et al, "Review of the tear break-up time and a closer look at the tear break-up time of Hong Kong Chinese", Optom Vis Sci, 1993;70(1):30-8.
Choi Ha-Soon et al, "Design and synthesis of 7H-pyrrolo[2,3-d]pyrimidines as focal adhesion kinase inhibitors. Part 1", Bioorg. & Med. Chem. Lett., 16(8):2173-2176 (2006).
Chu-Moyer, et al., "Preparation of the Four Regioisomeric 2-(Methylthio)oxazolopyridines: Useful Synthons for Elaboration to 2-(Amino substituted)oxazolopyridines", J. Org. Chem. 60(17): 5721-5725 (1995).
Cilloni et al., "Emerging drugs for chronic myeloid leukemia", Expert Opinion on Emerging Drugs, (Jun. 2010) vol. 15, No. 2, pp. 175-184.
Coligan, J.E. et al, Wiley Press; Methods in Molecular Biology: vol. 225, Inflammation Protocols., Winyard, P.G. and Willoughby, D.A., Humana Press (2003).
Communication dated Jan. 22, 2009 for European Appln. No. 06839328.9 (5 pgs.).
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (2005).
Daniels et al., "Imatinib mesylate inhibits the profibrogenic activity of TGF-? and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand, 73:501-505 (1995).
De Paiva, et al, "IL-17 disrupts corneal barrier following desiccating stress", Mucosal Immunol. 2(3):243-53 (2009).
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J. Haematol, 109(4): 823-8.
Deng Jun, et al, "Rh-catalyzed asymmetric hydrogenation of gamma-phthalimido-substituted esters: an efficient enantioselective synthesis of beta-aryl-gamma-amino acids", Org. Lett. 9(23):4825-4827 (2007).

Deuse, T. et al., "Novel Immunosuppression: R348, a JAK3- and Syk-Inhibitor Attenuates Acute Cardiac Allograft Rejection", Transplantation, 2008, 85(6) 885-892.
Doane, "An instrument for in vivo tear film interferometry", Optom Vis Sci, 1989; 66: 383-8.
Doleschall G., et al., "Thermal and Acid Catalysed Degradations of 3-alkylthio-6,7-dihydro[1.2.4]triazino[1,6-c]quinazolin-5-ium-1-olates", Tetrahedron, 30:3997-4012, 1974.
Dudley, A.C., et al. "AVEGF/JAK2/STAT5 axis may partially mediate endothelial cell tolerance to hypoxia", Biochem. J. 2005, 390(Pt 2):427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl, et al., "Therapeutic applications of viscous and injectable poly(ortho esters)", Adv. Drug. Deliv. Rev. 53:45-73 (2001).
Eliason, et al., "Staining of the conjunctiva and conjunctival tear film", Br J Ophthalmol, 1990;74:519-22.
Fabrizio Saettone, "Ocular inserts for topical delivery", Advanced Drug Delivery Reviews 16:95-106 (1998).
Farrell et al., "A classification for dry eyes following comparison of tear thinning time with Schirmer tear test", Acta Ophthalmol (Copenh), 1992; 70(3):357-60.
Farrell et al., "A clinical procedure to predict the value of temporary occlusion therapy in keratoconjunctivitis sicca" Ophthal Physiol Opt, 2003;23:1-8.
Farris, "Tear osmolarity—a new gold standard?" Adv Exp Med Biol, 350:495-503, 1994.
Flex E., et al., "Somatically acquired JAK1 mutations in adult acute lymphoblastic leukemia", J. Exp Med. 205:751-8, (2008).
Fonseca, J.E. et al., "Interleukin-6 as a key player in systemic inflammation and joint destruction", Autoimmunity Reviews, 8:538-42, (2009).
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fujihara et al., "Evaluation of human conjunctival epithelium by a combination of brush cytology and flow cytometry: an approach to the quantitative technique", Diagn Cytopathol, 1997;17:456-60.
Fujii, C. et al., "Aberrant expression of serine.threeonine kinase Pim-3 in hepatocellular carcinoma development and its role in the proliferation of human hepatoma cell lines" International Journal of Cancer 114: 209-218, (2005).
Fukagawa et al., "Histological evaluation of brush cytology of rabbit conjunctiva", Nippon Ganka Gakkai Zasshi, 1993;97:1173-8 (contains English abstract within the article).

(56) References Cited

OTHER PUBLICATIONS

Gaertner, "Cyclization of 1-Alkylamino-3-halo-2-alkanolst o 1-Alkyl-3-azetidinols," J. Org. Chem., 1967, 32, 2972-76.
Ghelardi, et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother. 48:3396-3401 (2004).
Glasson et al., "Differences in clinical parameters and tear film of tolerant and intolerant contact lens wearers", Invest Ophthalmol Vis Sci, 2003;44:5116-5124.
Glattfeld, "Improvements in the Preparation of DL-Threonic and DL-Erythronic Acids", J. Am. Chem. Soc. 62:974-977 (1940).
Gobbels et al., Tear secretion in dry eyes as assessed by objective fluorophotometry. Ger J Ophthalmol, 1992; 1:350-353.
Golding et al., "X-ray and scanning electron microscopic analysis of the structural composition of tear ferns", Cornea Jan. 1994;13(1):58-66.
Gomtsyan, et al, "Design, synthesis, and structure-activity relationship of 6-alkynylpyrimidines as potent adenosine kinase inhibitors", J. Med. Chem. 45(17):3639-3648 (2002).
Gooseman, et al., "The intramolecular b-fluorine . . . ammonium interaction in 4- and 8-membered rings", Chem. Common, vol. 30, pp. 3190-3192 (2006).
Gorre, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303 (12 pp.).
Goto et al. Color mapping of tear lipid layer thickness distribution from the image analysis in DR-1 tear lipid layer interference images (ARVO abstract). ARVO 2004.
Goto et al., "Computer-synthesis of an interference color chart of human tear lipid layer by a colorimetric approach",Invest Ophthalmol Vis Sci, 2003;44:4693-7.
Goto et al., "Differentiation of lipid tear deficiency dry eye by kinetic analysis of tear interference images", Arch Ophthalmol, 2003;121:173-80.
Goto et al., "Evaluation of the tear film stability after laser in situ keratomileusis using the tear film stability analysis system", Am J Ophthalmol, Jan. 2004b;137(1):116-20.
Goto et al., "Tear Film Stability Analysis System: Introducing a new application for videokeratography", Cornea, Nov. 2004a;23(8):S65-S70.
Goto, et al., Kinetic analysis of tear interference images in aqueous tear deficiency dry eye before and after punctal occlusion. Invest Ophthalmol Vis Sci, 2003;44:1897-905.
Gottlieb, A.B., et al, "Psoriasis: Emerging Therapeutic Strategies", Nat Rev Drug Disc., 4:19-34 (2005).
Grabbe, et al., "Immunoregulatory mechanisms involved in elicitation of allergic-contact hypersensitivity", Immunol Today, Jan; 19(1):37-44 (1998) (only 1 page provide and marked "best available copy").
Green, T.W. and Wuts, P.G,M.. Protective Groups in Organic Synthesis, 3rd. Ed., Wiley & Sons, Inc., New York (1999).
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Guillon, Jean-Pierre, "Tear film photography and contact lens wear", J Br Contact Lens Assoc, 1982;5:84-7.
Guschin, et al, "A major role for the protein tyrosine kinase JAK1 in the JAKISTAT signal transduction pathway in response to interleukin-6", Embo J 14:1421-1429 (1995).

Hamze' et al., "Synthesis of Various 3-Substituted 1,2,4-Oxadiazole-Containing Chiral B3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Higuchi, et al., "Pro-drugs as Novel Delivery Systems," vol. 14 of the A.C.S. Symposium Series (1975).
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
International Preliminary Report on Patentability (with Written Opinion) dated Jun. 18, 2008 for International Appln. No. PCT/US2006/047369 (10 pgs.).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability (with Written Opinion) dated Mar. 6, 2012 for International Appln. No. PCT/US2010/047252 (7 pgs.).
International Preliminary Report on Patentability for International Appln. No. PCT/US2008/066662 dated Dec. 17, 2009 (7 pgs.).
International Preliminary Report on Patentability for International Appln. No. PCT/US2008/66658 mailed Dec. 17, 2009 (7 pages).
International Preliminary Report on Patentability for International Appln. No. PCT/US2009/036635 mailed Sep. 14, 2010 (6 pages).
International Preliminary Report on Patentability for International Appln. No. PCT/US2009/059203 mailed Apr. 5, 2011 (6 pages).
International Preliminary Report on Patentability for International Appln. No. PCT/US2010/021003 mailed Jul. 19, 2011(11 pages).
International Preliminary Report and Written Opinion dated Feb. 9, 2010 for International Appln. No. PCT/US2009/059203 (10 pages).
International Preliminary Report and Written Opinion for International Appln. No. PCT/US2005/046207 dated May 15, 2007 (6 pages).
International Preliminary Report and Written Opinion for International Appln. No. PCT/US2008/066662 dated Dec. 23, 2008 (11 pgs.).
International Preliminary Report and Written Opinion for International Appln. No. PCT/US2009/036635 dated Jun. 3, 2009 14 pages.
International Preliminary Report and Written Opinion for PCT/US2006/047369, 16 pages (Apr. 24, 2007).
International Preliminary Report and Written Opinion for PCT/US2011/027665 mailed Jun. 27, 2011 (14 pages).
International Search Report and Written Opinion for PCT/US2011/061374 mailed Mar. 27, 2012 (10 pages).
International Search Report and Written Opinion for PCT/US2011/061351 mailed Feb. 17, 2012 (12 pages).
International Search Report for PCT/US2008/66658 mailed Dec. 23, 2008 (4 pages).
International Search Report for PCT/US2009/036635 mailed Jun. 3, 2009 (2 pages).
International Search Report and Written Opinion for PCT/US2010/021003 mailed Aug. 16, 2010 (23 pages).
International Search Report for PCT/US2010/035728 mailed Jul. 8, 2010 (3 pages).
International Search Report for PCT/US2010/035783 mailed Aug. 23, 2010 (4 pages).

(56) References Cited

OTHER PUBLICATIONS

International Search Report for PCT/US2010/047252 mailed Nov. 17, 2010 (4 pages).
International Search Report for PCT/US2010/052011 mailed Nov. 30, 2010 (3 pages).
Iranpoor, N.; Firouzabadi, H.; Aghapour, "A Rapid and Facile Conversion of Primary Amides and Aldoximes to Nitriles and Ketoximes to Amides with Triphenylphosphine and N-Chlorosuccinimide", G Syn. Commun 32:2535-41 (2002).
Ishizaki, et al., "Pharmacological Properties of Y-27632, a Specific Inhibitor of Rho-Associated Kinases", Molecular Pharmacology, 2000, 57, 976-983.
Itagaki, et al,"Expedient Synthesis of Potent Cannabinoid Receptor Agonist (−)-CP55,940", Organic Letters, 2005; 7(19); 4181-4183.
James, et al., "A unique clonal JAK2 mutation leading to constitutive signalling causes polycythaemia vera", Nature, 434 (7037):1144-8 (2005).
Jee, et al., "Overview: animal models of osteopenia and osteoporosis", J Musculoskel. Neuron, Interact, 1(3):193-207 (2001).
Jester, et al., "In vivo biomcroscopy and photography of meibomian glands in a rabbit model of meibomian gland dysfunction", Invest Ophthalmol Vis Sci, 1982;22:660-7.
Johnson, et al., "The effect of instilled fluorescein solution volume on the values and repeatability of TBUT measurements", Cornea, 2005;24:811-7.
Kaercher, T., "Ocular symptoms and signs in patients with ectodermal dysplasia syndromes", Grafes Arch Clin Exp Ophthalmol, 2004;495-500.
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase: Mechanism of Activation and Downstream Effectors.", Cancer Res., 65(6):2047-2053, Mar. 15, 2005.
Kim, et al., "Zinc-Modified Cyanoborohydride as a Selective Reducing Agent", J. Org. Chem. 50: 1927-1932 (1985).
King-Smith et al., "Three interferometric methods for measuring the thickness of layers of the tear film", Optom Vis Sci, 1999; 76:19-32.
Kiss, Robert, "Recent developments on JAK2 inhibitors: A patent review", Expert Opinion on Therapeutic Patents, (Apr. 2010) vol. 20, No. 4, pp. 471-495.
Kojima et al., "A new noninvasive tear stability analysis system for the assessment of dry eyes", Invest Ophthalmol Vis Sci, May 2004;45(5):1369-74).
Komuro et al., "Assessment of meibomian gland function by a newly developed laser meibometer", Adv Exp Med Biol, 2002; 506:517-520.
Korb et al., "The effect of two novel lubricant eye drops on tear film lipid layer thickness in subjects with dry eye symptoms", Optom Vis Sci, 2005; 82: 594-601.
Korb, et al., "Increase in tear film lipid layer thickness following treatment of meibomian gland dysfunction", Adv Exp Med Biol, 1994;350:293-8.
Korolev, et al., "Pd-EDTA as an efficient catalyst for Suzuki-Miyaura reactions in water", Tet. Lett. 46: 5751-5754 (2005).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kuo, et al., "Pd-EDTA as an efficient catalyst for Suzuki-Miyaura reactions in water", Chem Common 301-3 (2007).
Kuppens et al., "Basal tear turnover and topical timolol in glaucoma patients and healthy controls by Fluorophotometry", Invest Ophthalmol Vis Sci, 1992; 33:3442-3448.
Lai, et al., "Mechanistic Study on the Inactivation of General Acyl-CoA Dehydrogenase by a Metabolite of Hypoglycin A", J. Am. Chem. Soc. 113: 7388-7397 (1991).
Lam, et al, "Tear Cytokine Profiles in Dysfunctional Tear Syndrome", Am J Ophthalmol., 147(2):198-205 (2009).
Larock, R., "Comprehensive Organic Transformations", Wiley-VCH, $2^{nd}$ Ed. (1999) pp. 1949-1950, 1958-1959, 1976, and 1983-1985.
Lemp "Report of National Eye Institute/Industry Workshop on clinical trials in dry eyes", CLAO J, 1995;21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter re Office Action received for Chilean Application No. 3496-2006 (Jul. 5, 2010) (4 pages).
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INC8018424 A Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Maffioli, et al., "Mild and Reversible Dehydration of Primary Amides with PdCl2 in Aqueous Acetonitrile", Organic Letters vol. 7 No. 23, 5237-39 (2005).
Main et al, "High throughput synthesis of diverse 2,5-disubstituted indoles using titanium carbenoids bearing boronate functionality", Tetrahedron, 64(5):901-914 (2007).
Mainstone et al., "Tear meniscus measurement in the diagnosis of dry eye", Curr Eye Res, 1996; 15:653-661.
Manjula, et al., "Rapid Method of Converting Primary Amides to Nitrites and Nitriles to Primary Amides by ZnCl2 using Microwaves under Different Reaction Conditions", Syn. Commun 37:1545-50 (2007).
Manning, et al., "The Protein Kinase Complement of the Human Genome", Science. 2002, 298(5600):1912-16 and 1933-34.

(56) References Cited

OTHER PUBLICATIONS

March, Jerry, *Advanced Organic Chemistry: Reactions, Mechanisms, and Structure*, 3rd ed., John Wiley & Sons:New York, pp. 845-855 (1985).

Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.

Maruyama et al., "Effect of environmental conditions on tear dynamics in soft contact lens wearers", Invest Ophthalmol Vis Sci, 2004;45(8):2563-8.

Mathers et al., "Assessment of the tear film with tandem scanning confocal microscopy", Cornea, 1997;16:162-8.

Mathers et al., "Tear film changes associated with normal aging", Cornea, 1996; 15:229-334.

Mathers et al., "Tear flow and evaporation in patients with and without dry eye", Ophthalmology, 1996; 103:664-669.

Mathers et al., "Video imaging of the meibomian gland", Arch Ophthalmol, 1994;112:448-9.

Mathers, "Evaporation from the ocular surface", Exp Eye Res, 2004; 78:389-394.

McNamara et al., "Fluorometry in contact lens research: The next step", Optom Vis Sci, 1998; 75:316-322.

Mengher et al., "Non-invasive tear film break-up time: sensitivity and specificity", Acta Ophthalmol (Copenh), 1986; 64(4):441-4.

Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).

Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.

Methods in Molecular Biology: vol. 225, Inflammation Protocols., Winyard, P.G. and Willoughby, D.A., Humana Press, 2003.

Meydan et al., "Inhibition of acute lymphoblastic leukaemia by a Jak-2 inhibitor", Nature. Feb. 15, 1996;379(6566):645-8.

Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).

Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).

Minegishi, et al., "Human Tyrosine Kinase 2 Deficiency Reveals Its Requisite Roles in Multiple Cytokine Signals Involved in Innate and Acquired Immunity", Immunity 25:745-55 (2006).

Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol, Sep. 2010;85(3):192-9. Epub Jun. 2, 2010.

Mishima, et al., "Determination of tear volume and tear flow", Invest Ophthalmol, 1966; 5:264-276.

Mishima, S., "Some physiological aspects of the precorneal tear film", Arch Ophthalmol, 1965;73:233-241.

Mitsunobu, O., "The Use of Diethyl Axodicarboxylate and Triphenylphosphine in Synthesis and Transformation of Natural Products." Synthesis (1): 1-28 (1981).

Miyata, et al., "Stereospecific nucleophilic addition reactions to olefins.", J. Org. Chem. 56:6556-6564 (1991).

Miyaura et al., "Palladium-Catalyzed Cross-Coupling Reactions of Organoboron Compounds," Chem. Rev., i 995, 95, 2457-2483.

Miyoshi et al., "Interleukin-8 concentrations in conjunctival epithelium brush cytology samples correlate with neutrophil, eosinophil infiltration, and corneal damage", Cornea, 2001;20:743-7.

Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).

Moriarty, et al., "The synthesis and SAR of 2-amino-pyrrolo[2,3-d]pyrimidines: A new class of Aurora-A kinase inhibitors", Bioorganic and Medicinal Chemistry Letters, 16(22), 5778-5783 (2006).

Mosby's Dictionary of Medicine, Nursing, & Health Professions, sicca complex, 2009, Elsevier, printed from http://www.credoreference.com/entry/ehsmosbymed/sicca_complex, 2 pages.

Mullighan, et al, "JAK mutations in high-risk childhood acute lymphoblastic leukemia", Proc Nati Acad Sci USA. 106:9414-8 (2009).

Naka T., "The paradigm of IL-6: from basic science to medicine", Arthritis Res. 2002;4 Suppl 3:S233-42. Epub May 9, 2002.

Nakagawara, Akira, "Trk receptor tyrosine kinases: A bridge between cancer and neural development." Cancer Letters, 169:107-114, 2001.

Nally et al., "Ocular discomfort and tear film break-up time in dry eye patients: A correlation", Invest Ophthalmol Vis Sci, 2000;41:4:1436 (Poster Presentation).

Naqvi, et al., "A potential role of ruxolitinib in leukemia", Expert Opinion on Investigational Drugs, (Aug. 2011) vol. 20, No. 8, pp. 1159-1166.

National Cancer Institute, "FDA Approval for Ruxolitinib Phosphate", http://www.cancer.gov/cancertopics/druginfo/fda-ruxolitinibphosphate Posted Nov. 18, 2011 (3 pages).

Naus, et al., "6-(Het)aryl-7-Deazapurine Ribonucleosides as Novel Potent Cytostatic Agents", J. Med. Chem., 53(1):460-470 (2010).

Neidle, Stephen, Cancer Drug Design and Discovery, (Elsevier/Academic Press, 2008) pp. 427-431.

Nelson et al., "Tear film osmolality determination: an evaluation of potential errors in measurement" Curr Eye Res, Sep;5(9):677-81, 1986.

Neubauer, H., et al., "Jak2 Deficiency Defines an Essential Developmental Checkpoint in Definitive Hematopoiesis", Cell, 93(3): 397-409 (1998).

Nicholoff et al., "Recent Insights into the immunopathogenesis of psoriasis provide new therapeutic opportunities", J. Clin. Invest., vol. 113, No. 12, 1664-1675 (2004).

Nichols et al., "The lack of association between signs and symptoms in patients with dry eye disease", Cornea, vol. 23(8):762-770 (2004).

Nichols et al., "The repeatability of clinical measurements of dry eye", Cornea, vol. 23(3):272-85 (2004).

Nishio, et al., "Tyrosine kinase-dependent modulation by interferon-α of the ATP-sensitive K+ current in rabbit ventricular myocytes", FEBS Letters, (1999), 445, 87-91.

Nitta, et al., "Peptide-Titanium Complex as Catalyst for Asymmetric Addition of Hydrogen Cyanide to Aldehyde", J. Am. Chem. Soc., 1992, 114, 7969-75 (1992).

Norn, M., "Quantitative tear ferning. Clinical investigations", Acta Ophthalmol (Copenh), Jun. 1994;72(3):369-72.

Notice of Allowance and Fee(s) Due dated Sep. 21, 2007 in connection with U.S. Appl. No. 11/313,394 (6 pages).

Office Action (Non-final) dated Aug. 22, 2007 in connection with U.S. Appl. No. 11/115,702 (9 pages).

Office Action (Non-final) dated Dec. 3, 2007 in connection with U.S. Appl. No. 11/524,641 (13 pages).

Office Action (Non-final) dated Feb. 25, 2009 for U.S. Appl. No. 12/137,892 (13 pgs.).

Office Action (Final) dated Feb. 7, 2008 for U.S. Appl. No. 11/115,702 (5 pages).

Office Action (Final) dated Nov. 30, 2009 for U.S. Appl. No. 12/137,892 (9 pgs.).

Office Action (Non-final) dated Apr. 20, 2007 in connection with U.S. Appl. No. 11/313,394 (16 pages).

Office Action received for European Application No. 06 839 328.9 (Jan. 22, 2009) (5 pages).

Office Action received for Japanese Application No. 2008-545733 dated Oct. 11, 2011 (5 pages).

Office Action received for New Zealand Application No. 569015 dated Feb. 24, 2010 (2 pages).

(56) References Cited

OTHER PUBLICATIONS

Office Action received for Singapore Application No. 2008-04386-1 (Aug. 24, 2010).
Office Action received for Vietnamese Patent Application No. 1-2011-03188 dated Mar. 8, 2012 as translated by foreign associate (10 pages).
Office Action, Eurasian Patent Office, prepared Feb. 5, 2010.
Office Action, European Patent Office, Application No. 06 839 328,9 mailed Oct. 21, 2010.
Office Action, European Patent Office, mailed Nov. 6, 2009.
Office Action, Mexican Patent Office, mailed Jun. 15, 2010.
Office Action, Mexican Patent Office, mailed Nov. 13, 2009.
Office Action/Examination Report received for Pakistan Application No. 211/2009 dated Jan. 18, 2010 (1 page).
Oguz, et al., "The height and radius of the tear meniscus and methods for examining these parameters", Cornea, 2000;19:497-500.
Opposition, Costa Rica, patent application No. 2011-620, translation from Foreign Associate dated Jun. 13, 2012 (6 pages).
Opposition, Ecuador Patent Office, mailed Nov. 18, 2008 1 page letter from Foreign Associate enclosing the translation (5 pages) of the Opposition.
Ortmann, et al., "Janus kinases and signal transducers and activators of transcription: their roles in cytokine signaling, development and immunoregulation." Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Ousler, et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer, et al., "Multiple roles of ephrins in morphogenesis, neuronal networking, and brain function." Genes & Dev,, 17:1429-1450, 2003.
Pardanani A., "JAK2 inhibitor therapy in myeloproliferative disorders: rationale, preclinical studies and ongoing clinical trialsJAK2 inhibitor therapy in MPD", Leukemia 22, 23-30 (Jan. 2008).
Parganas, E., D. Wang, et al., "Jak2 is Essential for Signaling through a Variety of Cytokine Receptors", (1998). Cell, 93(3): 385-95.
Park et al., "Homogeneous Proximity Tyrosine Kinase Assays: Scintillation Proximity Assay versus Homogeneous Time-Resolved Fluorescense", Analytical Biochemistry, 1999, 269, 94-104.
Patani, et al., "Bioisosterism: A Rational Approach in Drug Design", Chem. Rev., 1996, 96, 3147-3176.
Pearce et al., "Spatial location studies on the chemical composition of human tear ferns", Ophthalmic Physiol Opt, (2000) vol. 20(4):306-13.
Pearce, et al., "An improved fluorophotometric method for tear turnover assessment", Optom Vis Sci, (2001.) 78(1):30-36).
Pensyl et al., "The repeatability of tear mucus ferning grading", Optom Vis Sci, Aug. 1998;75(8):600-4.
Pernis, et al., "JAK-STAT signaling in asthma." J Clin Invest, 109(10): 1279-83 (2002).
Pflugfelder, et al., "Evaluation of subjective assessments and objective diagnostic tests for diagnosing tear-film disorders known to cause ocular irritation", Cornea, 1998;17(1):38-56.
Pirard, B. et al., "Classification of Kinase Inhibitors Using BCUT Descriptors", J. Chem. Inf. Comput. Sci., 2000, 40, 1431-1440.
Pisella et al., Flow cytometric analysis of conjunctival epithelium in ocular rosacea and keratoconjunctivitis sicca. Ophthalmology, 2000;107:1841-1849.
Pisella, et al., Conjunctival proinflammatory and proapoptotic effects of latanoprost, preserved timolol and unpreserved timolol: an ex vivo and in vitro study. Invest Ophthalmol Vis Sci, 2004;45:1360-1368).
Portnaya, et. al., "Azomethine dyes. IV. Indoaniline dyes derived from heterocyclic N-substituted 1-hydroxy-2-naphthamid", Ts Vses Nauchn Issled Kinofotoinst, Issue 40, (1960) pp. 106-168.
Press Release dated Sep. 18, 2008: "Incyte's Topical JAK Inhibitor Demonstrates Positive Proof-of-Concept Results in Patients with Mild to Moderate Psoriasis" (4 pages).

Prezent, et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al, "One-pot conversion of activated alcohols into 1,1-dibromoalkenes and terminal alkynes using tandem oxidation processes with manganese dioxide", Tetrahedron, 62 (2006) 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957.
Ravin, L., "Preformulation", Remington's Pharmaceutical Sciences, 17th ed., Mack Publishing Company, Easton, Pa., 1985, Chapter 76, pp. 1409-1423.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action of Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Robin et al., In vivo transillumination biomicroscopy and photography of meibomian gland dysfunction. Ophthalmology, 1985;92:1423-6.
Rodig, et al., "Disruption of the Jak1 gene demonstrates obligatory and nonredundant roles of the Jaks in cytokine-induced biologic responses." Cell, 93(3): 373-83 (1998).
Rolando et al., "Tear mucus crystallization in children with cystic fibrosis", Ophthalmologica, 1988;197(4):202-6).
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.
Rolando et al., "The effect of hyperosmolarity on tear mucus ferning", Fortschr Ophthalmol, 1986;83:644-646.
Rolando et al., The Ocular Surface and Tear Film and Their Dysfuntion in Dry Eye Disease, Survey of Ophthalmology, Mar. 2001, vol. 45, Supplement 2, S203-S210.
Rolando, M. "Tear mucus ferning test in natmal and keratoconjunctivitis sicca eyes." Chibret Int J Ophthalmol, 1984;2(4):32-41.
Roudebush et al., "Pharmacologic manipulation of a four day marine delayed type hyper sensitivity model", Agents Actions, 1993, 38(1-2):116-21.
Rousvoal, G. et al. "Janus kinase 3 inhibition with CP-690,550 prevents allograft vasculopathy", Transpl Int., 2006 19(12):1014-21.
Saemann, et al., "Prevention of CD40-triggered dendritic cell maturation and induction of T-cell hyporeactivity by targeting of Janus kinase 3." Am J. Transplant, 3(11): 1341-9 (2003).
Saettone et al. "Ocular inserts for topical delivery," Advanced Drug Delivery Reviews, 16: 95-106, 1995.
Samanta et al., "Janus kinase 2: a critical target in chronic myelogenous leukemia", Cancer Res. Jul. 1, 2006;66(13):6468-72.
Sawada et al, "Increased Lipophilicity and Subsequent Cell Partitioning Decrease Passive Transcellular Diffusion of Novel, Highly Lipophilic Antioxidents", The Journal of Pharmacology and Experimental Therapeutics, 1999, No. 288, vol. 3, pp. 1317-1326, p. 1321, compound 26.
Schindler et al., "Hormones and Signaling: Cytokines and STAT Signaling", Adv Phannacol. 2000; 47:113-74.

(56) References Cited

OTHER PUBLICATIONS

Schrader et al., "Animal Models of Dry Eye," Developmental Opthalmology, Karger 2008, 41, 298-312.
Scott, et al., "Jaks, STATs, Cytokines, and Sepsis." Clin Diagn Lab Immunol, 9(6): 1153-9 (2002).
Seefeld, et al, "Discovery of 5-pyrrolopyridinyl-2-thiophenecarboxamides as potent AKT kinase", Bioorganic & Medicinal Chemistry Letters, 19(8):2244-2248 (2009).
Seela, Frank; Muth, Heinz Peter; Roefing, Angefika, Helvetica Chimica, Acta, (1991), 74(3), 554-64.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimazaki et al., "Meibomian gland dysfunction in patients with Sjogren syndrome", Ophthalmology, 1998;105(8):1485-8.
Smith et al, "Basic pathogenic mechanisms operating in experimental model acute anterior uveitis," Immunology and Cell Biology, 1998, 76, 497-512.
Smolen, et al, "Effect of interleukin-6 receptor inhibition with tocilizumab in patients with rheumatoid arthritis (Option study): a double-blind, placebo-controlled, randomized trial", Lancet 371:987, 2008 (2008).
Sriram, K. et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol. Chem., 2004, 279(19):19936-47. Epub Mar. 2, 2004.
Staerk, J., et. al., "JAK1 and Tyk2 activation by the homologous polycythemia vera JAK2 V617F mutation: cross-talk with IGF1 receptor", J Biol Chem., 280:41893-41899 (2005).
State Intellectual Property Office, PR China, Office Action, prepared Sep. 3, 2010.
Stirewalt et al., "Predictors of relapse and overall survival in Philadelphia chromosome-positive acute lymphoblastic leukemia after transplantation", Biol Blood Marrow Transplant. Mar. 2003;9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Sullivan et al., "4th International Conference on the Lacrimal Gland, Tear Film & Ocular Surface and Dry Eye Syndromes, Nov. 20, 2004" (2 pages).
Takahashi, et al., "Solvent-Free Reaction Using Pmospwonium Salts: Chlorination of Hydroxyheteroaromatics and dehydration of Primary Amides", Heterocycles 68: 1973-1979 (2006).
Takano et al., "Inflammatory cells in brush cytology samples correlate with the severity of corneal lesions in atopic keratoconjunctivitis", Br J Ophthalmol, 2004;88:1504-5.
Takemoto, et al. (1997). "Proliferation of adult T cell leukemia/lymphoma cells is associated with the constitutive activation of JAK/STAT proteins." Proc Nati Acad Sci U S A, 94(25): 13897-902.
Tan, et al, "Racemization processes at a quaternary carbon center in the context of the asymmetric Michael reaction", Tetrahedron Lett., 42(30):5021-5023 (2001).
Tang et al., "Knowledge-based design of 7-azaindoles as selective B-Raf inhibitors", Bioorganic & Medicinal Chemistry Letters (2008), 18(16):4610-4614.
Tasian et al., "Understanding the biology of CRLF2-overexpressing acute lymphoblastic leukemia", Critical Reviews in Oncogenesis, (2011) vol. 16, No. 1-2, pp. 13-24.
Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp, 1188-1191.
Thompson, J., et al., "Photochemical Preparation of a Pyridone Containing Tetracycle: A Jak Protein Kinase Inhibitor", Bioorganic & Medicinal Chemistry Letters, 12 (2002) 1219-1223.
Tiffany et al., Meniscometry using the Tearscope-plus (ARVO abstract). Invest Ophthalmol Vis Sci, (2001);42, s37 (1 page).
Tiffany, J., "Refractive index of meibomian and other lipids", Curr Eye Res, (1986);5:887-9.
Toyonaga, "Blockade of constitutively activated Janus kinase/signal transducer and activator of transcription-3 pathway inhibits growth of human pancreatic cancer", Cancer Lett. 201(1):107-16 (2003).
Tsubota et al., "Brush cytology for the evaluation of dry-eye", Nippon Ganka Gakkai Zasshi, 1990a ;94:224-30; in Japanese with English abstract.
Tsubota et al., "Conjunctival brush cytology", Acta Cytol, (1990) vol. 34(2):233-5.
Tsubota et al., "Detection by brush cytology of mast cells and eosinophils in allergic and vernal conjunctivitis"; Cornea, (1991) vol. 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem. 50:760-763 (1985).
van Best et al., "Measurement of basal tear turnover using a standardized protocol", Graefe's Arch Chu Exp Ophthalmol, 1995; 233:1-7.
van Bijsterveld, O., "Diagnostic tests in the sicca syndrome", Arch Ophthalmol, 1969;82:10-14.
Vasilevsky, et al., "Ethyl Vinyl Ether—an Agent for Protection of the Pyrazole NH-Fragment. A Convenient Method for the Preparation of N-Unsubstituted 6Alkynylpyrazoles", Heterocycles, 60(4):879-886 (2003).
Verma, et al., "Jak family of kinases in cancer", Cancer and Metastasis Reviews, vol. 22, No. 4, 423-434, DOI: 10.1023/A:1023805715476 (2003).
Verstovsek, "Therapeutic Potential of JAK2 Inhibitors", Hematology Am Soc Hematol Educ Program, 2009:636-42.
Verstovsek, S. et al. "Characterization of JAK2 V617F Allele Burden in Advanced Myelofibrosis (MF) Patients: No Change in V617F:WT JAK2 Ratio in Patients with High Allele Burdens Despite Profound Clinical Improvement Following Treatment with the JAK Inhibitor INCB018424" Poster #2802 at the American Society of Hematology Annual Meeting (ASH), Dec. 7, 2008. (18 pages).
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), pre-

(56) References Cited

OTHER PUBLICATIONS sentation at the American Society of Hematology 49th Annual Meeting and Exposition, Dec. 10, 2007 (16 pages).
Vitali et al. "The European Community Study Group on diagnostic criteria for Sjogren's syndrome. Sensitivity and specificity of tests for ocular and oral involvement in Sjogren's syndrome." 1994; Ann Rheum Dis, 53(10): 637-47.
Wagh, et al., "Polymers used in ocular dosage form and drug delivery systems", Asian J. Pharm., pp. 12-17 (Jan. 2008).
Webster's New World Medical Dictionary, Sjogren's syndrome, 2003, Wiley Publishing, printed fro http://www.credoreference.com/entry/webstermed/sjogren_s_syndrome, 2 pages.
Weiss, et al., "Evaluation of a Series of Naphthamides as Potent, Orally Active Vascular Endothelial Growth Factor Receptor-2 Tyrosine Kinase Inhibitors", J. Med Chem., 51:1668-1680 (2008).
Welch et al., "An approach to a more standardized method of evaluating tear film break-up time", Invest Ophthalmol Vis Sci, 2003; 2485/B324 (abstract only—2 pages).
White et al., "Human basic tear fluid osmolality. I. Importance of sample collection strategy", Acta Ophthalmol (Copenh), Aug;71(4):524-9, 1993.
Williams et al., "Carbohydrate Chemistry: Recent Advances", Chem. Rev. 81:589-636 (1981).
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf, et al., "Burger's Medicinal Chemistry and Drug Discovery", 5$^{th}$ Ed. Part I, pp. 975-977 (1995).
Wu et al., One-Pot Two-Step Microwave-Assisted Reaction in Construction 4,5-Disubstituted Pyrazolopyrimidines Organic Letters, 2003, 5(20), 3587-3590.
Xiaoyang et al., "Knockdown of STAT3 Expression by RNA Interference Inhibits the Induction of Breast Tumors in Immunocompetent Mice", Cancer Res Apr. 1, 2005 65; 2532.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-☐B activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Yokoi et al., "A newly developed video-meibography system featuring a newly designed probe", Jpn J Ophthalmol, 2007; 51: 53-6).
Yokoi et al., "Assessment of meibomian gland function in dry eye using meibometry", Arch Ophthalmol, 1999;117:723-9).
Yokoi et al., "Correlation of tear lipid layer interference patterns with the diagnosis and severity of dry eye", Am J Ophthalmol, 1996;122:818-24.
Yokoi et al., "Non-invasive methods of assessing the tear film", Exp Eye Res, 2004;78:399-407).
Yu, et al., "Constitutive activation of the Janus kinase-STAT pathway in T lymphoma overexpressing the Lck protein tyrosine kinase", J Immunol. 159(11):5206-10 (1997).
Zheng, et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zoppellaro, et al., "A Multifunctional High-Spin Biradical Pyrazolylbipyridine-bisnitronylnitroxide", Org. Lett. 6(26):4929-4932 (2004).
Zou, et al., "Signaling Pathways Activated by Oncogenic Forms of Abl Tyrosine Kinase." Journal of Biological Chemistry, 274(26):18141-18144, 1999.
International Search Report and Written Opinion for PCT/US2011/037291, 11 pages (Apr. 19, 2012).
International Search Report and Written Opinion for PCT/US2008/083319, 29 pages mailed Mar. 13, 2009.
International Search Report and Written Opinion for PCT/US2011/025433, 12 pages (mailed Jul. 20, 2011).
Peters, K. G. et al., "Functional Significance of Tie2 Signaling in the Adult Vasculature", 2004, © The Endocrine Society.
Pillonel, Christian, "Evaluation of phenylaminopyrimidines as antifungal protein kinase inhibitors", Pest Management Science, Wiley & Sons, vol. 61, Jun. 13, 2005 pp. 1069-1076.
Office Action, Canadian Patent Office, Application No. 2,632,466, dated May 8, 2012 (3 pages).
Bosworth, "JAK1/JAK2 Inhibitor Ruxolitinib is a Rising Star", Clinical Oncology News 2011, 06:04 (3 pages).
International Preliminary Report on Patentability for PCT/US2011/027665 mailed Sep. 11, 2012 (7 pages).
International Preliminary Report on Patentability for PCT/US2010/052011 mailed Apr. 11, 2012 (4 pages).
International Preliminary Report on Patentability for PCT/US2011/025433 mailed Aug. 21, 2012 (7 pages).
International Search Report and Written Opinion for PCT/US2012/025581, 16 pages (mailed Apr. 26, 2012).
Janes, M. et al., "Effective and selective targeting of leukemia cells using a TORC1/2 kinase inhibitor.", *Nature Medicine* (2010) LNKD-PUBMED:20072130, vol. 16, No. 2, pp. 205-213 XP002673719.
Mancini, M. et al., "RAD 001 (everolimus) prevents mTOR and Akt late re-activation in response to imatinib in chronic myeloid leukemia.", *J. Cellular Biochemistry* (2010) LNKD-PUBMED:20014066, XP-002673720 vol. 109, No. 2 (2010) pp. 320-328.
Mesa, R. et al., "Emerging drugs for the therapy of primary and post essential thrombocythemia, post polycythemia vera myelofibrosis", *Expert Opinion on Emerging Drugs England*, vol. 14, No. 3 (2009) pp. 471-479.
Opposition for EP Patent 1966202, filed on Jun. 21, 2012 (30 pages).
Ting, et al., "The Synthesis of substituted bipiperidine amide compounds as CCR3 antagonists", Bioorg. Med. Chem. Lett., vol. 15, No. 5, 1 (2005) pp. 1375-1378.
Vannucchi, A. et al., "Inhibitors of PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742 ASH Annual Meeting Abstract 3835 American Society of Hematology (2011).
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.
Vannucchi A. et al., "The mTOR Inhibitor, RAD001, Inhibits the Growth of Cells From Patients with Myeloproliferative Neoplasms", Blood: ASH Annual Meeting Absracts, 51$^{st}$ Annual Meeting of the American Society of Hematology, vol. 114, No. 22 (2009) 2 pages.
Gura, "Cancer Models: Systems for Identifying New Drugs Are Often Faulty", *Science*, vol. 278, No. 5340, pp. 1041-1042 (Nov. 7, 1997).
Roberts, Jr., et al., "Trends in the Risks and Benefits to Patients with Cancer Participating in Phase 1 Clinical Trials", *JAMA* 292(17):2130-2140 (Nov. 3, 2004).
Kamb, "What's wrong with our cancer models?", *Nature Reviews Drug Discovery* 4, pp. 161-165 (2005).
Kola, "Can the pharmaceutical industry reduce attrition rates?", *Nature Reviews Drug Discovery* 3, pp. 711-715 (2004).
Leaf, Clifton, "Why are we losing the war on cancer (and how to win it)", *Health Administrator*, vol. XVII, No. 1:172-183 (2005).
Expert Scientific Group on Phase One Clinical Trials Final Report, Nov. 30, 2006, pp. C1, C35-C38.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the

(56) References Cited

OTHER PUBLICATIONS

American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
International Search Report and Written Opinion for PCT/US2012/043099, 11 pages (Sep. 13, 2012).
International Search Report and the Written Opinion, PCT/US2012/053921, mailed Nov. 7, 2012 (19 pages).
International Search Report and the Written Opinion, PCT/US2012/051439, mailed Nov. 30, 2012 (15 pages).
International Search Report and Written Opinion for PCT/US2012/050252 mailed Jan. 2, 2013, 17 pages.
Notice of Hearing and Preliminary Report for EP Patent 1966202, dated Mar. 18, 2013 (7 pages).
Opposition for India Patent Application No. 2365/KOLNP/2008 dated Nov. 12, 2012 (received by Applicants from Indian associate on Apr. 17, 2013) 37 pages.
Patrick, Graham L., "An Introduction to medicinal chemistry" *Oxford University Press Inc.*, New York (31 pages) (cited in Opposition from India dated Nov. 12, 2012.
Bhattacharya et al., "Brittain, ed. Polymorphism in Pharmaceutical Solids," 2009, p. 327-345.
Bock, C., et al. "Managing drug resistance in cancer: lessons from HIV therapy." Nature. (Jul. 2012), vol. 12, pp. 494-501.
Clark et al., "Discovery and Development of Janus Kinase (JAK) inhibitors for Inflammatory Diseases," J Med Chem., 2014, pp. A-P.
Costa Rican Office Action in CR Application No. 10065, dated Jul. 16, 2013, 8 pages.
International Preliminary Report on Patentability for PCT/US2011/037291 mailed Nov. 27, 2012 (7 pages).
International Preliminary Report on Patentability for PCT/US2011/061351 mailed May 30, 2013 (7 pages).
International Preliminary Report on Patentability for PCT/US2011/061374 mailed May 30, 2013 (5 pages).
International Preliminary Report on Patentability for PCT/US2012/043099 mailed Dec. 23, 2013, 6 pages.
International Preliminary Report on Patentability for PCT/US2012/050210 mailed Feb. 11, 2014, 8 pages.
International Preliminary Report on Patentability for PCT/US2012/051439 mailed Feb. 27, 2014, 7 pages.
International Preliminary Report on Patentability for PCT/US2012/053921 mailed Mar. 20, 2014, 8 pages.
International Search Report and Written Opinion in International Application No. PCT/US2014/020554, dated Jul. 16, 2014, 17 pages.
Lucet et al., "The structural basis of Janus kinas 2 inhibition by a potent and specific pan-Janus kinase inhibitor," Blood, 2006, 107(1):176-183.
Mandal, "Cancer Classification," 2014. Available from: <http://www.news-medical.net/health/Cancer-Classification.aspx, 6 pages.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoidarthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
MD Anderson Cancer Center. "Leukemia Prevention and Screening," 2014, 2 pages.
MD Anderson Cancer Center. "Myeloproliferative Disease Prevention and Screening," 2014, 2 pages.
Norman, "Selective JAK1 inhibitor and selective Tyk2 inhibitor patents," Expert Opinion, Informa Healthcare. 2012, available at: <http://informahealthcare.com/dol/pdfplus/10.1517/13543776.2012.723693>.
Office Action (Final) dated Jan. 29, 2014 in U.S. Appl. No. 13/043,986, 10 pages.
Office Action in U.S. Appl. No. 14/186,338, mailed May 5, 2014, 18 pages.
Office Action, China, Patent Application No. 201080033308.6 dated Aug. 2, 2013, 10 pages.
Opposition, Costa Rica, translation from Foreign Associate Dated Nov. 20, 2013, 9 pages.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
WebMD. "Diabetes Health Center." Available at: < http://diabetes.webmd.com/guide/diabetestreatment_care >. 3 pages, retrieved from the Internet May 28, 2013.
Ye et al., "The synthesis and the antitumor activity of 5,7-disubstituted pyrazolo [1,5-a] pyrimidines," Chinese J Med Chem., Feb. 28, 2007, 17(1):18-22.
Yongjun et al., "Advances in research of tyrosine kinases inhibitor of vascular endothelial growth factor receptor," Chinese J New Drugs, Dec. 31, 2008, 17(7):544-550.
Beck et al., "Brief Report: Alleviation of Systemic Manifestations of Castleman's Disease by Monoclonal Anti-Interleukin-6 Antibody," N. Engl. J. Med., 1994, 330(9):602-605.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3):333-337.
Chemical encyclopedia, vol. 1, pp. 242-243, publication "Soviet Encyclopedia," Moscow, 1988.
Choy et al., "Therapeutic Benefit of Blocking huericukin-6 Activity With an Anti-interleukin-6 Receptor Monoclonal Antibody in Rheumatoid Arthritis," Arthritis & Rheumatism, 2002, 46(12) 3143-3150.
Claridge; Bioorganic and Medicinal Chemistry Letters, 2008, 18,2793-2798.
Cottet and Schlosser, "Three Chloro(trifluoromethyl)pyridines as Model Substrates for Regioexhaustive Functionalization," Eur J Org Chem, 2004, 18:3793-3798.
Dorwald; "Side Reactions in Organic Synthesis: A Guide to Successful Synthesis Design" 2005 Wiley-VCH Verlag GmbH & Co. KGaA, Wienheim, chapter 1, 32 pages.
Fayad et al., "Interleukin-6 and interleukin-10 levels in chronic lymphocytic leukemia: correlation with phenotypic characteristics and outcome," Blood, Jan. 2001, 97(1): 256-263.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Gaestel et al., "Targeting innate immunity protein kinase signalling in inflammation," Nat Rev Drug Discov., Jun. 2009, 8(6):480-99.
Gilchrist et al., "5H-2-Pyridines from 2-Bromocyclopentene-1-carboxaldehyde," Tetrahedron, Jan. 1, 1995, pp. 9119-9126.
Goodman, et al., "IL-6 Signaling in Psoriasis Prevents Immune Suppression by T Cells" J. Immunol., Sep. 2009, 183: 3170-3176.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Hickenbottom "Reactions of organic compounds," State Scientific-Technical Publishing Association, Chemical Literature Section, Moscow, 1939, pp. 360-362.
International Preliminary Report on Patentability for PCT/US2013/041601, issued Nov. 18, 2014, 7 pages.

(56) References Cited

OTHER PUBLICATIONS

International Search Report in International Application No. PCT/US2013/041601, mailed Sep. 3, 2013, 3 pages.

International Search Report and Written Opinion in International Application No. PCT/US2013/067794, mailed Dec. 17, 2013, 14 pages.

Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.

Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.

Lima and Barreiro, "Bioisosterism: a useful strategy for molecular modification and drug design," Curr Med Chem. 2005;12(1):23-49.

Maxson et al., "Oncogenic CSF3R Mutations in Chronic Neutrophilic Leukemia and Atypical CML," N. Engl. J. Med., 2013, 368(19):1781-1790.

Neuner, et al., J. Invest. Dermatol. 1991, 97, 27-33.

Nishimoto et. al., "Improvement in Castleman's disease by humanized anti-interleukin-6 receptor antibody theraphy," Blood, 2000, 95(1):56-61.

Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.

Pedranzini, et al., Cancer Res., 66(19):9714-9721 (2006).

Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby-Elsevier, 2009.

Search Report in TW Application No. 100117866, dated Dec. 2014, 1 page.

Sonbol et al., "Comprehensive review of JAK inhibitors in myeloproliferative neoplasms," Therapeutic Advances in Hematology, 2013, 4(1): 15-35.

Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.

Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.

Tamura et al., "Involvement of Human Interleukin 6 in Experimental Cachexia Induced by a Human Uterine Cervical Carcinoma Xenograft," Clin. Cancer Res., Nov. 1995, 1: 1353-1358.

Trikha et al., "Targeted anti-interleukin-6 monoclonal antibody therapy for cancer: a review of the rationale and clinical evidence," Clinical Cancer Research, 2003, 9: 4653-4665.

van Rhee et al., "Anti-Interleukin-6 Monoclonal man's Disease," J. Clin. Oncol., 2010, 28(23):3701-3708.

Vaillant et al., "Turbidity of pulpy flint juice: A key factor for predicting cross-flow microfiltration performance," J Membrane Sci., 2008, 325:404-412.

Vanhoutte, Arthritis Rheum 64.10 (2012): S1051-1.

Verstovsek, et al., Blood (ASH Annual Meeting Abstracts) 2007 110: Abstract 558.

Verstovsek, et al., Blood (ASH Annual Meeting Abstracts) 2009 114: Abstract 311.

Verstovsek, et al., Blood (ASH Annual Meeting Abstracts) 2010 116: Abstract 313.

Xiong, "Inhibition or JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.

Yamamura et al., "Circulating interleukin-6 levels are elevated in adult T-cell leukaemia/lymphoma patients and correlate with adverse clinical features and survival," Br. J. Haematol., 1998, 100: 129-134.

Younes, J. Clin. Oncol., 30(33):1461-1467 (2012).

HETEROCYCLIC DERIVATIVES OF PYRAZOL-4-YL-PYRROLO[2,3-D] PYRIMIDINES AS JANUS KINASE INHIBITORS

This application claims the benefit of priority of U.S. Provisional Appl. No. 61/238,794, filed Sep. 1, 2009, which is incorporated herein by reference in its entirety.

FIELD OF THE INVENTION

The present invention provides heterocyclic derivatives of pyrazol-4-yl-pyrrolo[2,3-d]pyrimidines, as well as their compositions and methods of use, that modulate the activity of Janus kinases (JAKs) and are useful in the treatment of diseases related to the activity of JAKs including, for example, inflammatory disorders, autoimmune disorders, cancer, and other diseases.

BACKGROUND OF THE INVENTION

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus Meraz, et al. (1998) *Cell* 93(3): 373-83). Jak2-/- mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T, et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacal.* 2000; 47:113-74).

Accordingly, inhibitors of Janus kinases or related kinases are widely sought. For example, certain JAK inhibitors, including pyrrolopyridine and pyrrolopyrimidines, are reported in U.S. Ser. No. 11/637,545, filed Dec. 12, 2006.

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY OF THE INVENTION

The present invention provides, inter alia, compounds of Formula Ia:

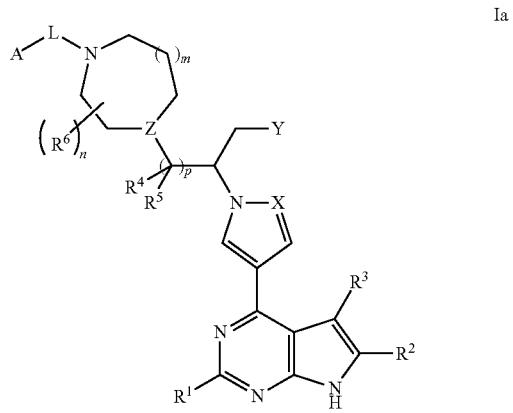

or pharmaceutically acceptable salts thereof, wherein constituent members are defined herein.

The present invention also provides compounds of Formula I:

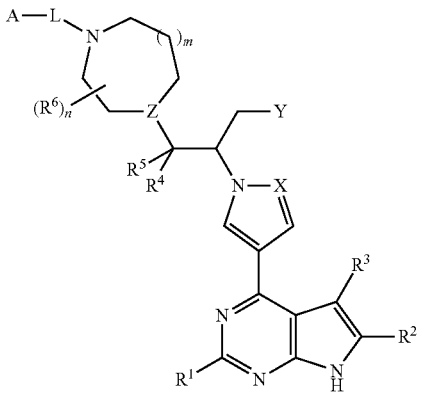

or pharmaceutically acceptable salts thereof.

The present invention further provides pharmaceutical compositions comprising a compound of Formula I or Ia, or a pharmaceutically acceptable salt thereof, and at least one pharmaceutically acceptable carrier.

The present invention further provides methods of modulating an activity of JAK1 comprising contacting JAK1 with a compound of Formula I or Ia, or a pharmaceutically acceptable salt thereof.

The present invention further provides methods of treating a disease or a disorder associated with abnormal kinase expression or activity in a patient by administering to a patient a therapeutically effective amount of a compound of Formula I or Ia, or a pharmaceutically acceptable salt thereof.

The present invention further provides methods of treating an autoimmune disease, a cancer, a myeloproliferative disorder, an inflammatory disease, a bone resorption disease, or organ transplant rejection in a patient in need thereof, comprising administering to said patient a therapeutically effective amount of a compound of Formula I or Ia, or a pharmaceutically acceptable salt thereof.

The present invention also provides compounds of Formula I or Ia as described herein, or pharmaceutically acceptable salts thereof, as described herein for use in methods of treating autoimmune diseases, cancer, myeloproliferative disorders, inflammatory diseases, a bone resorption disease, or organ transplant rejection.

The present invention further provides compounds of Formula I or Ia as described herein, or pharmaceutically acceptable salts thereof, for use in methods of modulating a JAM.

The present invention also provides uses of compounds of Formula I or Ia as described herein, or pharmaceutically acceptable salts thereof, for the preparation of medicaments for use in treating autoimmune diseases, cancer, myeloproliferative disorders, inflammatory diseases, a bone resorption disease, or organ transplant rejection.

The present invention further provides uses of compounds of Formula I or Ia as described herein, or pharmaceutically acceptable salts thereof, for the preparation of medicaments for use in methods of modulating a JAK1.

The details of one or more embodiments of the invention are set forth in the accompanying drawings and the description below. Other features, objects, and advantages of the invention will be apparent from the description and drawings, and from the claims.

DETAILED DESCRIPTION

The present invention provides, inter alia, compounds that modulate the activity of one or more JAKs and are useful, for example, in the treatment of various diseases such as those associated with expression or activity of one or more JAKs. The compounds of the invention include those of Formula Ia:

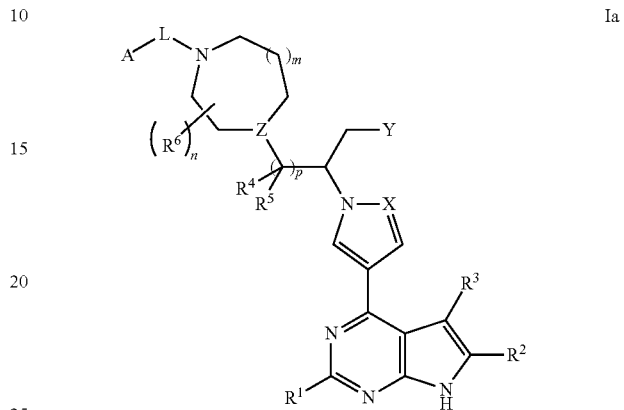

or a pharmaceutically acceptable salt thereof; wherein:

A is H, $C_{1-6}$ alkyl, $C_{2-6}$ alkenyl, $C_{2-6}$ alkynyl, $C_{3-14}$ cycloalkyl, $C_{2-13}$ heterocycloalkyl, $C_{6-14}$ aryl, $C_{1-14}$ heteroaryl, $C_{3-14}$ cycloalkyl-$C_{1-4}$ alkyl, $C_{2-13}$ heterocycloalkyl-$C_{1-4}$ alkyl, $C_{6-14}$ aryl-$C_{1-4}$ alkyl, or $C_{1-14}$ heteroaryl-$C_{1-4}$ alkyl, wherein said $C_{1-6}$ alkyl, $C_{2-6}$ alkenyl, $C_{2-6}$ alkynyl, $C_{3-14}$ cycloalkyl, $C_{2-13}$ heterocycloalkyl, $C_{6-14}$ aryl, $C_{1-14}$ heteroaryl, $C_{3-14}$ cycloalkyl-$C_{1-4}$ alkyl, $C_{2-13}$ heterocycloalkyl-$C_{1-4}$ alkyl, $C_{6-14}$ aryl-$C_{1-4}$ alkyl, and $C_{1-14}$ heteroaryl-$C_{1-4}$ alkyl are each optionally substituted with 1, 2, 3, 4, 5, or 6 independently selected $R^8$ substituents;

each $R^8$ is independently selected from halo, cyano, nitro, $C_{1-6}$ alkyl, $C_{1-6}$ haloalkyl, $C_{2-6}$ alkenyl, $C_{2-6}$ alkynyl, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl, —$OR^a$, —$SR^a$, —$S(\equiv O)R^b$, —$S(\equiv O)_2R^b$, —$S(\equiv O)NR^eR^f$, —$C(\equiv O)R^b$, —$C(\equiv O)OR^b$, —$C(\equiv O)NR^eR^f$, —$OC(\equiv O)R^b$, —$OC(\equiv O)NR^eR^f$, —$NR^eR^f$, —$NR^cC(\equiv O)R^d$, —$NR^cC(\equiv O)OR^d$, —$NR^cC(\equiv O)NR^d$, —$NR^c S(\equiv O)_2R^d$, and —$NR^bS(\equiv O)_2NR^eR^f$;

L is absent, $C(\equiv O)$, $C(\equiv O)NH$, $S(\equiv O)$, or $S(\equiv O)_2$;

X is CH or N;

Y is H, cyano, halo, $C_{1-4}$ alkyl, or $C_{1-4}$ haloalkyl;

Z is $CR^7$ or N;

$R^1$, $R^2$, and $R^3$ are each independently H, hydroxyl, halo, $C_{1-3}$ alkyl, or $C_{1-3}$ haloalkyl;

$R^4$ and $R^5$ are each independently H, $C_{1-3}$ alkyl, or $C_{1-3}$ haloalkyl;

or $R^4$ and $R^5$ together with the carbon atom to which they are attached can form a 3-, 4-, 5-, 6- or 7-membered cycloalkyl ring;

each $R^6$ is independently hydroxyl, fluorine, $C_{1-4}$ alkyl, hydroxy-$C_{1-4}$-alkyl, $C_{1-4}$alkoxy-$C_{1-4}$-alkyl, or $C_{1-4}$ fluoroalkyl;

$R^7$ is H, fluorine, $C_{1-4}$ alkyl, or $C_{1-4}$ fluoroalkyl;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$- alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^c$ and $R^d$, together with the moiety to which they are attached, can form a 3-, 4-, 5-, 6-, or 7-membered heterocycloalkyl ring optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

m is 0 or 1;

n is 0, 1, 2, 3, 4, 5, 6, 7, 8, 9, or 10; and p is 0 or 1;

provided that the valency of each atom in the optionally substituted moieties is not exceeded.

The compounds also include compounds of Formula I:

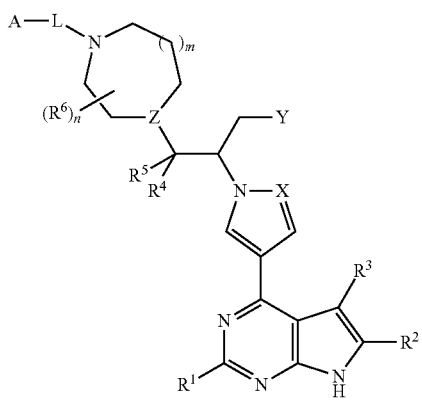

I or pharmaceutically acceptable salts thereof, wherein:

A is H, $C_{1-6}$ alkyl, $C_{2-6}$ alkenyl, $C_{2-6}$ alkynyl, $C_{3-14}$ cycloalkyl, $C_{2-13}$ heterocycloalkyl, $C_{6-14}$ aryl, $C_{1-14}$ heteroaryl, $C_{3-14}$ cycloalkyl-$C_{1-4}$ alkyl, $C_{2-13}$ heterocycloalkyl-$C_{1-4}$ alkyl, $C_{6-14}$ aryl-$C_{1-4}$ alkyl, or $C_{1-14}$ heteroaryl-$C_{1-4}$ alkyl, wherein said $C_{1-6}$ alkyl, $C_{2-6}$ alkenyl, $C_{2-6}$ alkynyl, $C_{3-14}$ cycloalkyl, $C_{2-13}$ heterocycloalkyl, $C_{6-14}$ aryl, $C_{1-14}$ heteroaryl, $C_{3-14}$ cycloalkyl-$C_{1-4}$ alkyl, $C_{2-13}$ heterocycloalkyl-$C_{1-4}$ alkyl, $C_{6-14}$ aryl-$C_{1-4}$ alkyl, and $C_{1-14}$ heteroaryl-$C_{1-4}$ alkyl are each optionally substituted with 1, 2, 3, 4, 5, or 6 independently selected $R^8$ substituents;

each $R^8$ is independently selected from halo, cyano, nitro, $C_{1-6}$ alkyl, $C_{1-6}$ haloalkyl, $C_{2-6}$ alkenyl, $C_{2-6}$ alkynyl, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl, —$OR^a$, —$SR^a$, —$S(=O)R^b$, —$S(=O)_2R^b$, —$S(=O)NR^eR^f$, —$C(=O)R^b$, —$C(=O)OR^b$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cC(=O)NR^d$, —$NR^cS(=O)_2R^d$, and —$NR^bS(=O)_2NR^eR^f$;

L is absent, C(=O), S(=O), or S(=O)$_2$;

X is CH or N;

Y is H, cyano, halo, $C_{1-4}$ alkyl, or $C_{1-4}$ haloalkyl;

Z is $CR^7$ or N;

$R^1$, $R^2$, and $R^3$ are each independently H, halo, $C_{1-3}$ alkyl, or $C_{1-3}$ haloalkyl;

$R^4$ and $R^5$ are each independently H, $C_{1-3}$ alkyl, or $C_{1-3}$ haloalkyl;

or $R^4$ and $R^5$ together with the carbon atom to which they are attached can form a 3-, 4-, 5-, 6- or 7-membered cycloalkyl ring;

each $R^6$ is independently fluorine, $C_{1-4}$ alkyl, or $C_{1-4}$ fluoroalkyl;

$R^7$ is H, fluorine, $C_{1-4}$ alkyl, or $C_{1-4}$ fluoroalkyl;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^c$ and $R^d$, together with the moiety to which they are attached, can form a 3-, 4-, 5-, 6-, or 7-membered heterocycloalkyl ring optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

m is 0 or 1; and n is 0, 1, 2, 3, 4, 5, 6, 7, 8, 9, or 10;

provided that the valency of each atom in the optionally substituted moieties is not exceeded.

In some embodiments, A is other than H.

In some embodiments, A is H, $C_{1-6}$ alkyl, $C_{2-6}$ alkenyl, $C_{2-6}$ alkynyl, $C_{3-14}$ cycloalkyl, $C_{2-13}$ heterocycloalkyl, $C_{6-14}$ aryl, or $C_{1-14}$ heteroaryl, wherein said $C_{1-6}$ alkyl, $C_{2-6}$ alkenyl, $C_{2-6}$ alkynyl, $C_{3-14}$ cycloalkyl, $C_{2-13}$ heterocycloalkyl, $C_{6-14}$ aryl, and $C_{1-14}$ heteroaryl are each optionally substituted with 1, 2, 3, 4, 5, or 6 independently selected $R^8$ substituents.

In some embodiments, A is H, $C_{1-6}$ alkyl, $C_{3-14}$ cycloalkyl, $C_{2-13}$ heterocycloalkyl, $C_{6-14}$ aryl, or $C_{1-14}$ heteroaryl, wherein said $C_{1-6}$ alkyl, $C_{3-14}$ cycloalkyl, $C_{2-13}$ heterocycloalkyl, $C_{6-14}$ aryl, and $C_{1-14}$ heteroaryl are each optionally substituted with 1, 2, 3, 4, 5, or 6 independently selected $R^8$ substituents.

In some embodiments, A is $C_{1-6}$ alkyl, $C_{3-14}$ cycloalkyl, $C_{6-14}$ aryl, or $C_{1-14}$ heteroaryl, each optionally substituted with 1, 2, 3, 4, 5, or 6 independently selected $R^8$ substituents.

In some embodiments, A is $C_{1-6}$ alkyl.

In some embodiments, A is methyl.

In some embodiments, A is $C_{3-14}$ cycloalkyl.

In some embodiments, A is cyclopropyl.

In some embodiments, A is $C_{6-14}$ aryl.

In some embodiments, A is phenyl.

In some embodiments, A is phenyl, which is optionally substituted with 1 or 2 substituents independently selected from halo and cyano.

In some embodiments, A is 4-cyanophenyl, 3,5-difluorophenyl, or 4-fluorophenyl.

In some embodiments, A is $C_{1-14}$ heteroaryl, which is optionally substituted with 1 or 2 substituents independently selected from $C_{1-6}$ alkyl.

In some embodiments, A is pyrazolyl.

In some embodiments, A is pyrazolyl, which is optionally substituted with 1 or 2 substituents independently selected from $C_{1-6}$ alkyl.

In some embodiments, A is $C_{1-6}$ alkyl, $C_{3-14}$ cycloalkyl, $C_{6-14}$ aryl, or $C_{1-14}$ heteroaryl, each of which is optionally substituted by 1, 2, 3, or 4 independently selected $R^8$ substituents.

In some embodiments, A is $C_{1-6}$ alkyl, $C_{3-14}$ cycloalkyl, $C_{6-14}$ aryl, or $C_{1-14}$ heteroaryl, wherein said $C_{3-14}$ cycloalkyl, $C_{6-14}$ aryl, and $C_{1-14}$ heteroaryl are each optionally substituted with 1 or 2 substituents independently selected from halo, cyano, and $C_{1-6}$ alkyl.

In some embodiments, A is $C_{1-6}$ alkyl, $C_{3-14}$ cycloalkyl, $C_{6-14}$ aryl, or $C_{1-14}$ heteroaryl, wherein said $C_{3-14}$ cycloalkyl, $C_{6-14}$ aryl, and $C_{1-14}$ heteroaryl are each optionally substituted with 1 or 2 substituents independently selected from halo, cyano, $C_{1-6}$ alkyl, $C_{1-6}$ haloalkyl, $-OR^a$, and $-NR^eR^f$.

In some embodiments, A is methyl, cyclopropyl, phenyl, a pyrazole ring, a pyridine ring, an indazole ring, a thiophene ring, a furan ring, a pyrimidine ring, or an imidazole ring; wherein said phenyl, pyrazole ring, pyridine ring, indazole ring, thiophene ring, furan ring, pyrimidine ring, and imidazole ring are each optionally substituted with 1, 2, or 3 substituents independently selected from halo, cyano, $C_{1-6}$ alkyl, $C_{1-6}$ haloalkyl, $-OR^a$, and $-NR^eR^f$.

In some embodiments, A is methyl, cyclopropyl, phenyl or pyrazolyl, wherein said phenyl or pyrazolyl are each optionally substituted with 1 or 2 substituents independently selected from halo, cyano, and $C_{1-6}$ alkyl.

In some embodiments, each $R^8$ is independently selected from halo, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{2-9}$ heterocycloalkyl, $C_{6-10}$ aryl, $C_{1-9}$ heteroaryl, $-OR^a$, $-SR^a$, $-S(=O)R^b$, $-S(=O)_2R^b$, $-S(=O)NR^eR^f$, $-C(=O)R^b$, $-C(=O)OR^b$, $-C(=O)NR^eR^f$, $-OC(=O)R^b$, $-OC(=O)NR^eR^f$, $-NR^eR^f$, $-NR^cC(=O)R^d$, $-NR^cC(=O)OR^d$, $-NR^cC(=O)NR^d$, $-NR^cS(=O)_2R^d$, and $-NR^bS(=O)_2NR^eR^f$.

In some embodiments, each $R^8$ is independently selected from halo, cyano, nitro, $C_{1-6}$ alkyl, $C_{1-6}$ haloalkyl, $-OR^a$, $-S(=O)_2R^b$, $-C(=O)OR^b$, $-C(=O)NR^eR^f$, $-NR^eR^f$, and $-NR^cC(=O)R^d$, In some embodiments, each $R^8$ is independently selected from halo, cyano, nitro, $C_{1-6}$ alkyl, $C_{1-6}$ haloalkyl, and $-OR^a$.

In some embodiments, each $R^8$ is independently selected from halo, cyano, $C_{1-6}$ alkyl, $C_{1-6}$ haloalkyl, $-OR^a$, and $-NR^eR^f$.

In some embodiments, each $R^8$ is independently selected from halo, cyano, and $C_{1-6}$ alkyl.

In some embodiments, L is absent.

In some embodiments, L is C(=O).

In some embodiments, L is S(=O).

In some embodiments, L is $S(=O)_2$.

In some embodiments, L is C(=O) or $S(=O)_2$.

In some embodiments, L is C(=O)NH.

In some embodiments, X is CH.

In some embodiments, X is N.

In some embodiments, Y is H, cyano, or halo (such as fluoro).

In some embodiments, Y is H, cyano, methyl or fluoro.

In some embodiments, Y is H.

In some embodiments, Y is cyano.

In some embodiments, Y is fluoro.

In some embodiments, Y is $C_{1-4}$ alkyl or $C_{1-4}$ haloalkyl.

In some embodiments, Y is $C_{1-4}$ alkyl.

In some embodiments, Y is methyl.

In some embodiments, Z is $CR^7$.

In some embodiments, Z is CH.

In some embodiments, Z is N.

In some embodiments, $R^1$, $R^2$, and $R^3$ are each independently H, halo, or $C_{1-3}$ alkyl.

In some embodiments, $R^1$, $R^2$, and $R^3$ are each H.

In some embodiments, $R^4$ and $R^5$ are each independently H or $C_{1-3}$ alkyl.

In some embodiments, $R^4$ and $R^5$ are each H.

In some embodiments, $R^4$ and $R^5$ together with the carbon atom to which they are attached can form a 3-, 4-, or 5-membered cycloalkyl ring.

In some embodiments, each $R^6$ is $C_{1-4}$ alkyl.

In some embodiments, m is 0.

In some embodiments, m is 1.

In some embodiments, n is 0.

In some embodiments, n is 1.

In some embodiments, n is 0, 1, or 2.

In some embodiments, n is 0 or 1.

In some embodiments, p is 0.

In some embodiments, p is 1.

In some embodiments, the compounds of the invention have a formula II:

In some embodiments, the compounds of the invention have a formula IIa:

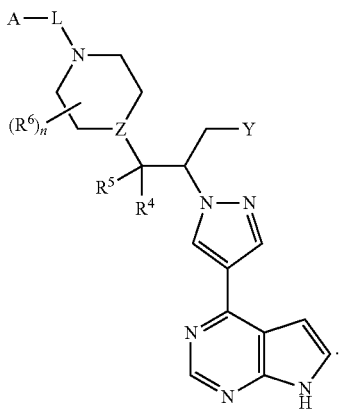

In some embodiments, the compounds of the invention have a formula IIb:

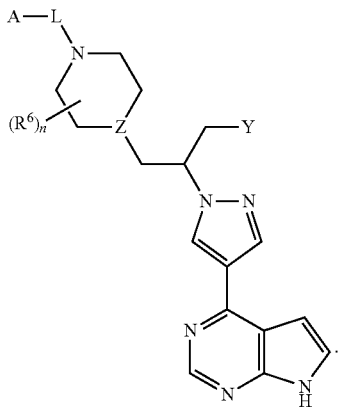

In some embodiments, A is $C_{1-6}$ alkyl, $C_{3-14}$ cycloalkyl, $C_{6-14}$ aryl, or $C_{1-14}$ heteroaryl, each optionally substituted with 1, 2, 3, 4, 5, or 6 independently selected $R^8$ substituents;

each $R^8$ is independently selected from halo, cyano, nitro, $C_{1-6}$ alkyl, $C_{1-6}$ haloalkyl, $C_{2-6}$ alkenyl, $C_{2-6}$ alkynyl, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl, —$OR^a$, —$SR^a$, —$S(=O)R^b$, —$S(=O)_2R^b$, —$S(=O)NR^eR^f$, —$C(=O)R^b$, —$C(=O)OR^b$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cC(=O)NR^d$, —$NR^eS(=O)_2R^d$, and —$NR^bS(=O)_2NR^eR^f$;

L is $C(=O)$ or $S(=O)_2$;
X is N;
Y is H, cyano, or halo;
Z is CH or N;
$R^1$, $R^2$, $R^3$, $R^4$, and $R^5$ are each H;
m is 0;
n is 0; and
each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^c$ and $R^d$, together with the moiety to which they are attached, can form a 3-, 4-, 5-, 6-, or 7-membered heterocycloalkyl ring optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

In some embodiments, A is $C_{1-6}$ alkyl, $C_{3-14}$ cycloalkyl, $C_{6-14}$ aryl, or $C_{1-14}$ heteroaryl, each optionally substituted with 1, 2, 3, 4, 5, or 6 independently selected $R^8$ substituents;

each $R^8$ is independently selected from halo, cyano, nitro, $C_{1-6}$ alkyl, $C_{1-6}$ haloalkyl, —$OR^a$, —$S(=O)_2R^b$, —$C(=O)OR^b$, —$C(=O)NR^eR^f$, —$NR^eR^f$, and —$NR^cC(=O)R^d$;

L is $C(=O)$ or $S(=O)_2$;
X is N;
Y is H, cyano, or halo;
Z is CH or N;
$R^1$, $R^2$, $R^3$, $R^4$, and $R^5$ are each H;
m is 0;
n is 0; and
each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^c$ and $R^d$, together with the moiety to which they are attached, can form a 3-, 4-, 5-, 6-, or 7-membered heterocycloalkyl ring optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

In some embodiments:

A is $C_{1-6}$ alkyl, $C_{3-14}$ cycloalkyl, $C_{6-14}$ aryl, or $C_{1-14}$ heteroaryl, wherein said $C_{3-14}$ cycloalkyl, $C_{6-14}$ aryl, and $C_{1-14}$ heteroaryl are each optionally substituted with 1, 2, or 3 independently selected $R^8$ substituents;

each $R^8$ is independently selected from halo, cyano, $C_{1-6}$ alkyl, $C_{1-6}$ haloalkyl, $-OR^a$, and $-NR^eR^f$;

L is absent, C(=O), C(=O)NH, or S(=O)$_2$;

X is N or CH;

Y is H, cyano, methyl, or fluoro;

Z is CH or N;

$R^1$, $R^2$, $R^3$, $R^4$, and $R^5$ are each H;

each $R^6$ is $C_{1-4}$ alkyl;

m is 0 or 1;

n is 0 or 1;

p is 0 or 1;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

In some embodiments, A is $C_{1-6}$ alkyl, $C_{3-14}$ cycloalkyl, $C_{6-14}$ aryl, or $C_{1-14}$ heteroaryl, each optionally substituted with 1, 2, 3, 4, 5, or 6 independently selected $R^8$ substituents;

each $R^8$ is independently selected from halo, cyano, and $C_{1-6}$ alkyl;

L is C(=O) or S(=O)$_2$;

X is N;

Y is H, cyano, or fluoro;

Z is CH or N;

$R^1$, $R^2$, $R^3$, $R^4$, and $R^5$ are each H;

m is 0; and n is 0.

In some embodiments, the compounds of the invention have a formula IIc, IId, IIe, or IIf:

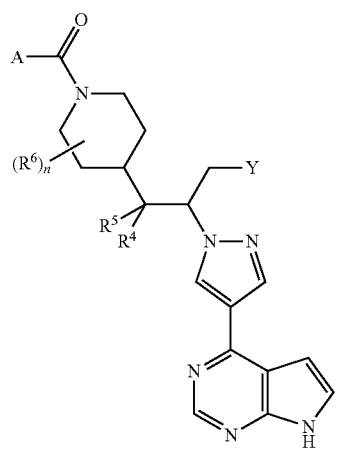

IIc

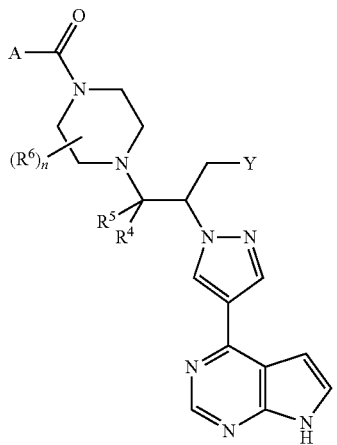

IId

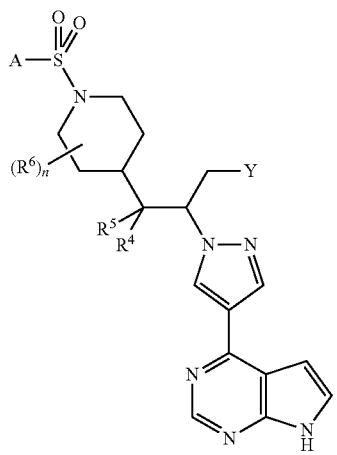

IIe

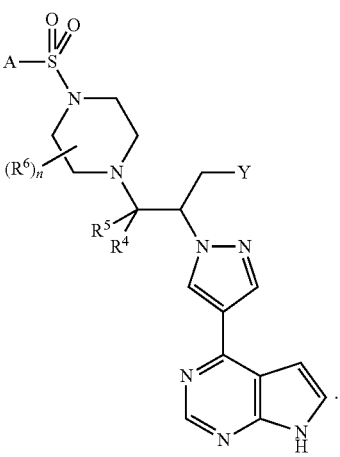

IIf

In some embodiments, the compounds of the invention have a formula IIg or IIh:
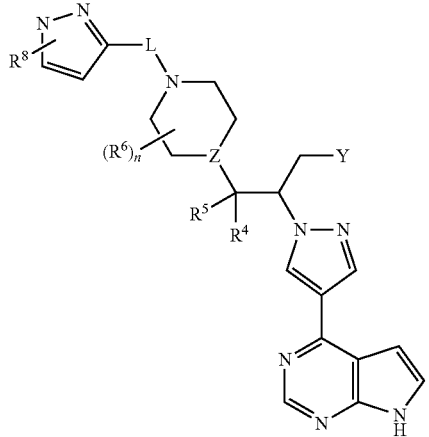
In some embodiments, the compounds of the invention have a formula IIj or IIk:
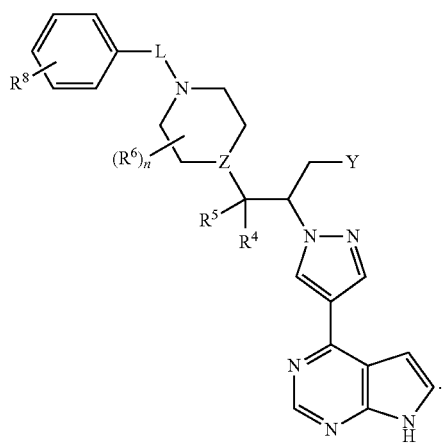
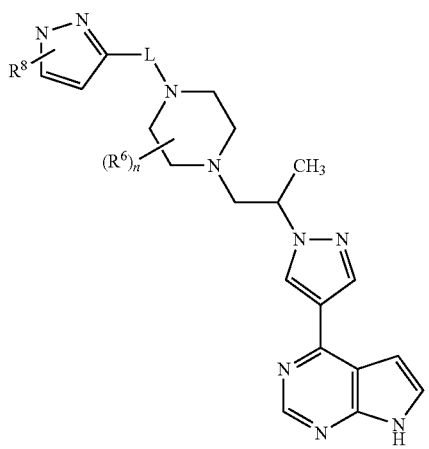
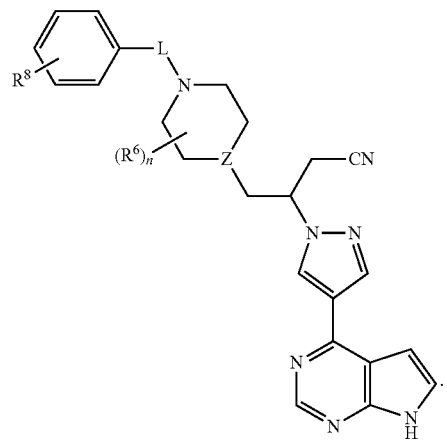
In some embodiments, the compounds of the invention have a formula III:
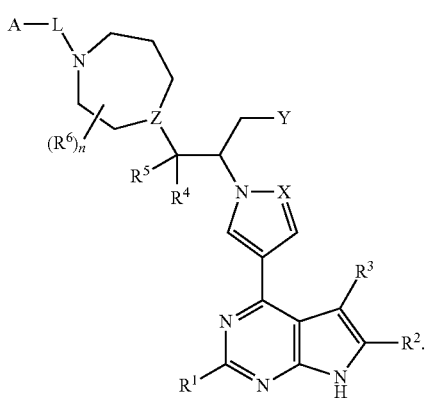
In some embodiments, the compounds of the invention have a formula IIIa or IIIb:
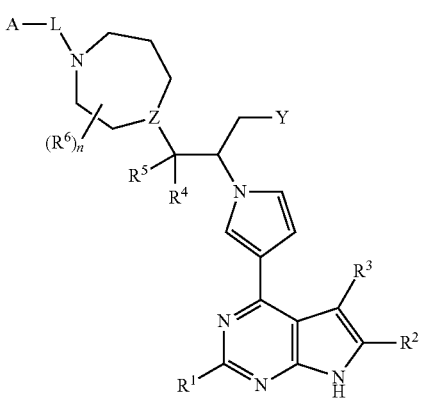

15
-continued

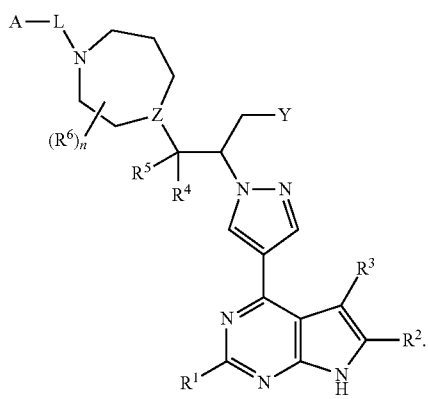

IIIb

In some embodiments, the compounds of the invention have a formula IIIc or IIId:

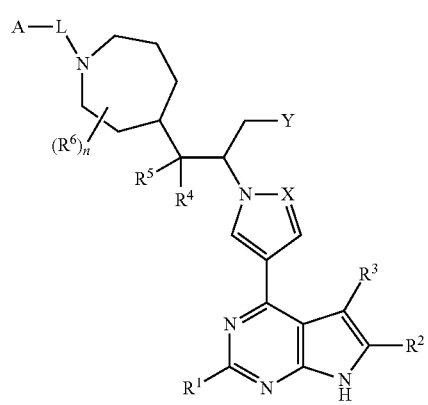

IIIc

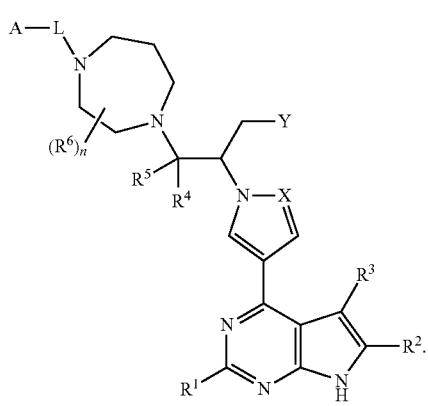

IIId

16

In some embodiments, the compounds of the invention have a formula IV:

[Formula IV structure]

IV

In some embodiments, the compound has Formula V:

[Formula V structure]

V

In some embodiments, the compound is the (R)-enantiomer.

In some embodiments, the compound is the (S)-enantiomer.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is to be understood that the "alkyl" or "aryl" represents a linking alkylene group or arylene group, respectively.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

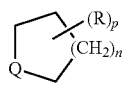

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 12, 1 to 8, 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, n-octyl, and the like.

As used herein, "$C_{n-m}$ alkenyl", employed alone or in combination with other terms, refers to an alkyl group having one or more carbon-carbon double bonds and n to m carbon atoms. In some embodiments, the alkenyl moiety contains 2 to 6, or 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl", employed alone or in combination with other terms, refers to an alkyl group having one or more carbon-carbon triple bonds and n to m carbon atoms. Example alkynyl groups include, but are not limited to, ethy-nyl, propyn-1-yl, propyn-2-yl, and the like. In some embodiments, the alkynyl moiety contains 2 to 6 or 2 to 4 carbon atoms.

As used herein, the term "$C_{n-m}$ cycloalkyl", employed alone or in combination with other terms, refers to a non-aromatic cyclic hydrocarbon including cyclized alkyl, alkenyl, and alkynyl groups, and which has n to m ring member carbon atoms. Cycloalkyl groups can include mono- or polycyclic (e.g., having 2, 3, or 4 fused, bridged, or Spiro rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. Ring-forming carbon atoms of a cycloalkyl group can be optionally substituted by oxo. Cycloalkyl groups also include cycloalkylidenes. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as admantan-1-yl. As used herein, "spirocycloalkyl groups" refers to non-aromatic hydrocarbon moieties containing at least two rings fused at a single carbon atom, such as spiro [2.5]octane and the like. In some embodiments, the cycloalkyl group has 3 to 14 ring members, 3 to 10 ring members, or 3 to 7 ring members. In some embodiments, the cycloalkyl group is monocyclic, bicyclic or tricyclic. In some embodiments, the cycloalkyl group is monocyclic. In some embodiments, the cycloalkyl group is a $C_{3-7}$ monocyclic cycloalkyl group. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, tetrahydronaphthalenyl, octahydronaphthalenyl, indanyl, and the like.

As used herein, the term "$C_{n-m}$ cycloalkyl-$C_{o-p}$ alkyl", employed alone or in combination with other terms, refers to a group of formula -alkylene-cycloalkyl, wherein the cycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the cycloalkyl portion has 3 to 14 ring members, 3 to 10 ring members, or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "$C_{n-m}$ heterocycloalkyl", "$C_{n-m}$ heterocycloalkyl ring", or "$C_{n-m}$ heterocycloalkyl group", employed alone or in combination with other terms, refers to non-aromatic ring or ring system, which may optionally contain one or more alkenylene or alkynylene groups as part of the ring structure, which has at least one heteroatom ring member independently selected from nitrogen, sulfur oxygen and phosphorus, and which has n to m ring member carbon atoms. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 hetereoatoms independently selected from nitrogen, sulfur and oxygen. Also included in the definition of heterocycloalkyl are moieties that have one or more aromatic rings fused (i.e., having a bond in common with) to the non-aromatic ring, for example, 1,2,3,4-tetrahydro-quinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azaadmantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 14 ring-forming atoms, 3 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or hetereoatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group.

As used herein, the term "$C_{n-m}$ heterocycloalkyl-$C_{o-p}$ alkyl", employed alone or in combination with other terms, refers to a group of formula -alkylene-heterocycloalkyl, wherein the heterocycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heterocycloalkyl portion has 3 to 14 ring members, 3 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "$C_{n-m}$ aryl", employed alone or in combination with other terms, refers to a monocyclic or polycyclic (e.g., having 2, 3 or 4 fused rings) aromatic hydrocarbon moiety having n to m ring member carbon atoms, such as, but not limited to, phenyl, 1-naphthyl, 2-naphthyl, anthracenyl, phenanthrenyl, and the like. In some embodiments, aryl groups have from 6 to 20 carbon atoms, from 6 to 14 carbon atoms, from 6 to 10 carbon atoms, or 6 carbon atoms. In some embodiments, the aryl group is a monocyclic or bicyclic group.

As used herein, the term "$C_{n-m}$ aryl-$C_{o-p}$-alkyl", employed alone or in combination with other terms, refers to a group of formula -alkylene-aryl, wherein the aryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the aryl portion is phenyl. In some embodiments, the aryl group is a monocyclic or bicyclic group. In some embodiments, the arylalkyl group is benzyl.

As used herein, the term "$C_{n-m}$ heteroaryl", "$C_{n-m}$ heteroaryl ring", or "$C_{n-m}$ heteroaryl group", employed alone or in combination with other terms, refers to a monocyclic or polycyclic (e.g., having 2, 3 or 4 fused rings) aromatic hydrocarbon moiety, having one or more heteroatom ring members independently selected from nitrogen, sulfur and oxygen and having n to m ring member carbon atoms. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. The carbon atoms or hetereoatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 1 to 20 carbon atoms, from 3 to 20 carbon atoms, from 3 to 15 carbon atoms, from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "$C_{n-m}$ heteroaryl-$C_{o-p}$-alkyl", employed alone or in combination with other terms, refers to a group of formula -alkylene-heteroaryl, wherein the heteroaryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heteroaryl portion is a monocyclic or bicyclic group having 1, 2, 3, or 4 hetereoatoms independently selected from nitrogen, sulfur and oxygen. In some embodiments, the heteroaryl portion has 5 to 10 carbon atoms.

As used herein, the appearance of the term "bicyclic" before the name of a moiety indicates that the moiety has two fused rings.

As used herein, the appearance of the term "monocyclic" before the name of a moiety indicates that the moiety has a single ring.

As used herein, "halo" or "halogen", employed alone or in combination with other terms, includes fluoro, chloro, bromo, and iodo.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "$C_{n-m}$ fluoroalkyl", employed alone or in combination with other terms, refers to a $C_{n-m}$ haloalkyl wherein the halogen atoms are selected from fluorine. In some embodiments, $C_{n-m}$ fluroalkyl is fluoromethyl, difluoromethyl, or trifluoromethyl.

As used herein, the term "$C_{n-m}$ alkoxy", employed alone or in combination with other terms, refers to an group of formula —O-alkyl, wherein the alkyl group has n to m carbon atoms. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "$C_{n-m}$ haloalkoxy", employed alone or in combination with other terms, refers to a group of formula —O-(haloalkyl), wherein the haloalkyl group has n to m carbon atoms. In some embodiments, the alkyl group has 1 to 6 or 1 to 4 carbon atoms. An example haloalkoxy group is —$OCF_3$.

As used herein, "amino", employed alone or in combination with other terms, refers to $NH_2$.

As used herein, the term "$C_{n-m}$ alkylamino", employed alone or in combination with other terms, refers to a group of formula —NH(alkyl), wherein the alkyl group has n to m carbon atoms. In some embodiments, alkyl group has 1 to 6 or 1 to 4 carbon atoms. Example $C_{n-m}$ alkylamino groups include methylamino, ethylamino, propylamino (e.g., n-propylamino and isopropylamino), and the like.

As used herein, the term "di-$C_{n-m}$-alkylamino", employed alone or in combination with other terms, refers to a group of formula —N(alkyl)$_2$, wherein each alkyl group has independently n to m carbon atoms. Example di-$C_{n-m}$-alkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "$C_{1-4}$alkoxy-$C_{1-4}$-alkyl" refers to a group of formula —$C_{1-4}$ alkyl-O—$C_{1-4}$ alkyl.

As used herein, the term "hydroxy-$C_{1-4}$-alkyl" refers to a group of formula —$C_{1-4}$ alkyl-OH.

As used herein, wherein a ring is indicated as "a pyridine ring", "a pyrazole ring", "a pyridimine ring", etc., the ring can be attached at any position of the ring, provided that the valency of the atom at the point of attachment is not exceeded.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of a-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alco hols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

Synthesis

Compounds of the invention, including salts and N-oxides thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compound 5 (Formula I, wherein Z═CN) can be made by methods analogous to that depicted in Scheme I. Accordingly, the conjugate addition of a protected pyrazol-4-yl-pyrrolo[2,3-d]pyrimidine or pyrrol-3-yl-pyrrolo[2,3-d]pyrimidine of formula 1 with a butanenitrile derivative 2 in the presence of a coupling agent, typically a base, can provide an adduct 3. The protecting groups, Pg$^1$ and Pg$^2$, can be any appropriate protecting group, including, but not limited to, the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, Pg$^2$ is 2-(trimethylsilyl) ethoxymethyl (SEM). In some embodiments, the Pg$^1$ protecting group is one that can be selectively removed in the presence of the Pg$^2$ protecting group. In some embodiments, the Pg$^1$ protecting group is t-butoxycarbonyl (BOC) or benzyloxycarbonyl (Cbz).

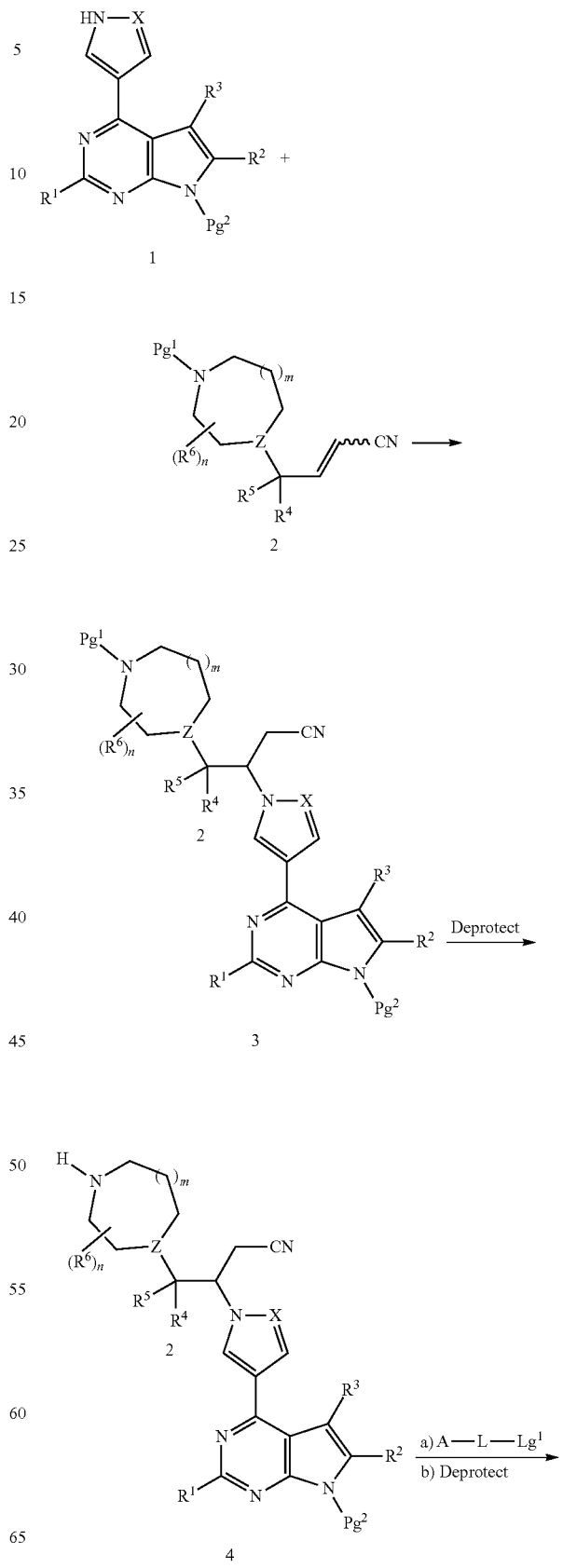

Scheme I

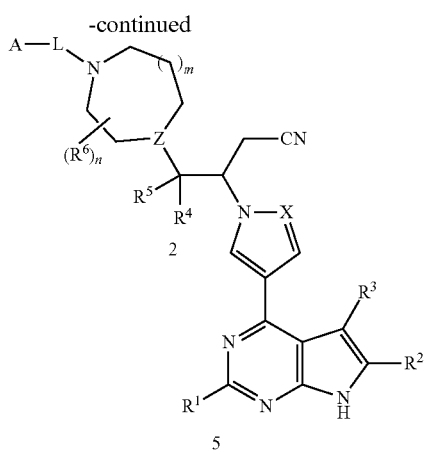

5

The coupling agent can be any appropriate coupling agent useful for conjugate addition, including, but not limited to a tetraalkylammonium halide, tetraalkylammonium hydroxide, guanidine, amidine, hydroxide, alkoxide, silicate, alkali metal phosphate, oxide, tertiary amine, alkali metal carbonate, alkali metal bicarbonate, alkali metal hydrogen phosphate, phosphine, or alkali metal salt of a carboxylic acid. In some embodiments, the coupling agent is tetramethyl guanidine, 1,8-diazabicyclo[5.4.0]undec-7-ene (DBU), 1,5-diazabicyclo(4.3.0)non-5-ene (DBN), 1,4-diazabicyclo(2.2.2)octane, tert-butyl ammonium hydroxide, sodium hydroxide, potassium hydroxide, sodium methoxide, sodium ethoxide, tripotassium phosphate, sodium silicate, calcium oxide, triethylamine, sodium carbonate, potassium carbonate, sodium bicarbonate, potassium bicarbonate, potassium hydrogen phosphate, triphenyl phosphine, triethyl phosphine, potassium acetate, or potassium acrylate. In some embodiments, the coupling agent is 1,8-diazabicyclo[5.4.0]undec-7-ene (DBU). The conjugate addition of the compounds of formulas 1 and 2 can be conducted in an appropriate solvent (e.g., acetonitrile). The conjugate addition product 3 can then be deprotected to remove the $Pg^1$ protecting group to form the free amine 4. For example, when $Pg^1$ is BOC, the protecting group can be removed through treatment with HCl in dioxane, whereas when $Pg^1$ is Cbz, the protecting group can be removed under hydrogenation conditions (e.g., hydrogen gas in the presence of 10% palladium on carbon). The amine 4 can then be reacted with a compound of formula A-L-$Lg^1$ with either concomitant or subsequent deprotection of the $Pg^2$ protecting group to provide the desired compound of formula 5. Appropriate leaving groups for $Lg^1$, include, but are not limited to, chloro, bromo, fluoro, —$OSO_2CH_3$, —$OSO_2CF_3$, tosylate, and thio (SH). The reaction can be carried out in the presence of a base (such as a tertiary amine, e.g., diisopropylethylamine) in a solvent such as N-methylpyrrolidone (NMP), dioxane, or ethanol (EtOH) at an elevated temperature (e.g., 60 to 135° C.).

Compounds of formula 1 may be formed by methods analogous to that depicted in Scheme II. Accordingly, Suzuki-coupling of a protected 4-chloro-pyrrolo[2,3-d]pyrimidine 6 with a protected or unprotected (e.g., wherein $Pg^3$ is H or a protecting group) pyrrol-3-yl or pyrazol-4-yl boronic acid or ester 7 (wherein R" is hydrogen, alkyl or two R" join together with the oxygen and boron atoms to form a optionally substituted heterocycloalkyl ring such as a pinacol ring) in the presence of a suitable catalyst (e.g., tetrakis(triphenylphosphine)palladium(0) or tetrakis(tri(o-tolylphosphine))palladium(0)) and a base (e.g., potassium carbonate) can provide the desired starting material 1 (see, e.g., Example 65 of US 20070135461, which is incorporated herein by reference in its entirety). The pyrrol-3-yl or pyrazol-4-yl boronic ester or acid can be protected with any appropriate protecting group. Similarly, the $Pg^2$ protecting group can be any appropriate protecting group (e.g., diethoxymethyl (DEM) or 2-(trimethylsilyl)ethoxymethyl (SEM)).

Scheme II

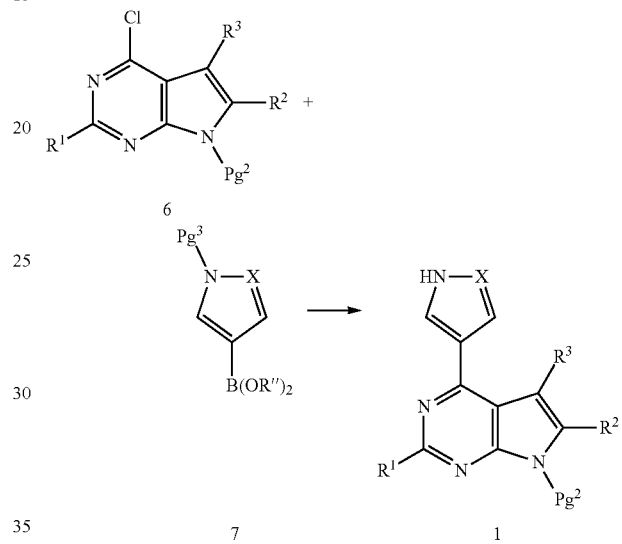

The butanenitrile 2 can be formed by reaction of the aldehyde 9 with a Horner-Wadsworth-Emmons reagent in the presence of a base (e.g., potassium tert-butoxide) as shown in Scheme III. The $Pg^1$ protecting group can be any of the protecting groups summarized above (e.g., BOC or Cbz). The aldehydes 9 can be obtained by the oxidation (such as, Swern or Dess-Martin oxidation) of the corresponding alcohols 8.

Scheme III

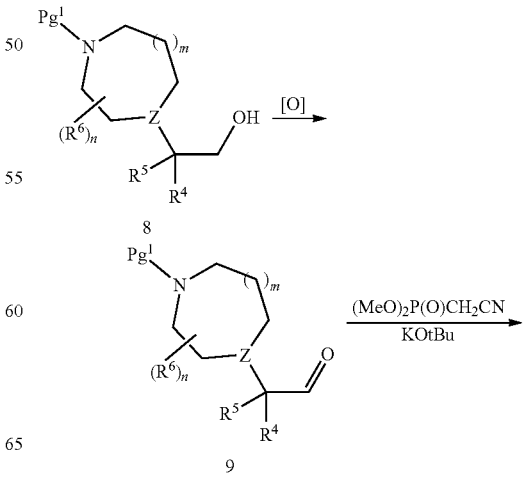

-continued

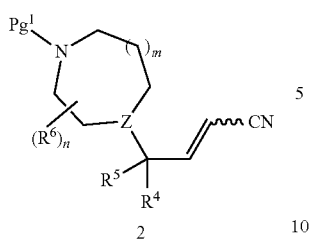
2

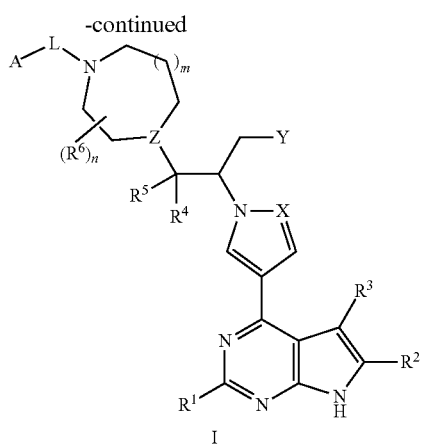
I

Compounds of Formula I can alternatively be obtained by a $S_N2$ displacement reaction of a compound 11 with a compound 1 in the presence of a base (such as those described above) as depicted in Scheme IV. The leaving group $Lg^2$ in 11 can be any one of those described above for $Lg^1$. The compounds 11 can be obtained in general by the conversion of the hydroxyl group in compound 10 into $Lg^2$ through methods well known in the art. Secondary alcohols, such as, 10 can be obtained either through the opening of epoxides 13 with the nucleophiles 12 (especially when Z=NH). In some embodiments, the epoxide opening is performed in the presence of a Lewis acid such as trialkylaluminum. In another method, the nucleophiles 12 can displace a leaving group such as $Lg^3$ in 14. The leaving group $Lg^3$ in 14 can be any one of those described above for $Lg^1$. In some embodiments, the hydroxyl group in 14 can be protected with a suitable hydroxyl protecting group including, but not limited to, the protecting groups for amines delineated in Wuts and Greene, Protective Groups in Organic Synthesis, 4th ed., John Wiley & Sons: New Jersey, pages 16-366 (2007)

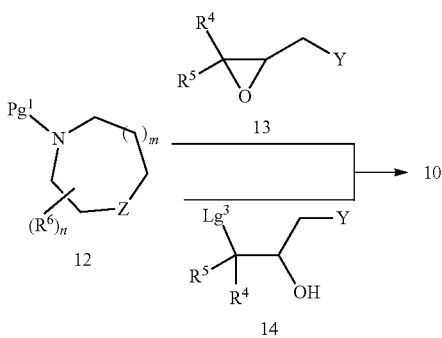

Compounds of Formula Ia, where p is 0, can be formed as shown in Scheme V. Accordingly, a protected compound of formula a can be reacted with a vinyl compound of formula b in the presence of a coupling agent such as DBU to give a compound of formula c. Compound c can then be selectively deprotected to give a compound of formula d. Compound d can then reacted as shown for compound 4 (except where cyano is Y) in Scheme I to give a compound of Formula Ia.

Scheme IV

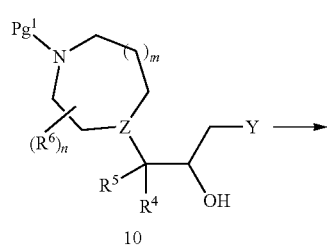
10

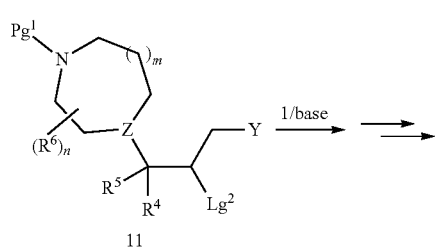
11

Scheme V

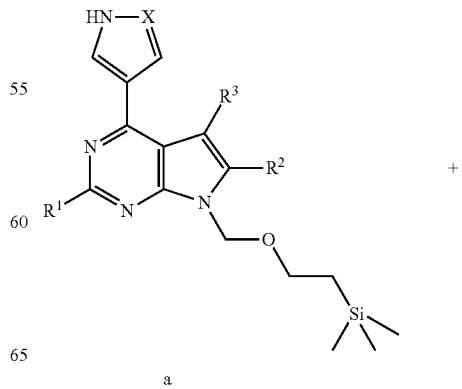
a

+

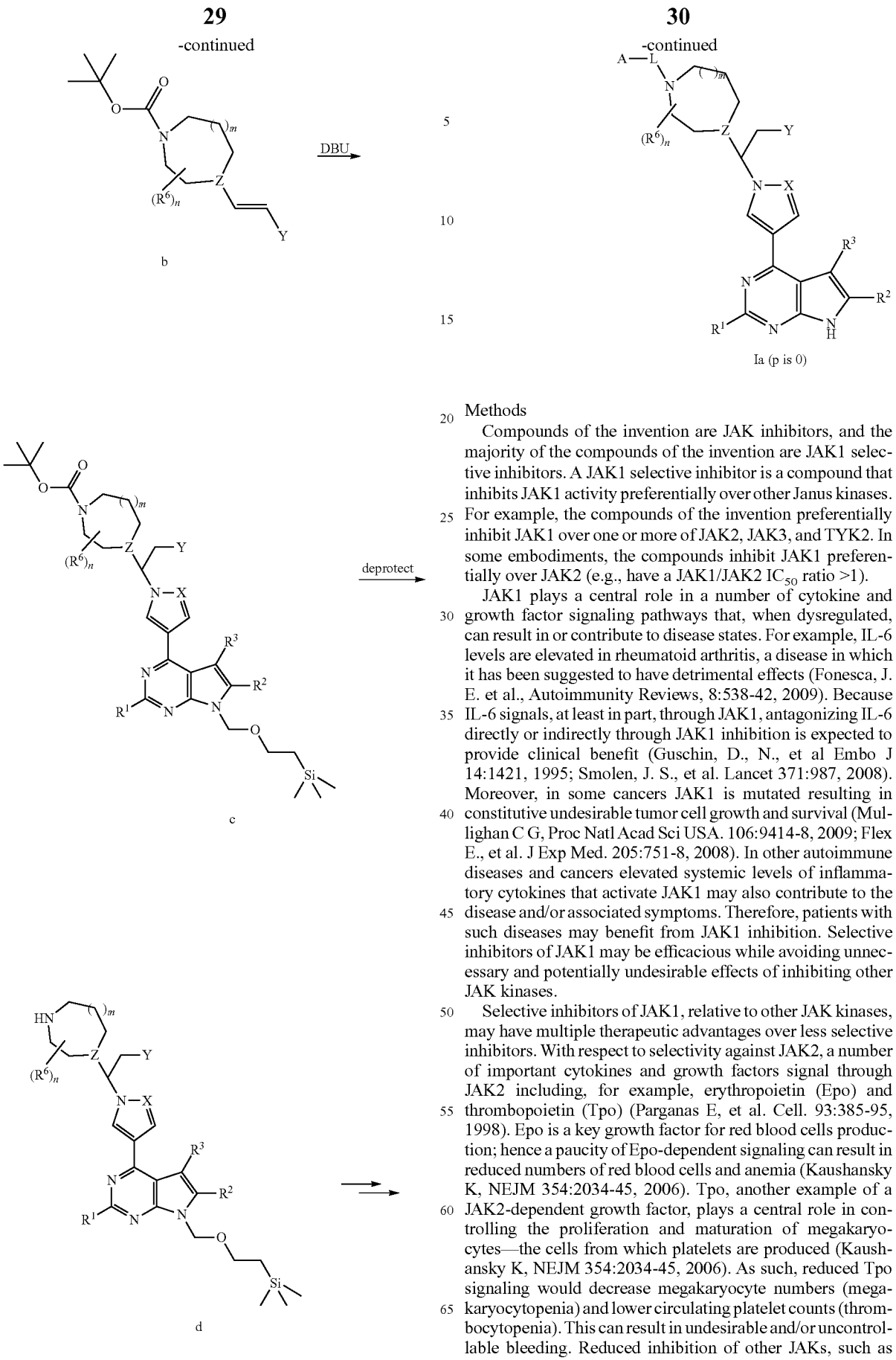

Methods

Compounds of the invention are JAK inhibitors, and the majority of the compounds of the invention are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 $IC_{50}$ ratio >1).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106:9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity. In some embodiments, the JAK-associated disease is a JAK1-associated disease.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemics, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)).

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface,* 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a compound of Formula I, pharmaceutically acceptable salt thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt thereof, for use in a method of modulating a JAK1. In some embodiments, the present invention also provides use of a compound of Formula I as described herein, or a pharmaceutically acceptable salt thereof, for the preparation of a medicament for use in a method of modulating a JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holies Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is an topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid. In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly (dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid). In some embodiments, the film is a soft-contact lens, such as ones made from copolymers of N,N-diethylacrylamide and methacrylic acid crosslinked with ethyleneglycol dimethacrylate.

In some embodiments, the ophthalmic compositon comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exhange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro JAK labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}$, I, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

EXAMPLES

The example compounds below containing one or more chiral centers were obtained in enantiomerically pure form or as scalemic mixtures, unless otherwise specified. The following abbreviations are used throughout the text: NMP (N-methylpyrrolidone), TFA (trifluoroacetic acid), DCM (dichloromethane), MeOH (methanol), DIPEA (diisopropylethylamine), MsCl (mesyl chloride), DMF (dimethylformamide), THF (tetrahydrofuran), HPLC (high performance liquid chromatography), LC (liquid chromatography), MS (mass spectrometry), LCMS (liquid chromatography-mass spectrometry), TMS (trimethylsilyl), MeCN (acetonitrile), iPrOH (isopropanol), EtOAc (ethyl acetate), DMSO (dimethylsulfoxide), tBu (tert-butyl), SEM (2-(trimethylsilyl)ethoxymethyl), RT (room temperature), h (hour or hours), and min (minute or minutes).

Example 1

4-[4-(methylsulfonyl)piperazin-1-yl]-3-[4-(7H-pyrrolo[2,3-d]pyrimidin-4-yl)-1H-pyrazol-1-yl]butanenitrile

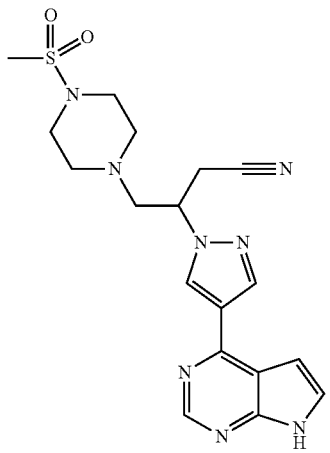 [SMILES: CS(=O)(=O)N1CCN(CC(CC#N)n2cc(-c3ncnc4[nH]ccc34)cn2)CC1]

Step 1. tert-butyl 4-(2-oxoethyl)piperazine-1-carboxylate

Oxalyl chloride (3.6 mL, 0.0425 mol) was dissolved in DCM (87 mL) at −78° C. Dimethyl sulfoxide (6.58 mL, 0.0927 mol) was added and the solution was held at −78° C. for 10 min. To the resultant mixture was added a solution of tert-butyl 4-(2-hydroxyethyl)piperazine-1-carboxylate (from Oakwood, 8.90 g, 0.0386 mol) in DCM (44 mL) over 15 min. The reaction was stirred at −78° C. for 1 h, then triethylamine (26.9 mL, 0.193 mol) was added. The mixture was warmed to RT over 30 minutes and then stirred at RT for another 30 min. The mixture was diluted with DCM, washed with water (2×), brine (1×), dried over sodium sulfate, and concentrated. The crude product (8.10 g, 91.8%) was used directly in next step without further purification. $^1$H NMR (400 MHz, CDCl$_3$): δ 9.70 (1H, s), 3.48 (4H, m), 3.19 (2H, s), 2.47 (4H, m), 1.45 (9H, s) ppm.

Step 2. tert-butyl 4-[(2E)-3-cyanoprop-2-en-1-yl]piperazine-1-carboxylate

To a solution of 1 M of potassium tert-butoxide in THF (45.5 mL, 0.0455 mol) at 0° C. was added drop wise a solution of diethyl cyanomethylphosphonate (7.72 mL, 0.0477 mol) in THF (70 mL). The reaction mixture was warmed up to at RT, cooled to 0° C. again, and a solution of tert-butyl 4-(2-oxoethyl)piperazine-1-carboxylate (9.90 g, 0.0434 mol) in THF (10 mL) was added. The reaction mixture was allowed to warm up to RT and stirred for 2 more hours. After being quenched with water, the mixture was extracted with EtOAc. The organic layers were dried and concentrated. The residue was purified by silica gel column eluting with DCM to give the desired product (7.5 g, 69%).

Step 3. (R)- and (S)-tert-butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate tert-Butyl 4-[(2E)-3-cyanoprop-2-en-1-yl]piperazine-1-carboxylate (1.0 g, 0.00398 mol) was combined with 4-(1H-pyrazol-4-yl)-7-{[2-(trimethylsilyl)ethoxy]methyl}-7H-pyrrolo[2,3-d]pyrimidine (prepared as described in WO 2007/070514 Example 65; 0.4183 g, 0.001326 mol) and 1,8-diazabicyclo[5.4.0]undec-7-ene (DBU, 40 μL, 0.26 mmol) in acetonitrile (8.3 mL) under nitrogen. The mixture was stirred at RT over the weekend. Solvents were removed under reduced pressure. The residue was purified with silica gel column eluting with 0 to 10% MeOH in DCM, providing the desired product (690 mg, 91.8%). LCMS calculated for $C_{28}H_{43}N_8O_3Si(M+H)^+$: m/z=567.3; Found: 567.0. $^1$H NMR (300 MHz, CDCl$_3$): δ 8.90 (1H, s), 8.38 (1H, s), 8.37 (1H, s), 7.47 (1H, d, J=3.9 Hz), 6.85 (1H, d, J=3.9 Hz), 5.73 (2H, s), 4.72 (1H, m), 4.31 (2H, t, J=7.2 Hz), 3.60 (2H, dd, J=9.6 and 8.1 Hz), 3.47 (4H, m), 3.19 (2H, dd, J=5.7 and 2.1 Hz), 2.51 (4H, m), 1.50 (9H, s), 1.46 (2H, t, J=7.2 Hz), 0.03 (9H, s) ppm. The enantiomers (retention times: first peak, 2.08 min; second peak, 3.58 min) were separated on a ChiralCel OD-H column (4.6×250 mm, 5 μM), eluting with a gradient of ethanol in hexanes at 1 mL/min.

Step 4. 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride tert-Butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate (second peak from chiral purification, 0.70 g, 0.0012 mol) was stirred with 4.0 M of hydrogen chloride in p-dioxane (5.0 mL, 0.020 mol) at RT for 30 min. After evaporating to dryness, the resulting HCl salt was used directly in next step. LCMS calculated for $C_{23}H_{34}N_9OSi(M+H)^+$: m/z=467.3; Found: 467.0.

Step 5. 4-[4-(methylsulfonyl)piperazin-1-yl]-3-[4-(7H-pyrrolo[2,3-d]pyrimidin-4-yl)-1H-pyrazol-1-yl]butanenitrile Methanesulfonyl chloride (137 mg, 0.00119 mol), 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (0.5 g, 0.994 mmol) and triethylamine (416 μL, 0.00298 mol) were mixed in acetonitrile (5 mL). The mixture was stirred at RT for 1 h. The completion of the reaction was checked with LC/MS. Solvents were evaporated. The crude product was treated with DCM (1 mL) and trifluoroacetic acid (1 mL, 0.01 mol) for 30 min. The reaction mixture was evaporated under reduced pressure. To the resultant residue was added methanol (3 mL, 0.07 mol) and ethylenediamine (0.3 mL, 0.004 mol) and stirred at RT for 30 min, and concentrated to dryness under reduced pressure. The residue was purified on RP-HPLC (XBridge C-18 Column, eluting with a gradient of acetonitrile/water containing 0.15% NH$_4$OH, at flow rate 60 mL/min) to give 110 mg (27%) of the desired product. LCMS calculated for $C_{18}H_{23}N_8O_2S(M+H)^+$: m/z=415.2; Found: 415.0. $^1$H NMR (400 MHz, CD$_3$OD): δ 8.66 (1H, s), 8.63 (1H, s), 8.37 (1H, s), 7.51 (1H, d, J=3.6 Hz), 6.95 (1H, d, J=4.0 Hz), 4.95 (1H, m), 3.19-3.14 (6H, m), 2.95 (2H, m), 2.77 (3H, s), 2.67 (2H, m), 2.65 (2H, m) ppm.

Example 2

4-[(4-{3-cyano-2-[4-(7H-pyrrolo[2,3-d]pyrimidin-4-yl)-1H-pyrazol-1-yl]propyl}piperazin-1-yl)carbonyl]benzonitrile

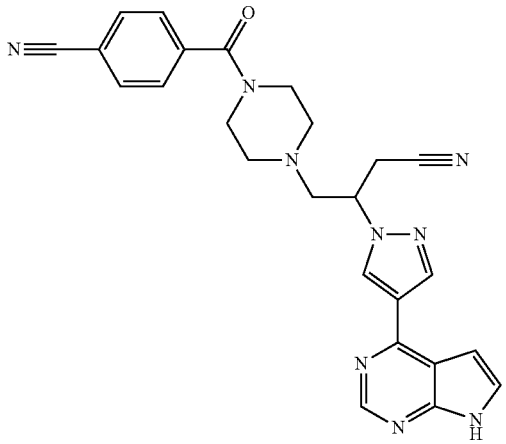 [SMILES: N#CCC(CN1CCN(C(=O)c2ccc(C#N)cc2)CC1)n1cc(-c2ncnc3[nH]ccc23)cn1]

4-Cyanobenzoyl chloride (7.91 mg, 0.0478 mmol), 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (from example 1, step 4; 0.02 g, 0.0398 mol) and triethylamine (16.6 μL, 0.119 mmol) were dissolved in acetonitrile (0.2 mL). The mixture was stirred at RT for 1 h. Solvents were evaporated and the crude product was treated with DCM (0.2 mL) and trifluoroacetic acid (0.2 mL, 0.002 mol) for 30 min. The reaction mixture was concentrated under reduced pressure. To the residue was added methanol (1 mL) and ethylenediamine (0.1 mL, 0.001 mol) and the resultant mixture was stirred at RT for 30 min and evaporated under reduced pressure. The residue was purified on RP-HPLC (XBridge C-18 Column, eluting with a gradient of acetonitrile/water containing 0.15% NH$_4$OH, at flow rate 30 mL/min) to give the desired product. LCMS calculated for C$_{25}$H$_{24}$N$_9$O(M+H)$^+$: m/z=466.2; Found 466.0.

Example 3

4-[4-(3,5-difluorobenzoyl)piperazin-1-yl]-3-[4-(7H-pyrrolo[2,3-d]pyrimidin-4-yl)-1H-pyrazol-1-yl]butanenitrile

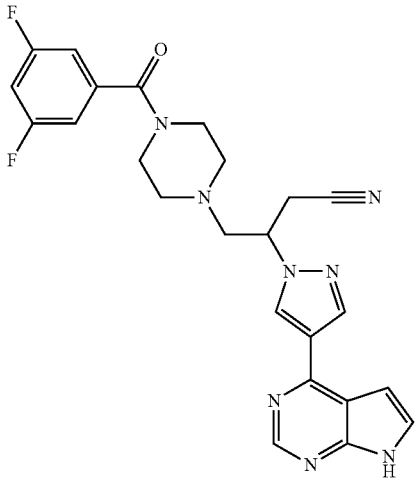 [SMILES: N#CCC(CN1CCN(C(=O)c2cc(F)cc(F)c2)CC1)n1cc(-c2ncnc3[nH]ccc23)cn1]

3,5-Difluorobenzoyl chloride (8.44 mg, 0.0478 mmol), 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (from example 1, step 4; 0.02 g, 0.0398 mmol) and triethylamine (16.6 μL, 0.119 mmol) were mixed in acetonitrile (0.2 mL). The mixture was stirred at RT for 1 h. Solvents were evaporated. The crude product was treated with DCM (0.2 mL) and trifluoroacetic acid (0.2 mL, 0.002 mol) for 30 min. The reaction mixture was evaporated under reduced pressure. To the resultant residue was added methanol (1 mL) and ethylenediamine (0.1 mL, 0.001 mol). The reaction mixture was stirred at RT for 30 min and concentrated under reduced pressure. The residue was purified on RP-HPLC (XBridge C-18 Column, eluting with a gradient of acetonitrile/water containing 0.15% NH$_4$OH, at flow rate 30 mL/min) to give the desired product. LCMS calculated for C$_{24}$H$_{23}$F$_2$N$_8$O(M+H)$^+$: m/z=477.2; Found: 477.0.

Example 4

4-{4-[(1-methyl-1H-pyrazol-3-yl)sulfonyl]piperazin-1-yl}-3-[4-(7H-pyrrolo[2,3-d]pyrimidin-4-yl)-1H-pyrazol-1-yl]butanenitrile

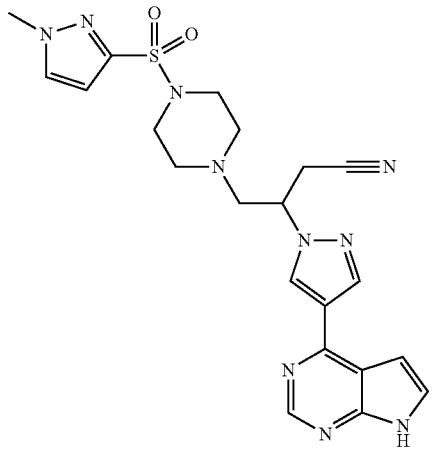 [SMILES: Cn1ccc(S(=O)(=O)N2CCN(CC(CC#N)n3cc(-c4ncnc5[nH]ccc45)cn3)CC2)n1]

1-Methyl-1H-pyrazole-3-sulfonyl chloride (130 mg, 0.72 mmol), 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (from example 1, step 4; 300 mg, 0.6 mmol), and triethylamine (250 μL, 0.0018 mol) were dissolved in acetonitrile (3 mL). The mixture was stirred at RT for 1 h, and evaporated to dryness under reduced pressure. The residue was treated with DCM (0.5 mL) and trifluoroacetic acid (0.5 mL, 0.006 mol) for 30 min. The reaction mixture was evaporated under reduced pressure. To the resultant residue was added methanol (2 mL) and ethylenediamine (0.2 mL, 0.003 mol). The reaction mixture was stirred at RT for 30 min, and evaporated under reduced pressure. The crude product was purified on RP-HPLC (XBridge C-18 Column, eluting with a gradient of acetonitrile/water containing 0.15% NH$_4$OH, at flow rate 60 mL/min) to give the desired product (259 mg, 90.4%). LCMS calculated for C$_{21}$H$_{25}$N$_{10}$O$_2$S(M+H)$^+$: m/z=481.2; Found: 481.0. $^1$H NMR (300 MHz, CD$_3$OD): δ 8.95 (1H, s), 8.90 (1H, s), 8.52 (1H, s), 7.88 (1H, d, J=3.6 Hz), 7.71 (1H, d, J=2.4 Hz), 7.27 (1H, d, J=3.6 Hz), 6.62 (1H, d, J=2.4 Hz), 5.15 (1H, m), 3.89 (3H, s), 3.20~3.12 (8H, m), 2.94 (2H, m), 2.77 (2H, m) ppm.

Example 5

4-[1-(cyclopropylsulfonyl)piperidin-4-yl]-3-[4-(7H-pyrrolo[2,3-d]pyrimidin-4-yl)-1H-pyrazol-1-yl]butanenitrile

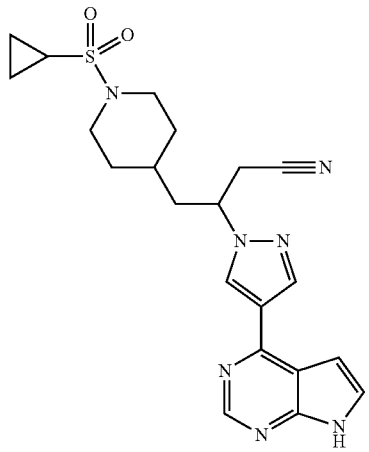 [SMILES: N#CCC(CC1CCN(S(=O)(=O)C2CC2)CC1)n1cc(-c2ncnc3[nH]ccc23)cn1]

Step 1. tert-butyl 4-(2-oxoethyl)piperidine-1-carboxylate

Dimethyl sulfoxide (7.43 mL, 0.105 mol) was added to oxalyl chloride (5.53 mL, 0.0654 mol) in DCM (244.2 mL) at −78° C. After 10 min, tert-butyl 4-(2-hydroxyethyl)piperidine-1-carboxylate (from Aldrich, 10.0 g, 0.0436 mol) in DCM (488.4 mL) was added and the resultant mixture was stirred at −78° C. for 30 min. Triethylamine (30.4 mL, 0.218 mol) was then added and the mixture was stirred for 5 h and the temperature allowed to gradually warm up to RT. After being quenched with water, the mixture was extracted with DCM. The organic layers were combined, washed with brine, dried, and evaporated to dryness. LCMS calculated for $C_{12}H_{21}NO_3Na(M+Na)^+$: m/z=250.2; Found: 250.0.

Step 2. tert-butyl 4-[(2E)-3-cyanoprop-2-en-1-yl]piperidine-1-carboxylate

To a solution of 1.0 M of potassium tert-butoxide in THF (45.8 mL, 0.0458 mol) at 0° C. was added dropwise a solution of diethyl cyanomethylphosphonate (7.8 mL, 0.0480 mol) in THF (58.4 mL). The reaction was warmed to RT and then cooled to 0° C. again. To the reaction mixture was added a solution of tert-butyl 4-(2-oxoethyl)piperidine-1-carboxylate (9.91 g, 0.0436 mol) in THF (11.7 mL). The reaction was allowed to warm up to RT and stirred at RT overnight. After being quenched with water, the mixture was extracted with EtOAc. The combined organic layers were washed with brine, dried and evaporated to dryness. The crude mixture was purified on silica gel, eluting with 0 to 40% EtOAc in hexanes, to provide the desired product (8.22 g, 75.3%). LCMS calculated for $C_{14}H_{22}N_2O_2Na(M+Na)^+$: m/z=273.2; Found: 273.0.

Step 3. (R)- and (S)-tert-butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperidine-1-carboxylate tert-Butyl 4-[(2E)-3-cyanoprop-2-en-1-yl]piperidine-1-carboxylate (3.10 g, 0.0124 mol) was combined with 4-(1H-pyrazol-4-yl)-7-{[2-(trimethylsilyl)ethoxy]methyl}-7H-pyrrolo[2,3-d]pyrimidine (prepared as described in WO 2007/070514, Example 65; 2.0 g, 0.00634 mol) and 1,8-diazabicyclo[5.4.0]undec-7-ene (0.2 g, 0.0013 mol) in acetonitrile (39 mL) under nitrogen. The mixture was stirred at RT over the weekend. Solvents were removed under reduced pressure. The residue was purified on silica gel column eluting with 0 to 100% EtOAc in hexanes to give the desired product (3.50 g, 97.5% yield). LCMS calculated for $C_{29}H_{44}N_7O_3Si(M+H)^+$: m/z=566.3; Found: 566.0. The enantiomers were separated on a ChiralCel OD-H column (4.6× 250 mm, 5 μM), eluting with a gradient of ethanol in hexanes at 1 mL/min. First peak retention time 11.39 min; second peak retention time 17.42 min.

Step 4. 4-piperidin-4-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride tert-Butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperidine-1-carboxylate (second peak from chiral purification, 1.12 g, 0.00198 mol) was stirred with 4.0 M of hydrogen chloride in p-dioxane (5 mL, 0.02 mol) at RT for 30 min. After being concentrated to dryness under reduced pressure, the resultant HCl salt was used directly in next step. LCMS calculated for $C_{24}H_{36}N_7OSi(M+H)^+$: m/z=466.3; Found: 466.2.

Step 5. 4-[1-(cyclopropylsulfonyl)piperidin-4-yl]-3-[4-(7H-pyrrolo[2,3-d]pyrimidin-4-yl)-1H-pyrazol-1-yl]butanenitrile Cyclopropanesulfonyl chloride (77.0 mg, 0.548 mmol), 4-piperidin-4-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (250 mg, 0.498 mmol), and triethylamine (208 μL, 0.00149 mol) were dissolved in acetonitrile (1.0 mL). The mixture was stirred at RT for 1 h, water was added to make a homogeneous solution and purified with preparative LCMS (pH=10) to provide the desired product. The product was treated with DCM (0.5 mL) and trifluoroacetic acid (0.5 mL, 0.006 mol) for 30 min. The reaction mixture was evaporated under reduced pressure. To the resulting residue was added methanol (5 mL) and ethylenediamine (0.5 mL, 0.007 mol) and the resultant mixture was stirred at RT for 30 min. The reaction mixture was concentrated under reduced pressure. The residue was purified on RP-HPLC (XBridge C-18 Column, eluting with a gradient of acetonitrile/water containing 0.15% $NH_4OH$, at flow rate 60 mL/min) to give the desired product (185 mg, 84.5%). LCMS calculated for $C_{21}H_{26}N_7O_2S(M+H)^+$: m/z=440.2; Found: 440.0. $^1$H NMR (300 MHz, $CD_3OD$): δ 8.98 (1H, s), 8.88 (1H, s), 8.53 (1H, s), 7.85 (1H, d, J=3.6 Hz), 7.28 (1H, d, J=3.6 Hz), 4.98 (1H, m), 3.68 (2H, m), 3.15 (2H, m), 2.73 (2H, m), 2.37 (1H, m), 2.23 (1H, m), 1.98 (1H, m), 1.87 (1H, m), 1.62 (1H, m), 1.29 (3H, m), 0.97 (4H, m) ppm.

Example 6

4-[1-(2,4-difluorobenzoyl)piperidin-4-yl]-3-[4-(7H-pyrrolo[2,3-d]pyrimidin-4-yl)-1H-pyrazol-1-yl]butanenitrile

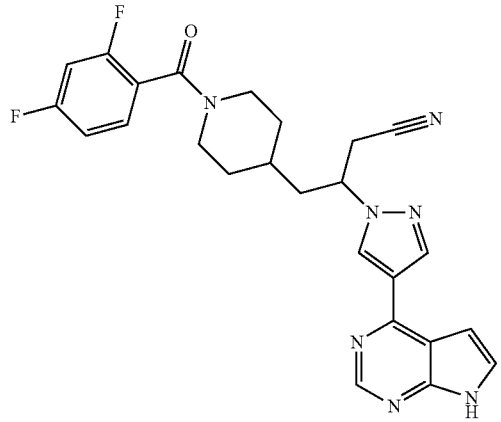 [SMILES: N#CCC(CC1CCN(C(=O)c2ccc(F)cc2F)CC1)n1cc(-c2ncnc3[nH]ccc23)cn1]

2,4-Difluorobenzoyl chloride (110 mg, 0.621 mmol), 4-piperidin-4-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (from example 5, step 4; 0.26 g, 0.52 mmol), and triethylamine (216 μL, 0.00155 mol) were dissolved in acetonitrile (2.5 mL). The mixture was stirred at RT for 1 h. Solvents were evaporated. The crude product was treated with DCM (3 mL, 0.05 mol) and trifluoroacetic acid (3 mL, 0.04 mol) for 30 min, and evaporated to dryness under reduced pressure. To the resultant residue was added methanol (5 mL) and ethylenediamine (0.5 mL, 0.007 mol). The reaction mixture was stirred at RT for 30 min, and concentrated under reduced pressure. The residue was purified on RP-HPLC (XBridge C-18 Column, eluting with a gradient of acetonitrile/water containing 0.15% $NH_4OH$, at flow rate 60 mL/min) to give the desired product. LCMS calculated for $C_{25}H_{24}F_2N_7O(M+H)^+$: m/z=476.2; Found: 476.0. $^1H$ NMR (400 MHz, $CD_3OD$): δ 8.96 (1H, d, J=10.0 Hz), 8.87 (1H, s), 8.51 (1H, s), 7.84 (1H, m), 7.38 (1H, m), 7.26 (1H, m), 7.06 (2H, m), 4.96 (1H, m), 4.59 (1H, m), 3.49 (2H, m), 3.15 (2H, m), 2.74 (1H, m), 2.23 (2H, m), 2.03 (1H, m), 1.86 (2H, m), 1.39 (1H, m), 1.28 (1H, m) ppm.

Example 7

4-{1-[(1-methyl-1H-pyrazol-3-yl)sulfonyl]piperidin-4-yl}-3-[4-(7H-pyrrolo[2,3-d]pyrimidin-4-yl)-1H-pyrazol-1-yl]butanenitrile

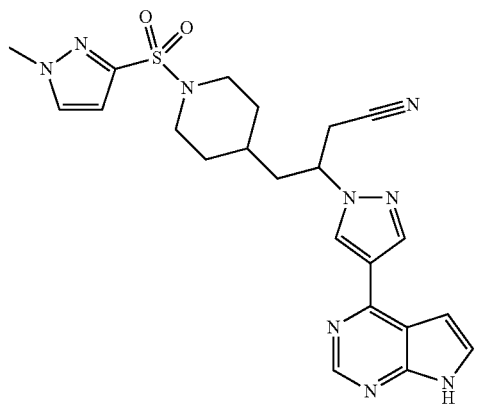 [SMILES: Cn1ccc(S(=O)(=O)N2CCC(CC(CC#N)n3cc(-c4ncnc5[nH]ccc45)cn3)CC2)n1]

1-Methyl-1H-pyrazole-3-sulfonyl chloride (108 mg, 0.597 mmol), 4-piperidin-4-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (from example 5, step 4; 250 mg, 0.498 mmol), and triethylamine (208 μL, 0.00149 mol) were dissolved in acetonitrile (2.5 mL). The mixture was stirred at RT for 1 h. Solvents were evaporated. The crude product was treated with DCM (4 mL) and trifluoroacetic acid (4 mL, 0.05 mol) for 30 min, evaporated under reduced pressure. To the resultant residue was added methanol (5 mL) and ethylenediamine (0.5 mL, 0.007 mol). The resulting mixture was stirred at RT for 30 min, and concentrated under reduced pressure. The residue was purified on RP-HPLC (XBridge C-18 Column, eluting with a gradient of acetonitrile/water containing 0.15% $NH_4OH$, at flow rate 60 mL/min) to give the desired product (183 mg, 76.6%). LCMS calculated for $C_{22}H_{26}N_9O_2S(M+H)^+$: m/z=480.2; Found: 480.0. $^1H$ NMR (300 MHz, $CD_3OD$): δ 8.92 (1H, s), 8.86 (1H, s), 8.49 (1H, s), 7.83 (1H, d, J=3.6 Hz), 7.69 (1H, d, J=2.1 Hz), 7.23 (1H, d, J=3.6 Hz), 6.59 (1H, d, J=2.1 Hz), 4.94 (1H, m), 3.89 (3H, s), 3.70 (2H, m), 3.12 (2H, m), 2.33 (2H, m), 2.19 (1H, m), 1.94 (1H, m), 1.82 (1H, m), 1.58 (1H, m), 1.32 (2H, m), 1.05 (1H, m) ppm.

Example 8

4-[1-(4-fluorobenzoyl)piperidin-4-yl]-3-[4-(7H-pyrrolo[2,3-d]pyrimidin-4-yl)-1H-pyrazol-1-yl]butanenitrile

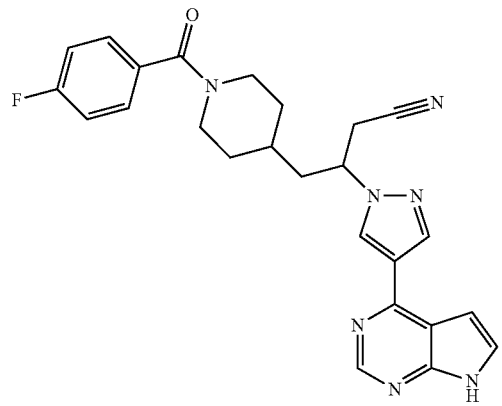 [SMILES: N#CCC(CC1CCN(C(=O)c2ccc(F)cc2)CC1)n1cc(-c2ncnc3[nH]ccc23)cn1]

4-Fluoro benzoyl chloride (94.7 mg, 0.597 mmol), 4-piperidin-4-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (from example 5, step 4; 0.250 g, 0.498 mmol), and triethylamine (208 μL, 0.00149 mol) were dissolved in acetonitrile (2.5 mL). The mixture was stirred at RT for 1 h. Solvents were evaporated. The crude product was treated with DCM (3 mL) and trifluoroacetic acid (3 mL, 0.04 mol) for 30 min, and evaporated to dryness under reduced pressure. To the resultant residue was added methanol (5 mL) and ethylenediamine (0.5 mL, 0.007 mol) and the resulting mixture was stirred at RT for 30 min. After being concentrated under reduced pressure, the residue was purified on RP-HPLC (XBridge C-18 Column, eluting with a gradient of acetonitrile/water containing 0.15% $NH_4OH$, at flow rate 60 mL/min) to give the desired product. LCMS calculated for $C_{25}H_{25}FN_7O(M+H)^+$: m/z=458.2; Found: 458.0. NMR (300 MHz, $CD_3OD$) δ 9.01 (1H, s), 8.90 (1H, s), 8.54 (1H, s), 7.89

(1H, d, J=3.6 Hz), 7.42 (2H, m), 7.31 (1H, d, J=3.6 Hz), 7.17 (2H, m), 4.98 (1H, m), 4.55 (1H, m), 3.52 (2H, m), 3.16 (2H, m), 2.73 (1H, m), 2.25 (2H, m), 2.03 (1H, m), 1.88 (2H, m), 1.38 (1H, m), 1.28 (1H, m) ppm.

Example 9

4-[1-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine, phosphoric acid salt

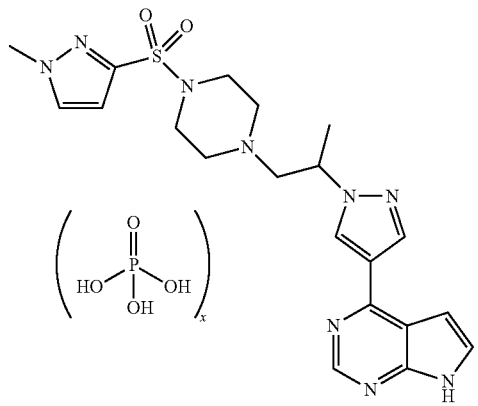

Step 1. benzyl 4-(2-hydroxypropyl)piperazine-1-carboxylate

To a solution of propylene oxide (4.0 mL, 57 mmol) in DCM (160 mL) was added 2.0 M of trimethylaluminum in toluene (27 mL, 54 mmol) at −78° C. under $N_2$. After being stirred at that temperature for 10 min, a solution of benzyl piperazine-1-carboxylate (from Aldrich, 9 mL, 40 mmol) in DCM (60 mL) was added. The resulting reaction mixture was stirred at −78° C. for 30 min. The reaction was then allowed to warm up to 0° C., stirring for another 30 min. To the reaction mixture was added sodium fluoride (8.2 g, 200 mmol) in one portion, followed by water (5.2 mL, 290 mmol) slowly and periodically at 0° C. The resulting suspension was rapidly stirred for 1 h at 0° C. and filtered through a short column of Celite and the column was subsequently washed with DCM (120 mL). The combined filtrates were dried over $Na_2SO_4$, concentrated and purified on silica gel (eluting with 0-10% MeOH in DCM) to provide the desired product (9.6 g, 76%). LCMS calculated for $C_{15}H_{23}N_2O_3(M+H)^+$: m/z=279.2; Found: 279.3. $^1$H NMR (500 MHz, DMSO-$d_6$): δ 7.39~7.31 (5H, m), 8.07 (2H, s), 4.29 (1H, J=4.0 Hz), 3.75 (1H, m), 3.38 (4H, br s), 2.38 (4H, m), 2.24 (1H, dd, J=12.5 and 7.0 Hz), 2.17 (1H, dd, J=12.5 and 7.0 Hz), 1.04 (3H, d, J=6.0 Hz) ppm.

Step 2. benzyl 4-{2-[(methylsulfonyl)oxy]propyl}piperazine-1-carboxylate

To a mixture of benzyl 4-(2-hydroxypropyl)piperazine-1-carboxylate (from step 1, 1.7 g, 6.1 mmol) in DCM (20 mL) was added DIPEA (2.1 mL, 12 mmol) followed by methanesulfonyl chloride (0.70 mL, 9.0 mmol) at 0° C. The reaction was stirred at 0° C. for 2 h. The reaction was quenched with saturated $NaHCO_3$ solution and extracted with DCM. The combined organic layers were washed with brine, dried over $MgSO_4$ and concentrated to provide crude product (2.22 g) which was used in next step without further purification. LCMS calculated for $C_{16}H_{25}N_2O_5S(M+H)^+$: m/z=357.1; Found: 357.3.

Step 3. (R)- and (S)-benzyl 4-(2-(4-(7-((2-(trimethylsilyl)ethoxy)methyl)-7H-pyrrolo[2,3-d]pyrimidin-4-yl)-1H-pyrazol-1-yl)propyl)piperazine-1-carboxylate A mixture of 4-(1H-pyrazol-4-yl)-7-{[2-(trimethylsilyl)ethoxy]methyl}-7H-pyrrolo[2,3-d]pyrimidine (prepared as described in WO 2007/070514 Example 65; 3.50 g, 0.0111 mol) in 1.0 M of potassium tert-butoxide in tert-butyl alcohol (11.6 mL, 0.0116 mol) was stirred at RT for 10 min. To the resulting mixture was added a solution of benzyl 4-{2-[(methylsulfonyl)oxy]propyl}piperazine-1-carboxylate (3.46 g) in 1,4-dioxane (70 mL). The reaction was stirred at 65° C. overnight. The reaction was quenched with saturated $NH_4Cl$ solution and extracted with EtOAc. The combined organic layers were washed with brine, dried over $MgSO_4$, and concentrated. The residue was purified on silica gel (eluting with 0-85% EtOAc in hexanes) to give a mixture of the titled products (3.57 g, in a ratio of 1:4 based on chiral column). The mixtures were separated on a ChiralCel OD-H column (3×25 cm, 5 μM), eluting with a gradient of 5% ethanol in hexanes at flow rate 28 mL/min, to give four peaks. Peak 1 with retention time 10.638 min and peak 2 with retention time 11.553 min were confirmed as the two enantiomers of titled compound. LCMS calculated for $C_{30}H_{42}N_7O_3Si(M+H)^+$: m/z=576.3; Found: 576.4. Peak 3 with retention time 13.642 min and peak 4 with retention time 26.764 min were confirmed to be the two enantiomers of a byproduct, benzyl 4{1-methyl-2-[4-(7-{[2-(trimethylsilyl)ethoxy]methyl}-7H-pyrrolo[2,3-d]pyrimidin-4-yl)-1H-pyrazol-1-yl]ethyl}piperazine-1-carboxylate, LCMS calculated for $C_{30}H_{42}N_7O_3Si(M+H)^+$: m/z=576.3; Found: 576.4. $^1$H NMR (500 MHz, DMSO-$d_6$): δ 8.84 (1H, s), 8.78 (1H, s), 8.39 (1H, s), 7.85 (1H, d, J=3.5 Hz), 7.45 (5H, m), 7.16 (1H, d, J=3.5 Hz), 5.73 (2H, s), 5.16 (2H, s), 4.43 (1H, dd, J=13.5 and 7.5 Hz), 4.24 (1H, dd, J=13.5 and 7.5 Hz), 3.63 (2H, t, J=8.0 Hz), 3.42 (4H, br s), 3.32 (1H, m), 2.72 (2H, m), 2.51 (2H, m), 1.03 (3H, d, J=7.0 Hz), 0.94 (3H, t, J=8.0 Hz), 0.00 (9H, s) ppm.

Step 4. 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine A mixture of benzyl 4-{2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate (0.30 g, 0.52 mmol; peak 1 from chiral separation) in methanol (10 mL) was hydrogenated in the presence of 10% palladium on carbon (10:90, Palladium:carbon black, 0.2 g, 0.2 mmol) under balloon pressure of hydrogen for 2 h. After filtering off catalyst, the filtrate was concentrated to give the desired product (0.20 g). LCMS calculated for $C_{22}H_{36}N_7OSi(M+H)^+$: m/z=442.3; Found: 442.4.

Step 5. 4-[1-(1-methyl-2-{4-[(1-methyl-1H-pyrazol-3-yl)sulfonyl]piperazin-1-yl}ethyl)-1H-pyrazol-4-yl]-7-{[2-(trimethylsilyl)ethoxy]methyl}-7H-pyrrolo[2,3-d]pyrimidine To a mixture of 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine (0.21 g, 0.48 mmol) and DIPEA (0.26 mL, 0.0015 mol) in DCM (5 mL) was added 1-methyl-1H-pyrazole-3-sulfonyl chloride (0.14 g, 0.78 mmol) in portions at 0° C. The reaction mixture was stirred at RT overnight, quenched with water, and extracted with DCM. The organic layers were dried over MgSO$_4$, concentrated and purified on silica gel (eluting with 0-5% MeOH in DCM) to give the desired product. LCMS calculated for C$_{26}$H$_{40}$N$_9$O$_3$SSi(M+H)$^+$: m/z=586.3; Found: 586.4.

Step 6. 4-[1-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine To a solution of 4-[1-(1-methyl-2-{4-[(1-methyl-1H-pyrazol-3-yl)sulfonyl]piperazin-1-yl}ethyl)-1H-pyrazol-4-yl]-7-{[2-(trimethylsilyl)ethoxy]methyl}-7H-pyrrolo[2,3-d]pyrimidine (0.243 g, 0.415 mmol) in acetonitrile (10 mL) and water (1 mL; ~8% water/acetonitrile) was added lithium tetrafluoroborate (1.02 g, 10.7 mmol). The solution was refluxed at 100° C. overnight. The mixture was cooled down and 7.2 M of ammonium hydroxide in water (0.346 mL, 2.49 mmol) was added in portions over a period of 5 min at RT, adjusting pH to 9-10 with stirring for 2 h. The solids were removed by filtration and the filtrate was purified on RP-HPLC (XBridge C-18 Column, eluting with a gradient of acetonitrile/water containing 0.15% NH$_4$OH, at flow rate 60 mL/min) to give the desired product (0.159 g, 84.1%). LCMS calculated for C$_{20}$H$_{26}$N$_9$O$_2$S(M+H)$^+$: m/z=456.2; Found: 456.4.

Step 7. 4-[1-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine phosphoric acid salt A suspension of 4-[1-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine (0.165 g, 0.362 mmol) in isopropyl alcohol (60 mL) was heated at 60° C. until becoming clear. Phosphoric acid (0.0373 g, 0.373 mmol) in isopropyl alcohol (1.0 mL) was added to the solution at 60° C. The solution was cooled down but no precipitation formed. Solvents were reduced in vacuo until white solid precipitated and held at RT for 30 min. The solid was filtered off, air dried, rinsed with some Et$_2$O and again air dried to give a phosphoric acid salt (150 mg, 74.8%). The number of phosphoric acids in the salt was not determined. LCMS calculated for C$_{20}$H$_{26}$N$_9$O$_2$S(M+H)$^+$: m/z=456.2 (free base); Found: 456.4.
$^1$H NMR (400 MHz, DMSO-d$_6$): δ 8.62 (1H, s), 8.59 (1H, s), 8.22 (1H, s), 7.86 (1H, d, J=2.2 Hz), 7.54 (1H, d, J=3.6 Hz), 6.91 (1H, d, J=3.6 Hz), 6.58 (1H, d, J=2.2 Hz), 4.63 (1H, m), 3.82 (3H, s), 2.85~2.78 (5H, m), 2.61~2.54 (3H, m), 2.36 (2H, m), 1.40 (3H, d, J=6.4 Hz) ppm.

Example 10

(±)-4-(1-(1-fluoro-3-(4-(1-methyl-1H-pyrazol-3-ylsulfonyl)piperazin-1-yl)propan-2-yl)-1H-pyrazol-4-yl)-7H-pyrrolo[2,3-d]pyrimidine

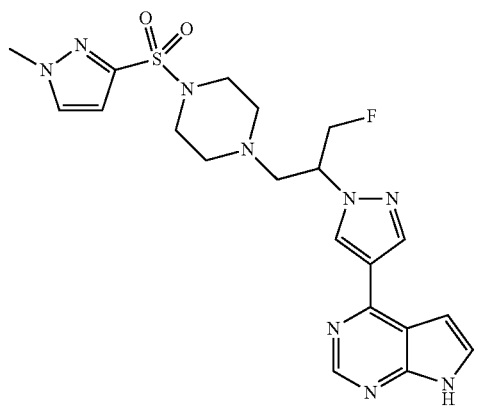 [SMILES: Cn1ccc(S(=O)(=O)N2CCN(CC(CF)n3cc(-c4ncnc5[nH]ccc45)cn3)CC2)n1]

Step 1. 3-fluoro-2-hydroxypropyl 4-methylbenzenesulfonate

To a mixture of 3-fluoropropane-1,2-diol (from Sigma, 0.750 g, 7.97 mmol) and triethylamine (1.39 mL, 9.96 mmol) in DCM (20 mL) was added p-toluenesulfonyl chloride (1.60 g, 8.37 mmol). The reaction was stirred at RT for 2 h. The mixture was concentrated to dryness and used in next step.

Step 2. benzyl 4-(3-fluoro-2-hydroxypropyl)piperazine-1-carboxylate

To the crude 3-fluoro-2-hydroxypropyl 4-methylbenzenesulfonate (1.98 g, 7.98 mmol) in methanol (40 mL) was added benzyl piperazine-1-carboxylate (1.76 g, 7.98 mmol). The reaction was stirred at RT over the weekend. After being evaporated to dryness, the residue was purified on silica gel, eluting with 0 to 10% MeOH in DCM to yield the desired product (443 mg, 18.7%). LCMS calculated for C$_{15}$H$_{22}$FN$_2$O$_3$(M+H)$^+$: m/z=297.2; Found: 297.4.

Step 3. benzyl 4-{3-fluoro-2-[(methylsulfonyl)oxylpropyl}piperazine-1-carboxylate To a mixture of benzyl 4-(3-fluoro-2-hydroxypropyl)piperazine-1-carboxylate (0.443 g, 1.49 mmol) and triethylamine (0.312 mL, 2.24 mmol) in DCM (10 mL) was added methanesulfonyl chloride (0.127 mL, 1.64 mmol). The reaction was stirred at RT for 1 h and quenched with saturated sodium bicarbonate. The organic layers were combined, washed with brine, dried over magnesium sulfate, and evaporated to dryness. The residue was used directly in next step (600 mg, 107.2%). LCMS calculated for C$_{16}$H$_{24}$FN$_2$O$_5$S(M+H)$^+$: m/z=375.1; Found: 375.3.

Step 4. (±)-benzyl 4-{3-fluoro-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate To a mixture of 4-(1H-pyrazol-4-yl)-7-{[2-(trimethylsilyl)ethoxy]methyl}-7H-pyrrolo[2,3-d]pyrimidine (prepared as described in WO 2007/070514 Example 65; 0.248 g, 0.785 mmol) in 1,4-dioxane (4 mL) was added 1.0 M of potassium tert-butoxide in tert-butyl alcohol (0.822 mL, 0.822 mmol). The reaction was stirred at RT for 10 min. To the resulting mixture was added benzyl 4-{3-fluoro-2-[(methylsulfonyl)oxy]propyl}piperazine-1-carboxylate (0.280 g, 0.748 mmol). The reaction was stirred at 95° C. for 2 h, quenched with aqueous ammonium chloride, and extracted with EtOAc. The combined organic layers were washed with water, brine, dried and evaporated to dryness. The residue was purified on silica gel column, eluting with 0 to 80% EtOAc in hexanes, to provide the desired product and (±)-benzyl 4-(2-fluoro-1-{[4-(7-{[2-(trimethylsilyl)ethoxy]methyl}-7H-pyrrolo[2,3-d]pyrimidin-4-yl)-1H-pyrazol-1-yl]methyl}ethyl)piperazine-1-carboxylate (128 mg, 28.8%). LCMS calculated for C$_{30}$H$_{41}$FN$_7$O$_3$Si(M+H)$^+$: m/z=594.3; Found: 594.3.

Step 5. (±)-4-{1-[2-fluoro-1-(piperazin-1-ylmethyl)ethyl]-1H-pyrazol-4-yl}-7-{[2-(trimethylsilyl)ethoxy]methyl}-7H-pyrrolo[2,3-d]pyrimidine A mixture of (±)-benzyl 4-{3-fluoro-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate (0.064 g, 0.11 mmol) and (±)-benzyl 4-(2-fluoro-1-{[4-(7-{[2-(trimethylsilyl)ethoxy]methyl}-7H-pyrrolo[2,3-d]pyrimidin-4-yl)-1H-pyrazol-1-yl]methyl}ethyl)piperazine-1-carboxylate (0.064 g, 0.11 mmol) in 5 mL of methanol was hydrogenated in the presence of 5% Pd/C, under balloon pressure of hydrogen, for 2 h. After filtering off the catalyst, the filtrate was concentrated and used directly in next step. LCMS calculated for $C_{22}H_{35}FN_7OSi(M+H)^+$: m/z=460.3; Found: 460.4.

Step 6. (±)-4-(1-(1-fluoro-3-(4-(1-methyl-1H-pyrazol-3-ylsulfonyl)piperazin-1-yl)propan-2-yl)-1H-pyrazol-4-yl)-7H-pyrrolo[2,3-d]pyrimidine To a mixture of (±)-4-{1-[2-fluoro-1-(piperazin-1-ylmethyl)ethyl]-1H-pyrazol-4-yl}-7-{[2-(trimethylsilyl)ethoxy]methyl}-7H-pyrrolo[2,3-d]pyrimidine (0.050 g, 0.11 mmol) and (±)-4-[1-(3-fluoro-2-piperazin-1-ylpropyl)-1H-pyrazol-4-yl]-7-{[2-(trimethylsilyl)ethoxy]methyl}-7H-pyrrolo[2,3-d]pyrimidine (0.050 g, 0.11 mmol) in acetonitrile (2 mL) was added triethylamine (0.0606 mL, 0.435 mmol) followed by 1-methyl-1H-pyrazole-3-sulfonyl chloride (0.0491 g, 0.272 mmol). The reaction was stirred at RT for 1 h and evaporated to dryness. LCMS calculated for $C_{26}H_{39}FN_9O_3SSi(M+H)^+$: m/z=604.3; Found: 604.4.

The crude mixture from above was treated with 2 mL of TFA at RT for 1 h, evaporated to dryness. The residue was dissolved in 3 mL of methanol and treated with 100 μL ethylenediamine at RT for 1 h. The reaction mixture was purified on RP-HPLC (XBridge C-18 Column, eluting with a gradient of acetonitrile/water containing 0.1% TFA to give the desired products as TFA salts. First peak, with retention time 0.844 min at Waters SunFire HPLC column (C18, 2.1× 50 mm, 5 μM, injection volume 2 μL, flow rate 3 mL/min, eluting with a gradient from 2 to 80% of acetonitrile/water with 0.025% TFA, was found to be titled compound, LCMS calculated for $C_{20}H_{25}FN_9O_2S(M+H)^+$: m/z=474.2; Found: 474.1. Second peak with retention time 0.961 min at the same analytical HPLC conditions was isomer (±)-4-(1-(3-fluoro-2-(4-(1-methyl-1H-pyrazol-3-ylsulfonyl)piperazin-1-yl)propyl)-1H-pyrazol-4-yl)-7H-pyrrolo[2,3-d]pyrimidine, LCMS calculated for $C_{20}H_{25}FN_9O_2S(M+H)^+$: m/z=474.2; Found 474.1.

Example 11

4-[1-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine bis(phosphate) Salt

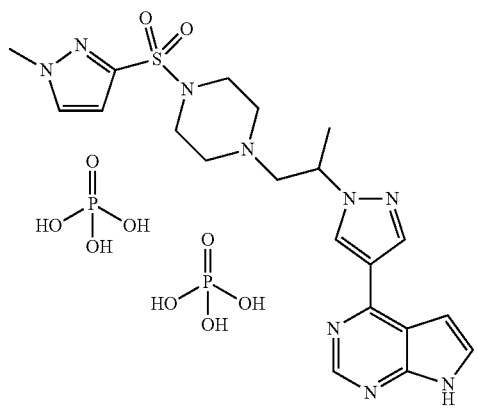

Step 1. tert-butyl 4-(2-chloropropanoyl)piperazine-1-carboxylate

To a mixture of tert-butyl piperazine-1-carboxylate (2.0 g, 11 mmol) in methylene chloride (20 mL) was added triethylamine (3.0 mL, 21 mmol) followed by 2-chloropropanoyl chloride (1.5 g, 12 mmol) drop-wise at 0° C. The reaction was stirred for 1 h, quenched with water, and extracted with dichloromethane. The combined organic layers were washed with water, brine, dried over magnesium sulfate and then evaporated to dryness to provide the crude product (3 g, 101%). LCMS calculated for $C_8H_{14}ClN_2O_3$ (M-Bu+H)$^+$: m/z=221.1; Found: 221.1.

Step 2. tert-butyl 4-{2-[4-(7-{[2-(trimethylsilyl)ethoxy]methyl}-7H-pyrrolo[2,3-d]pyrimidin-4-yl)-1H-pyrazol-1-yl]propanoyl}piperazine-1-carboxylate A mixture of 4-(1H-pyrazol-4-yl)-7-{([2-(trimethylsilyl)ethoxy]methyl}-7H-pyrrolo[2,3-d]pyrimidine (2.56 g, 0.00812 mol) in 1.0 M of potassium tert-butoxide in tert-butyl alcohol(10.8 mL, 0.0108 mol) was stirred at RT for 10 min. To the resulting mixture was added a solution of tert-butyl 4-(2-chloropropanoyl)piperazine-1-carboxylate (2.99 g, 0.0108 mol) in 1,4-dioxane (40 mL). The reaction was stirred at 80° C. overnight, then cooled and quenched with saturated ammonium chloride. The mixture was extracted with EtOAc. The combined organic layers were washed with brine, dried over sodium sulfate, then concentrated to dryness under reduced pressure. The residue was purified on silica gel, eluting with 0 to 100% EtOAc in hexanes, to give the desired product (3.74 g, 82.9%). LCMS calculated for $C_{27}H_{42}N_7O_4Si(M+H)^+$: m/z=556.3; Found: 556.3.

Step 3. 4-[1-(1-methyl-2-oxo-2-piperazin-1-ylethyl)-1H-pyrazol-4-yl]-7-{[2-(trimethylsilyl)ethoxy]methyl}-7H-pyrrolo[2,3-d]pyrimidine To a mixture of tert-butyl 4-{2-[4-(7-{[2-(trimethylsilyl)ethoxy]methyl}-7H-pyrrolo[2,3-d]pyrimidin-4-yl)-1H-pyrazol-1-yl]propanoyl}piperazine-1-carboxylate (3.14 g, 5.65 mmol) in methylene chloride (20 mL) was added 4.0 M of hydrogen chloride in 1,4-dioxane (7.06 mL, 28.2 mmol). The reaction mixture was stirred at RT for 1 h, then evaporated to dryness under reduced pressure. The residue was diluted with EtOAc and washed with 1 N NaOH, brine, dried over magnesium sulfate, and concentrated to dryness under reduced pressure to give the desired product (2.57 g, 99.8%). LCMS calculated for $C22H_{34}N_7O_2Si$ (M+H)$^+$: m/z=456.3; Found: 456.2.

Step 4. 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine To a mixture of 1.0 M of lithium tetrahydroaluminate in THF (11.3 mL. 11.3 mmol) in THF (40 mL) was added drop-wise, a solution of 4-[1-(1-methyl-2-oxo-2-piperazin-1-ylethyl)-1H-pyrazol-4-yl]-7-{[2-(trimethylsilyl)ethoxy]methyl}-7H-pyrrolo[2,3-d]pyrimidine (2.57 g, 5.64 mmol) in THF (20 mL). The mixture was refluxed for 30 min. The mixture was cooled at 0° C., quenched with 0.44 mL of water, followed by 0.44 mL of 15% NaOH, then 1.32 mL of water. The mixture was stirred at RT for 30 min, filtered through Celite. The filtrate was dried over sodium sulfate, concentrated to dryness under reduced pressure. The resultant residue was purified on silica gel, eluting with 0 to 10% methanol (containing 10% 2M $NH_3$/EtOH) in dichloromethane, to give the desired product (690 mg, 27.7%). LCMS calculated for $C_{22}H_{36}N_7OSi$ $(M+H)^+$: m/z=442.3; Found: 442.3.

Step 5. 4-[1-(1-methyl-2-{4-[(1-methyl-1H-pyrazol-3-yl)sulfonyl]piperazin-1-yl}ethyl)-1H-pyrazol-4-yl]-7-{[2-(trimethylsilyl)ethoxy]methyl}-7H-pyrrolo[2,3-d]pyrimidine To a mixture of 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine (1.1 g, 2.5 mmol) in dichloromethane (20 mL) was added triethylamine (0.52 mL, 3.7 mmol) followed by 1-methyl-1H-pyrazole-3-sulfonyl chloride (0.54 g, 3.0 mmol). The reaction was stirred at RT for 1 h, then quenched with saturated sodium bicarbonate, and extracted with dichloromethane. The combined organic layers were washed with brine and dried over sodium sulfate. After being concentrated to dryness, the residue was purified on silica gel, eluting with 0 to 10% methanol in dichloromethane to provide the product (1.28 g, 87.7%). LCMS calculated for $C_{26}H_{40}N_9O_3SSi$ $(M+H)^+$: m/z=586.3; Found: 586.2. The product was separated on a ChiralCel OD-H column (3×25 cm, 5 μM), eluting with a gradient of ethanol in hexanes at flow rate 28 mL/min, to give the two enantiomers. First peak with retention time 20.76 min and second peak with retention time 24.72 min.

Step 6. 4-[1-(1-methyl-2-{4-[1-methyl-1H-pyrazol-3-yl)sulfonyl]piperazin-1-yl}ethyl)-1H-pyrazol-4-yl]-7H-pyrrolo[2,3-d]pyrimidine A mixture of 4-[1-(1-methyl-2-{4-[(1-methyl-1H-pyrazol-3-yl)sulfonyl]piperazin-1-yl}ethyl)-1H-pyrazol-4-yl]-7-{[2-(trimethylsilyl)ethoxy]methyl}-7H-pyrrolo[2,3-d]pyrimidine ($1^{st}$ peak from chiral separation, 0.496 g, 0.847 mmol) in 10 mL of dichloromethane was treated with trifluoroacetic acid (10 mL, 100 mmol) at RT for 1 h. After evaporating to dryness, the residue was dissolved in 10 mL of methanol and treated with ethylenediamine (0.58 mL, 8.7 mmol) at RT for 1 h. The mixture was purified on RP-HPLC (XBridge C-18 Column, eluting with a gradient of acetonitrile/water containing 0.15% $NH_4OH$, at flow rate 60 mL/min) to give the desired product (324 mg, 84%). LCMS calculated for $C_{20}H_{26}FN_9O_2S$ $(M+H)^+$: m/z=456.2; Found: 456.2. Chiral HPLC comparison with an authentic sample from Example 9 confirmed this product made from $1^{st}$ peak of chiral separation to be the active enantionmer.

Step 7. 4-[7-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine bis(phosphate)

To a solution of 4-[1-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine (0.324 g, 0.711 mmol) in isopropyl alcohol (4.62 mL) was added phosphoric acid (0.1534 g, 0.001564 mol) in 1.0 mL isopropyl alcohol (while solution was hot) at 60° C. The phosphate salt precipitated while heating was continued, but did not affect dissolution. The solution was allowed to cool, filtered and the residue was air dried, rinsed with some ethyl ether and air dried further (355 mg, 72%). NMR showed the sample to contain 6% isopropyl alcohol. NMR titration of the salt, with triphenylphosphine, confirmed it is a bis(phosphate). $^1$H NMR (500 MHz, DMSO-$d_6$): δ 12.06 (1H, s), 8.65 (1H, s), 8.60 (1H, s), 8.24 (1H, s), 7.87 (1H, d, J=2.0 Hz), 7.56 (1H, dd, J=3.5 and 2.5 Hz), 6.92 (1H, dd, J=3.5 and 2.5 Hz), 6.60 (1H, d, J=2.0 Hz), 4.64 (1H, m), 3.85 (3H, s), 2.89~2.82 (5H, m), 2.65~2.58 (3H, m), 2.40 (2H, m), 1.42 (3H, d, J=6.5 Hz) ppm.

Example 12

4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile trifluoroacetate Salt (Single Enantiomer Isolated)

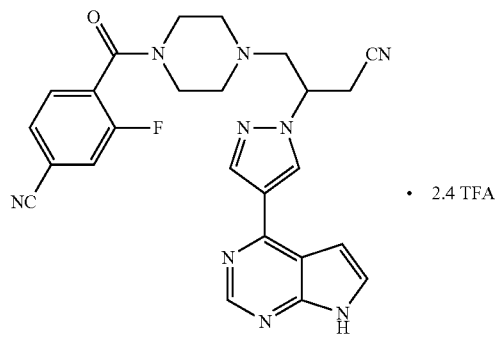 [SMILES: N#CCC(CN1CCN(C(=O)c2ccc(C#N)cc2F)CC1)n1cc(-c2ncnc3[nH]ccc23)cn1]

• 2.4 TFA

Step 1. (R)- and (S)-tert-butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate

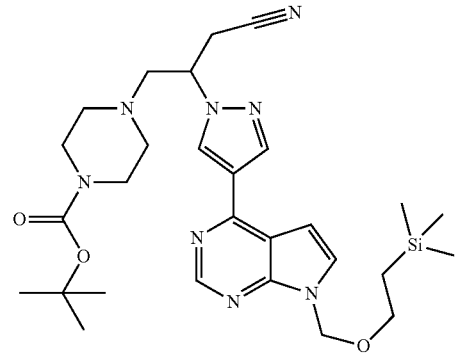 [SMILES: CC(C)(C)OC(=O)N1CCN(CC(CC#N)n2cc(-c3ncnc4c3ccn4COCC[Si](C)(C)C)cn2)CC1]

1,8-Diazabicyclo[5.4.0]undec-7-ene (5.5 mL, 0.037 mol) was added to a solution of (E)- and (Z)-tert-butyl 4-(3-cyanoallyl)piperazine-1-carboxylate (11.1 g, 0.0441 mol, prepared as in Example 1, Steps 1-2) and 4-(1H-pyrazol-4-yl)-7-{[2-(trimethylsilyl)ethoxy]methyl}-7H-pyrrolo[2,3-d]pyrimidine (11.6 g, 0.0368 mol, prepared as described in WO2007/070514, Example 65) in acetonitrile (70 mL). The mixture was stirred at 50° C. for 15 hours. Solvents were removed in vacuo. The residue was dissolved in ethyl acetate, washed with water (3 times), brine (once), dried over sodium sulfate and concentrated. Flash column chromatography, followed by preparative HPLC-MS (eluting with a gradient of MeCN/$H_2O$ containing 0.15% $NH_4OH$) afforded product as a white foam (8.20 g, 39%).

Chiral HPLC was used to separate the racemic mixture into single enantiomers (Phenomenex Lux-Cellulose-2, 21.2×250 mm, 5 μm, eluting with 30% EtOH/70% Hexanes, at 20 mL/min). Peak 1 (first to elute): 4.0 g and peak 2 (second to elute): 4.0 g. $^1$H NMR Peak 1 (400 MHz, CDCl$_3$): δ 8.84 (s, 1H), 8.33 (s, 1H), 8.31 (s, 1H), 7.40 (d, 1H), 6.79 (d, 1H), 5.68 (s, 2H), 4.70-4.62 (m, 1H), 3.58-3.51 (m, 2H), 3.44-3.35 (br m, 4H), 3.16 (dd, 1H), 3.10 (dd, 1H), 2.99 (dd, 1H), 2.89 (dd, 1H), 2.50-2.40 (br m, 4H), 1.44 (s, 9H), 0.95-0.89 (m, 2H), −0.06 (s, 9H); LCMS (M+H)$^+$: 567.3. $^1$H NMR Peak 2 (400 MHz, CDCl$_3$): δ 8.84 (s, 1H), 8.32 (s, 1H), 8.31 (s, 1H), 7.40 (d, 1H), 6.79 (d, 1H), 5.68 (s, 2H), 4.70-4.62 (m, 1H), 3.58-3.51 (m, 2H), 3.45-3.34 (br m, 4H), 3.16 (dd, 1H), 3.10 (dd, 1H), 2.99 (dd, 1H), 2.90 (dd, 1H), 2.50-2.40 (br m, 4H), 1.44 (s, 9H), 0.95-0.89 (m, 2H), −0.06 (s, 9H); LCMS (M+H)$^+$: 567.3.

Step 2. 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride Salt

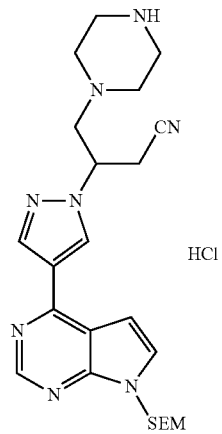 [SMILES: C[Si](C)(C)CCOCn1ccc2c(-c3cnn(C(CC#N)CN4CCNCC4)c3)ncnc21 ; Cl]

tert-Butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate (4.0 g, 7.0 mmol; Peak 2 from Step 1) was dissolved in 1,4-dioxane (40 mL), and 4.0 M of HCl in dioxane (25 mL, 100 mmol) was added. The mixture was stirred at room temperature for 80 min. Solvent was removed in vacuo to afford the product as the hydrochloride salt. LCMS (M+H)$^+$: 467.3.

Step 3. 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile trifluoroacetate Salt A mixture of 4-cyano-2-fluorobenzoic acid (138 mg, 0.836 mmol, Alfa Aesar), N,N,N',N'-tetramethyl-O-(7-azabenzotriazol-1-yl)uronium hexafluorophosphate (254 mg, 0.669 mmol) and triethylamine (0.466 mL, 3.34 mmol) in THF (10.0 mL) was stirred at room temperature for 15 minutes. 4-Piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (0.33 g, 0.56 mmol; from Step 2) was added. The reaction was stirred at room temperature for one hour. The reaction was diluted with ethyl acetate and water. The layers were separated and the organic layer was washed successively with water, 0.1N NaOH and brine, dried over sodium sulfate and concentrated. The residue was dissolved in a 2:1 mixture of DCM:TFA, stirred for 3 hours, concentrated, then in a mixture of 8 mL methanol to which 0.8 mL of ethylenediamine was added. After stirring for one hour, the product was purified via HPLC-MS, eluting with a gradient of MeCN and H$_2$O containing 0.2% TFA. Eluent frozen and lyophilized to afford a white powder (200 mg, 47%). $^1$H NMR (400 MHz, d$_6$-dmso): δ 12.64 (br s, 1H), 8.97 (s, 1H), 8.97 (s, 1H), 8.83 (s, 1H), 8.51 (s, 1H), 7.99 (dd, 1H), 7.82-7.76 (m, 2H), 7.61 (t, 1H), 7.15-7.11 (m, 1H), 5.13 (br m, 1H), 3.82-2.37 (br, 12H); $^{19}$F NMR (400 MHz, d$_6$-dmso): δ −74.97 (s, 7.2F), −114.49 (br s, 1F); LCMS (M+H)$^+$: 484.2.

Example 13

4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile trifluoroacetate Salt (Single Enantiomer Isolated)

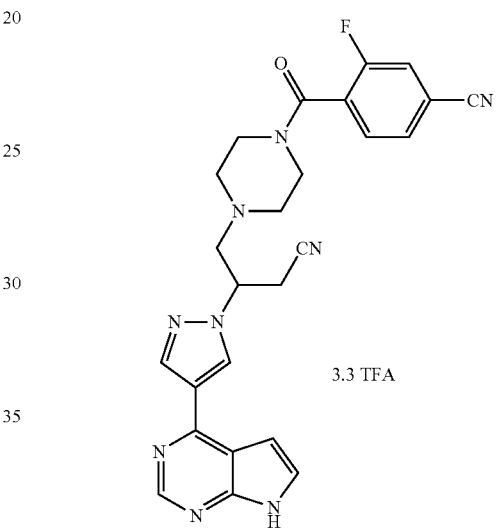

Step 1. tert-butyl 4-{3-cyano-2-[3-(7-{[2-(trimethylsilyl)ethoxy]methyl}-7H-pyrrolo[2,3-d]pyrimidin-4-yl)-1H-pyrrol-1-yl]propyl}piperazine-1-carboxylate

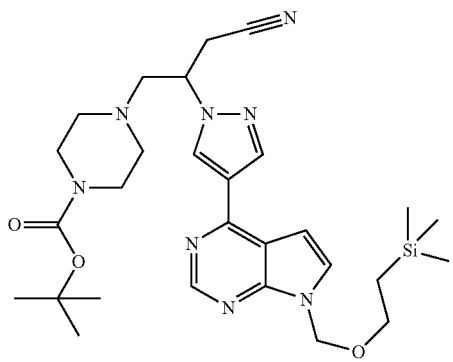 [SMILES: CC(C)(C)OC(=O)N1CCN(CC(CC#N)n2cc(-c3ncnc4c3ccn4COCC[Si](C)(C)C)cn2)CC1]

To a mixture of (E)- and (Z)-tert-butyl 4-(3-cyanoallyl)piperazine-1-carboxylate (4.0 g, 0.016 mol; prepared as in Example 1, Steps 1-2) and 4-(1H-pyrrol-3-yl)-7-{[2-(trimethylsilyl)ethoxy]methyl}-7H-pyrrolo[2,3-d]pyrimidine (4.2 g, 0.013 mol, prepared as in WO2009/114512, Example 82) in N,N-Dimethylformamide (25 mL) was added potassium carbonate (5.540 g, 0.0401 mol). The mixture was stirred at 60° C. for 17 hours. Additional (E)- and (Z)-tert-butyl 4-(3-cyanoallyl)piperazine-1-carboxylate (4.0 g, 0.016 mol) was added and the reaction was stirred at 60° C. for 24 hours. A further portion of (E)- and (Z)-tert-butyl 4-(3-cyanoallyl)piperazine-1-carboxylate (4.0 g, 0.016 mol) was added. After 3 nights of heating, most of the starting material had been converted to desired product as determined by LCMS. The mixture was then filtered, diluted with EtOAc, washed with water (3 times), brine (once), dried over sodium sulfate, decanted and concentrated. Purification via preparative HPLC-MS (eluting with a gradient of MeCN/H$_2$O containing 0.15% NH$_4$OH) afforded a brown foam (4.20 g, 55%). $^1$H NMR (300 MHz, CDCl$_3$): δ 8.81 (s, 1H), 7.66 (t, 1H), 7.34 (d, 1H), 6.97 (dd, 1H), 6.89 (t, 1H), 6.84 (d, 1H), 5.66 (s, 2H), 4.47-4.36 (m, 1H), 3.57-3.50 (m, 2H), 3.45-3.37 (m, 4H), 3.06 (dd, 1H), 3.00-2.90 (m, 2H), 2.83 (dd, 1H), 2.57-2.35 (m, 4H), 1.45 (s, 9H), 0.96-0.86 (m, 2H), −0.06 (s, 9H); LCMS (M+H)$^+$: 566.3.

Chiral HPLC was used to separate the racemate into single enantiomers (Chiral Technologies ChiralPAK IA 20×250 mm, 5 μm, mobile phase 30% EtOH/70% hexanes, flow rate 12 mL/min). Peak 1 (first enantiomer to elute), 1.8 g; Peak 2 (second enantiomer to elute): 1.9 g.

Step 2. 4-piperazin-1-yl-3-[3-(7-{[2-(trimethylsilyl)ethoxy]methyl}-7H-pyrrolo[2,3-d]pyrimidin-4-yl)-1H-pyrrol-1-yl]butanenitrile hydrochloride Salt

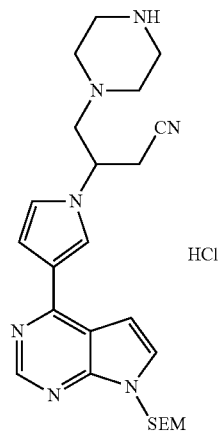 [SMILES: C[Si](C)(C)CCOCn1ccc2c(-c3ccn(C(CC#N)CN4CCNCC4)c3)ncnc21 ; Cl]

HCl

To a solution of tert-butyl 4-{3-cyano-2-[3-(7-{[2-(trimethylsilyl)ethoxy]methyl}-7H-pyrrolo[2,3-d]pyrimidin-4-yl)-1H-pyrrol-1-yl]propyl}piperazine-1-carboxylate (1.9 g, 0.0034 mol; peak 2 of Step 1) in 1,4-dioxane (20 mL) was added 4.0 M of HCl in p-dioxane (12 mL, 48 mmol). The mixture was stirred at room temperature for 80 minutes. Solvent was removed in vacua, to afford product as a light yellow solid (1.90 g, 100%). LCMS (M+H)$^+$: 466.3.

Step 3. 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile trifluoroacetate Salt A mixture of 4-cyano-2-fluorobenzoic acid (44 mg, 0.26 mmol, Alfa Aesar), N,N,N',N'-Tetramethyl-O-(7-azabenzotriazol-1-yl)uronium Hexafluorophosphate (93 mg, 0.24 mmol) and triethylamine (171 uL, 1.22 mmol) in THF (2.4 mL) was stirred at room temperature for 15 minutes. 4-Piperazin-1-yl-3-[3-(7-{[2-(trimethylsilyl)ethoxy]methyl}-7H-pyrrolo[2,3-d]pyrimidin-4-yl)-1H-pyrrol-1-yl]butanenitrile hydrochloride salt (110 mg, 0.20 mmol; from Step 2) was added. The reaction was stirred for 2 hours. Ethyl acetate and water were added. The layers were separated and the organic layer was washed successively with water, 1N NaOH and brine, dried over sodium sulfate and concentrated. The residue was dissolved first in a 1:1 mixture of DCM:TFA for 1 hour, was concentrated, then was stirred in methanol (2 mL) containing ethylenediamine (0.2 mL) for one hour. Purification via preparative HPLC-MS (eluting with a gradient of MeCN/H$_2$O containing 0.1% TFA afforded product as the 3.3×TFA salt (84 mg, 48%). $^1$H NMR (300 MHz, d$_6$-dmso): δ 13.22 (br s, 1H), 8.90 (s, 1H), 8.38 (s, 1H), 8.00 (dd, 1H), 7.97-7.93 (m, 1H), 7.80 (dd, 1H), 7.61 (t, 1H), 7.35 (s, 2H), 7.18-7.13 (m, 1H), 5.00-4.80 (m, 1H), 3.75-3.49 (br m, 2H), 3.35-2.33 (m, 10H); $^{19}$F NMR (300 MHz, d$_6$-dmso): δ −74.82 (s, 10F), −114.53 (s, 1F); LCMS (M+H)$^+$: 483.2.

Example 14

4-{4-[4-(difluoromethyl)-2-fluorobenzoyl]piperazin-1-yl}-3-[4-(7H-pyrrolo[2,3-d]pyrimidin-4-yl)-1H-pyrazol-1-yl]butanenitrile

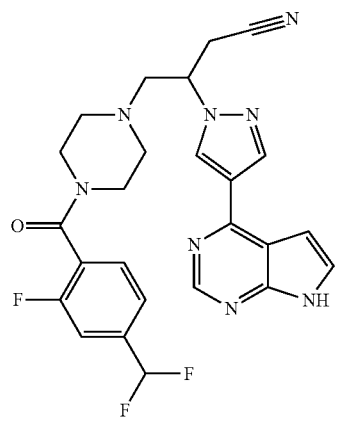 [SMILES: N#CCC(CN1CCN(C(=O)c2ccc(C(F)F)cc2F)CC1)n1cc(-c2ncnc3[nH]ccc23)cn1]

Step 1. 2-fluoro-4-formylbenzoic acid

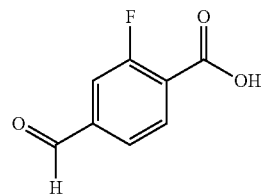 [SMILES: O=Cc1ccc(C(=O)O)c(F)c1]

2-Fluoro-4-methylbenzoic acid (1.0 g, 6.5 mmol, Matrix Scientific), N-bromosuccinimide (2.8 g, 16 mmol) and benzoyl peroxide (78 mg, 0.32 mmol) in carbon tetrachloride (15 mL) was heated to reflux for 40 hours. Solids were filtered off and washed with CCl$_4$. Solvent was removed from the filtrate in vacuo to afford 1.37 g light yellow solid. The crude product in was dissolved in ethanol (15 mL) and heated to 50° C. A solution of silver nitrate (1.6 g, 9.7 mmol) in hot water (2.3 mL) was introduced dropwise. The mixture was stirred at this temperature for 45 minutes. Upon cooling to room temperature, the mixture was poured into 1N HCl (7 ml) and filtered. The residue was washed with ethanol and volatiles were removed from the filtrate in vacuo. The remaining aqueous solution was extracted with EtOAc (twice). The extracts were washed with brine, dried over sodium sulfate and concentrated afford a yellow solid. Flash column chromatography, eluting with a gradient of 0-9% isopropanol in DCM containing 1% HOAc afforded product as a light yellow solid (310 mg, 23%). $^1$H NMR (300 MHz, d$_6$-dmso): δ 13.69 (br s, 1H), 10.05 (d, 1H), 8.09-8.02 (m, 1H), 7.87-7.76 (m, 2H); LCMS (M+H)$^+$: 169.0.

Step 2. methyl 2-fluoro-4-formylbenzoate

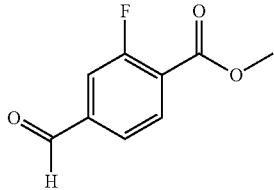

Sodium hydride (69 mg, 1.7 mmol) was added portionwise to a solution of 2-fluoro-4-formylbenzoic acid (0.30 g, 1.4 mmol) in N,N-Dimethylformamide (5.0 mL) at 0° C. The mixture was allowed to warm to room temperature and was stirred for 30 minutes. Methyl iodide (0.18 mL, 2.9 mmol) was introduced dropwise. After 2 hours, the mixture was quenched with 1 N HCl, and extracted with EtOAc. The extracts were washed with water (twice), brine (once), dried over sodium sulfate and concentrated. Flash column chromatography, eluting with a gradient from 0-15% ethyl acetate in hexanes afforded product as a white solid (190 mg, 72%). $^1$H NMR (300 MHz, CDCl$_3$): δ 10.05 (d, 1H), 8.11 (dd, 1H), 7.73 (dd, 1H), 7.65 (dd, 1H), 3.98 (s, 3H); LCMS (M+H)$^+$: 183.0.

Step 3. methyl 4-(difluoromethyl)-2-fluorobenzoate

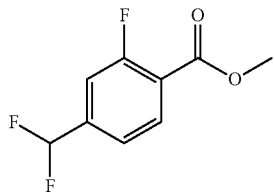

A mixture of methyl 2-fluoro-4-formylbenzoate (78 mg, 0.43 mmol) and 2-methoxy-N-(2-methoxyethyl)-N-(trifluoro-λ(4)-sulfanyl)ethanamine (160 uL, 0.86 mmol) in ethanol (2.0 uL, 0.034 mmol) was stirred at room temperature for 5 hours and quenched by the addition of 5% Sodium bicarbonate. The mixture was extracted with ethyl acetate. The extracts were washed successively with with 1N HCl, water, and brine, then dried over sodium sulfate and concentrated to afford product which was used without further purification (66 mg, 68%). $^1$H NMR (300 MHz, CDCl$_3$): δ 8.04 (t, 1H), 7.36 (d, 1H), 7.31 (d, 1H), 6.66 (t, 1H), 3.96 (s, 3H); LCMS (M+H)$^+$: 205.0.

Step 4. 4-(difluoromethyl)-2-fluorobenzoic acid

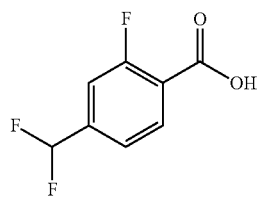 [SMILES: O=C(O)c1ccc(C(F)F)cc1F]

To a solution of methyl 4-(difluoromethyl)-2-fluorobenzoate (61 mg, 0.27 mmol) in THF (2.7 mL), was added a solution of lithium hydroxide, monohydrate (170 mg, 4.0 mmol) in water (0.90 mL). The mixture was stirred for 3.5 hours. Hydrochloric acid (1 N) was added to adjust the pH to 2, and the product was extracted with ethyl acetate. The extracts were washed twice with water, once with brine, dried over sodium sulfate and concentrated to afford crude acid, used directly in the next step (51 mg, 99%). $^1$H NMR (300 MHz, d$_6$-dmso): δ 13.56 (br s, 1H), 8.00 (t, 1H), 7.53 (t, 2H), 7.11 (t, 1H).

Step 5. 4-{4-[4-(difluoromethyl)-2-fluorobenzoyl]piperazin-1-yl}-3-[4-(7H-pyrrolo[2,3-d]pyrimidin-4-yl)-1H-pyrazol-1-yl]butanenitrile 4-(Difluoromethyl)-2-fluorobenzoic acid (10.1 mg, 0.0532 mmol) was dissolved in THF (0.39 mL). Triethylamine (29.7 uL, 0.213 mmol) and N,N,N',N'-tetramethyl-O-(7-azabenzotriazol-1-yl)uronium hexafluorophosphate (16.2 mg, 0.0426 mmol) were added, followed by 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (21 mg, 0.035 mmol, prepared as in Example 12, step 2). The reaction was stirred for 30 minutes. Ethyl acetate and water were added, shaken, and layers separated. The organic layer was washed successively with water, 0.1N NaOH and brine, dried over sodium sulfate and concentrated. The residue was stirred in a 1:1 mixture of DCM:TFA for 1 hour, concentrated, then stirred in a solution of methanol (1 mL) containing ethylenediamine (0.2 mL) for one hour. Purification via preparative HPLC-MS (eluting with a gradient of MeCN/H$_2$O containing 0.15% NH$_4$OH) afforded product as the free base (7 mg, 39%). $^1$H NMR (300 MHz, d$_6$-dmso): δ 12.06 (br s, 1H), 8.81 (s, 1H), 8.67 (s, 1H), 8.36 (s, 1H), 7.60 (d, 1H), 7.57-7.43 (m, 3H), 7.07 (t, 1H), 6.97 (d, 1H), 4.98 (tt, 1H), 3.63-3.55 (m, 2H), 3.25-3.18 (m, 2H), 3.317-3.10 (m, 2H), 2.91-2.77 (m, 2H), 2.66-2.26 (m, 4H); LCMS (M+H)$^+$: 509.2.

Example 15

4-[(4-{3-cyano-2-[4-(7H-pyrrolo[2,3-d]pyrimidin-4-yl)-1H-pyrazol-1-yl]propyl}piperazin-1-yl)carbonyl]-3,5-difluorobenzonitrile phosphate Salt

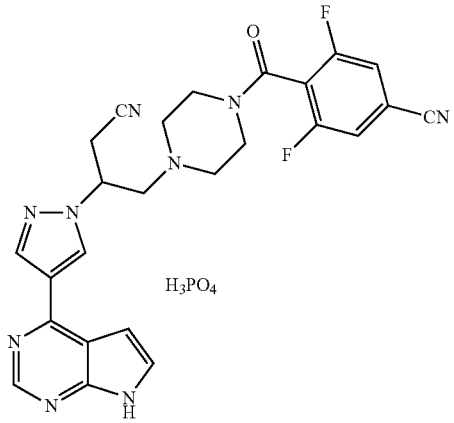

Step 1. 4-cyano-2,6-difluorobenzoic acid

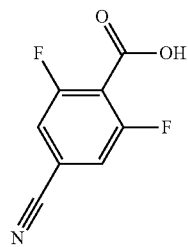 [SMILES: N#Cc1cc(F)c(C(=O)O)c(F)c1]

Potassium phosphate, monobasic (1.0 g, 7.5 mmol) in water (10 mL) was added to a solution of 3,5-difluoro-4-formylbenzonitrile (0.50 g, 0.0030 mol, Aldrich) in DMSO (10 mL). Sodium chlorite (0.7 g, 0.006 mol) in water (10 mL) was added and the reaction was stirred for 1 hour. Ethyl acetate and water were added. Layers were separated, and the aqueous was saturated with solid NaCl and extracted with further ethyl acetate. The combined organic extracts were washed with sat. NaCl, dried and rotovapped to give a white solid. $^1$H NMR (300 MHz, d$_6$-dmso): δ 7.98-7.91 (m, 2H).

Step 2. 4-[(4-{3-cyano-2-[4-(7H-pyrrolo[2,3-d]pyrimidin-4-yl)-1H-pyrazol-1-yl]propyl}piperazin-1-yl)carbonyl]-3,5-difluorobenzonitrile

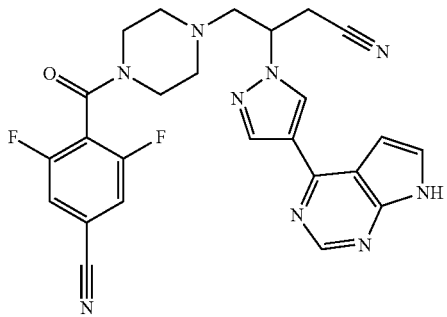 [SMILES: N#CCC(CN1CCN(C(=O)c2c(F)cc(C#N)cc2F)CC1)n1cc(-c2ncnc3[nH]ccc23)cn1]

4-Cyano-2,6-difluorobenzoic acid (82 mg, 0.32 mmol), Benzotriazol-1-yloxytris(dimethylamino)phosphonium hexafluorophosphate (110 mg, 0.00025 mol) and triethylamine (180 uL, 0.0013 mol) were stirred together in DMF (0.5 mL) for 15 minutes. 4-Piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (125 mg, 0.211 mmol; from Example 12, Step 2) was added and the reaction stirred for 16 hours. To push the reaction to completion, additional 4-cyano-2,6-difluorobenzoic acid (82 mg, 0.32 mol) and triethylamine (58.9 uL, 0.000422 mol) were mixed, in a separate vial, in N,N-Dimethylformamide (1.6 mL) and benzotriazol-1-yloxytris(dimethylamino)phosphonium hexafluorophosphate (110 mg, 0.25 mmol) was added. This mixture was stirred separately for 15 minutes, and then was added to the incomplete original reaction mixture. The reaction was continued for 1.5 hours, then was diluted with a large quantity of ethyl acetate. The solution was washed with three portions of water, once with brine, dried over sodium sulfate and concentrated. The residue was stirred in a mixture of 1:1 dichloromethane (DCM):TFA for one hour, was concentrated, then was stirred in methanol (3 mL) containing ethylenediamine (0.5 mL) until deprotection was complete as evidenced by LCMS. Two successive purifications vial HPLC-MS (eluting first with a gradient of MeCN/H$_2$O containing 0.1% TFA, then repurification eluting with a gradient of MeCN/H$_2$O containing 0.15% NH$_4$OH afforded clean product (46 mg, 43%). $^1$H NMR (400 MHz, d$_6$-dmso): δ 12.11 (br s, 1H), 8.81 (s, 1H), 8.67 (s, 1H), 8.37 (s, 1H), 7.98-7.91 (m, 2H), 7.60 (d, 1H), 6.97 (d, 1H), 5.02-4.93 (tt, 1H), 3.66-3.54 (m, 2H), 3.25-3.16 (m, 4H), 2.91-2.78 (m, 2H), 2.63-2.54 (m, 1H), 2.52-2.38 (m, 2H), 2.37-2.28 (m, 1H); LCMS (M+H)$^+$: 502.1.

Step 3. 4-[4-{3-cyano-2-[4-(7H-pyrrolo[2,3-d]pyrimidin-4-yl)-1H-pyrazol-1-yl]propyl}piperazin-1-yl)carbonyl]-3,5-difluorobenzonitrile phosphate Salt A solution of phosphoric acid (8.81 mg, 0.0899 mmol) in isopropyl alcohol (0.38 mL) was added dropwise to a solution of 4-[(4-{3-cyano-2-[4-(7H-pyrrolo[2,3-d]pyrimidin-4-yl)-1H-pyrazol-1-yl]propyl}piperazin-1-yl)carbonyl]-3,5-difluorobenzonitrile (41 mg, 0.082 mmol; from Step 2) in hot isopropyl alcohol (6 mL). The mixture was heated to give a clear solution. Upon cooling to room temperature, white precipitate formed. Some of the isopropanol was removed in vacuo. The solid was filtered off and rinsed with ether, then dried under high vacuum at 40-50° C. to afford product as a 1:1 phosphate salt. $^1$H NMR (400 MHz, CDCl$_3$): δ 12.12 (br s, 1H), 8.81 (s, 1H), 8.68 (s, 1H), 8.37 (s, 1H), 7.98-7.91 (m, 2H), 7.60 (dd, 1H), 6.97 (dd, 1H), 5.02-4.93 (m, 1H), 3.67-3.55 (m, 2H), 3.25-3.12 (m, 4H), 2.91-2.77 (m, 2H), 2.62-2.27 (m, 4H): LCMS (M+H)$^+$: 502.1.

Example 16

4-{4-[(5-chloro-3-fluoropyridin-2-yl)carbonyl]piperazin-1-yl}-3-[4-(7H-pyrrolo[2,3-d]pyrimidin-4-yl)-1H-pyrazol-1-yl]butanenitrile

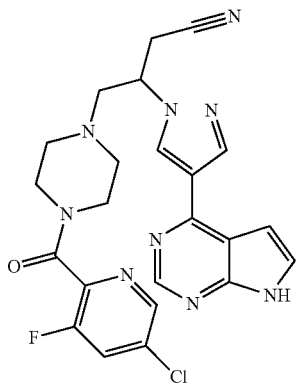 [SMILES: N#CCC(CN1CCN(C(=O)c2ncc(Cl)cc2F)CC1)N/C=C(\C=N)c1ncnc2[nH]ccc12]

To a solution of 5-chloro-3-fluoropyridine-2-carboxylic acid (23.5 mg, 0.134 mmol, prepared as described in Eur. J. Org. Chem. (24), 4174-4180; 2002) and triethylamine (86.2 uL, 0.618 mmol) in THF (1.1 mL) was added N,N,N',N'-tetramethyl-O-(7-azabenzotriazol-1-yl)uronium Hexafluorophosphate (47.0 mg, 0.124 mol). After stirring for 15 minutes, 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (61 mg, 0.10 mmol; from Example 12, Step 2) was added. The reaction was stirred for two hours. The reaction mixture was partitioned between water and ethyl acetate. The organic layer was washed successively with water, 0.1 N NaOH and brine, dried over sodium sulfate and concentrated. The residue was stirred in a 1:1 mixture of DCM:TFA for 1 hour, concentrated, and stirred in methanol (1 mL) containing ethylenediamine (0.2 mL) for 1 hour. Preparative HPLC-MS, eluting with a gradient of MeCN/H$_2$O containing 0.15% NH$_4$OH, was used to purify the product (29 mg, 57%). $^1$H NMR (300 MHz, d$_6$-dmso): δ □12.10 (br s, 1H), 8.81 (s, 1H), 8.61 (s, 1H), 8.55 (dd, 1H), 8.37 (s, 1H), 8.24 (dd, 1H), 7.60 (d, 1H), 6.97 (d, 1H), 4.98 (tt, 1H), 3.65-3.56 (m, 2H), 3.26-3.12 (m, 4H), 2.92-2.77 (m, 2H), 2.64-2.25 (m, 4H); LCMS (M+H)$^+$: 494.2.

Example 17

6-[(4-{3-cyano-2-[4-(7H-pyrrolo[2,3-d]pyrimidin-4-yl)-1H-pyrazol-1-yl]propyl}piperazin-1-yl)carbonyl]-5-fluoronicotinonitrile

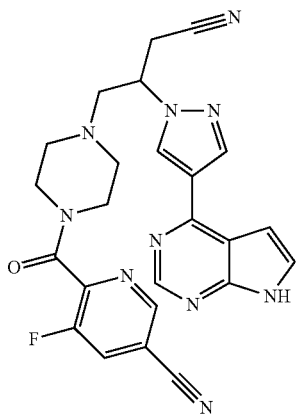 [SMILES: N#CCC(CN1CCN(C(=O)c2ncc(C#N)cc2F)CC1)n1cc(-c2ncnc3[nH]ccc23)cn1]

A mixture of 4-{4-[(5-chloro-3-fluoropyridin-2-yl)carbonyl]piperazin-1-yl}-3-[4-(7H-pyrrolo[2,3-d]pyrimidin-4-yl)-1H-pyrazol-1-yl]butanenitrile (15 mg, 0.030 mmol, from Example 1), 2-(Dicyclohexylphosphino)-2',6'-dimethoxy-1,1'-biphenyl (3.7 mg, 0.0091 mmol), Tris(dibenzylideneacetone)dipalladium(0) (3.3 mg, 0.0036 mmol) and zinc cyanide (18 mg, 0.15 mmol) in DMF (0.50 mL, 6.4 mmol) and one drop of water was degassed by purging with a stream of nitrogen for 5 minutes, then was heated in the microwave for 15 minutes at 150° C. Preparative HPLC-MS, eluting with a gradient of MeCN/H$_2$O containing 0.15% NH$_4$OH, was used to purify the product (6 mg, 40%). $^1$H NMR (300 MHz, d$_6$-dmso): δ 12.10 (br s, 1H), 8.93 (t, 1H), 8.81 (s, 1H), 8.68 (s, 1H), 8.59 (dd, 1H), 8.37 (s, 1H), 7.60 (d, 1H), 6.97 (d, 1H), 4.98 (tt, 1H), 3.65-3.58 (m, 2H), 3.25-3.19 (m, 2H), 3.19-3.13 (m, 2H), 2.92-2.78 (m, 2H), 2.66-2.25 (m, 4H); LCMS (M+H)$^+$: 485.2.

Example 18

4-[4-(3-fluoro-4-methoxybenzoyl)piperazin-1-yl]-3-[4-(7H-pyrrolo[2,3-d]pyrimidin-4-yl)-1H-pyrazol-1-yl]butanenitrile phosphate Salt

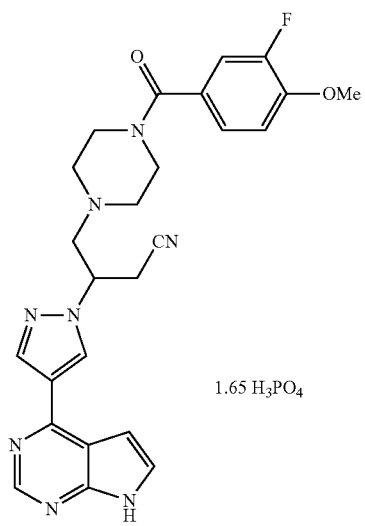 [SMILES: COc1ccc(C(=O)N2CCN(CC(CC#N)n3cc(-c4ncnc5[nH]ccc45)cn3)CC2)cc1F ; "1.65 H3PO4"]

1.65 H$_3$PO$_4$

Step 1. 4-[4-(3-fluoro-4-methoxybenzoyl)piperazin-1-yl]-3-[4-(7H-pyrrolo[2,3-d]pyrimidin-4-yl)-1H-pyrazol-1-yl]butanenitrile To a solution of 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (125 mg, 0.211 mmol; from Example 12, Step 2) in DCM (2 mL) was added triethylamine (177 uL, 1.27 mmol) followed by 3-fluoro-4-methoxybenzoyl chloride (80 mg, 0.4 mmol). The reaction was stirred at for 16 hours. 4-Dimethylaminopyridine (5 mg, 0.04 mmol) was added. Acetonitrile (0.30 mL) was added to aid in solubility and additional 3-fluoro-4-methoxybenzoyl chloride (80 mg, 0.4 mmol) was added. When reaction was complete as evidenced by LCMS, solvent was removed in vacuo. The residue was stirred in a mixture of 1:1 DCM:TFA for 1 hour, concentrated, then stirred in MeOH (3 mL) containing ethylenediamine (0.5 mL). Preparative HPLC-MS, eluting with a gradient of MeCN/H$_2$O containing 0.15%

NH$_4$OH, was used to purify the product (50 mg, 48%). $^1$H NMR (400 MHz, d$_6$-dmso): δ 12.12 (br s, 1H), 8.81 (s, 1H), 8.68 (s, 1H), 8.37 (s, 1H), 7.60 (d, 1H), 7.27-7.15 (m, 3H), 6.98 (d, 1H), 4.99 (tt, 1H), 3.86 (s, 3H), 3.57-3.17 (m, 6H), 2.89-2.77 (m, 2H), 2.60-2.32 (m, 4H); LCMS (M+H)$^+$: 489.1.

Step 2. 4-[4-(3-fluoro-4-methoxybenzoyl)piperazin-1-yl]-3-[4-(7H-pyrrolo[2,3-d]pyrimidin-4-yl)-1H-pyrazol-1-yl]butanenitrile phosphate Salt Phosphoric acid (10.4 mg, 0.106 mmol) in isopropyl alcohol (0.45 mL) was added dropwise to a solution of 4-[4-(3-fluoro-4-methoxybenzoyDpiperazin-1-yl]-3-[4-(7H-pyrrolo[2,3-d]pyrimidin-4-yl)-1H-pyrazol-1-yl]butanenitrile (47 mg, 0.096 mmol; from Step 1) in hot isopropyl alcohol (7 mL). The clear solution was stirred with cooling to room temperature. The volume of solvent was reduced in vacuo. The solid was filtered and triturated with ether to afford product as 1.65:1 phosphate salt (40 mg). $^1$H NMR (400 MHz, d$_6$-dmso): δ 12.12 (s, 1H), 8.81 (s, 1H), 8.68 (s, 1H), 8.37 (s, 1H), 7.60 (dd, 1H), 7.27-7.15 (m, 3H), 6.98 (dd, 1H), 4.99 (tt, 1H), 3.85 (s, 3H), 3.64-3.18 (m, 6H), 2.86 (dd, 1H), 2.81 (dd, 1H), 2.60-2.33 (m, 4H); LCMS (M+H)$^+$: 489.2.

Example 19

4-(4-{[3-fluoro-5-(trifluoromethyl)pyridin-2-yl]carbonyl}piperazin-1-yl)-3-[4-(7H-pyrrolo[2,3-d]pyrimidin-4-yl)-1H-pyrazol-1-yl]butanenitrile

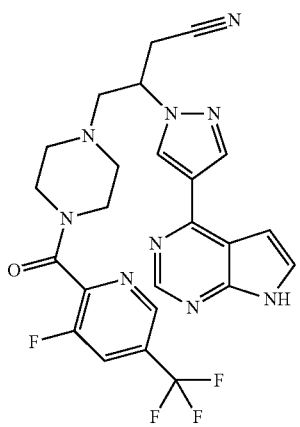 [SMILES: N#CCC(CN1CCN(C(=O)c2ncc(C(F)(F)F)cc2F)CC1)n1cc(-c2ncnc3[nH]ccc23)cn1]

Step 1. 2-bromo-3-fluoro-5-(trifluoromethyl)pyridine

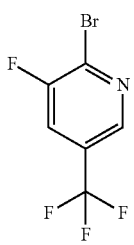

3-Fluoro-5-(trifluoromethyl)pyridin-2-ol (1.0 g, 5.5 mmol, Matrix) and phosphorus tribromide oxide (1.6 g, 5.5 mmol) in DMF (2.9 mL, 38 mmol) was heated at 130° C. for 70 minutes. After cooling to ambient temperature, the mixture was poured onto crushed ice and sodium bicarbonate to achieve a pH of 8. The product was extracted with diethyl ether, the extracts were washed twice with water and once with brine, dried over sodium sulfate, decanted and concentrated. Flash column chromatography, eluting with a gradient from 0-10% ethyl acetate in hexanes was used to purify the product (590 mg, 44%).
$^1$H NMR (400 MHz, CDCl$_3$): δ □8.52 (s, 1H), 7.66 (dd, 1H); LCMS (M+H)$^+$: 243.1.

Step 2. 3-fluoro-5-(trifluoromethyl)pyridine-2-carboxylic acid

2-bromo-3-fluoro-5-(trifluoromethyl)pyridine (0.59 g, 2.4 mmol) in toluene (0.50 mL) was added to a solution of 2.50 M of n-butyllithium in hexane (1.1 mL, 2.7 mmol) in toluene (3.0 mL) at −75° C. After one hour at −75° C., CO$_2$ gas was bubbled through the solution for 15 minutes at this temperature and continued as the reaction was allowed to slowly warm to room temperature. Solvent was removed in vacuo. Water was added, and the aqueous was washed with ether twice while basic, then was acidifed using concentrated HCl. A light yellow precipitate formed, which was collected by filtration (300 mg, 59%). $^1$H NMR (300 MHz, CDCl$_3$): δ 8.78 (s, 1H), 7.93 (d, 1H); LCMS (M+H)$^+$: 210.1.

Step 3. 4-(4-{[3-fluoro-5-(trifluoromethyl)pyridin-2-yl]carbonyl}piperazin-1-yl)-3-[4-(7H-pyrrolo[2,3-d]pyrimidin-4-yl)-1H-pyrazol-1-yl]butanenitrile N,N,N',N-Tetramethyl-O-(7-azabenzotriazol-1-yl)uronium hexafluorophosphate (16.2 mg, 0.0000426 mol) was added to a solution of 3-fluoro-5-(trifluoromethyl)pyridine-2-carboxylic acid (11 mg, 0.053 mmol) and triethylamine (30 microL, 0.21 mmol) in THF (0.4 mL). After stirring for 15 minutes, 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (21 mg, 0.035 mmol; from Example 12, Step 2) was added and the reaction was stirred for two hours. The reaction mixture was partitioned between ethyl acetate and water. The organic layer was washed successively with water, 0.1N NaOH and brine, dried over sodium sulfate and concentrated. The residue was dissolved and stirred in a 1:1 mixture of DCM:TFA for 1 hour, concentrated, then stirred in methanol (1 mL) containing ethylenediamine (0.2 mL) for one hour. Preparative HPLC-MS, eluting with a gradient of MeCN/H$_2$O containing 0.15% NH$_4$OH, was used to purify the product (9 mg, 48%). $^1$H NMR (300 MHz, d$_6$-dmso): δ □8.88 (s, 1H), 8.81 (s, 1H), 8.67 (s, 1H), 8.48 (dd, 1H), 8.37 (s, 1H), 7.60 (d, 1H), 6.97 (d, 1H), 4.99 (tt, 1H), 3.67-3.56 (m, 2H), 3.25-3.12 (m, 4H), 2.92-2.79 (m, 2H), 2.66-2.55 (m, 1H), 2.55-2.38 (m 2H), 2.38-2.25 (m, 1H); LCMS (M+H)⁺: 528.3.

Example 20

6-[(4-{3-cyano-2-[4-(7H-pyrrolo[2,3-d]pyrimidin-4-yl)-1H-pyrazol-1-yl]propyl}piperazin-1-yl)carbonyl]nicotinonitrile

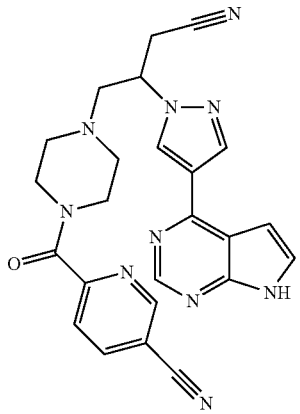 [SMILES: N#CCC(CN1CCN(C(=O)c2ccc(C#N)cn2)CC1)n1cc(-c2ncnc3[nH]ccc23)cn1]

Step 1. 4-{4-[(5-bromopyridin-2-yl)carbonyl]piperazin-1-yl}-3-[4-(7H-pyrrolo[2,3-d]pyrimidin-4-yl)-1H-pyrazol-1-yl]butanenitrile

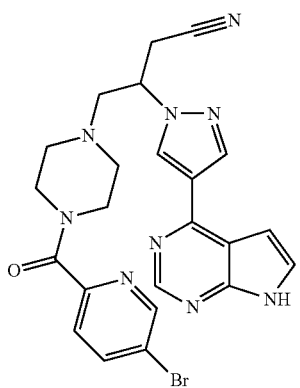 [SMILES: N#CCC(CN1CCN(C(=O)c2ccc(Br)cn2)CC1)n1cc(-c2ncnc3[nH]ccc23)cn1]

Triethylamine (72 uL, 0.52 mol) and N,N,N',N'-tetramethyl-O-(7-azabenzotriazol-1-yl)uronium hexafluorophosphate (39 mg, 0.103 mmol) were added to a solution of 5-bromopyridine-2-carboxylic acid (26 mg, 0.13 mmol) in THF (0.95 mL). After 15 minutes, 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (51 mg, 0.086 mmol; from Example 12, Step 2) was added and the reaction was stirred for two hours. The reaction was partitioned between ethyl acetate and water. The organic layer was washed successively with water, 0.1 N NaOH and brine, dried over sodium sulfate and concentrated. The residue was dissolved and stirred in a 1:1 mixture of DCM:TFA for 1 hour, concentrated, then stirred in methanol (1 mL) containing ethylenediamine (0.2 mL) for one hour. Preparative HPLC-MS, eluting with a gradient of MeCN/H₂O containing 0.15% NH₄OH, was used to purify the product (20 mg, 44%). ¹H NMR (400 MHz, d₆-dmso): δ 12.10 (br s, 1H), 8.81 (s, 1H) 8.70 (dd, 1H), 8.67 (s, 1H), 8.37 (s, 1H), 8.16 (dd, 1H), 7.60 (d, 1H), 7.52 (dd, 1H), 6.97 (d, 1H), 4.98 (tt, 1H), 3.61-3.54 (m, 2H), 3.37-3.28 (m, 2H), 3.24-3.19 (m, 2H), 2.86 (dd, 1H), 2.81 (dd, 1H), 2.63-2.54 (m, 1H), 2.52-2.40 (m, 2H), 2.39-2.31 (m, 1H); LCMS (M+H)⁺: 520.2/522.2.

Step 2. 6-[(4-{3-cyano-2-[4-(7H-pyrrolo[2,3-d]pyrimidin-4-yl)-1H-pyrazol-1-yl]propyl}piperazin-1-yl)carbonyl]nicotinonitrile Zinc cyanide (24 mg, 0.20 mmol) and tetrakis(triphenylphosphine)palladium(0) (17 mg, 0.014 mmol) were added to a solution of 4-{4-[(5-bromopyridin-2-yl)carbonyl]piperazin-1-yl}-3-[4-(7H-pyrrolo[2,3-d]pyrimidin-4-yl)-1H-pyrazol-1-yl]butanenitrile (15 mg, 0.029 mmol) in N,N-Dimethylformamide (0.48 mL). The mixture was degassed, then heated in the microwave at 150° C. for 15 minutes. The mixture was diluted with MeCN (1 mL), filtered and purified via preparative HPLC-MS, eluting with a gradient of MeCN/H₂O containing 0.15% NH₄OH (9 mg, 67%). ¹H NMR (400 MHz, d₆-dmso): δ ☐12.12 (br s, 1H), 9.03 (dd, 1H), 8.81 (s, 1H), 8.68 (s, 1H), 8.43 (dd, 1H), 8.37 (s, 1H), 7.74 (dd, 1H), 7.60 (d, 1H), 6.97 (d, 1H), 4.99 (tt, 1H), 3.62-3.56 (m, 2H), 3.27-3.19 (m, 4H), 2.86 (dd, 1H), 2.82 (dd, 1H), 2.64-2.56 (m, 1H), 2.53-2.41 (m, 2H), 2.39-2.31 (m, 1H); LCMS (M+H)⁺: 467.3.

Example 21

4-{4-[(5-fluoropyridin-2-yl)carbonyl]piperazin-1-yl}-3-[4-(7H-pyrrolo[2,3-d]pyrimidin-4-yl)-1H-pyrazol-1-yl]butanenitrile trifluoroacetate Salt

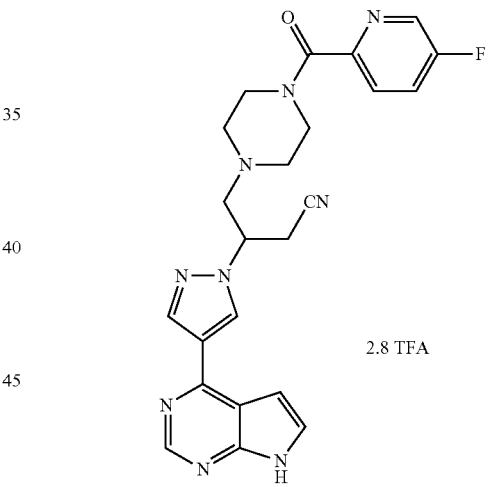

Step 1. 5-fluoropyridine-2-carboxylic acid

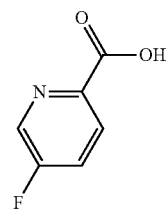

Potassium phosphate monobasic (1.4 g, 10 mmol) in water (10 mL) was added to a solution of 5-fluoropyridine-2-carbaldehyde (0.50 g, 4.0 mmol, Frontier) in DMSO (10 mL).

Sodium chlorite (0.9 g, 0.008 mol) in water (10 mL) was added, and the reaction continued for 1 hour. The mixture was saturated with NaCl, then diluted with EtOAc. The organic layer was further washed with brine, dried over sodium sulfate and concentrated to afford product (370 mg, 65%). $^1$H NMR (400 MHz, CDCl$_3$): δ 8.50 (d, 1H), 8.29 (ddd, 1H), 7.66 (ddd, 1H); LCMS (M+H)$^+$: 142.0.

Step 2. 4-{4-[(5-fluoropyridin-2-yl)carbonyl]piperazin-1-yl}-3-[4-(7H-pyrrolo[2,3-d]pyrimidin-4-yl)-1H-pyrazol-1-yl]butanenitrile trifluoroacetate Salt Triethylamine (155 uL, 1.12 mmol) and N,N,N',N'-Tetramethyl-O-(7-azabenzotriazol-1-yl)uronium Hexafluorophosphate (85 mg, 0.22 mmol) were added to a solution of 5-fluoropyridine-2-carboxylic acid (39 mg, 0.28 mol) in THF (2.0 mL). After stirring for 15 minutes, 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (110 mg, 0.18 mmol, from Example 12, Step 2) was added. The reaction was stirred for 16 hours. The reaction was partitioned between water and ethyl acetate. The organic layer was washed successively with water, 0.1N NaOH and brine, dried over sodium sulfate and concentrated. The residue was stirred in a 1:1 mixture of DCM:TFA for 2 hours, concentrated, and stirred in methanol (2 mL) containing ethylenediamine (0.2 mL) for one hour. Purification via preparative HPLC-MS, eluting with a gradient of MeCN/H$_2$O containing 0.1% TFA, afforded the product as the trifluoroacetate salt (72 mg, 50%). $^1$H NMR (400 MHz, d$_6$-dmso): δ 12.50 (br s, 1H), 8.99 (s, 1H), 8.82 (s, 1H), 8.58 (d, 1H), 8.53 (s, 1H), 7.87 (dt, 1H), 7.78 (br s, 1H), 7.71 (dd, 1H), 7.12 (br s, 1H), 5.29-5.14 (br m, 1H), 3.99-2.54 (br, 12H); LCMS (M+H)$^+$: 460.2.

Example 22

4-[4-(1H-indazol-5-ylsulfonyl)piperazin-1-yl]-3-[4-(7H-pyrrolo[2,3-d]pyrimidin-4-yl)-1H-pyrazol-1-yl]butanenitrile

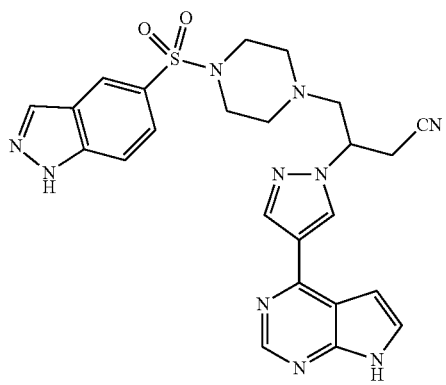 [SMILES: N#CCC(CN1CCN(S(=O)(=O)c2ccc3[nH]ncc3c2)CC1)n1cc(-c2ncnc3[nH]ccc23)cn1]

Step 1. 1H-indazole-5-sulfonyl chloride

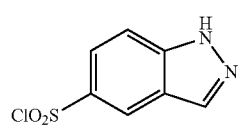 [SMILES: O=S(=O)(Cl)c1ccc2[nH]ncc2c1]

To a solution of concentrated HCl (1.35 mL, 16.2 mmol) diluted with water (0.80 mL) was added 5-aminoindazole (0.50 g, 3.8 mmol, Aldrich). The mixture was cooled at 0° C., and a solution of sodium nitrite (259 mg, 3.76 mmol) in water (0.30 mL) was added. The slurry was stirred at 0° C. for 20 minutes, then was poured into a freshly prepared cold saturated solution of SO$_2$ in acetic acid (4.0 mL). To this mixture was added a solution of copper(II) chloride (217 mg, 1.61 mmol) in water (0.30 mL). The mixture was allowed to stir with warming to room temperature for one hour. The reaction was then diluted with a small amount of water, and filtered to collect the crude product, which was used without further purification in the next step.

Step 2. 4-[4-(1H-indazol-5-ylsulfonyl)piperazin-1-yl]-3-[4-(7H-pyrrolo[2,3-d]pyrimidin-4-yl)-1H-pyrazol-1-yl]butanenitrile 1H-Indazole-5-sulfonyl chloride (26 mg, 0.12 mmol; from Step 1) was added to a solution of 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (24 mg, 0.041 mmol; from Example 12, Step 2) and triethylamine (57 uL, 0.40 mmol) in acetonitrile (0.30 mL). The mixture was stirred for 16 hours, then solvent was removed in vacuo. The residue was stirred in a 1:1 mixture of DCM:TFA for 1 hour, concentrated, and stirred in a solution of methanol (1 mL) containing ethylenediamine (0.2 mL) for one hour. Purification via preparative HPLC-MS, eluting with a gradient of MeCN/H$_2$O containing 0.15% NH$_4$OH afforded product as the free base (5 mg, 24%). $^1$H NMR (300 MHz, d$_6$-dmso): δ 12.08 (br s, 1H), 8.70 (s, 1H), 8.60 (s, 1H), 8.31-8.30 (m, 2H), 8.26-8.23 (m, 1H), 7.72 (d, 1H), 7.61 (dd, 1H), 7.52 (d, 1H), 6.87 (d, 1H), 4.93-4.81 (m, 1H), 3.39-2.41 (m, 12H); LCMS (M+H)$^+$: 517.1.

Example 23

4-(2-(4-(7H-pyrrolo[2,3-d]pyrimidin-4-yl)-1H-pyrazol-1-yl)-3-cyanopropyl)-N-(4-fluoro-2-methylphenyl)piperazine-1-carboxamide

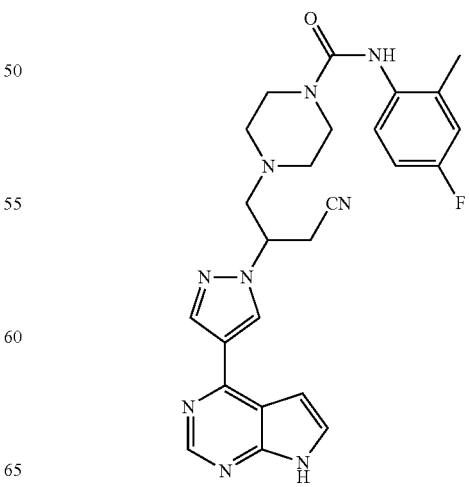

Step 1. 4-fluoro-1-isocyanato-2-methylbenzene

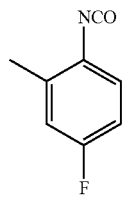

20% Phosgene in toluene (0.25 mL, 0.48 mmol) and triethylamine (0.11 mL, 0.76 mmol) were added to a solution of 4-fluoro-2-methyl-benzenamine (12 mg, 0.095 mmol) in a mixture of THF (0.30 mL) and DCM (0.10 mL). The reaction was stirred for two hours, then solvents were removed in vacuo and the product used without further purification in the next step.

Step 2. 4-(2-(4-(7H-pyrrolo[2,3-d]pyrimidin-4-yl)-1H-pyrazol-1-yl)-3-cyanopropyl)-N-(4-fluoro-2-methylphenyl)piperazine-1-carboxamide 4-Fluoro-1-isocyanato-2-methylbenzene (10 mg, 0.068 mmol) was added to a solution of 4-piperazin-1-yl-3-[4-(7-{[2-(trimethylsilyl)ethoxy]methyl}-7H-pyrrolo[2,3-d]pyrimidin-4-yl)-1H-pyrazol-1-yl]butanenitrile hydrochloride (20 mg, 0.034 mmol; from Example 12, Step 2) and triethylamine (28 uL, 0.20 mmol) in THF (0.39 mL). The reaction was stirred for one hour, then solvent was removed in vacuo. The residue was stirred in a 1:1 mixture of DCM:TFA for 1 hour, concentrated, and stirred in a solution of methanol (1 mL) containing ethylenediamine (0.2 mL) for one hour. Purification via preparative HPLC-MS, eluting with a gradient of MeCN/H$_2$O containing 0.15% NH$_4$OH afforded product as the free base (11 mg, 67%). $^1$H NMR (400 MHz, d$_6$-dmso): δ 12.12 (br s, 1H), 8.82 (s, 1H), 8.69 (s, 1H), 8.38 (s, 1H), 8.01 (s, 1H), 7.61 (d, 1H), 7.11 (dd, 1H), 7.02 (dd, 1H), 6.98 (d, 1H), 6.92 (dt, 1H), 5.01 (tt, 1H), 3.42-3.29 (m, 4H), 3.26-3.19 (m, 2H), 2.86 (dd, 1H), 2.81 (dd, 1H), 2.54-2.46 (m, 2H), 2.43-2.34 (m, 2H), 2.11 (s, 3H); LCMS (M+H)$^+$: 488.3.

Example 24

4-[((3R)-4-{3-cyano-2-[4-(7H-pyrrolo[2,3-d]pyrimidin-4-yl)-1H-pyrazol-1-yl]propyl}-3-methylpiperazin-1-yl)carbonyl]-3-fluorobenzonitrile (Single Diastereomers Isolated)

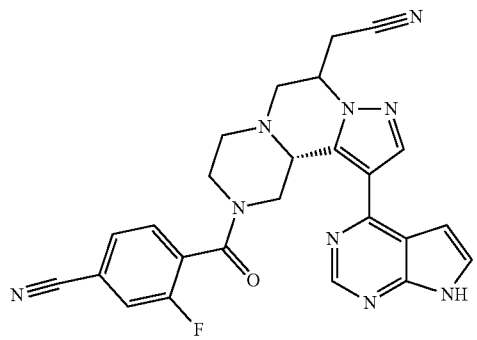

Step 1. tert-butyl (3R)-4-(2-hydroxyethyl)-3-methylpiperazine-1-carboxylate

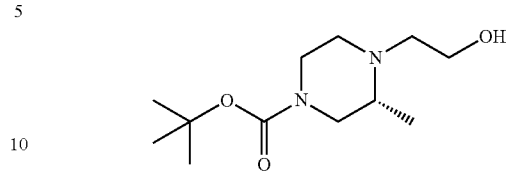

2-Bromoethanol (1.1 mL, 15 mmol) was added to a mixture of tert-butyl (3R)-3-methylpiperazine-1-carboxylate (2.0 g, 10 mmol, Aldrich) and potassium carbonate (4.1 g, 30 mmol) in acetonitrile (35 mL). The mixture was heated to reflux for 10 hours, cooled to room temperature, filtered and concentrated. Flash column chromatography, eluting with a gradient from 0-10% ethyl acetate/hexanes, afforded product as a colorless oil (1.40 g, 57%). $^1$H NMR (300 MHz, CDCl$_3$): δ 3.70-2.85 (m, 5H), 2.80 (ddd, 1H), 2.59-2.46 (m, 1H), 2.39-2.20 (m, 2H), 1.75-1.55 (m, 2H), 1.46 (s, 9H), 1.04 (d, 3H); LCMS (M+H)$^+$: 245.2.

Step 2. tert-butyl (3R)-3-methyl-4-(2-oxoethyl)piperazine-1-carboxylate

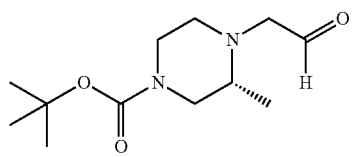 [SMILES: C[C@@H]1CN(C(=O)OC(C)(C)C)CCN1CC=O]

Dimethyl sulfoxide (0.732 mL, 10.3 mmol) was added to a solution of oxalyl chloride (0.582 mL, 6.88 mmol) in DCM (13 mL) at −78° C. After stirring for 10 minutes, tert-butyl (3R)-4-(2-hydroxyethyl)-3-methylpiperazine-1-carboxylate (1.4 g, 5.7 mmol) in DCM (6.6 mL) was added over 15 minutes. The reaction was stirred at −78° C. for 1 hour, then triethylamine (3.99 mL, 28.6 mmol) was added. The reaction was stirred, with warming to room temperature, for 1 hour. The reaction mixture was diluted with DCM, washed twice with water and once with brine, dried over sodium sulfate and concentrated to afford product, used without further purification (1.20 g, 86%). $^1$H NMR (300 MHz, CDCl$_3$): δ 9.72 (t, 1H), 3.90-3.65 (m, 2H), 3.43 (d, 1H), 3.15 (ddd, 1H), 3.04 (dd, 1H), 2.89-2.67 (m, 2H), 2.52-2.34 (m, 2H), 1.46 (s, 9H), 1.02 (d, 3H); LCMS (M+H$_2$O+H)$^+$: 261.2.

Step 3. (E)- and (Z)- (R)-tert-butyl 4-(3-cyanoallyl)-3-methylpiperazine-1-carboxylate

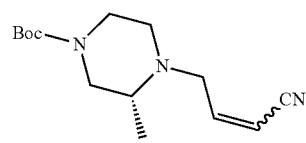 [SMILES: C[C@@H]1CN(C(=O)OC(C)(C)C)CCN1CC=CC#N]

A solution of diethyl cyanomethylphosphonate (0.841 mL, 5.20 mmol) in THF (10 mL) was added dropwise to a solution of 1 M of potassium tert-butoxide in THF (5.05 mL, 5.05 mmol) at 0° C. The reaction mixture was allowed to warm to room temperature and stir for 20 minutes. The solution was re-cooled to 0° C. and a solution of tert-butyl (3R)-3-methyl-4-(2-oxoethyl)piperazine-1-carboxylate (1.2 g, 5.0 mmol) in THF (5 mL) was added. The reaction mixture was warmed to room temperature and stirred for 3.5 hours. After quenching with water, the mixture was extracted with EtOAc. The combined extracts were washed twice with water, once with brine, dried over sodium sulfate and concentrated to afford crude product as an oil, which was used in the without further purification. $^1$H NMR (300 MHz, CDCl$_3$): δ 6.74 (ddd, 1H trans), 6.58 (ddd, 1H cis), 5.64 (dt, 1H trans), 5.47 (dt, 1H cis), 3.84-2.13 (m, 18H for both isomers), 1.45 (s, 18H), 1.07 (d, 3H), 1.01 (d, 3H); LCMS (M+H)$^+$: 266.2.

Step 4. tert-butyl (3R)-4-{3-cyana-2-[4-(7-{[2-(trimethylsilyl)ethoxy]methyl}-7H-pyrrolo[2,3-d]pyrimidin-4-yl)-1H-pyrazol-1-yl]propyl}-3-methylpiperazine-1-carboxylate

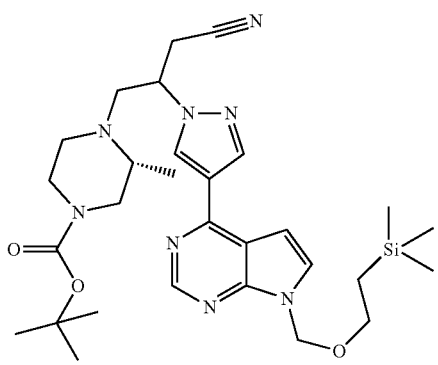 [SMILES: C[C@@H]1CN(C(=O)OC(C)(C)C)CCN1CC(CC#N)n1cc(-c2ncnc3c2ccn3COCC[Si](C)(C)C)cn1]

A mixture of (E)- and (Z)- (R)-tert-butyl 4-(3-cyanoallyl)-3-methylpiperazine-1-carboxylate (1.30 g, 4.90 mmol) and 4-(1H-pyrazol-4-yl)-7-{[2-(trimethylsilyl)ethoxy]methyl}-7H-pyrrolo[2,3-d]pyrimidine (1.03 g, 3.27 mmol, prepared as described in WO2007/070514, Example 65) and potassium carbonate (1.45 g, 10.5 mmol) in N,N-dimethylformamide (5.0 mL) was stirred for 16 hours. The mixture was filtered to remove potassium carbonate, and diluted with EtOAc. The solution was washed with three portions of water, once with brine, dried over sodium sulfate and concentrated. Flash column chromatography, eluting with a gradient of 0-80% (50% EtOAc/40% hexanes/10% IPA): hexanes afforded product as a mixture of diastereomers (1.40 g, 74%). NMR (300 MHz, CDCl$_3$): δ 8.85 (s, 1H), 8.35-8.28 (m, 2H), 7.40 (d, 1H), 6.79 (dd, 1H), 5.68 (s, 2H), 4.63-4.51 (m, 1H), 3.70-0.86 (m, 18H), 1.44 (s, 9H), −0.06 (s, 9H); LCMS (M+H)$^+$: 581.5.

Step 5. 4-[(2R)-2-methylpiperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloride Salt

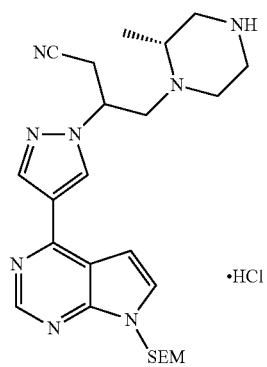 [SMILES: C[C@@H]1CNCCN1CC(CC#N)n1cc(-c2ncnc3c2ccn3COCC[Si](C)(C)C)cn1 ; Cl]

4.0 M of HCl in p-dioxane (3.0 mL, 0.012 mol) was added to a solution of diastereomeric tert-butyl (3R)-4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-methylpiperazine-1-carboxylate (0.50 g, 0.86 mmol) in 1,4-dioxane (5 mL). The reaction was stirred at room temperature for 80 minutes. Solvent was removed in vacuo to afford the product as a mixture of diastereomers and as the hydrochloride salt (470 mg, 98%). LCMS (M+H)$^+$: 481.3.

Step 6. 4-[((3R)-4-{3-cyano-2-[4-(7H-pyrrolo[2,3-d]pyrimidin-4-yl)-1H-pyrazol-1-yl]propyl}-3-methylpiperazin-1-yl)carbonyl]-3-fluorobenzonitrile A mixture of 4-cyano-2-fluorobenzoic acid (50.4 mg, 0.305 mmol, Alfa Aesar), N,N,N',N'-tetramethyl-O-(7-azabenzotriazol-1-yl)uronium hexafluorophosphate (107 mg, 0.282 mmol) and triethylamine (196 uL, 1.41 mmol) in THF (2.8 mL) was stirred for 15 minutes, followed by the addition of the diastereomeric 4-[(2R)-2-methylpiperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloride salt (130 mg, 0.23 mmol). After stirring for 2 hours, the reaction was partitioned between ethyl acetate and water. The organic layer was washed successively with water, 0.1 N NaOH and brine, dried over sodium sulfate and concentrated. To separate diastereomers, preparative HPLC-MS was used: Waters mass directed fractionation system, Waters SunFire C18 column, 5 μm particle size, 30×100 mm, mobile phase system: Aq(0.1% TFA)/AcN; flow rate 60 mL/min; separating gradient: 30.4-48.4% B in 12 minutes. Peak 1 (first to elute), and Peak 2 (second to elute) were subjected to the deprotection step separately: stirred for 1 hour in a 1:1 mixture of DCM/TFA, concentrated, then stirred for 30 minutes in a solution of ethylenediamine (0.2 mL) in methanol (1.5 mL). Purification via preparative HPLC-MS, eluting with a gradient of MeCN/H$_2$O containing 0.15% NH$_4$OH afforded product (peak 1: 19 mg, peak 2: 23 mg, total 36% of theoretical). Peak 1: ¹H NMR (400 MHz, d₆-dmso) (rotamers): δ 12.11 (br s, 1H), 8.81 (d, 1H), 8.67 (s, 1H), 8.36 (s, 1H), 7.99-7.93 (m, 1H), 7.79-7.68 (m, 1H), 7.62-7.54 (m, 2H), 6.97 (dd, 1H), 4.93-4.83 (m, 1H), 3.85-3.66 (m, 1H), 3.36-2.08 (m, 10H), 0.90 and 0.71 ((each as d) together=3H); LCMS (M+H)⁺: 498.1. Peak 2: ¹H NMR (400 MHz, d₆-dmso) (rotamers): δ □12.08 (br s, 1H), 8.82 (d, 1H), 8.68 (d, 1H), 8.37 (d, 1H), 8.01-7.93 (m, 1H), 7.80-7.71 (m, 1H), 7.63-7.54 (m, 2H), 6.98 (t, 1H), 4.94-4.81 (m, 1H), 3.87-2.26 (m, 11H), 1.05 and 0.87 ((each as d) together=3H); LCMS (M+H)⁺: 498.1.

Example 25

4-[((3S)-4-{3-cyano-2-[4-(7H-pyrrolo[2,3-d]pyrimidin-4-yl)-1H-pyrazol-1-yl]propyl}-3-methylpiperazin-1-yl)carbonyl]-3-fluorobenzonitrile (Single Diastereomers Isolated)

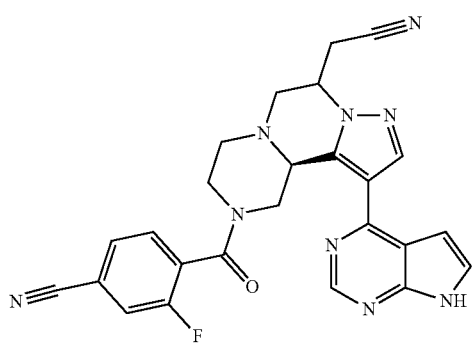

Step 1. (E)- and (Z)- (S)-tert-butyl 4-(3-cyanoallyl)-3-methylpiperazine-1-carboxylate

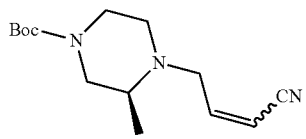 [SMILES: C[C@H]1CN(C(=O)OC(C)(C)C)CCN1CC=CC#N]

To a mixture of olefin isomers (2E)- and (2Z)-4-bromobut-2-enenitrile (1.2 g, 8.0 mmol, prepared as described in *J. Am. Chem. Soc.* 1940, 62, pp. 974-7) in acetonitrile (10.6 mL), was added tert-butyl (3S)-3-methylpiperazine-1-carboxylate (1.6 g, 8.0 mmol, Aldrich), followed by sodium bicarbonate (1.34 g, 16.0 mmol). The reaction was stirred for 24 hours, then was filtered, and solvent removed in vacuo. 1N HCl was added, this aqueous solution was washed with EtOAc, and the washes were discarded. The aqueous layer was then made basic by the addition of solid sodium bicarbonate, and the product was extracted with two portions of ethyl acetate. The combined extracts were washed with brine, dried over sodium sulfate and concentrated to afford product, used without further purification (1.60 g, 75%). ¹H NMR (300 MHz, CDCl₃): δ 6.73 (ddd, 1H), 6.58 (ddd, 1H), 5.63 (dt, 1H), 5.46 (dt, 1H), 4.00-2.14 (m, 18H), 1.45 (s, 18H), 1.08 and 1.07 and 1.01 ((each as d, together=3H); LCMS (M+H)⁺: 266.2.

Step 2. tert-butyl (3S)-4-{3-cyano-2-[4-(7-{[2-(trimethylsilyl)ethoxy]methyl}-7H-pyrrolo[2,3-d]pyritnidin-4-yl)-1H-pyrazol-1-yl]propyl}-3-methylpiperazine-1-carboxylate

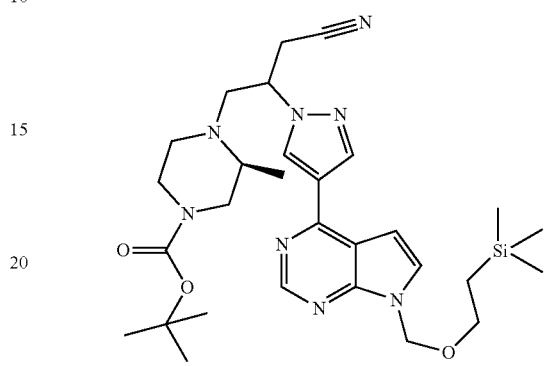

Potassium carbonate (1.57 g, 11.4 mmol) was added to the mixture of olefin isomers (E)- and (Z)- (S)-tert-butyl 4-(3-cyanoallyl)-3-methylpiperazine-1-carboxylate (1.6 g, 6.0 mmol) and 4-(1H-pyrazol-4-yl)-7-{[2-(trimethylsilyl)ethoxy]methyl}-7H-pyrrolo[2,3-d]pyrimidine (1.12 g, 3.55 mmol, prepared as described in WO2007/070514, Example 65) in DMF (5.4 mL). The reaction was stirred for 16 hours. The mixture was filtered to remove potassium carbonate, was diluted with EtOAc, washed three times with water, once with brine, dried over sodium sulfate and concentrated. Flash column chromatography, eluting with a gradient from 0-80% (50% EtOAc/40% hexanes/10% IPA):hexanes afforded product as a mixture of diastereomers (1.70 g, 82%). ¹H NMR (300 MHz, CDCl₃): δ 8.85 (s, 1H), 8.33-8.30 (m, 2H), 7.40 (d, 1H), 6.79 (dd, 1H), 5.67 (s, 2H), 4.64-4.50 (m, 1H), 4.13-2.20 (m, 13H), 1.44 (s, 9H), 1.30-0.88 (m, 5H), −0.06 (s, 9H); LCMS (M+H)⁺: 581.3.

Step 3. 4-[(2S)-2-methylpiperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloride Salt

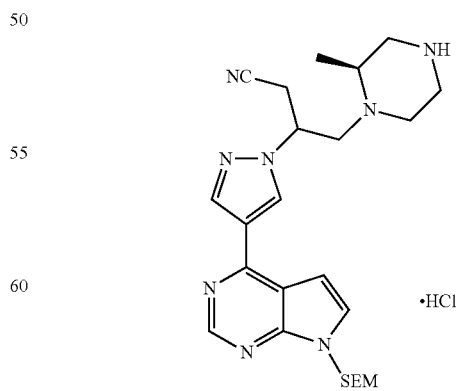

4.0 M of HCl in p-dioxane (3.0 mL) was added to the diastereomeric mixture of tert-butyl (3S)-4-{3-cyano-2-[4-

(7-{[2-(trimethylsilyl)ethoxy]methyl}-7H-pyrrolo[2,3-d]pyrimidin-4-yl)-1H-pyrazol-1-yl]propyl}-3-methylpiperazine-1-carboxylate (0.50 g, 0.86 mmol) in 1,4-dioxane (5 mL). The mixture was stirred at room temperature for 80 minutes, then solvent was removed in vacuo to afford the hydrochloride salt as a light yellow solid (480 mg, 100%). LCMS (M+H)+: 481.3.

Step 4. 4-[((3S)-4-{3-cyano-2-[4-(7H-pyrrolo[2,3-d]pyrimidin-4-yl)-1H-pyrazol-1-yl]propyl}-3-methylpiperazin-1-yl)carbonyl]-3-fluorobenzonitrile Following the procedure of Example 24, Step 6, the diastereomeric mixture of 4-[(2S)-2-methylpiperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloride salt (101 mg, 0.182 mmol; from Step 3) was converted to single diasteromers of 4-[((3S)-4-{3-cyano-2-[4-(7H-pyrrolo[2,3-d]pyrimidin-4-yl)-1H-pyrazol-1-yl]propyl}-3-methylpiperazin-1-yl)carbonyl]-3-fluorobenzonitrile. To separate diastereomers just prior to the SEM deprotection step, preparative HPLC-MS was used: Waters mass directed fractionation system, Waters SunFire C18 column, 5 μm particle size, 30×100 mm, mobile phase system: Aq(0.1% TFA)/AcN; flow rate 60 mL/min; separating gradient: 30.4-48.4% B in 12 minutes. (peak 1: 21 mg, peak 2: 19 mg, total 44% of theoretical). Peak 1: $^1$H NMR (400 MHz, $d_6$-dmso) (rotamers): δ 12.09 (br s, 1H), 8.81 (d, 1H), 8.67 (s, 1H), 8.36 (s, 1H), 8.00-7.93 (m, 1H), 7.79-7.69 (m, 1H), 7.62-7.53 (m, 2H), 6.97 (dd, 1H), 4.94-4.82 (m, 1H), 3.87-3.68 (m, 1H), 3.37-2.08 (m, 10H), 0.90 and 0.70 (each as d, together=3H); LCMS (M+H)+: 498.2. Peak 2: $^1$H NMR (400 MHz, $d_6$-dmso) (rotamers): δ 12.10 (br s, 1H), 8.82 (d, 1H), 8.68 (d, 1H), 8.37 (d, 1H), 8.00-7.94 (m, 1H), 7.64-7.54 (m, 2H), 6.98 (t, 1H), 4.95-4.82 (m, 1H), 3.85-3.76 (m, 1H), 3.38-2.25 (m, 10H), 1.05 and 0.87 (each as d, together=3H); LCMS (M+H)+: 498.2. See table below for more detail.

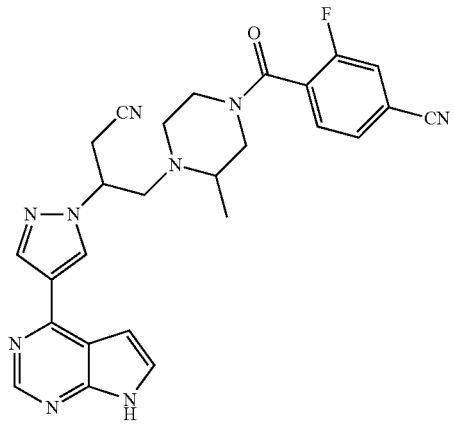 [SMILES: CC1CN(C(=O)c2ccc(C#N)cc2F)CCN1CC(CC#N)n1cc(-c2ncnc3[nH]ccc23)cn1]

| Ex No. | Name | NMR | MS (M + H) |
|---|---|---|---|
| R-1 | 4-(4-(2-(4-(7H-pyrrolo[2,3-d]pyrimidin-4-yl)-1H-pyrazol-1-yl)-3-cyanopropyl)-3-methylpiperazine-1-carbonyl)-3-fluorobenzonitrile | (400 MHz, $d_6$-dmso) (rotamers): δ 12.11 (br s, 1H), 8.81 (d, 1H), 8.67 (s, 1H), 8.36 (s, 1H), 7.99-7.93 (m, 1H), 7.79-7.68 (m, 1H), 7.62-7.54 (m, 2H), 6.97 (dd, 1H), 4.93-4.83 (m, 1H), 3.85-3.66 (m, 1H), 3.36-2.08 (m, 10H), 0.90 and 0.71 (each as d, together = 3H) | 498.2 |
| R-2 | 4-(4-(2-(4-(7H-pyrrolo[2,3-d]pyrimidin-4-yl)-1H-pyrazol-1-yl)-3-cyanopropyl)-3-methylpiperazine-1-carbonyl)-3-fluorobenzonitrile | (400 MHz, $d_6$-dmso) (rotamers): δ 12.08 (br s, 1H), 8.82 (d, 1H), 8.68 (d, 1H), 8.37 (d, 1H), 8.01-7.93 (m, 1H), 7.80-7.71 (m, 1H), 7.63-7.54 (m, 2H), 6.98 (t, 1H), 4.94-4.81 (m, 1H), 3.86-3.67 (m, 1H), 3.37-2.25 (m, 10H), 1.05 and 0.87 (each as d, together = 3H) | 498.1 |
| S-1 | 4-(4-(2-(4-(7H-pyrrolo[2,3-d]pyrimidin-4-yl)-1H-pyrazol-1-yl)-3-cyanopropyl)-3-methylpiperazine-1-carbonyl)-3-fluorobenzonitrile | (400 MHz, $d_6$-dmso) (rotamers): δ 12.09 (br s, 1H), 8.81 (d, 1H), 8.67 (s, 1H), 8.36 (s, 1H), 8.00-7.93 (m, 1H), 7.79-7.69 (m, 1H), 7.62-7.53 (m, 2H), 6.97 (dd, 1H), 4.94-4.82 (m, 1H), 3.87-3.68 (m, 1H), 3.37-2.08 (m, 10H), 0.90 and 0.70 (each as d, together = 3H) | 498.2 |
| S-2 | 4-(4-(2-(4-(7H-pyrrolo[2,3-d]pyrimidin-4-yl)-1H-pyrazol-1-yl)-3-cyanopropyl)-3-methylpiperazine-l-carbonyl)-3-fluorobenzonitrile | (400 MHz, $d_6$-dmso) (rotamers): δ 12.10 (br s, 1H), 8.82 (d, 1H), 8.68 (d, 1H), 8.37 (d, 1H), 8.00-7.94 (m, 1H), 7.80-7.71 (m, 1H), 7.64-7.54 (m, 2H), 6.98 (t, 1H), 4.95-4.82 (m, 1H), 3.85-3.76 (m, 1H), 3.38-2.25 (m, 10H), 1.05 and 0.87 (each as d, together = 3H) | 498.2 |

The following compounds were prepared by methods analogous to those described above. MS and ¹H NMR data are shown in the following tables.

| Ex No. | R = | Name | Salt Form | MS (M + H) |
|---|---|---|---|---|
| 26 | (2-fluoro-4-chlorobenzoyl) | 3-(4-(7H-pyrrolo[2,3-d]pyrimidin-4-yl)-1H-pyrazol-1-yl)-4-(4-(4-chloro-2-fluorobenzoyl)piperazin-1-yl)butanenitrile | — | 493.0 |
| 27 | (2,6-difluoro-4-chlorobenzoyl) | 3-(4-(7H-pyrrolo[2,3-d]pyrimidin-4-yl)-1H-pyrazol-1-yl)-4-(4-(4-chloro-2,6-difluorobenzoyl)piperazin-1-yl)butanenitrile | — | 511.1 |
| 28 | (2-fluoro-4-methylbenzoyl) | 3-(4-(7H-pyrrolo[2,3-d]pyrimidin-4-yl)-1H-pyrazol-1-yl)-4-(4-(2-fluoro-4-methylbenzoyl)piperazin-1-yl)butanenitrile | — | 473.2 |
| 29 | (2,4,6-trifluorobenzoyl) | 3-(4-(7H-pyrrolo[2,3-d]pyrimidin-4-yl)-1H-pyrazol-1-yl)-4-(4-(2,4,6-trifluorobenzoyl)piperazin-1-yl)butanenitrile | — | 495.1 |
| 30 | (2,4-difluorobenzoyl) | 3-(4-(7H-pyrrolo[2,3-d]pyrimidin-4-yl)-1H-pyrazol-1-yl)-4-(4-(2,4-difluorobenzoyl)piperazin-1-yl)butanenitrile | — | 477.1 |
| 31 | (2-fluoro-4-hydroxybenzoyl) | 3-(4-(7H-pyrrolo[2,3-d]pyrimidin-4-yl)-1H-pyrazol-1-yl)-4-(4-(2-fluoro-4-hydroxybenzoyl)piperazin-1-yl)butanenitrile trifluoroacetate salt | 3TFA | 475.1 |
| 32 | (2-fluoro-5-(trifluoromethyl)benzoyl) | 3-(4-(7H-pyrrolo[2,3-d]pyrimidin-4-yl)-1H-pyrazol-1-yl)-4-(4-(2-fluoro-5-(trifluoromethyl)benzoyl)piperazin-1-yl)butanenitrile | — | 527.2 |

-continued

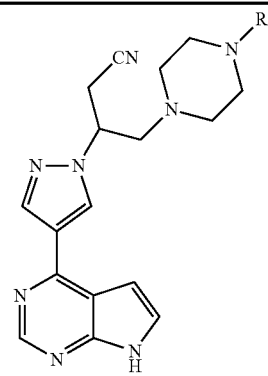

| Ex No. | R = | Name | Salt Form | MS (M + H) |
|---|---|---|---|---|
| 33 | (2,3-difluorobenzoyl) | 3-(4-(7H-pyrrolo[2,3-d]pyrimidin-4-yl)-1H-pyrazol-1-yl)-4-(4-(2,3-difluorobenzoyl)piperazin-1-yl)butanenitrile | — | 477.2 |
| 34 | (2,3-difluoro-4-methoxybenzoyl) | 3-(4-(7H-pyrrolo[2,3-d]pyrimidin-4-yl)-1H-pyrazol-1-yl)-4-(4-(2,3-difluoro-4-methoxybenzoyl)piperazin-1-yl)butanenitrile | — | 507.0 |
| 35 | (2-fluoro-6-hydroxybenzoyl) | 3-(4-(7H-pyrrolo[2,3-d]pyrimidin-4-yl)-1H-pyrazol-1-yl)-4-(4-(2-fluoro-6-hydroxybenzoyl)piperazin-1-yl)butanenitrile | — | 475.2 |
| 36 | (4-fluorobenzoyl) | 3-(4-(7H-pyrrolo[2,3-d]pyrimidin-4-yl)-1H-pyrazol-1-yl)-4-(4-(4-fluorobenzoyl)piperazin-1-yl)butanenitrile | — | 459.2 |
| 37 | (4-fluoro-3-methylbenzoyl) | 3-(4-(7H-pyrrolo[2,3-d]pyrimidin-4-yl)-1H-pyrazol-1-yl)-4-(4-(4-fluoro-3-methylbenzoyl)piperazin-1-yl)butanenitrile | — | 473.2 |
| 38 | (5-chloropicolinoyl) | 3-(4-(7H-pyrrolo[2,3-d]pyrimidin-4-yl)-1H-pyrazol-1-yl)-4-(4-(5-chloropicolinoyl)piperazin-1-yl)butanenitrile | — | 476.2 |
| 39 | (2-chloro-4-fluorobenzoyl) | 3-(4-(7H-pyrrolo[2,3-d]pyrimidin-4-yl)-1H-pyrazol-1-yl)-4-(4-(2-chloro-4-fluorobenzoyl)piperazin-1-yl)butanenitrile | — | 493.1 |
| 40 | (3,5-difluoropicolinoyl) | 3-(4-(7H-pyrrolo[2,3-d]pyrimidin-4-yl)-1H-pyrazol-1-yl)-4-(4-(3,5-difluoropicolinoyl)piperazin-1-yl)butanenitrile | — | 478.3 |

-continued

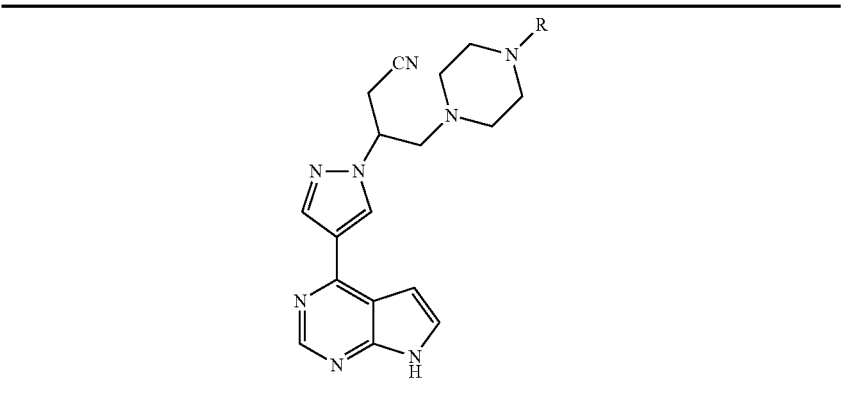

| Ex No. | R = | Name | Salt Form | MS (M + H) |
|---|---|---|---|---|
| 41 | (2-fluoro-5-(trifluoromethoxy)benzoyl) | 3-(4-(7H-pyrrolo[2,3-d]pyrimidin-4-yl)-1H-pyrazol-1-yl)-4-(4-(2-fluoro-5-(trifluoromethoxy)benzoyl)piperazin-1-yl)butanenitrile | — | 543.2 |
| 42 | (thiophene-2-carbonyl) | 3-(4-(7H-pyrrolo[2,3-d]pyrimidin-4-yl)-1H-pyrazol-1-yl)-4-(4-(thiophene-2-carbonyl)piperazin-1-yl)butanenitrile | — | 447.1 |
| 43 | (4-fluoro-3-methoxybenzoyl) | 3-(4-(7H-pyrrolo[2,3-d]pyrimidin-4-yl)-1H-pyrazol-1-yl)-4-(4-(4-fluoro-3-methoxybenzoyl)piperazin-1-yl)butanenitrile | — | 489.2 |
| 44 | (3-chloro-4-methoxybenzoyl) | 3-(4-(7H-pyrrolo[2,3-d]pyrimidin-4-yl)-1H-pyrazol-1-yl)-4-(4-(3-chloro-4-methoxybenzoyl)piperazin-1-yl)butanenitrile trifluoroacetate salt | 3TFA | 505.0 |
| 45 | (2-fluoro-4-(trifluoromethyl)benzoyl) | 3-(4-(7H-pyrrolo[2,3-d]pyrimidin-4-yl)-1H-pyrazol-1-yl)-4-(4-(2-fluoro-4-(trifluoromethyl)benzoyl)piperazin-1-yl)butanenitrile trifluoroacetate salt | 3TFA | 527.2 |
| 46 | (3-chloro-5-fluorobenzoyl) | 3-(4-(7H-pyrrolo[2,3-d]pyrimidin-4-yl)-1H-pyrazol-1-yl)-4-(4-(3-chloro-5-fluorobenzoyl)piperazin-1-yl)butanenitrile trifluoroacetate salt | 3TFA | 493.1 |
| 47 | (4-fluoro-2-methylbenzoyl) | 3-(4-(7H-pyrrolo[2,3-d]pyrimidin-4-yl)-1H-pyrazol-1-yl)-4-(4-(4-fluoro-2-methylbenzoyl)piperazin-1-yl)butanenitrile | — | 473.3 |

-continued

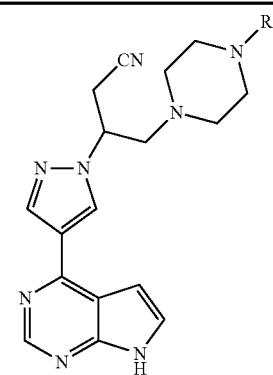

| Ex No. | R = | Name | Salt Form | MS (M + H) |
|---|---|---|---|---|
| 48 | 2,3,4-trifluorobenzoyl | 3-(4-(7H-pyrrolo[2,3-d]pyrimidin-4-yl)-1H-pyrazol-1-yl)-4-(4-(2,3,4-trifluorobenzoyl)piperazin-1-yl)butanenitrile phosphate salt | — | 495.2 |
| 49 | 4-fluoro-3-(trifluoromethoxy)benzoyl | 3-(4-(7H-pyrrolo[2,3-d]pyrimidin-4-yl)-1H-pyrazol-1-yl)-4-(4,-(4-fluoro-3-(trifluoromethoxy)benzoyl)piperazin-1-yl)butanenitrile | — | 543.2 |
| 50 | 3,4-difluorobenzoyl | 3-(4-(7H-pyrrolo[2,3-d]pyrimidin-4-yl)-1H-pyrazol-1-yl)-4-(4-(3,4-difluorobenzoyl)piperazin-1-yl)butanenitrile | — | 477.2 |
| 51 | 2-fluoro-3-(trifluoromethoxy)benzoyl | 3-(4-(7H-pyrrolo[2,3-d]pyrimidin-4-yl)1H-pyrazol-1-yl)-4-(4-(2-fluoro-3-(trifluoromethoxy)benzoyl)piperazin-1-yl)butanenitrile | — | 543.2 |
| 52 | 4-methoxythiophene-3-carbonyl | 3-(4-(7H-pyrrolo[2,3-d]pyrimidin-4-yl)-1H-pyrazol-1-yl)-4-(4-(4-methoxythiophene-3-carbonyl)piperazin-1-yl)butanenitrile | — | 477.1 |
| 53 | 3-chloro-5-(trifluoromethoxy)benzoyl | 3-(4-(7H-pyrrolo[2,3-d]pyrimidin-4-yl)-1H-pyrazol-1-yl)-4-(4-(3-chloro-5-(trifluoromethoxy)benzoyl)piperazin-1-yl)butanenitrile | — | 559.2 |
| 54 | 3-chloro-4-hydroxybenzoyl | 3-(4-(7H-pyrrolo[2,3-d]pyrimidin-4-yl)-1H-pyrazol-1-yl)-4-(4-(3-chloro-4-hydroxybenzoyl)piperazin-1-yl)butanenitrile trifluoroacetate salt | 3TFA | 491.0 |

-continued

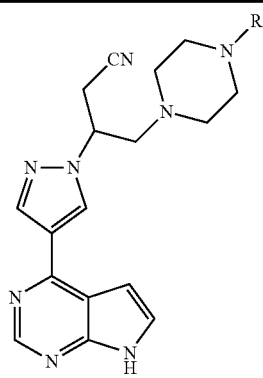

| Ex No. | R = | Name | Salt Form | MS (M + H) |
|---|---|---|---|---|
| 55 | (3,5-difluoro-4-methoxybenzoyl) | 3-(4-(7H-pyrrolo[2,3-d]pyrimidin-4-yl)-1H-pyrazol-1-yl)-4-(4-(3,5-difluoro-4-methoxybenzoyl)piperazin-1-yl)butanenitrile | — | 507.0 |
| 56 | (3-fluoro-4-(trifluoromethyl)benzoyl) | 3-(4-(7H-pyrrolo[2,3-d]pyrimidin-4-yl)-1H-pyrazol-1-yl)-4-(4-(3-fluoro-4-(trifluoromethyl)benzoyl)piperazin-1-yl)butanenitrile | — | 527.2 |
| 57 | (4-fluoro-3-(trifluoromethyl)benzoyl) | 3-(4-(7H-pyrrolo[2,3-d]pyrimidin-4-yl)-1H-pyrazol-1-yl)-4-(4-(4-fluoro-3-(trifluoromethyl)benzoyl)piperazin-1-yl)butanenitrile | — | 527.2 |
| 58 | picolinoyl | 3-(4-(7H-pyrrolo[2,3-d]pyrimidin-4-yl)-1H-pyrazol-1-yl)-4-(4-picolinoylpiperazin-1-yl)butanenitrile | — | 442.2 |
| 59 | (4-fluoro-2-(trifluoromethyl)benzoyl) | 3-(4-(7H-pyrrolo[2,3-d]pyrimidin-4-yl-1H-pyrazol-1-yl)-4-(4-(4-fluoro-2-(trifluoromethyl)benzoyl)piperazin-1-yl)butanenitrile | — | 527.2 |
| 60 | (2-cyanophenyl)sulfonyl | 2-(4-(2-(4-(7H-pyrrolo[2,3-d]pyrimidin-4-yl)-1H-pyrazol-1-yl)-3-cyanopropyl)piperazin-1-ylsulfonyl)benzonitrile | — | 502.1 |
| 61 | (3,5-difluorophenyl)sulfonyl | 3-(4-(7H-pyrrolo[2,3-d]pyrimidin-4-yl)-1H-pyrazol-1-yl)-4-(4-(3,5-difluorophenylsulfonyl)piperazin-1-yl)butanenitrile trifluoroacetate salt | 3TFA | 513.2 |

-continued

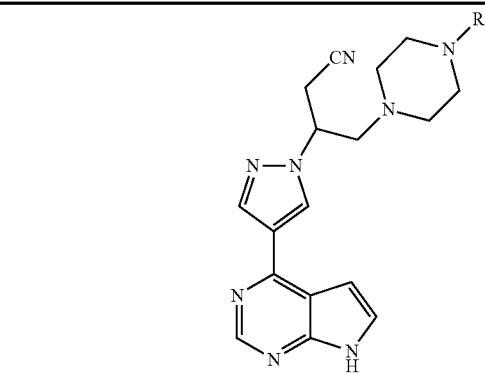

| Ex No. | R = | Name | Salt Form | MS (M + H) |
|---|---|---|---|---|
| 62 | (2,5-difluorophenylsulfonyl) | 3-(4-(7H-pyrrolo[2,3-d]pyrimidin-4-yl)-1H-pyrazol-1-yl)-4-(4-(2,5-difluorophenylsulfonyl)piperazin-1-yl)butanenitrile trifluoroacetate salt | 3TFA | 513.2 |
| 63 | (5-methylpyridin-2-ylsulfonyl) | 3-(4-(7H-pyrrolo[2,3-d]pyrimidin-4-yl)-1H-pyrazol-1-yl)-4-(4-(5-methylpyridin-2-ylsulfonyl)piperazin-1-yl)butanenitrile | — | 492.1 |
| 64 | (6-methylpyridin-2-ylsulfonyl) | 3-(4-(7H-pyrrolo[2,3-d]pyrimidin-4-yl)-1H-pyrazol-1-yl)-4-(4-(6-methylpyridin-2-ylsulfonyl)piperazin-1-yl)butanenitrile | — | 492.1 |
| 65 | (pyridin-3-ylsulfonyl) | 3-(4-(7H-pyrrolo[2,3-d]pyrimidin-4-yl)-1H-pyrazol-1-yl)-4-(4-(pyridin-3-ylsulfonyl)piperazin-1-yl)butanenitrile | — | 478.1 |
| 66 | (2-(trifluoromethyl)phenylsulfonyl) | 3-(4-(7H-pyrrolo[2,3-d]pyrimidin-4-yl)-1H-pyrazol-1-yl)-4-(4-(2-(trifluoromethyl)phenylsulfonyl)piperazin-1-yl)butanenitrile | — | 545.1 |
| 67 | (thiophen-2-ylsulfonyl) | 3-(4-(7H-pyrrolo[2,3-d]pyrimidin-4-yl)-1H-pyrazol-1-yl)-4-(4-(thiophen-2-ylsulfonyl)piperazin-1-yl)butanenitrile | — | 483.1 |
| 68 | (5-chlorothiophen-2-ylsulfonyl) | 3-(4-(7H-pyrrolo[2,3-d]pyrimidin-4-yl)-1H-pyrazol-1-yl)-4-(4-(5-chlorothiophen-2-ylsulfonyl)piperazin-1-yl)butanenitrile | — | 517.0 |
| 69 | (2,6-difluorophenyl)carboxamide | 4-(2-(4-(7H-pyrrolo[2,3-d]pyrimidin-4-yl)-1H-pyrazol-1-yl)-3-cyanopropyl)-N-(2,6-difluorophenyl)piperazine-1-carboxamide | — | 492.3 |

-continued

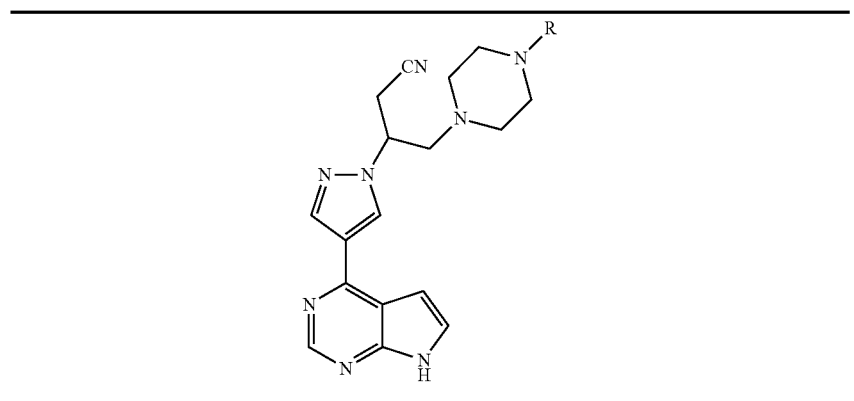

| Ex No. | R = | Name | Salt Form | MS (M + H) |
|---|---|---|---|---|
| 70 | 2,6-dichlorophenyl-NHC(O)- | 4-(2-(4-(7H-pyrrolo[2,3-d]pyrimidin-4-yl)-1H-pyrazol-1-yl)-3-cyanopropyl)-N-(2,6-dichlorophenyl)piperazine-1-carboxamide | — | 524.2 |
| 71 | 2-chloro-6-methylphenyl-NHC(O)- | 4-(2-(4-(7H-pyrrolo[2,3-d]pyrimidin-4-yl)-1H-pyrazol-1-yl)-3-cyanopropyl)-N-(2-chloro-6-methylphenyl)piperazine-1-carboxamide | — | 504.2 |
| 72 | 2,4-difluorophenyl-NHC(O)- | 4-(2-(4-(7H-pyrrolo[2,3-d]pyrimidin-4-yl)-1H-pyrazol-1-yl)-3-cyanopropyl)-N-(2,4-difluorophenyl)piperazine-1-carboxamide | — | 492.3 |
| 73 | 2-fluoro-3-(trifluoromethyl)phenyl-NHC(O)- | 4-(2-(4-(7H-pyrrolo[2,3-d]pyrimidin-4-yl)-1H-pyrazol-1-yl)-3-cyanopropyl)-N-(2-fluoro-3-(trifluoromethyl)phenyl)piperazine-1-carboxamide | — | 542.2 |
| 74 | 2-(difluoromethoxy)phenyl-NHC(O)- | 4-(2-(4-(7H-pyrrolo[2,3-d]pyrimidin-4-yl)-1H-pyrazol-1-yl)-3-cyanopropyl)-N-(2-(difluoromethoxy)phenyl)piperazine-1-carboxamide | — | 522.2 |
| 75 | 2-(trifluoromethoxy)phenyl-NHC(O)- | 4-(2-(4-(7H-pyrrolo[2,3-d]pyrimidin)-4-yl)-1H-pyrazol-1-yl)-3-cyanopropyl)-N-(2-(trifluoromethoxy)phenyl)piperazine-1-carboxamide | — | 540.2 |

-continued

| Ex No. | R = | Name | Salt Form | MS (M + H) |
|---|---|---|---|---|
| 76 | (phenyl with NHC(O)- and CF3 substituent) | 4-(2-(4-(7H-pyrrolo[2,3-d]pyrimidin-4-yl)-1H-pyrazol-1-yl)-3-cyanopropyl)-N-(2-(trifluoromethyl)phenyl)piperazine-1-carboxamide | — | 524.2 |
| 77 | (2-hydroxy-4-cyanobenzoyl) | 4-(4-(2-(4-(7H-pyrrolo[2,3-d]pyrimidin-4-yl)-1H-pyrazol-1-yl)-3-cyanopropyl)piperazine-1-carbonyl)-3-hydroxybenzonitrile | — | 491.0 |

| Ex No. | R = | NMR |
|---|---|---|
| 26 | (2-fluoro-4-chlorobenzoyl) | (400 MHz, d₆-dmso): δ 8.81 (s, 1H), 8.67 (s, 1H), 8.37 (s, 1H), 7.60 (d, 1H), 7.54 (dd, 1H), 7.41 (t, 1H), 7.35 (dd, 1H), 6.97 (d, 1H), 4.98 (tt, 1H), 3.63-3.52 (m, 2H), 3.24-3.18 (m, 2H), 3.17-3.12 (m, 2H), 2.86 (dd, 1H), 2.81 (dd, 1H), 2.94-2.38 (m, 3H), 2.37-2.28 (m, 1H). |
| 27 | (2,6-difluoro-4-chlorobenzoyl) | (400 MHz, d₆-dmso): δ 8.81 (s, 1H), 8.67 (s, 1H), 8.36 (s, 1H), 7.60 (d, 1H), 7.53-7.47 (m, 2H), 6.97 (d, 1H), 5.03-4.92 (m, 1H), 3.63-3.56 (m, 2H), 3.24-3.16 (m, 4H), 2.90-2.78 (m, 2H), 2.62-2.28 (m, 4H). |

-continued

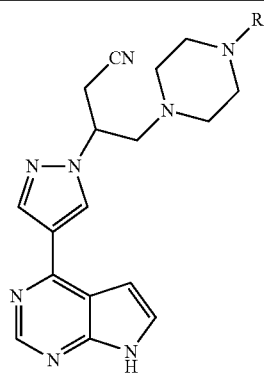

| Ex No. | R = | NMR |
|---|---|---|
| 28 | 2-fluoro-4-methylbenzoyl | (300 MHz, d$_6$-dmso): δ 12.06 (br s, 1H), 8.81 (s, 1H), 8.68 (s, 1H), 8.37 (s, 1H), 7.60 (d, 1H), 7.22 (t, 1H), 7.13-7.03 (m, 2H), 6.97 (d, 1H), 5.04-4.92 (m, 1H), 3.62-3.52 (m, 2H), 3.25-3.08 (m, 4H), 2.89-2.76 (m, 2H), 2.63-2.30 (m, 4H), 2.32 (s, 3H). |
| 29 | 2,4,6-trifluorobenzoyl | (400 MHz, d$_6$-dmso): δ 12.08 (br s, 1H), 8.81 (s, 1H), 8.67 (s, 1H), 8.37 (s, 1H), 7.60 (d, 1H), 7.37-7.28 (m, 2H), 6.97 (d, 1H), 4.98 (tt, 1H), 3.61-3.55 (m, 2H), 3.23-3.14 (m, 4H), 2.85 (dd, 1H), 2.80 (dd, 1H), 2.60-2.51 (m, 1H), 2.47-2.37 (m, 2H), 2.36-2.28 (m, 1H). |
| 30 | 2,4-difluorobenzoyl | (400 MHz, d$_6$-dmso): δ 12.10 (br s, 1H), 8.79 (s, 1H), 8.66 (s, 1H), 8.35 (s, 1H), 7.59 (d, 1H), 7.46-7.38 (m, 1H), 7.33 (dt, 1H), 7.13 (dt, 1h), 6.96 (d, 1H), 4.96 (tt, 1H), 3.60-3.52 (m, 2H), 3.23-3.17 (m, 2H), 3.16-3.09 (m, 2H), 2.88-2.75 (m, 2H), 2.62-2.25 (m, 4H). |
| 31 | 2-fluoro-4-hydroxybenzoyl | (400 MHz, d$_6$-dmso): δ 12.64 (br s, <1H), 10.39 (br s, <1H), 9.00 (s, 1H), 8.83 (s, 1H), 8.53 (s, 1H), 8.02 (br s, <1H), 7.81-7.76 (m, 1H), 7.19 (t, 1H), 7.15-7.11 (m, 1H), 6.65 (dd, 1h), 6.59 (dd, 1H), 5.22 (br s, 1H), 3.85-2.50 (br, 12H). |
| 32 | 2-fluoro-5-(trifluoromethyl)benzoyl | (400 MHz, d$_6$-dmso): δ 12.11 (br s, 1H), 8.81 (s, 1H), 8.68 (s, 1H), 8.37 (s, 1H), 7.92-7.87 (m, 1H), 7.86-7.81 (m, 1H), 7.60 (d, 1H), 7.54 (t, 1H), 6.97 (d, 1H), 4.99 (tt, 1H), 3.60 (br s, 2H), 3.25-3.10 (m, 4H), 2.85 (dd, 1H), 2.80 (dd, 1H), 2.70-2.29 (m, 4H). |
| 33 | 2,3-difluorobenzoyl | (400 MHz, d$_6$-dmso): δ 12.10 (br s, 1H), 8.81 (s, 1H), 8.68 (s, 1H), 8.37 (s, 1H), 7.60 (d, 1H), 7.55-7.46 (m, 1H), 7.31-7.23 (m, 1H), 7.18 (t, 1H), 6.97 (d, 1H), 4.99 (tt, 1H), 3.60 (br s, 2H), 3.25-3.10 (m, 4H), 2.85 (dd, 1H), 2.80 (dd, 1H), 2.70-2.29 (m, 4H). |
| 34 | 2,3-difluoro-4-methoxybenzoyl | (300 MHz, d$_6$-dmso): δ 12.04 (br s, 1H), 8.81 (s, 1H), 8.68 (s, 1H), 8.37 (s, 1H), 7.60 (d, 1H), 7.17-7.09 (m, 1H), 7.09-7.01 (m, 1H), 6.97 (d, 1H), 4.98 (tt, 1H), 3.89 (s, 3H), 3.60-3.52 (m, 2H), 3.37-3.14 (m, 4H), 2.91-2.77 (m, 2H)), 2.64-2.24 (m, 4H). |

-continued

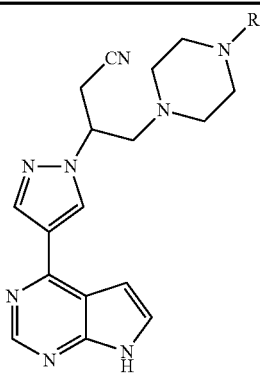

| Ex No. | R = | NMR |
|---|---|---|
| 35 | 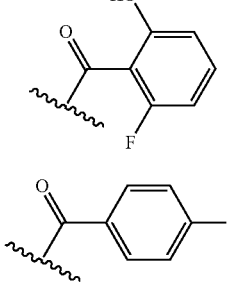 | (400 MHz, d₆-dmso): δ 8.80 (s, 1H), 8.67 (s, 1H), 8.36 (s, 1H), 7.60 (d, 1H), 7.14 (q, 1H), 6.97 (d, 1H), 6.63 (d, 1H), 6.54 (q, 1H), 4.97 (tt, 1H), 3.78-2.14 (m, 12H). |
| 36 | 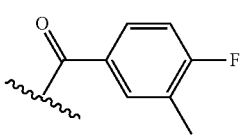 | (400 MHz, d₆-dmso): δ 12.10 (br s, 1H), 8.81 (s, 1H), 8.68 (s, 1H), 8.37 (s, 1H), 7.60 (d, 1H), 7.45-7.39 (m, 2H), 7.27-7.20 (m, 2H), 6.98 (d, 1H), 4.98 (tt, 1H), 3.62-3.15 (m, 6H), 2.86 (dd, 1H), 2.81 (dd, 1 H), 2.68-2.16 (m, 4H). |
| 37 | 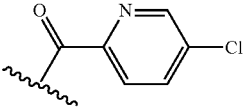 | (400 MHz, d₆-dmso): δ 12.10 (br s, 1H), 8.81 (s, 1H), 8.68 (s, 1H), 8.37 (s, 1H), 7.61 (d, 1H), 7.30 (dd, 1H), 7.22 (ddd, 1H), 7.17 (dd, 1H), 6.98 (d, 1H), 4.99 (tt, 1H), 3.65-3.13 (m, 6H), 2.86 (dd, 1H), 2.81 (dd, 1H), 2.62-2.26 (m, 4H), 2.22 (s, 3H). |
| 38 | 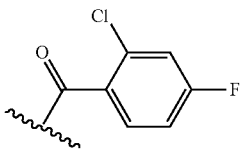 | (400 MHz, d₆-dmso): δ 8.81 (s, 1H), 8.68 (s, 1H), 8.63 (dd, 1H), 8.37 (s, 1H), 8.04 (dd, 1H), 7.61-7.58 (m, 2H), 6.97 (d, 1H), 4.99 (tt, 1H), 3.62-3.55 (m, 2H), 3.40-3.27 (m, 2H), 3.25-3.18 (m, 2H), 2.86 (dd, 1H), 2.81 (dd, 1H), 2.63-2.54 (m, 1H), 2.52-2.41 (m, 2H), 2.40-2.31 (m, 1H). |
| 39 | 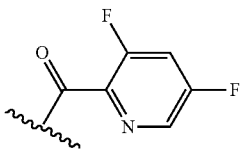 | (300 MHz, d₆-dmso): δ 12.07 (br s, 1H), 8.80 (s, 1H), 8.67 (s, 1H), 8.36 (s, 1H), 7.60 (d, 1H), 7.56-7.49 (m, 1H), 7.40 (dd, 1H), 7.33-7.21 (m, 1H), 6.97 (d, 1H), 4.98 (tt, 1H), 3.66-3.49 (m, 2H), 3.24-3.16 (m, 2H), 3.09-3.00 (m, 2H), 2.92-2.76 (m, 2H), 2.67-2.25 (m, 4H). |
| 40 | 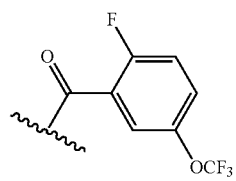 | (300 MHz, d₆-dmso): δ 11.89 (br s, 1H), 8.81 (s, 1H), 8.68 (s, 1H), 8.54 (d, 1H), 8.37 (s, 1H), 8.09 (dt, 1H), 7.60 (d, 1H), 6.97 (d, 1H), 4.98 (tt, 1H), 3.65-3.55 (m, 2H), 3.25-3.18 (m, 2H), 3.18-3.11 (m, 2H), 2.91-2.77 (m, 2H), 2.64-2.54 (m, 1H), 2.52-2.38 (m, 2H), 2.38-2.27 (m, 1H). |
| 41 | 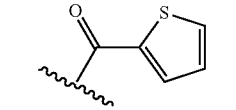 | (400 MHz, d₆-dmso): δ 12.06 (br s, 1H), 8.81 (s, 1H), 8.68 (s, 1H), 8.37 (s, 1H), 7.60 (d, 1H), 7.55-7.41 (m, 3H), 6.97 (d, 1H), 4.98 (tt, 1H), 3.63-3.13 (m, 6H), 2.90-2.78 (m, 2H), 2.65-2.30 (m, 4H). |
| 42 |  | (400 MHz, d₆-dmso): δ 12.06 (br s, 1H), 8.82 (s, 1H), 8.68 (s, 1H), 8.38 (s, 1H), 7.74 (dd, 1H), 7.60 (d, 1H), 7.36 (dd, 1H), 7.10 (dd, 1H), 6.97 (d, 1H), 5.00 (tt, 1H), 3.61-3.53 (m, 4H), 3.26-3.19 (m, 2H), 2.87 (dd, 1H), 2.82 (dd, 1H), 2.58-2.50 (m, 2H), 2.47-2.39 (m, 2H). |

-continued

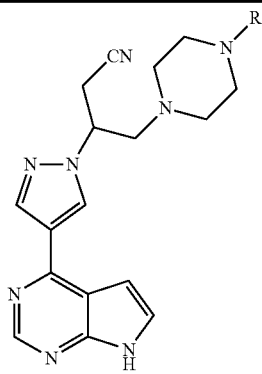

| Ex No. | R = | NMR |
|---|---|---|
| 43 | ![OMe, F benzoyl] | (300 MHz, d₆-dmso): δ 12.01 (br s, 1H), 8.81 (s, 1H), 8.68 (s, 1H), 8.37 (s, 1H), 7.60 (d, 1H), 7.23 (dd, 1H), 7.13 (dd, 1H), 6.97 (d, 1H), 6.92 (ddd, 1H), 4.99 (tt, 1H), 3.82 (s, 3H), 3.60-3.18 (br, 6H), 2.92-2.77 (br, 2H), 2.66-2.26 (br, 4H). |
| 44 | ![Cl, OMe benzoyl] | (400 MHz, d₆-dmso): δ 12.52 (br s, 1H), 8.97 (s, 1H), 8.80 (s, 1H), 8.51 (s, 1H), 7.77-7.73 (m, 1H), 7.46 (d, 1H), 7.36 (dd, 1H), 7.17 (d, 1H), 7.13-7.07 (m, 1H), 5.29-5.13 (m, 1H), 3.88 (s, 3H), 3.74-2.52 (br, 12H). |
| 45 | ![F, CF₃ benzoyl] | (400 MHz, d₆-dmso): δ 12.60 (br s, 1H), 8.97 (s, 1H), 8.82 (s, 1H), 8.51 (s, 1H), 7.86-7.74 (m, 2H), 7.70-7.60 (m, 2H), 7.14-7.11 (m, 1H), 5.22-5.08 (br, 1H), 3.87-2.44 (m, 12H). |
| 46 | ![F, Cl benzoyl] | (400 MHz, d₆-dmso): δ 12.51 (br s, 1H), 8.96 (s, 1H), 8.80 (s, 1H), 8.50 (s, 1H), 7.94 (br s, <1H), 7.76-7.73 (m, 1H), 7.55 (dt, 1H), 7.32 (s, 1H), 7.27 (ddd, 1H), 7.12-7.08 (m, 1H), 5.25-5.10 (br m, 1H), 3.66-2.44 (br m, 12H). |
| 47 | ![Me, F benzoyl] | (400 MHz, d₆-dmso): δ 8.80 (s, 1H), 8.67 (s, 1H), 8.36 (s, 1H), 7.60 (d, 1H), 7.21-6.97 (br m, 3H), 6.96 (d, 1H), 4.98 (tt, 1H), 3.61-3.17 (m, 4H), 3.07-3.02 (m, 2H), 2.86 (dd, 1H), 2.80 (dd, 1H), 2.63-2.22 (m, 4H), 2.17 (s, 3H). |
| 48 | ![F,F,F benzoyl] | (400 MHz, d₆-dmso): δ 12.08 (br s, 1H), 8.81 (s, 1H), 8.68 (s, 1H), 8.37 (s, 1H), 7.60 (d, 1H), 7.43-7.34 (m, 1H), 7.29-7.21 (m, 1H), 6.97 (d, 1H), 4.98 (tt, 1H), 3.62-3.14 (m, 6H), 2.87 (dd, 1H), 2.82 (dd, 1H), 2.63-2.53 (m, 1H), 2.51-2.38 (m, 2H), 2.36-2.28 (m, 1H). |
| 49 | ![OCF₃, F benzoyl] | (300 MHz, d₆-dmso): δ 12.08 (br s, 1H), 8.81 (s, 1H), 8.68 (s, 1H), 8.37 (s, 1H), 7.64-7.53 (m, 3H), 7.48 (ddd, 1H), 6.97 (d, 1H), 4.99 (tt, 1H), 3.60-3.17 (m, 6H), 2.91-2.76 (m, 2H), 2.65-2.29 (m, 4H). |

-continued

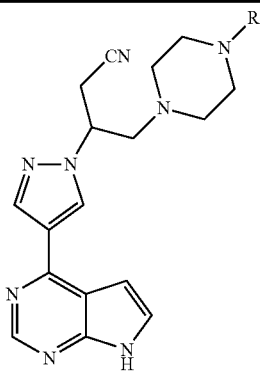

| Ex No. | R = | NMR |
|---|---|---|
| 50 | 3,4-difluorobenzoyl | (400 MHz, d₆-dmso): δ 12.10 (br s, 1H), 8.81 (s, 1H), 8.68 (s, 1H), 8.37 (s, 1H), 7.60 (d, 1H), 7.52-7.44 (m, 2H), 7.25-7.20 (m, 1H), 6.98 (d, 1H), 4.99 (tt, 1H), 3.60-3.14 (m, 6H), 2.86 (dd, 1H), 2.81 (dd, 1H), 2.62-2.29 (m, 4H). |
| 51 | 2-fluoro-3-(trifluoromethoxy)benzoyl | (400 MHz, d₆-dmso): δ 12.10 (br s, 1H), 8.81 (s, 1H), 8.68 (s, 1H), 8.37 (s, 1H), 7.68-7.63 (m, 1H), 7.60 (d, 1H), 7.46-7.41 (m, 1H), 7.37 (t, 1H), 6.97 (d, 1H), 4.98 (tt, 1H), 3.64-3.54 (br s, 2H), 3.25-3.19 (m, 2H), 3.18-3.12 (m, 2H), 2.87 (dd, 1H), 2.82 (dd, 1H), 2.64-2.29 (m, 4H). |
| 52 | 4-methoxythiophene-3-carbonyl | (400 MHz, d₆-dmso): δ 12.12 (br s, 1H), 8.81 (s, 1H), 8.68 (s, 1H), 8.37 (s, 1H), 7.60 (d, 1H), 7.53 (d, 1H), 6.97 (d, 1H), 6.65 (d, 1H), 4.98 (tt, 1H), 3.72 (s, 3H), 3.55-3.46 (br m, 2H), 3.24-3.19 (m, 2H), 3.17-3.12 (br m, 2H), 2.85 (dd, 1H), 2.80 (dd, 1H), 2.58-2.29 (m, 4H). |
| 53 | 3-chloro-5-(trifluoromethoxy)benzoyl | (400 MHz, d₆-dmso): δ 12.08 (br s, 1H), 8.81 (s, 1H), 8.68 (s, 1H), 8.37 (s, 1H), 7.67-7.65 (m, 1H), 7.60 (d, 1H), 7.52 (dd, 1H), 7.40-7.38 (m, 1H), 6.97 (d, 1H), 4.98 (tt, 1H), 3.60-3.14 (m, 6H), 2.87 (dd, 1H), 2.81 (dd, 1H), 2.64-2.30 (m, 4H). |
| 54 | 3-chloro-4-hydroxybenzoyl | (400 MHz, d₆-dmso): δ 12.56 (br s, 1H), 10.76 (br s, 1H), 8.99 (s, 1H), 8.82 (s, 1H), 8.53 (s, 1H), 7.79-7.74 (m, 1H), 7.38 (d, 1H), 7.21 (dd, 1H), 7.14-7.09 (br m, 1H), 6.98 (d, 1H), 5.32-5.17 (br m, 1H), 3.73-2.59 (br m, 12H). |
| 55 | 3,5-difluoro-4-methoxybenzoyl | (300 MHz, d₆-dmso): δ 12.10 (br s, 1H), 8.81 (s, 1H), 8.68 (s, 1H), 8.37 (s, 1H), 7.60 (d, 1H), 7.24-7.13 (m, 2H), 6.98 (d, 1H), 4.99 (tt, 1H), 3.95 (s, 3H), 3.59-3.17 (m, 6H), 2.87 (dd, 1H), 2.80 (dd, 1H), 2.63-2.25 (m, 4H). |
| 56 | 3-fluoro-4-(trifluoromethyl)benzoyl | (400 MHz, d₆-dmso): δ 12.12 (br s, 1H), 8.81 (s, 1H), 8.68 (s, 1H), 8.37 (s, 1H), 7.83 (t, 1H), 7.60 (d, 1H), 7.56 (d, 1H), 7.38 (d, 1H), 6.98 (d, 1H), 4.99 (tt, 1H), 3.60-3.51 (m, 2H), 3.25-3.13 (m, 4H), 2.87 (dd, 1H), 2.81 (dd, 1H), 2.64-2.27 (m, 4H). |

-continued

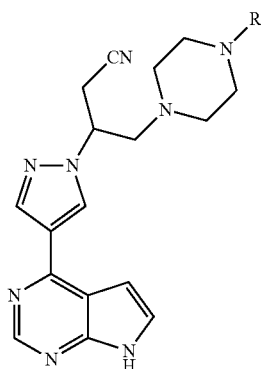

| Ex No. | R = | NMR |
|---|---|---|
| 57 | 3-CF₃, 4-F benzoyl | (300 MHz, d₆-dmso): δ 12.08 (br s, 1H), 8.81 (s, 1H), 8.68 (s, 1H), 8.37 (s, 1H), 7.80-7.73 (m, 2H), 7.63-7.52 (m, 2H), 6.97 (d, 1H), 4.99 (tt, 1H), 3.66-3.46 (m, 2H), 3.30-3.13 (m, 4H), 2.92-2.76 (m, 2H), 2.65-2.27 (m, 4H). |
| 58 | pyridine-2-carbonyl | (400 MHz, d₆-dmso): δ 12.08 (br s, 1H), 8.81 (s, 1H), 8.68 (s, 1H), 8.56 (ddd, 1H), 8.37 (s, 1H), 7.90 (dt, 1H), 7.60 (d, 1H), 7.53 (dt, 1H), 7.46 (ddd, 1H), 6.97 (d, 1H), 4.99 (tt, 1H), 3.63-3.54 (m, 2H), 3.37-3.28 (m, 2H), 3.24-3.19 (m, 2H), 2.86 (dd, 1H), 2.81 (dd, 1H), 2.63-2.54 (m, 1H), 2.51-2.42 (m, 2H), 2.40-2.32 (m, 1H). |
| 59 | 2-CF₃, 4-F benzoyl | (300 MHz, d₆-dmso): δ 12.08 (br s, 1H), 8.80 (s, 1H), 8.68 (s, 1H), 8.36 (s, 1H), 7.74 (dt, 1H), 7.66-7.47 (m, 3H), 6.97 (d, 1H), 4.97 (tt, 1H), 3.67-3.45 (m, 2H), 3.25-3.17 (m, 2H), 3.13-2.11 (m, 8H). |
| 60 | 2-CN phenylsulfonyl | (300 MHz, d₆-dmso): δ 12.06 (br s, 1H), 8.74 (s, 1H), 8.66 (s, 1H), 8.33 (s, 1H), 8.11 (dd, 1H), 7.96 (dt, 1H), 7.90 (dd, 1H), 7.85 (dt, 1H), 7.58 (d, 1H), 6.92 (d, 1H), 4.97-4.85 (m, 1H), 3.19-3.13 (m, 2H), 3.06-2.99 (m, 4H), 2.82-2.76 (m, 2H), 2.64-2.41 (m, 4H). |
| 61 | 3,5-diF phenylsulfonyl | (400 MHz, d₆-dmso): δ 12.72 (br s, 1H), 8.92 (s, 1H), 8.84 (s, 1H), 8.49 (s, 1H), 7.81-7.77 (m, 1H), 7.68 (tt, 1H), 7.52-7.44 (m, 2H), 7.11 (s, 1H), 5.09-4.99 (br m, 1H), 3.23-2.50 (br, 12H). |
| 62 | 2,5-diF phenylsulfonyl | (400 MHz, d₆-dmso): δ 12.73 (br s, 1H), 8.94 (s, 1H), 8.84 (s, 1H), 8.50 (s, 1H), 7.80 (br s, 1H), 7.69-7.51 (m, 3H), 7.27-6.94 (m, 1H), 5.04 (br m, 1H), 3.24-2.47 (br, 12H). |
| 63 | 5-methylpyridine-2-sulfonyl | (400 MHz, d₆-dmso): δ 12.12 (br s, 1H), 8.75 (s, 1H), 8.66 (s, 1H), 8.49-8.47 (m, 1H), 8.33 (s, 1H), 7.87 (ddd, 1H), 7.77 (d, 1H), 7.59 (d, 1H), 6.92 (d, 1H), 4.91 (tt, 1H), 3.19-3.12 (m, 2H), 3.08-2.99 (m, 2H), 2.85-2.73 (m, 2H), 2.60-2.50 (m, 2H), 2.47-2.37 (m, 2H), 2.35 (s, 3H). |

-continued

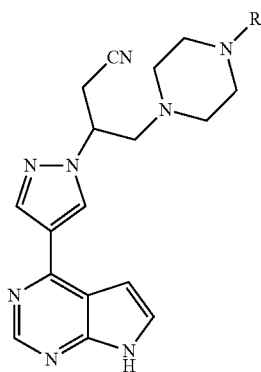

| Ex No. | R = | NMR |
|---|---|---|
| 64 | [2-methylpyridin-6-yl sulfonyl] | (400 MHz, d₆-dmso): δ 8.75 (s, 1H), 8.66 (s, 1H), 8.34 (s, 1H), 7.94 (t, 1H), 7.67 (d, 1H), 7.58 (d, 1H), 7.49 (d, 1H), 6.92 (d, 1H), 4.91 (tt, 1H), 3.19-3.13 (m, 2H), 3.10-3.04 (m, 4H), 2.84-2.74 (m, 2H), 2.60-2.36 (m, 4H), 2.41 (s, 3H). |
| 65 | [pyridin-3-yl sulfonyl] | (400 MHz, d₆-dmso): δ 12.09 (br s, 1H), 8.87 (dd, 1H), 8.85 (dd, 1H), 8.73 (s, 1H), 8.65 (s, 1H), 8.32 (s, 1H), 8.12 (ddd, 1H), 7.64 (ddd, 1H), 7.58 (d, 1H), 6.90 (d, 1H), 4.90 (tt, 1H), 3.16-3.12 (m, 2H), 2.92-2.85 (m, 4H), 2.81-2.76 (m, 2H), 2.61-2.53 (m, 2H), 2.49-2.42 (m, 2H). |
| 66 | [2-(trifluoromethyl)phenyl sulfonyl] | (400 MHz, d₆-dmso): δ 12.11 (br s, 1H), 8.76 (s, 1H), 8.66 (s,1H), 8.34 (s, 1H), 8.03-7.98 (m, 2H), 7.89-7.82 (m, 2H), 7.58 (d, 1H), 6.93 (d, 1H), 4.93 (tt, 1H), 3.20-3.15 (m, 2H), 3.11-3.05 (m, 4H), 2.84 (dd, 1H), 2.79 (dd, 1H), 2.61-2.52 (m, 2H), 2.50-2.42 (m, 2H). |
| 67 | [thiophen-2-yl sulfonyl] | (400 MHz, d₆-dmso): δ 12.11 (br s, 1H), 8.74 (s, 1H), 8.66 (s, 1H), 8.33 (s, 1H), 8.01-7.98 (m, 1H), 7.62-7.57 (m, 2H), 7.26-7.20 (m, 1H), 6.94-6.89 (m, 1H), 4.95-4.86 (m, 1H), 3.37-2.44 (br m, 12H). |
| 68 | [5-chlorothiophen-2-yl sulfonyl] | (400 MHz, d₆-dmso): δ 12.11 (br s, 1H), 8.76 (s, 1H), 8.67 (s, 1H), 8.34 (s, 1H), 7.59 (d, 1H), 7.52 (d, 1H), 7.32 (d, 1H), 6.93 (d, 1H), 4.92 (tt, 1H), 3.20-3.14 (m, 2H), 2.95-2.86 (m, 4H), 2.81 (app d, 2H), 2.65-2.55 (m, 2H), 2.54-2.46 (m, 2H). |
| 69 | [2,6-difluorophenyl carboxamide] | (400 MHz, d₆-dmso): δ 12.10 (br s, 1H), 8.83 (s, 1H), 8.68 (s, 1H), 8.38 (s, 1H), 8.22 (br s, 1H), 7.61 (d, 1H), 7.30-7.21 (m, 1H), 7.13-7.04 (m, 2H), 6.98 (d, 1H), 5.01 (tt, 1H), 3.42-3.30 (m, 4H), 3.25-3.20 (m, 2H), 2.89-2.78 (m, 2H), 2.54-2.46 (m, 2H), 2.44-2.34 (m, 2H). |
| 70 | [2,6-dichlorophenyl carboxamide] | (400 MHz, d₆-dmso): δ 8.83 (s, 1H), 8.69 (s, 1H), 8.38 (s, 1H), 7.61 (d, 1H), 7.49 (s, 1H), 7.26 (dd, 1H), 6.99 (d, 1H), 5.01 (tt, 1H), 3.43-3.35 (m, 4H), 3.25-3.20 (m, 2H), 2.86 (dd, 1H), 2.81 (dd, 1H), 2.55-2.47 (m, 2H), 2.44-2.36 (m, 2H). |

-continued

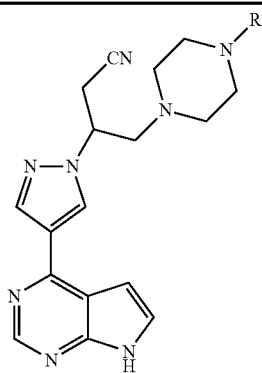

| Ex No. | R = | NMR |
|---|---|---|
| 71 | 2-methyl-6-chloro-phenyl carboxamide | (400 MHz, d₆-dmso): δ 12.08 (br s, 1H), 8.83 (s, 1H), 8.69 (s, 1H), 8.38 (s, 1H), 8.08 (s, 1H), 7.61 (d, 1H), 7.29 (ddd, 1H), 7.18 (ddd, 1H), 7.14 (dd, 1H), 6.99 (d, 1H), 5.02 (tt, 1H), 3.41-3.30 (m, 4H), 3.25-3.20 (m, 2H), 2.89-2.78 (m, 2H), 2.55-2.46 (m, 2H), 2.43-2.35 (m, 2H), 2.14 (s, 3H). |
| 72 | 2,4-difluoro-phenyl carboxamide | (400 MHz, d₆-dmso): δ 12.10 (br s, 1H), 8.82 (s, 1H), 8.68 (s, 1H), 8.38 (s, 1H), 8.28 (br s, 1H), 7.61 (d, 1H), 7.35 (dt, 1H), 7.22 (ddd, 1H), 7.02-6.95 (m, 2H), 5.01 (tt, 1H), 3.40-3.30 (m, 4H), 3.25-3.20 (m, 2H), 2.85 (dd, 1H), 2.81 (dd, 1H), 2.54-2.35 (m, 4H). |
| 73 | 2-fluoro-3-CF₃-phenyl carboxamide | (400 MHz, d₆-dmso): δ 8.83 (s, 1H), 8.68 (s, 1H), 8.39 (s, 1H), 7.71 (t, 1H), 7.61 (d, 1H), 7.45 (t, 1H), 7.30 (t, 1H), 6.99 (d, 1H), 5.01 (tt, 1H), 3.43-3.37 (m, 4H), 3.25-3.20 (m, 2H), 2.86 (dd, 1H), 2.82 (dd, 1H), 2.57-2.46 (m, 2H), 2.44-2.37 (m, 2H). |
| 74 | 2-OCHF₂-phenyl carboxamide | (400 MHz, d₆-dmso): δ 12.06 (br s, 1H), 8.82 (s, 1H), 8.68 (s, 1H), 8.38 (s, 1H), 8.09 (br s, 1H), 7.60 (d, 1H), 7.46 (dd, 1H), 7.20-7.11 (m, 3H), 7.00-6.97 (m, 1H), 6.97 (t, 1H), 5.01 (tt, 1H), 3.40-3.34 (m, 4H), 3.25-3.20 (m, 2H), 2.88-2.77 (m, 2H), 2.54-2.46 (m, 2H), 2.44-2.36 (m, 2H). |
| 75 | 2-OCF₃-phenyl carboxamide | (400 MHz, d₆-dmso): δ 12.12 (br s, 1H), 8.82 (s, 1H), 8.68 (s, 1H), 8.38 (s, 1H), 8.33 (s, 1H), 7.60 (d, 1H), 7.47 (dd, 1H), 7.34-7.26 (m, 2H), 7.18 (dt, 1H), 6.98 (d, 1H), 5.01 (tt, 1H), 3.40-3.35 (m, 4H), 3.25-3.20 (m, 2H), 2.84 (dd, 1H), 2.80 (dd, 1H), 2.54-2.33 (m, 4H). |
| 76 | 2-CF₃-phenyl carboxamide | (400 MHz, d₆-dmso): δ 12.04 (br s, 1H), 8.83 (s, 1H), 8.69 (s, 1H), 8.39 (s, 1H), 8.20 (br s, 1H), 7.66 (dd, 1H), 7.64-7.58 (m, 2H), 7.42-7.35 (m, 2H), 6.99 (d, 1H), 5.01 (tt, 1H), 3 41-3 28 (m, 4H), 3.26-3.19 (m, 2H), 2.85 (dd, 1H), 2.80 (dd, 1H), 2.53-2.46 (m, 2H), 2.43-2.35 (m, 2H). |

-continued
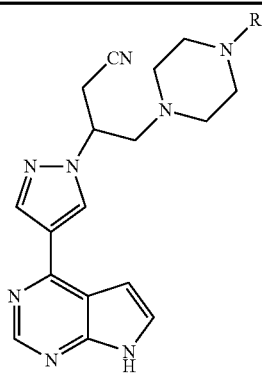
| Ex No. | R = | NMR |
|---|---|---|
| 77 | 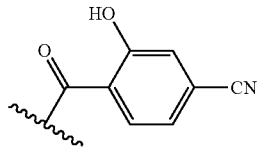 [SMILES: *C(=O)c1ccc(C#N)cc1O] | (400 MHz, d$_6$-dmso): δ 8.80 (s, 1H), 8.68 (s, 1H), 8.36 (s, 1H), 7.60 (d, 1H), 7.04 (d, 1H), 6.97 (d, 1H), 6.80 (d, 1H), 6.72 (dd, 1H), 4.97 (tt, 1H), 3.73-2.27 (br, 12H). |
| Ex No. | R = | Name | Salt Form | MS (M + H) |
|---|---|---|---|---|
| 78 | 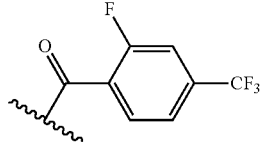 [SMILES: *C(=O)c1ccc(C(F)(F)F)cc1F] | 3-(3-(7H-pyrrolo[2,3-d]pyrimidin-4-yl)-1H-pyrrol-1-yl)-4-(4-(2-fluoro-4-(trifluoromethyl)benzoyl)piperazin-1-yl)butanenitrile | — | 526.2 |
| 79 | 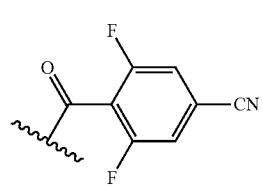 [SMILES: *C(=O)c1c(F)cc(C#N)cc1F] | 4-(4-(2-(3-(7H-pyrrolo[2,3-d]pyrimidin-4-yl)-1H-pyrrol-1-yl)-3-cyanopropyl)piperazine-1-carbonyl)-3,5-difluorobenzonitrile trifluoroacetate salt | 2TFA | 501.2 |

-continued

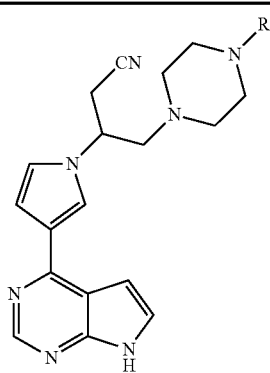

| Ex No. | R = | Name | Salt Form | MS (M + H) |
|---|---|---|---|---|
| 80 | (3,5-difluoropicolinoyl, C=O attached to pyridine with 3,5-F) | 3-(3-(7H-pyrrolo[2,3-d]pyrimidin-4-yl)-1H-pyrrol-1-yl)-4-(4-(3,5-difluoropicolinoyl)piperazin-1-yl)butanenitrile | — | 477.2 |
| 81 | (3,5-difluorobenzoyl) | 3-(3-(7H-pyrrolo[2,3-d]pyrimidin-4-yl)-1H-pyrrol-1-yl)-4-(4-(3,5-difluorobenzoyl)piperazin-1-yl)butanenitrile | — | 476.2 |
| 82 | (3-fluoro-4-methoxybenzoyl) | 3-(3-(7H-pyrrolo[2,3-d]pyrimidin-4-yl)-1H-pyrrol-1-yl)-4-(4-(3-fluoro-4-methoxybenzoyl)piperazin-1-yl)butanenitrile | — | 488.3 |
| 83 | (5-fluoropicolinoyl) | 3-(3-(7H-pyrrolo[2,3-d]pyrimidin-4-yl)-1H-pyrrol-1-yl)-4-(4-(5-fluoropicolinoyl)piperazin-1-yl)butanenitrile | — | 459.2 |
| 84 | (5-chloro-3-fluoropicolinoyl) | 3-(3-(7H-pyrrolo[2,3-d]pyrimidin-4-yl)-1H-pyrrol-1-yl)-4-(4-(5-chloro-3-fluoropicolinoyl)piperazin-1-yl)butanenitrile | — | 493.2 |
| 85 | (4-fluoro-3-(trifluoromethoxy)benzoyl) | 3-(3-(7H-pyrrolo[2,3-d]pyrimidin-4-yl)-1H-pyrrol-1-yl)-4-(4-(4-fluoro-3-(trifluoromethoxy)benzoyl)piperazin-1-yl)butanenitrile | — | 542.0 |

-continued

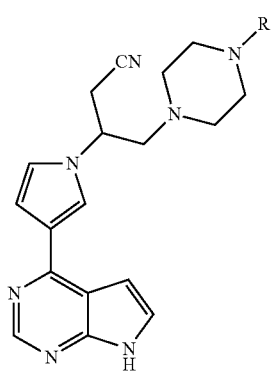

| Ex No. | R = | Name | Salt Form | MS (M + H) |
|---|---|---|---|---|
| 86 | 3-fluoro-5-cyanobenzoyl | 3-(4-(2-(3-(7H-pyrrolo[2,3-d]pyrimidin-4-yl)-1H-pyrrol-1-yl)-3-cyanopropyl)piperazine-1-carbonyl)-5-fluorobenzonitrile trifluoroacetate salt | 2TFA | 483.2 |
| 87 | 3-fluoro-5-cyanopicolinoyl | 6-(4-(2-(3-(7H-pyrrolo[2,3-d]pyrimidin-4-yl)-1H-pyrrol-1-yl)-3-cyanopropyl)piperazine-1-carbonyl)-5-fluoronicotinonitrile | — | 484.2 |
| 88 | 4-cyanobenzoyl | 4-(4-(2-(3-(7H-pyrrolo[2,3-d]pyrimidin-4-yl)-1H-pyrrol-1-yl)-3-cyanopropyl)piperazine-1-carbonyl)benzonitrile | — | 465.2 |
| 89 | 3-fluoro-5-(trifluoromethyl)picolinoyl | 3-(3-(7H-pyrrolo[2,3-d]pyrimidin-4-yl)-1H-pyrrol-1-yl)-4-(4-(3-fluoro-5-(trifluoromethyl)picolinoyl)piperazin-1-yl)butanenitrile | — | 527.2 |
| 90 | 2,4-difluorobenzoyl | 3-(3-(7H-pyrrolo[2,3-d]pyrimidin-4-yl)-1H-pyrrol-1-yl)-4-(4-(2,4-difluorobenzoyl)piperazin-1-yl)butanenitrile | — | 476.2 |
| 91 | 4-(difluoromethyl)-2-fluorobenzoyl | 3-(3-(7H-pyrrolo[2,3-d]pyrimidin-4-yl)-1H-pyrrol-1-yl)-4-(4-(4-(difluoromethyl)-2-fluorobenzoyl)piperazin-1-yl)butanenitrile | — | 508.2 |

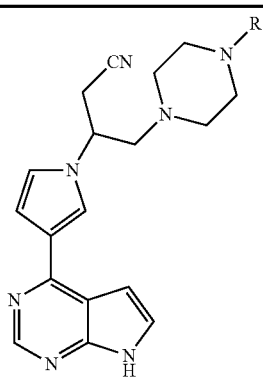

| Ex No. | R = | NMR |
|---|---|---|
| 78 | 2-F, 4-CF₃ benzoyl | (400 MHz, d₆-dmso): δ 11.95 (br s, 1H), 8.60 (s, 1H), 7.95 (t, 1H), 7.81 (d, 1H), 7.69-7.59 (m, 2H), 7.51 (d, 1H), 7.09 (t, 1H), 6.92 (d, 1H), 6.90 (dd, 1H), 4.75 (tt, 1H), 3.69-3.56 (m, 2H), 3.25-3.13 (m, 4H), 2.84 (dd, 1H), 2.75 (dd, 1H), 2.59-2.30 (m, 4H). |
| 79 | 2-F, 4-CN benzoyl | (300 MHz, d₆-dmso): δ 13.18 (br s, 1H), 8.89 (s, 1H), 8.36 (s, 1H), 8.00-7.91 (m, 3H), 7.34 (s, 2H), 7.14 (s, 1H), 4.94-4.80 (m, 1H), 3.70-3.57 (m, 2H), 3.33-3.17 (m, 4H), 3.05-2.27 (m, 6H). |
| 80 | 3,5-difluoropyridine-2-carbonyl | (300 MHz, d₆-dmso): δ 11.96 (br s, 1H), 8.60 (s, 1H), 8.55 (d, 1H), 8.09 (dt, 1H), 7.97-7.93 (m, 1H), 7.50 (d, 1H), 7.11-7.07 m, 1H), 6.92 (d, 1H), 6.89 (dd, 1H), 4.75 (tt, 1H), 3.67-3.58 (m, 2H), 3.27-3.13 (m, 4H), 2.84 (dd, 1H), 2.74 (dd, 1H), 2.58-2.51 (m, 2H), 2.41-2.34 (m, 2H). |
| 81 | 3,5-difluorobenzoyl | (300 MHz, d₆-dmso): δ 11.94 (br s, 1H), 8.60 (s, 1H), 7.95 (t, 1H), 7.50 (d, 1H), 7.34 (tt, 1H), 7.17-7.07 (m, 3H), 6.92 (d, 1H), 6.90 (dd, 1H), 4.75 (tt, 1H), 3.66-3.14 (m, 6H), 2.83 (dd, 1H), 2.74 (dd, 1H), 2.58-2.30 (m, 4H). |
| 82 | 3-F, 4-OMe benzoyl | (300 MHz, d₆-dmso): δ 11.91 (br s, 1H), 8.60 (s, 1H), 7.95 (t, 1H), 7.50 (d, 1H), 7.29-7.13 (m, 3H), 7.09 (t, 1H), 6.92 (d, 1H), 6.90 (dd, 1H), 4.75 (tt, 1H), 3.86 (s, 3H), 3.64-3.15 (m, 6H), 2.83 (dd, 1H), 2.73 (dd, 1H), 2.68-2.31 (m, 4H). |
| 83 | 5-fluoropyridine-2-carbonyl | (400 MHz, d₆-dmso): δ 11.91 (br s, 1H), 8.60 (s, 1H), 8.58 (d, 1H), 7.95 (t, 1H), 7.84 (dt, 1H), 7.67 (dd, 1H), 7.51 (d, 1H), 7.10 (dd, 1H), 6.92 (d, 1H), 6.90 (dd, 1H), 4.76 (tt, 1H), 3.64-3.57 (m, 2H), 3.40-3.18 (m, 4H), 2.83 (dd, 1H), 2.74 (dd, 1H), 2.56-2.51 (m, 2H), 2.43-2.38 (m, 2H). |
| 84 | 5-Cl, 3-F pyridine-2-carbonyl | (400 MHz, d₆-dmso): δ 11.95 (br s, 1H), 8.95 (s, 1H), 8.56 (dd, 1H), 8.25 (dd, 1H), 7.95 (t, 1H), 7.50 (d, 1H), 7.09 (t, 1H), 6.92 (d, 1H), 6.89 (dd, 1H), 4.75 (tt, 1H), 3.67-3.58 (m, 2H), 3.25-3.16 (m, 4H), 2.84 (dd, 1H), 2.74 (dd, 1H), 2.57-2.51 (m, 2H), 2.40-2.35 (m, 2H). |

-continued

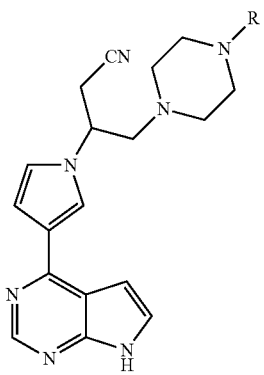

| Ex No. | R = | NMR |
|---|---|---|
| 85 | 3-OCF₃, 4-F benzoyl | (400 MHz, d₆-dmso): δ 11.96 (br s, 1H), 8.60 (s, 1H), 7.95 (t, 1H), 7.64-7.60 (m, 1H), 7.57 (dd, 1H), 7.52-7.46 (m, 2H), 7.09 (dd, 1H), 6.92 (d, 1H), 6.90 (dd, 1H), 4.75 (tt, 1H), 3.67-3.17 (m, 6H), 2.83 (dd, 1H), 2.74 (dd, 1H), 2.59-2.34 (m, 4H). |
| 86 | 3-F, 5-CN benzoyl | (300 MHz, d₆-dmso): δ 13.14 (br s, 1H), 8.88 (s, 1H), 8.36 (br s, 1H), 7.97 (ddd, 1H), 7.95-7.90 (m, 1H), 7.75 (t, 1H), 7.66 (ddd, 1H), 7.37-7.30 (m, 2H), 7.16-7.12 (m, 1H), 4.98-4.83 (m, 1H), 3.69-2.39 (m, 12H). |
| 87 | 5-CN-pyridin-2-yl carbonyl | (400 MHz, d₆-dmso): δ 11.95 (br s, 1H), 8.94 (t, 1H), 8.59 (s, 1H), 8.59 (dd, 1H), 7.95 (t, 1H), 7.50 (d, 1H), 7.09 (dd, 1H), 6.92 (d, 1H), 6.89 (dd, 1H), 4.75 (tt, 1H), 3.67-3.61 (m, 2H), 3.26-3.15 (m, 4H), 2.84 (dd, 1H), 2.75 (dd, 1H), 2.58-2.52 (m, 2H), 2.39-2.34 (m, 2H). |
| 88 | 4-CN benzoyl | (300 MHz, d₆-dmso): δ 11.94 (br s, 1H), 8.60 (s, 1H), 7.95 (t, 1H), 7.93-7.88 (m, 2H), 7.57-7.52 (m, 2H), 7.51 (d, 1H), 7.09 (dd, 1H), 6.92 (d, 1H), 6.90 (dd, 1H), 4.75 (tt, 1H), 3.66-3.11 (m, 6H), 2.83 (dd, 1H), 2.74 (dd, 1H), 2.59-2.31 (m, 4H). |
| 89 | 3-F, 5-CF₃-pyridin-2-yl carbonyl | (300 MHz, d₆-dmso): δ 11.92 (br s, 1H), 8.89 (s, 1H), 8.60 (s, 1H), 8.49 (dd, 1H), 7.97-7.95 (m, 1H), 7.50 (d, 1H), 7.10 (t, 1H), 6.92 (d, 1H), 6.90 (dd, 1H), 4.75 (tt, 1H), 3.70-3.60 (m, 2H), 3.37-3.15 (m 4H), 2.85 (dd, 1H), 2.75 (dd, 1H), 2.59-2.52 (m, 2H), 2.41-2.33 (m, 2H). |
| 90 | 2,4-diF benzoyl | (300 MHz, d₆-dmso): δ 11.94 (br s, 1H), 8.60 (s, 1H), 7.95 (t, 1H), 7.50 (d, 1H), 7.45 (ddd, 1H), 7.35 (dt, 1H), 7.16 (t, 1H), 7.09 (d, 1H), 6.92 (d, 1H), 6.90 (dd, 1H), 4.75 (tt, 1H), 3.65-3.54 (m, 2H), 3.26-3.13 (m, 4H), 2.84 (dd, 1H), 2.73 (dd, 1H), 2.56-2.31 (m, 4H). |
| 91 | 2-F, 4-CHF₂ benzoyl | (300 MHz, d₆-dmso): δ 11.95 (br s, 1H), 8.60 (s, 1H), 7.95 (br t, 1H), 7.57-7.44 (m, 4H), 7.09 (t, 1H), 7.08 (t, 1H), 6.92 (d, 1H), 6.91-6.87 (m, 1H), 4.75 (tt, 1H), 3.67-3.56 (m, 2H), 3.26-3.12 (m, 4H), 2.84 (dd, 1H), 2.74 (dd, 1H), 2.59-2.34 (m, 4H). |

Example 92

4-{1-[1-methyl-2-(4-{[5-methyl-2-(trifluoromethyl)-3-furyl]sulfonyl}piperazin-1-yl)ethyl]-1H-pyrazol-4-yl}-7H-pyrrolo[2,3-d]pyrimidine

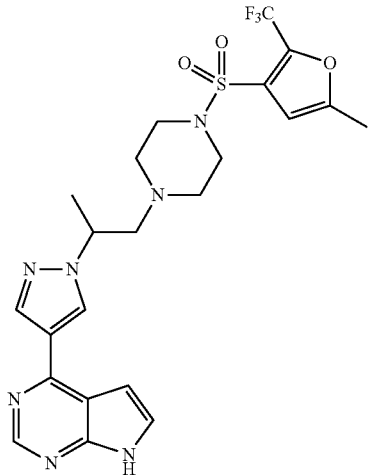 [SMILES: Cc1cc(S(=O)(=O)N2CCN(CC(C)n3cc(-c4ncnc5[nH]ccc45)cn3)CC2)c(C(F)(F)F)o1]

To a solution of 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine (16.0 mg, 0.036 mmol) in DCM (0.3 mL) was added triethylamine (7.6 µL, 0.054 mmol) followed by 5-methyl-2-(trifluoromethyl)furan-3-sulfonyl chloride (11 mg, 0.043 mmol). The reaction was stirred at room temperature for 1 h and trifluoroacetic acid (0.5 mL) was added to reaction vial. After stirring for 1 hour, the solvent was removed in vacuo. The residue was dissolved in methanol (1 mL) and treated with ethylenediamine (0.1 mL). The reaction solution was stirred for 1 hour and diluted with methanol and purified with preparative LCMS (C18 column eluting with a gradient of MeCN/H$_2$O containing 0.15% NH$_4$OH) to give the desired product as white solid (7.8 mg, 41%). $^1$H NMR (300 MHz, DMSO-D6): δ 12.17 (s, 1H); 8.73 (s, 2H); 8.34 (s, 1H); 7.64 (d, 1H); 7.59 (d, 1H); 7.03 (d, 1H); 4.76 (m, 1H); 3.02 (m, 5H); 2.78-2.50 (m, 5H); 1.53 (d, 3H); LCMS calculated for C$_{22}$H$_{25}$F$_3$N$_7$O$_3$S(M+H)$^+$: m/z=524.1.

Example 93

4-[1-(2-{4-[(5-chloro-2-thienyl)sulfonyl]piperazin-1-yl}-1-methylethyl)-1H-pyrazol-4-yl]-7H-pyrrolo[2,3-d]pyrimidine

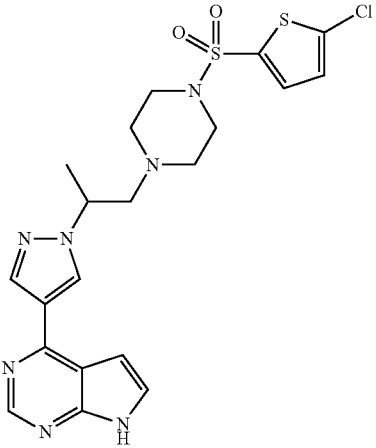 [SMILES: CC(CN1CCN(S(=O)(=O)c2ccc(Cl)s2)CC1)n1cc(-c2ncnc3[nH]ccc23)cn1]

This compound was prepared according to the procedure of Example 92, using 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine and 5-chlorothiophene-2-sulfonyl chloride as the starting materials. $^1$H NMR (300 MHz, DMSO-D6): δ 12.05 (s, 1H); 8.62 (s, 1H); 8.60 (s, 1H); 8.22 (s, 1H); 7.54 (d, 1H); 7.48 (d, 1H); 7.28 (d, 1H); 6.90 (d, 1H); 4.63 (m, 1H); 2.85 (m, 5H); 2.61 (m, 3H); 2.41 (m, 2H); 1.41 (d, 3H); LCMS calculated for C$_{20}$H$_{23}$ClN$_7$O$_2$S$_2$(M+H)+: m/z=492.0.

Example 94

2-[(4-{2-[4-(7H-pyrrolo[2,3-d]pyrimidin-4-yl)-1H-pyrazol-1-yl]propyl}piperazin-1-yl)sulfonyl]benzonitrile

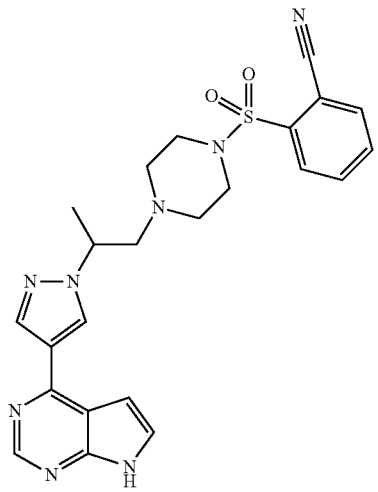 [SMILES: CC(CN1CCN(S(=O)(=O)c2ccccc2C#N)CC1)n1cc(-c2ncnc3[nH]ccc23)cn1]

This compound was prepared according to the procedure of Example 92, using 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine and 2-cyanobenzenesulfonyl chloride as the starting materials. $^1$H NMR (300 MHz, DMSO-D6): δ 12.05 (s, 1H); 8.61 (s, 1H); 8.58 (s, 1H); 8.21 (s, 1H); 8.07 (m, 1H); 7.95-7.78 (m, 3H); 7.53 (m, 1H); 6.88 (d, 1H); 4.62 (m, 1H); 2.98 (m, 4H); 2.82 (m, 1H); 2.59 (m, 3H); 2.36 (m, 2H); 1.40 (d, 3H); LCMS calculated for C$_{23}$H$_{25}$N$_8$O$_2$S (M+H)+: m/z=477.0.

Example 95

4-(1-{2-[4-(2,4-difluorobenzoyl)piperazin-1-yl]-1-methylethyl}-1H-pyrazol-4-yl)-7H-pyrrolo[2,3-d]pyrimidine bis(trifluoroacetate)

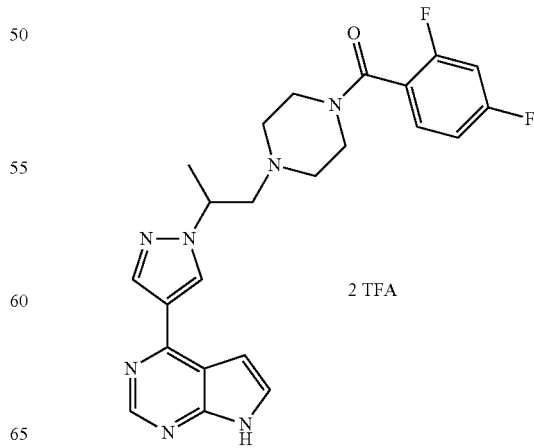

This compound was prepared according to the procedure of Example 92, using 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine and 2,4-difluorobenzoyl chloride as the starting materials. ¹H NMR (300 MHz, CD₃OD): δ 8.91 (d, 2H), 8.51 (s, 1H), 7.87 (d, 1H), 7.48 (q, 1H), 7.30 (d, 1H), 7.10 (t, 2H), 5.18 (m, 1H), 4.10-3.83 (br. m, 3H), 3.64-3.36 (br. m, 4H), 3.22-3.03 (br. m, 3H), 1.65 (d, 3H); LCMS calculated for C₂₃H₂₄F₂N₇O(M+H)+: m/z=452.1.

Example 96

4-[1-(2-{4-[(3-fluorophenyl)sulfonyl]piperazin-1-yl}-1-methylethyl)-1H-pyrazol-4-yl]-7H-pyrrolo[2,3-d]pyrimidine bis(trifluoroacetate)

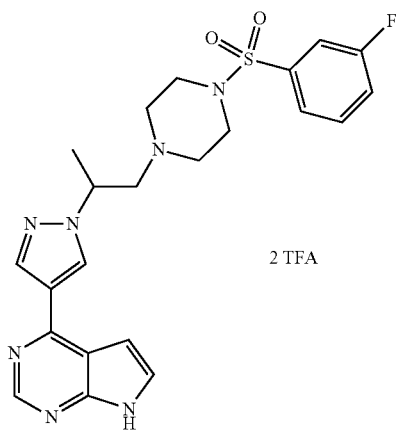 [SMILES: CC(CN1CCN(S(=O)(=O)c2cccc(F)c2)CC1)n1cc(-c2ncnc3[nH]ccc23)cn1]

This compound was prepared according to the procedure of Example 92, using 4-[1-(1-methyl-2-piperazin-1-ylethyl)-1H-pyrazol-4-yl]-7-{[2-(trimethylsilyl)ethoxy]methyl}-7H-pyrrolo[2,3-d]pyrimidine and 3-fluorobenzenesulfonyl chloride as the starting materials. ¹H NMR (300 MHz, CD₃OD): δ 8.83 (d, 2H), 8.42 (s, 1H), 7.79 (d, 1H), 7.72-7.36 (br. m, 4H), 7.20 (d, 1H), 5.01 (m, 1H), 3.30-2.95 (br. m, 6H), 1.59 (d, 3H), 1.30 (t, 4H); LCMS calculated for C₂₂H₂₅FN₇O₂S (M+H)+: m/z=470.1.

Example 97

4-[4-(2-fluoro-4-hydroxybenzoyl)-1,4-diazepan-1-yl]-3-[4-(7H-pyrrolo[2,3-d]pyrimidin-4-yl)-1H-pyrazol-1-yl]butanenitrile bis(trifluoroacetate)

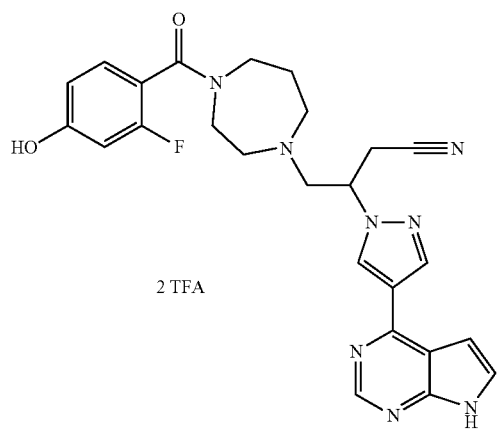 [SMILES: N#CCC(CN1CCCN(C(=O)c2ccc(O)cc2F)CC1)n1cc(-c2ncnc3[nH]ccc23)cn1]

Step 1. tert-butyl 4-(3-cyano-2-hydroxypropyl)-1,4-diazepane-1-carboxylate

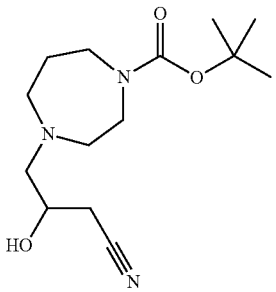 [SMILES: CC(C)(C)OC(=O)N1CCCN(CC(O)CC#N)CC1]

To a solution of tert-butyl 1,4-diazepane-1-carboxylate (4.65 g, 23.2 mmol) and 4-chloro-3-hydroxybutanenitrile (2.0 g, 17 mmol) in ethanol (40 mL) was added sodium bicarbonate (2.1 g, 25 mmol). The mixture was stirred at 90° C. for 19 hours. After cooling to room temperature, ethanol was evaporated. The remaining mixture was diluted with ethyl acetate and washed with water and brine. The organic was dried over MgSO4, filtered, and concentrated. The residue was purified by silica gel column (0% to 10% methanol/DCM) to give the desired product as yellow oil (3.2 g, 68%). LCMS calculated for C₁₄H₂₆N₃O₃(M+H)⁺: m/z=284.1.

Step 2. tert-butyl 4-{3-cyano-2-[(methylsulfonyl)oxy]propyl}-1,4-diazepane-1-carboxylate

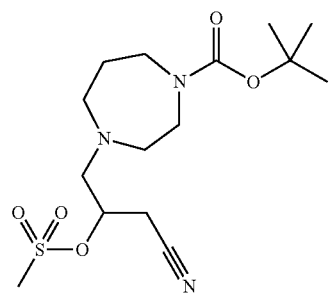 [SMILES: CC(C)(C)OC(=O)N1CCCN(CC(CC#N)OS(C)(=O)=O)CC1]

A solution of tert-butyl 4-(3-cyano-2-hydroxypropyl)-1,4-diazepane-1-carboxylate (3.2 g, 11 mmol) and triethylamine (3.1 mL, 22 mmol) in DCM (60 mL) was cooled to 0° C. and treated with methanesulfonyl chloride (1.2 mL, 16 mmol). After stirring at 0° C. for 1 hour, the reaction solution was diluted with water and DCM. The organic layer was washed with water twice, dried over MgSO4, filtered, and concentrated to give the desired product as oil (4 g, 98%). The crude product was used immediately in the next step. LCMS calculated for C₁₅H₂₈N₃O₅S(M+H)⁺: m/z=362.1.

Step 3. tert-butyl 4-{3-cyano-2-[4-(7-{[2-(trimethyl-silyl)ethoxy]methyl}-7H-pyrrolo[2,3-d]pyrimidin-4-yl)-1H-pyrazol-1-yl]propyl}-1,4-diazepane-1-carboxylate

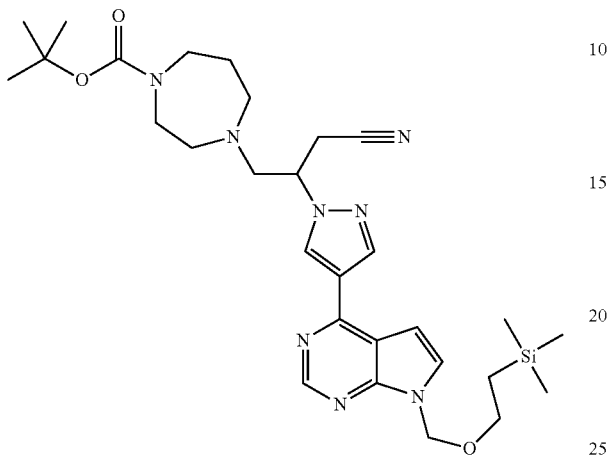

To a solution of tert-butyl 4-{3-cyano-2-[(methylsulfonyl)oxy]propyl}-1,4-diazepane-1-carboxylate (4.00 g, 11.1 mmol) and 4-(1H-pyrazol-4-yl)-7-{[2-(trimethylsilyl)ethoxy]methyl}-7H-pyrrolo[2,3-d]pyrimidine (3.50 g, 11.1 mmol) in DMF (30 mL) was added potassium carbonate (4.6 g, 33 mmol). The resulting mixture was stirred at room temperature for 66 hours. The reaction solution was diluted with ethyl acetate (~300 mL) then washed with water twice and brine. The organic solutions were dried over MgSO4, filtered, and concentrated. The residue was purified by silica gel column (0% to 10% methanol/DCM) to give the desired product as clear oil (6.5 g, 100%). LCMS calculated for $C_{29}H_{45}N_8O_3Si(M+H)^+$: m/z=581.3.

Step 4. 4-(1,4-diazepan-1-yl)-3-[4-(7-{[2-(trimethyl-silyl)ethoxy]methyl}-7H-pyrrolo[2,3-d]pyrimidin-4-yl)-1H-pyrazol-1-yl]butanenitrile

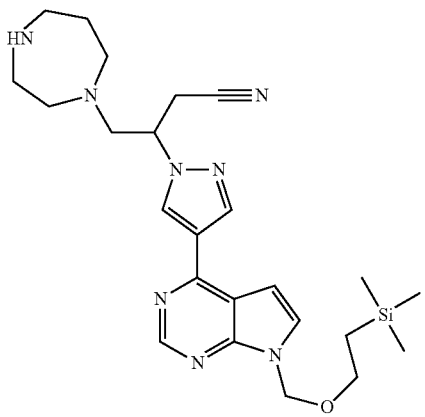 [SMILES: C[Si](C)(C)CCOCn1ccc2c(-c3cnn(C(CC#N)CN4CCCNCC4)c3)ncnc21]

To a solution of tert-butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-1,4-diazepane-1-carboxylate (6.4 g, 11 mmol;) in DCM (10 mL) was added 4.0 M of hydrogen chloride in 1,4-dioxane (22 mL, 88 mmol). The reaction solution was stirred at room temperature for 90 minutes. The solvent was removed in vacuo and the residue was dissolved in ethyl acetate. The organic layer was washed with 1.0 N NaOH solution. The aqueous was extracted with ethyl acetate. The combined extracts were dried over MgSO4, filtered, and concentrated to give the desired product as a brown sticky gum (4.1 g, 77%). LCMS calculated for $C_{24}H_{37}N_8OSi$ $(M+H)^+$: m/z=481.2.

Step 5. 4-[4-(2-fluoro-4-hydroxybenzoyl)-1,4-diazepan-1-yl]-3-[4-(7H-pyrrolo[2,3-d]pyrimidin-4-yl)-1H-pyrazol-1-yl]butanenitrile bis(trifluoroacetate)

To a vial was added 4-(1,4-diazepan-1-yl)-3-[4-(7-{[2-(trimethylsilyl)ethoxy]methyl}-7H-pyrrolo[2,3-d]pyrimidin-4-yl)-1H-pyrazol-1-yl]butanenitrile (20 mg, 0.04 mmol) followed by 2-fluoro-4-hydroxybenzoic acid (9.7 mg, 0.062 mmol), DMF (0.2 mL), triethylamine (12 µL, 0.083 mmol) and N,N,N',N'-tetramethyl-O-(7-azabenzotriazol-1-yl)uronium hexafluorophosphate (23.7 mg, 0.0624 mmol) (HATU). The reaction solution was stirred at room temperature overnight. The reaction was quenched with saturated sodium bicarbonate and extracted with ethyl acetate three times. The combined extracts were dried over MgSO4, filtered, and concentrated. The residue was dissolved in DCM (0.2 mL) and TFA (0.2 mL) and stirred at ambient temperature for 90 min. After removal of solvent, the residue was treated with methanol (0.5 mL) and ethylenediamine (100 µL) for 30 min. The reaction solution was diluted with methanol and purified by preparative LCMS (C18 column eluting with a gradient of MeCN/H2O containing 0.15% NH4OH) to give the desired product (15.5 mg, 52%). $^1$H NMR (300 MHz, CD3OD): δ 9.09 (s, 1H), 8.92 (s, 1H), 8.60 (s, 1H), 7.88 (d, 1H), 7.29 (m, 1H), 7.19 (t, 1H), 6.63 (m, 111), 6.51 (m, 1H), 4.05 (m, 1H), 3.89 (br. s, 1H), 3.68 (m, 2H), 3.49 (m, 2H), 3.35-3.15 (m, 6H), 2.08 (m, 2H), 1.29 (s, 2H); LCMS calculated for $C_{25}H_{26}FN_8O_2(M+H)^+$: m/z=489.1.

Examples 98-114

The examples in the table below were made by procedures analogous to those for producing Examples 97, step 5.

| Ex. | Structure | Name | M + H |
|-----|-----------|------|-------|
| 98  | 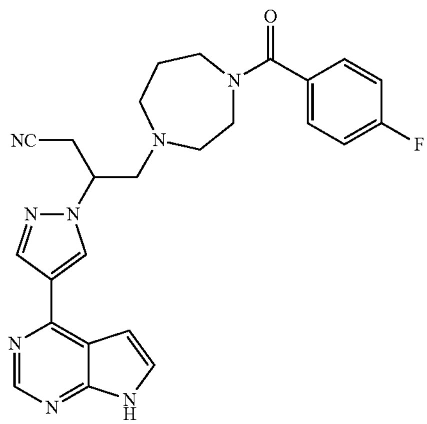 [SMILES: N#CCC(CN1CCCN(C(=O)c2ccc(F)cc2)CC1)n1cc(-c2ncnc3[nH]ccc23)cn1]          | 4-[4-(4-fluorobenzoyl)-1,4-diazepan-1-yl]-3-[4-(7H-pyrrolo[2,3-d]pyrimidin-4-yl)-1H-pyrazol-1-yl]butanenitrile | 473.2 |
| 99  | 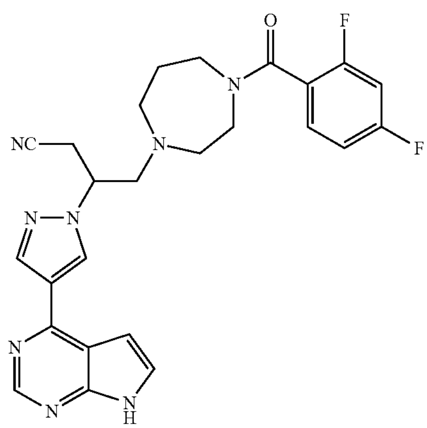 [SMILES: N#CCC(CN1CCCN(C(=O)c2ccc(F)cc2F)CC1)n1cc(-c2ncnc3[nH]ccc23)cn1]          | 4-[4-(2,4-difluorobenzoyl)-1,4-diazepan-1-yl]-3-[4-(7H-pyrrolo[2,3-d]pyrimidin-4-yl)-1H-pyrazol-1-yl]butanenitrile | 491.2 |
| 100 | 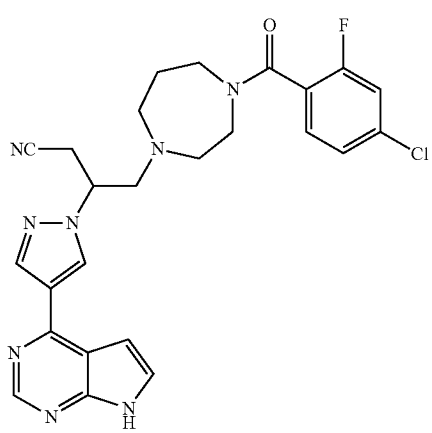 [SMILES: N#CCC(CN1CCCN(C(=O)c2ccc(Cl)cc2F)CC1)n1cc(-c2ncnc3[nH]ccc23)cn1]          | 4-[4-(4-chloro-2-fluorobenzoyl)-1,4-diazepan-1-yl]-3-[4-(7H-pyrrolo[2,3-d]pyrimidin-4-yl)-1H-pyrazol-1-yl]butanenitrile | 507.0 |

| Ex. | Structure | Name | M + H |
|---|---|---|---|
| 101 | 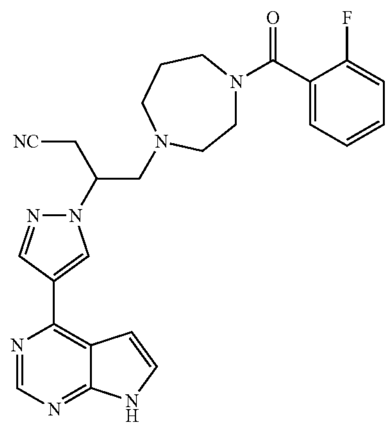 [SMILES: N#CCC(CN1CCCN(C(=O)c2ccccc2F)CC1)n1cc(-c2ncnc3[nH]ccc23)cn1] | 4-[4-(2-fluorobenzoyl)-1,4-diazepan-1-yl]-3-[4-(7H-pyrrolo[2,3-d]pyrimidin-4-yl)-1H-pyrazol-1-yl]butanenitrile | 473.2 |
| 102 | 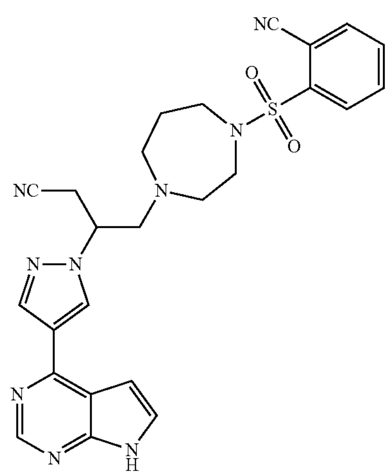 [SMILES: N#CCC(CN1CCCN(S(=O)(=O)c2ccccc2C#N)CC1)n1cc(-c2ncnc3[nH]ccc23)cn1] | 2-[(4-{3-cyano-2-[4-(7H-pyrrolo[2,3-d]pyrimidin-4-yl)-1H-pyrazol-1-yl]propyl}-1,4-diazepan-1-yl)sulfonyl]benzonitrile | 516.2 |
| 103 | 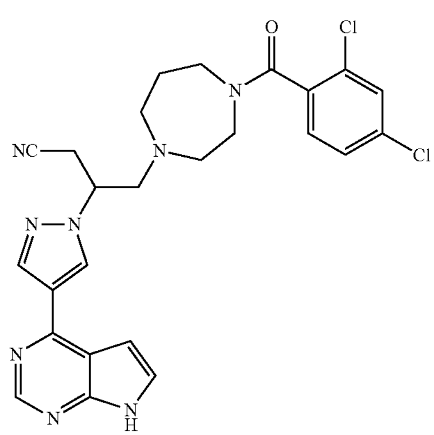 | 4-[4-(2,4-dichlorobenzoyl)-1,4-diazepan-1-yl]-3-[4-(7H-pyrrolo[2,3-d]pyrimidin-4-yl)-1H-pyrazol-1-yl]butanenitrile | 523.1 |

| Ex. | Structure | Name | M + H |
|---|---|---|---|
| 104 | 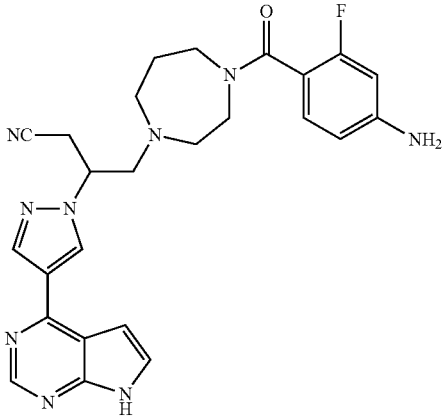 [SMILES: N#CCC(CN1CCCN(C(=O)c2ccc(N)cc2F)CC1)n1cc(-c2ncnc3[nH]ccc23)cn1] | 4-[4-(4-amino-2-fluorobenzoyl)-1,4-diazepan-1-yl]-3-[4-(7H-pyrrolo[2,3-d]pyrimidin-4-yl)-1H-pyrazol-1-yl]butanenitrile | 488.1 |
| 105 | 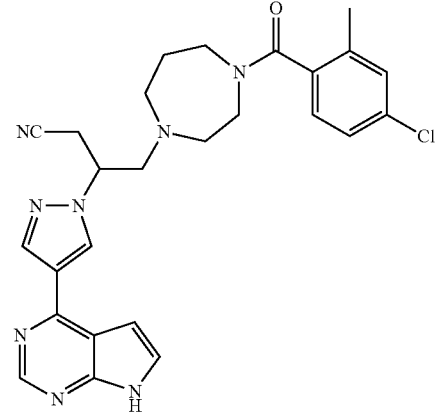 [SMILES: Cc1cc(Cl)ccc1C(=O)N1CCCN(CC(CC#N)n2cc(-c3ncnc4[nH]ccc34)cn2)CC1] | 4-[4-(4-chloro-2-methylbenzoyl)-1,4-diazepan-1-yl]-3-[4-(7H-pyrrolo[2,3-d]pyrimidin-4-yl)-1H-pyrazol-1-yl]butanenitrile | 503.1 |
| 106 | 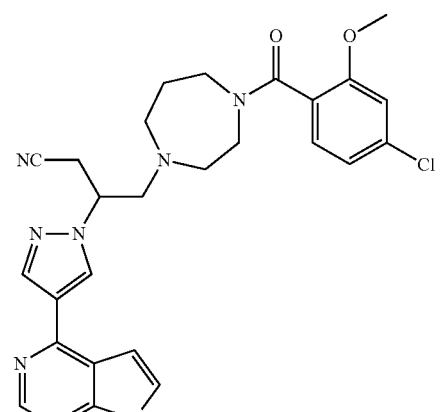 | 4-[4-(4-chloro-2-methoxybenzoyl)-1,4-diazepan-1-yl]-3-[4-(7H-pyrrolo[2,3-d]pyrimidin-4-yl)-1H-pyrazol-1-yl]butanenitrile | 519.1 |

-continued

| Ex. | Structure | Name | M + H |
|---|---|---|---|
| 107 | 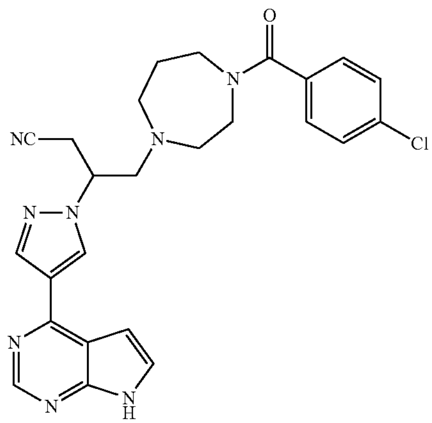 [SMILES: N#CCC(CN1CCCN(C(=O)c2ccc(Cl)cc2)CC1)n1cc(-c2ncnc3[nH]ccc23)cn1] | 4-[4-(4-chlorobenzoyl)-1,4-diazepan-1-yl]-3-[4-(7H-pyrrolo[2,3-d]pyrimidin-4-yl)-1H-pyrazol-1-yl]butanenitrile | 489.1 |
| 108 | 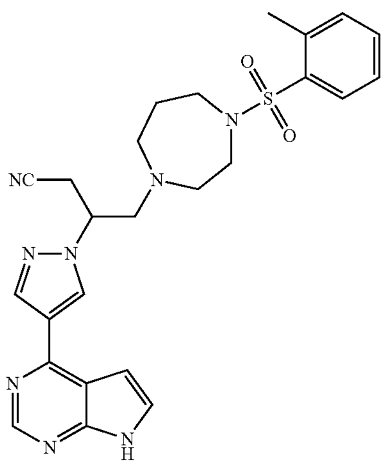 [SMILES: Cc1ccccc1S(=O)(=O)N1CCCN(CC(CC#N)n2cc(-c3ncnc4[nH]ccc34)cn2)CC1] | 4-{4-[(2-methylphenyl)sulfonyl]-1,4-diazepan-1-yl}-3-[4-(7H-pyrrolo[2,3-d]pyrimidin-4-yl)-1H-pyrazol-1-yl]butanenitrile | 505.1 |
| 109 | 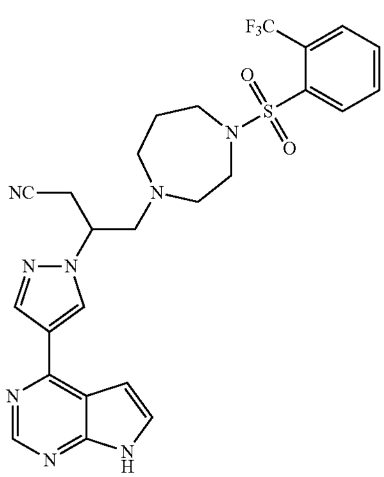 | 3-[4-(7H-pyrrolo[2,3-d]pyrimidin-4-yl)-1H-pyrazol-1-yl]-4-(4-{[2-(trifluoromethyl)phenyl]sulfonyl}-1,4-diazepan-1-yl)butanenitrile | 559.1 |

-continued

| Ex. | Structure | Name | M + H |
|---|---|---|---|
| 110 | 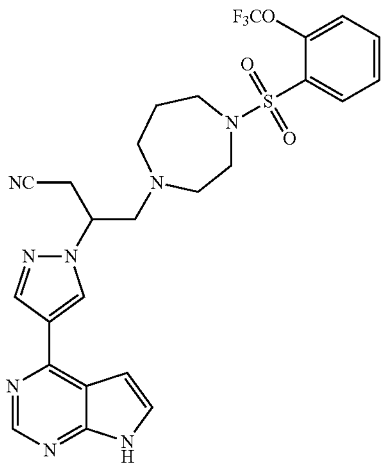 [SMILES: N#CCC(CN1CCCN(S(=O)(=O)c2ccccc2OC(F)(F)F)CC1)n1cc(-c2ncnc3[nH]ccc23)cn1] | 3-[4-(7H-pyrrolo[2,3-d]pyrimidin-4-yl)-1H-pyrazol-1-yl]-4-(4-{[2-(trifluoromethoxy)phenyl]sulfonyl}-1,4-diazepan-1-yl)butanenitrile | 575 |
| 111 | 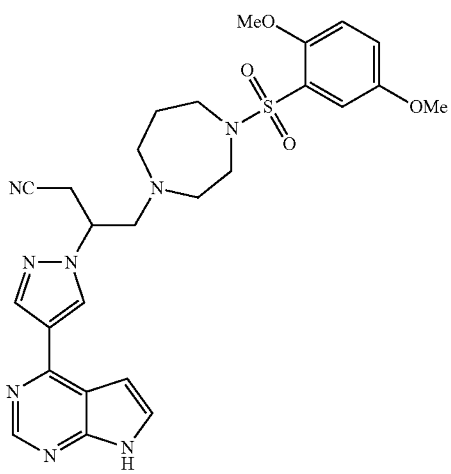 [SMILES: COc1ccc(OC)c(S(=O)(=O)N2CCCN(CC(CC#N)n3cc(-c4ncnc5[nH]ccc45)cn3)CC2)c1] | 4-{4-[(2,5-dimethoxyphenyl)sulfonyl]-1,4-diazepan-1-yl}-3-[4-(7H-pyrrolo[2,3-d]pyrimidin-4-yl)-1H-pyrazol-1-yl]butanenitrile | 551 |
| 112 | 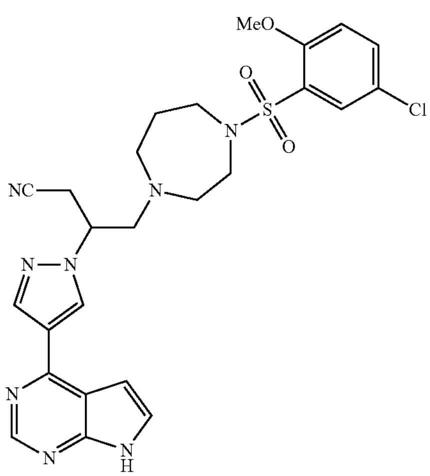 [SMILES: COc1ccc(Cl)cc1S(=O)(=O)N1CCCN(CC(CC#N)n2cc(-c3ncnc4[nH]ccc34)cn2)CC1] | 4-{4-[(5-chloro-2-methoxyphenyp)sulfonyl]-1,4-diazepan-1-yl}-3-[4-(7H-pyrrolo[2,3-d]pyrimidin-4-yl)-1H-pyrazol-1-yl]butanenitrile | 555.2 |

-continued

| Ex. | Structure | Name | M + H |
|---|---|---|---|
| 113 | 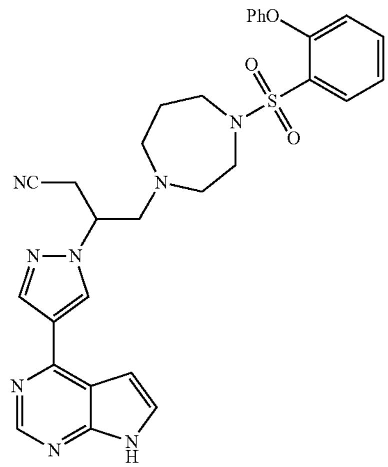 | 4-{4-[(2-phenoxyphenyl)sulfonyl]-1,4-diazepan-1-yl}-3-[4-(7H-pyrrolo[2,3-d]pyrimidin-4-yl)-1H-pyrazol-1-yl]butanenitrile | 583.3 |
| 114 | 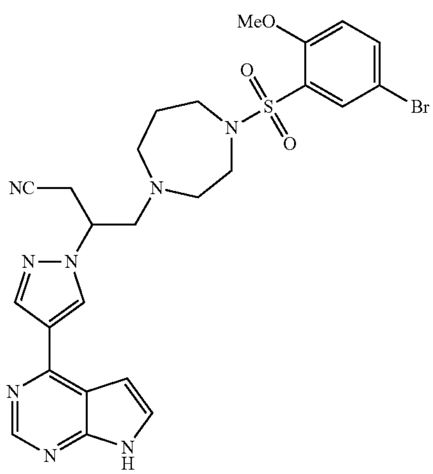 [SMILES: COc1ccc(Br)cc1S(=O)(=O)N1CCCN(CC(CC#N)n2cc(-c3ncnc4[nH]ccc34)cn2)CC1] | 4-{4-[(5-bromo-2-methoxyphenyl)sulfonyl]-1,4-diazepan-1-yl}-3-[4-(7H-pyrrolo[2,3-d]pyrimidin-4-yl)-1H-pyrazol-1-yl]butanenitrile | 599.2 |

Example 115

4-{1-[1-({4-[(1-methyl-1H-pyrazol-3-yl)sulfonyl]piperazin-1-yl}methyl)propyl]-1H-pyrazol-4-yl}-7H-pyrrolo[2,3-d]pyrimidine

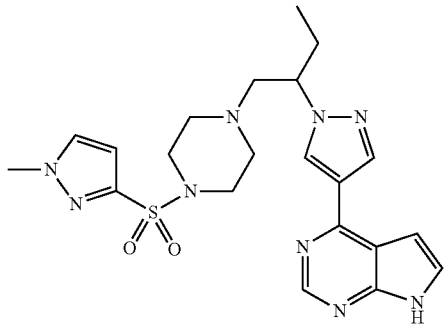 [SMILES: CCC(CN1CCN(S(=O)(=O)c2ccn(C)n2)CC1)n1cc(-c2ncnc3[nH]ccc23)cn1]

Step 1. Ethyl 2-(4-(7-((2-(trimethylsilyl)ethoxy)methyl)-7H-pyrrolo[2,3-d]pyrimidin-4-yl)-1H-pyrazol-1-yl)butanoate

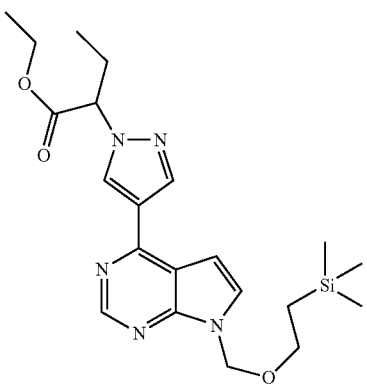 [SMILES: CCOC(=O)C(CC)n1cc(-c2ncnc3c2ccn3COCC[Si](C)(C)C)cn1]

To a 0° C. solution of 4-(1H-pyrazol-4-yl)-7-{[2-(trimethylsilyl)ethoxy]methyl}-7H-pyrrolo[2,3-d]pyrimidine (2.0 g, 0.0063 mol) in N,N-dimethylformamide (40 mL, 0.5 mol) was added sodium hydride (0.30 g, 0.0076 mol). After 15 minutes, ethyl 2-bromobutyrate (1.4 mL, 0.0095 mol) was added. After 4.5 hours, ethyl acetate and water were added. The organic phase was washed with water twice and saturated NaCl. The organic phase was then and the solvent was removed by rotary evaporation to give 3.02 g of a thick orange oil (110% yield). $^1$H NMR (400 MHz, CDCl3): δ 8.92 (1H, s); 8.49 (1H, s); 8.35 (1H, s); 7.45 (1H, d); 6.85 (1H, d); 6.75 (2H, s); 5.0 (1H, t); 4.35 (2H, m); 3.6 (2H, t); 2.35 (2H, m); 1.35 (6H, m); (1.0 (3H, m); 0 (9H, s). LCMS (M+1): 430.

Step 2. 2-[4-(7-{[2-(trimethylsilyl)ethoxy]methyl}-7H-pyrrolo[2,3-d]pyrimidin-4-yl)-1H-pyrazol-1-yl]butanal

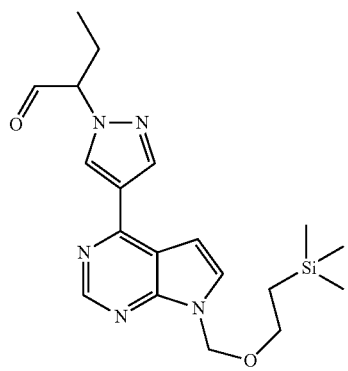 [SMILES: CCC(C=O)n1cc(-c2ncnc3c2ccn3COCC[Si](C)(C)C)cn1]

A solution of ethyl 2-[4-(7-{[2-(trimethylsilyl)ethoxy]methyl}-7H-pyrrolo[2,3-d]pyrimidin-4-yl)-1H-pyrazol-1-yl]butanoate (1.0 g, 2.3 mmol) in toluene (10 mL, 90 mmol) was cooled at −78° C. 1.0 M of Diisobutylaluminum hydride in toluene (2.8 mL, 2.8 mmol) was added dropwise over 10 minutes. Another 1.0 M of diisobutylaluminum hydride in toluene (3.0 mL, 3.0 mmol) was added. The mixture was warmed to −55° C. After quenching with 2.8 M of sodium hydroxide in water (10 mL, 30 mmol), the mixture formed an emulsion. Ethyl acetate was then added, and the aqueous phase was extracted with ethyl acetate. The combined organic layer was washed with 2.8 M of sodium hydroxide in water, water, saturated NH$_4$Cl, and saturated NaCl. The organic phase was dried and the solvent was evaporated by rotary evaporation at 35° C. to give an orange oil. The orange oil was then twice redissolved in toluene and then the solvent was removed by rotary evaporation to give 0.8 g orange oil (90% yield). LCMS: 386.

Step 3. tert-butyl 4-{2-[4-(7-{[2-(trimethylsilyl)ethoxy]methyl}-7H-pyrrolo[2,3-d]pyrimidin-4-yl)-1H-pyrazol-1-yl]butyl}piperazine-1-carboxylate

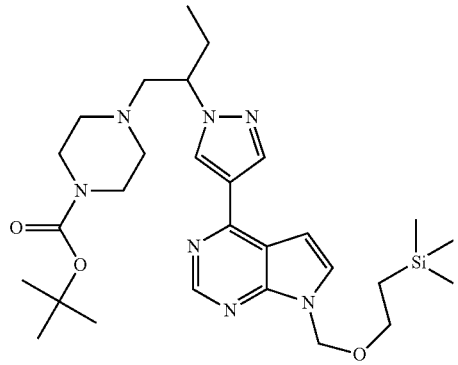 [SMILES: CCC(CN1CCN(C(=O)OC(C)(C)C)CC1)n1cc(-c2ncnc3c2ccn3COCC[Si](C)(C)C)cn1]

A solution of 2-[4-(7-{[2-(trimethylsilyl)ethoxy]methyl}-7H-pyrrolo[2,3-d]pyrimidin-4-yl)-1H-pyrazol-1-yl]butane-1,1-diol (0.80 g, 1.6 mmol) and tert-butyl piperazine-1-carboxylate (0.46 g, 2.5 mmol) in methylene chloride (8 mL, 100 mmol) was stirred for 1.6 hours. Acetic acid (150 uL, 2.6 mmol) was added. After 1 hour, sodium triacetoxyborohydride (0.74 g, 3.5 mmol) was added and was stirred overnight. The organic layer was washed with saturated NaHCO$_3$ and saturated NaCl. The organic phase was dried and the solvent was evaporated by rotary evaporation to give 1.32 g of a pale orange oil with a small amount of a solid. DCM was added, then decanted, and the resultant material was chromatographed with 0-10% MeOH/DCM, 0-1% NH$_4$OH to give 0.55 orange foam (62% yield). $^1$H NMR (400 MHz, CDCl3): δ 8.88 (1H, s); 8.35 (1H, s); δ 8.33 (1H, s); 7.45 (1H, d); 6.8 (1H, d); 5.75 (2H, s); 4.28 (1H, m); 4.25 (2H, m); 3.6 (2H, t); 2.0 (10H, m); 1.0 (12H, m); 0 (9H, s). LCMS (M+1): 556.

Step 4. 4-{1-[1-(piperazin-1-ylmethyl)propyl]-1H-pyrazol-4-yl}-7-{[2-(tritmethylsilyl)ethoxy]methyl}-7H-pyrrolo[2,3-d]pyrimidine

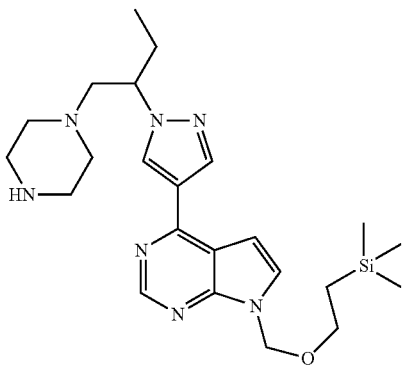 [SMILES: CCC(CN1CCNCC1)n1cc(-c2ncnc3c2ccn3COCC[Si](C)(C)C)cn1]

A suspension of tert-butyl 4-{2-[4-(7-{[2-(trimethylsilyl)ethoxy]methyl}-7H-pyrrolo[2,3-d]pyrimidin-4-yl)-1H-pyrazol-1-yl]butyl}piperazine-1-carboxylate (0.115 g, 0.207 mmol) in 1,4-dioxane (1 mL, 10 mmol) was dissolved after stirring for 10 minutes. 4.0 M of Hydrogen chloride in 1,4-dioxane(2.0 mL, 8.0 mmol) was added. After 1 hour, the solvent was evaporated by rotary evaporation to give 150 mg solid/glass. Ethyl acetate and saturated NaHCO₃ were added. The organic layer was washed with saturated NaCl, then the organic layer was dried and the solvent was evaporated by rotary evaporation to give 81 mg pale orange oil (85% yield). ¹H NMR (400 MHz, CDCl3): ☐ 9.9 (1H, s); 8.35 (1H, s); 8.33 (1H, s); 7.45 (1H, d); 6.85 (1H, d); 5.75 (2H, s); 4.33 (1H, m); 4.19 (H, m); 3.83-3.76 (1H, m); 2.98-2.3 (8H, m); 2.0 (2H, m); 0.99 (3H, m); 0.90 (3H, m); (9H, s). LCMS (M+1): 456.

A solution of 4-{1-[1-(piperazin-1-ylmethyl)propyl]-1H-pyrazol-4-yl}-7-{[2-(trimethylsilyl)ethoxy]methyl}-7H-pyrrolo[2,3-d]pyrimidine (0.040 g, 0.088 mmol) in dichloromethane (1 mL, 20 mmol), 1-methyl-1H-pyrazole-3-sulfonyl chloride (0.021 g, 0.12 mmol), and triethylamine (0.020 mL, 0.14 mmol) in dichloromethane was stirred overnight. 1 mL TFA was added. After 1 hour, the solvent was evaporated by rotary evaporation to give a glass which was stirred in 1 mL MeOH and 50 uL EDA for 2 h. The reaction was purified by LCMS (pH 10) to give 8.6 mg white solid (21% yield). ¹H NMR (400 MHz, DMSO): δ 12.05 (1H, br); 8.63 (1H, s); 8.61 (1H, s); 8.25 (1H, s); 7.85 (1H, d); 7.57 (1H, d); 6.95 (1H, d); 6.59 (1H, d); 4.4 (1H, m); 3.81 (2H, s); 2.84 (4H, m); 2.6 (2H, m); 2.47 (3H, s); 2.37 (2H, m); 1.78 (2H, m); 0.65 (3H, t). LCMS (M+1): 470.

Example 116

(4-(2-(4-(7H-pyrrolo[2,3-d]pyrimidin-4-yl)-1H-pyrazol-1-yl)butyl)piperazin-1-yl)(4-fluorophenyl)methanone

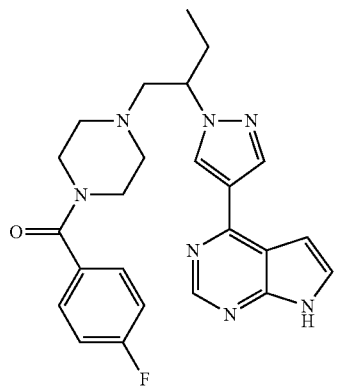 [SMILES: CCC(CN1CCN(C(=O)c2ccc(F)cc2)CC1)n1cc(-c2ncnc3[nH]ccc23)cn1]

A solution of 4-{1-[1-(piperazin-1-ylmethyl)propyl]-1H-pyrazol-4-yl}-7-{[2-(trimethylsilyl)ethoxy]methyl}-7H-pyrrolo[2,3-d]pyrimidine (0.010 g, 0.022 mmol, from step 4 in example 1) and benzoyl chloride, 4-fluoro-(3.4 uL, 0.028 mmol) in dichloromethane (1 mL, 20 mmol) was stirred for 2 hour. 1 mL TFA was added. After 1 hour, the solvent was evaporated by rotary evaporation to give a glass which was stirred in 1 mL MeOH and 50 microL EDA for 2 hours. The reaction was purified by LCMS (pH 10) to give 3.1 mg white solid (52% yield). ¹H NMR (400 MHz, DMSO): δ 12.0 (1H, br); 8.62 (1H, s); 8.599 (1H, s); 8.22 (1H, s); 7.55 (1H, m); 7.18 (1H, m); 6.95 (1H, d); 6.91 (1H, d); 4.4 (1H, m); 3.43 (2H, br); 3.18 (2H, br); 2.82 (1H, m); 2.61 (1H, m); 2.47 (2H, br); 2.24 (2H, br); 1.78 (2H, m); 0.65 (3H, t). LCMS (M+1); 448.

Example 117

2-[(4-{2-[4-(7H-pyrrolo[2,3-d]pyrimidin-4-yl)-1H-pyrazol-1-yl]butyl}piperazin-1-yl)carbonyl]phenol

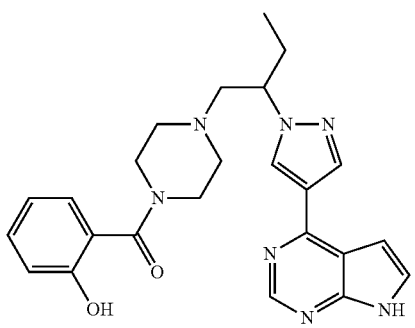 [SMILES: CCC(CN1CCN(C(=O)c2ccccc2O)CC1)n1cc(-c2ncnc3[nH]ccc23)cn1]

To a solution of 2-hydroxybenzoic acid (0.0045 g, 0.033 mmol) in tetrahydrofuran (0.5 mL, 6 mmol) was added N,N,N',N'-tetramethyl-O-(7-azabenzotriazol-1-yl)uronium hexafluorophosphate (0.012 g, 0.033 mmol) and N,N-diisopropylethylamine (5.7 uL, 0.033 mmol) and mixed for 1 hour until dissolution. The reaction was stirred overnight, then 4-{1-[1-(piperazin-1-ylmethyl)propyl]-1H-pyrazol-4-yl}-7-{[2-(trimethylsilyl)ethoxy]methyl}-7H-pyrrolo[2,3-d]pyrimidine (0.010 g, 0.022 mmol from step 4 in example 115 and 0.5 mL THF were added. After 0.5 hour, the reaction was purified by LCMS (pH 10) to give 14 mg white solid which was stirred in 1 mL MeOH and 50 microL EDA for 2 hours. The reaction was purified by LCMS (pH 10) to give 2.2 mg white solid. ¹H NMR (400 MHz, DMSO): δ 8.64 (1H, s); 8.6 (1H, s); 8.22 (1H, s); 7.55 (1H, d); 7.35 (1H, m); 6.99 (1H, m); 6.93 (1H, m); 688 (1H, m); 6.75 (1H, m); 4.39 (1H, m); 3.5-2.2 (10H, br); 1.78 (2H, m); 0.65 (3H, t). LCMS (M+1); 446.

Example 146

3-[1-(6-anilino-5-methylpyrimidin-4-yl)piperidin-4-yl]-3-[4-(7H-pyrrolo[2,3-d]pyrimidin-4-yl)-1H-pyrazol-1-yl]propanenitrile

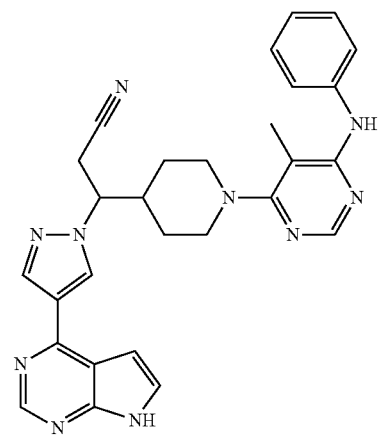 [SMILES: Cc1c(Nc2ccccc2)ncnc1N1CCC(C(CC#N)n2cc(-c3ncnc4[nH]ccc34)cn2)CC1]

Step 1. tert-butyl 4-{2-cyano-1-[4-(7-{[2-(trimethylsilyl)ethoxy]methyl}-7H-pyrrolo[2,3-d]pyrimidin-4-yl)-1H-pyrazol-1-yl]ethyl}piperidine-1-carboxylate

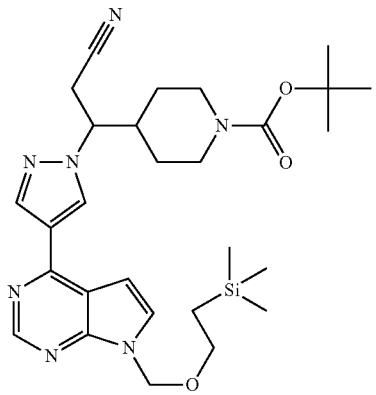 [SMILES: CC(C)(C)OC(=O)N1CCC(C(CC#N)n2cc(-c3ncnc4c3ccn4COCC[Si](C)(C)C)cn2)CC1]

A mixture of 4-(1H-pyrazol-4-yl)-7-{[2-(trimethylsilyl)ethoxy]methyl}-7H-pyrrolo[2,3-d]pyrimidine (10.0 g, 0.0317 mol), tert-butyl 4-[(E)-2-cyanovinyl]piperidine-1-carboxylate (10.7 g, 0.0430 mol) and 1,8-diazabicyclo[5.4.0]undec-7-ene (470 uL, 0.0032 mol) in acetonitrile (100 mL, 2 mol) was heated at 55° C. overnight. The solvent was removed by rotary evaporation to give an orange foam. The resultant material was chromatographed with 0-100 ethyl acetate/hexane to give 15.5 g white solid/foam (100% yield). ¹H NMR (400 MHz, CDCl3): δ 8.93 (1H, s); 8.41 (1H, s); 8.38 (1H, s); 7.45 (1H, d); 6.85 (1H, d); 5.75 (2H, s); 4.32 (2H, m); 4.15 (1H, br); 3.6 (2H, t); 3.22-3.05 (2H, m); 2.95-2.6 (2H, m); 2.15 (1H, m); 1.95 (1H, m); 1.45 (9H, s); 1.35 (3H, m); 0.97 (3H, t); 0 (9H, s). LCMS (M+1): 552.

Step 2. 3-piperidin-4-yl-3-[4-(7H-pyrrolo[2,3-d]pyrimidin-4-yl)-1H-pyrazol-1-yl]propanenitrile

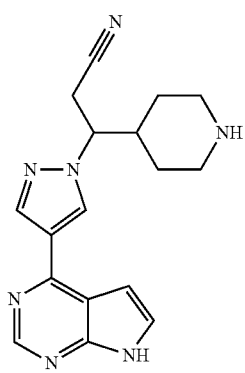 [SMILES: N#CCC(C1CCNCC1)n1cc(-c2ncnc3[nH]ccc23)cn1]

A solution of tert-butyl 4-{2-cyano-1-[4-(7-{[2-(trimethylsilyl)ethoxy]methyl}-7H-pyrrolo[2,3-d]pyrimidin-4-yl)-1H-pyrazol-1-yl]ethyl}piperidine-1-carboxylate (2.0 g, 0.0036 mol) in 1,2-dichloroethane (20 mL, 0.2 mol) and trifluoroacetic acid (20 mL, 0.2 mol) was stirred for 1.1 hour, then the solvent was removed by rotary evaporation to give a colorless oil. The thick oil was dissolved in methanol (15 mL, 0.37 mol) and ethylenediamine (1.0 mL, 0.015 mol) was added. After 1.1 hours, the reaction was purified by preparative-LCMS (pH 10) to give 0.95 g white solid (82% yield). LCMS (M+1): 322.

Step 3. 3-[1-(6-chloro-5-methylpyrimidin-4-yl)piperidin-4-yl]-3-[4-(7H-pyrrolo[2,3-d]pyrimidin-4-yl)-1H-pyrazol-1-yl]propanenitrile

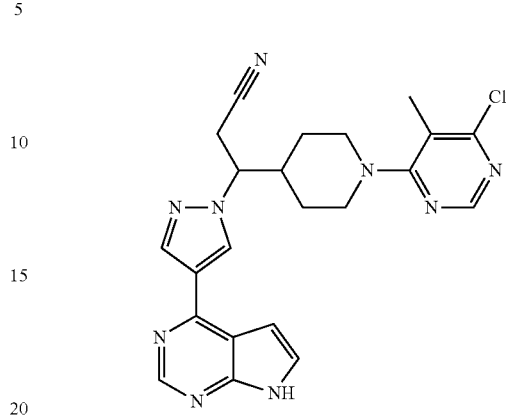

A solution of 3-piperidin-4-yl-3-[4-(7H-pyrrolo[2,3-d]pyrimidin-4-yl)-1H-pyrazol-1-yl]propanenitrile (0.20 g, 0.00062 mol), 4,6-dichloro-5-methylpyrimidine (0.11 g, 0.00067 mol) and N,N-diisopropylethylamine (130 microL, 0.00076 mol) in ethanol (2.0 mL, 0.034 mol) was heated to reflux for 1.2 hours, then the reaction was purified by preparative-LCMS (pH 10) to give 123 mg white solid (44% yield). LCMS (M+1): 448.

Step 4: A solution of 3-[1-(6-chloro-5-methylpyrimidin-4-yl)piperidin-4-yl]-3-[4-(7H-pyrrolo[2,3-d]pyrimidin-4-yl)-1H-pyrazol-1-yl]propanenitrile (0.0081 g, 0.018 mmol) in Aniline (95 uL, 1.0 mmol) was heated at 180° C. for 2.5 hours. The reaction was purified by preparative-LCMS (pH 10) to give 3.2 mg white solid (35% yield). ¹H NMR (400 MHz, DMSO): δ 12.05 (1H, br); 8.77 (1H, s); 8.61 (1H, s); 8.58 (1H, s); 8.15 (1H, s); 8.1 (1H, s); 7.55 (1H, d); 7.53 (2H, m); 7.2 (2H, t); 6.92 (1H, d); 6.9 (1H, m); 4.57 (1H, m); 3.6 (1H, m); 3.45 (1H, m); 3.27 (2H, m); 2.7 (1H, m); 2.58 (1H, m); 2.02 (1H, m); 1.98 (3H, s); 1.85 (1H, m); 1.3 (2H, m); 1.01 (1H, m). LCMS (M+1): 505.

Example 147

3-(4-(7H-pyrrolo[2,3-d]pyrimidin-4-yl)-1H-pyrazol-1-yl)-3-(1-(6-(2-fluorophenylamino)-5-methylpyrimidin-4-yl)piperidin-4-yl)propanenitrile

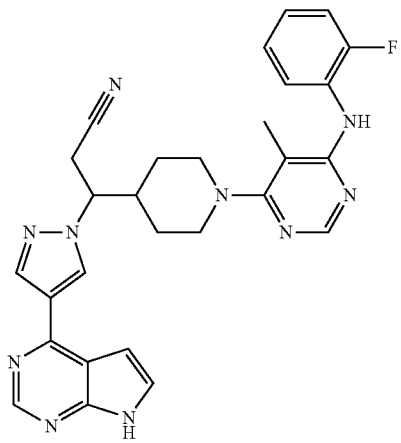 [SMILES: Cc1c(Nc2ccccc2F)ncnc1N1CCC(C(CC#N)n2cc(-c3ncnc4[nH]ccc34)cn2)CC1]

A solution of 3-[1-(6-chloro-5-methylpyrimidin-4-yl)piperidin-4-yl]-3-[4-(7H-pyrrolo[2,3-d]pyrimidin-4-yl)-1H-pyrazol-1-yl]propanenitrile (0.010 g, 0.022 mmol from step 3 in example 146) and 3 mg TSA.H$_2$O in 2-fluoro-aniline (95 microL, 1.0 mmol) was heated at 160° C. for 1.7 hours. The reaction was purified by preparative-LCMS (pH 10) to give 3.2 mg white solid (50% yield). $^1$H NMR (400 MHz, DMSO): δ 12.07 (1H, s); 8.78 (1H, s); 8.61 (1H s); 8.37 (1H, s); 8.02 (1H, s); 7.99 (1H, s); 7.55 (1H, d); 7.38 (1H, m); 7.1.5 (1H, m); 7.06 (2H, m); 6.95 (1H, s); 4.57 (1H, m); 3.61 (1H, m); 3.45 (1H, m); 3.27 (2H, m); 2.7 (1H, m); 2.58 (1H, m); 2.02 (1H, m); 1.98 (3H, s); 1.82 (1H, m); 1.3 (2H, m); (1.01 (1H, m). LCMS (M+1): 523.

| Ex. No. | Structure | Name | MS (M + H) | Prep. Ex. No. |
|---|---|---|---|---|
| 118 | 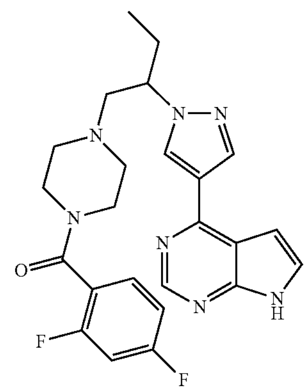 [SMILES: CCC(CN1CCN(C(=O)c2ccc(F)cc2F)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(2,4-difluorophenyl)methanone | 466 | 116 |
| 119 | 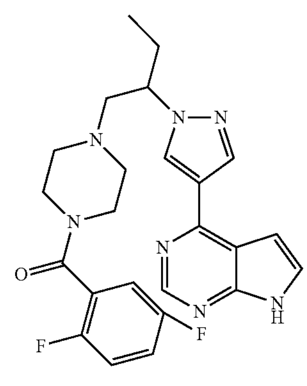 [SMILES: CCC(CN1CCN(C(=O)c2cc(F)ccc2F)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(2,5-difluorophenyl)methanone | 466 | 116 |
| 120 | 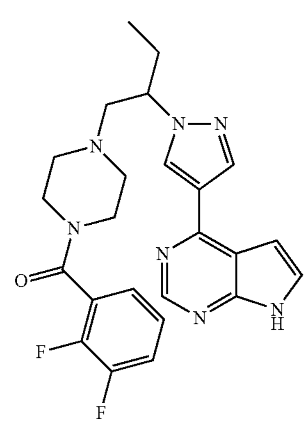 [SMILES: CCC(CN1CCN(C(=O)c2cccc(F)c2F)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(2,3-difluorophenyl)methanone | 466 | 116 |

-continued

| Ex. No. | Structure | Name | MS (M + H) | Prep. Ex. No. |
|---|---|---|---|---|
| 121 | 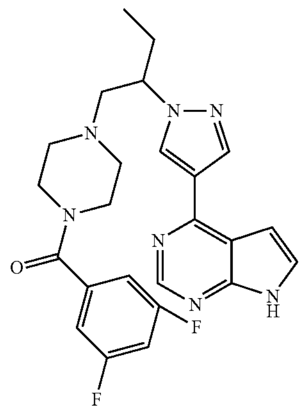 [SMILES: CCC(CN1CCN(C(=O)c2cc(F)cc(F)c2)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(3,5-difluorophenyl)methanone | 466 | 116 |
| 122 | 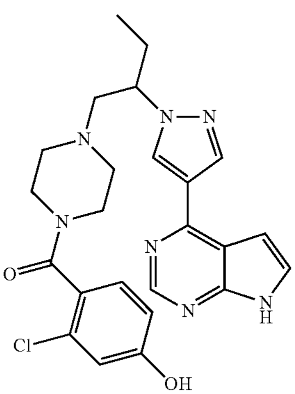 [SMILES: CCC(CN1CCN(C(=O)c2ccc(O)cc2Cl)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(2-chloro-4-hydroxyphenyl)methanone | 480 | 117 |
| 123 | 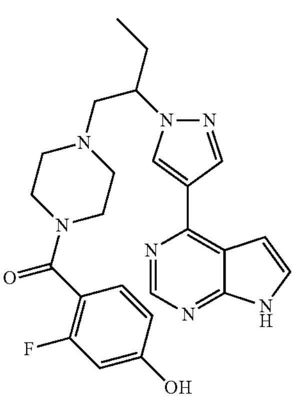 [SMILES: CCC(CN1CCN(C(=O)c2ccc(O)cc2F)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(2-fluoro-4-hydroxyphenyl)methanone | 464 | 117 |

-continued

| Ex. No. | Structure | Name | MS (M + H) | Prep. Ex. No. |
|---|---|---|---|---|
| 124 | 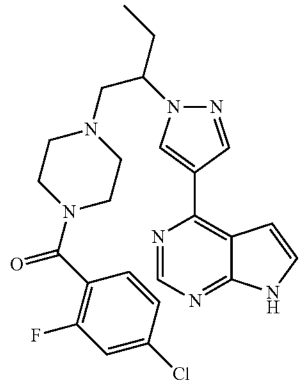 [SMILES: CCC(CN1CCN(C(=O)c2ccc(Cl)cc2F)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(4-chloro-2-fluorophenyl)methanone | 482 | 116 |
| 125 | 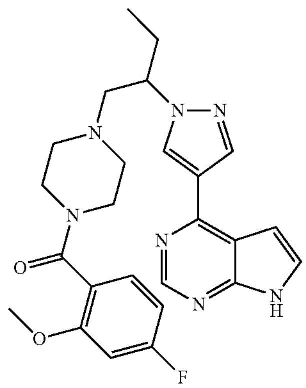 [SMILES: CCC(CN1CCN(C(=O)c2ccc(F)cc2OC)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(4-fluoro-2-methoxyphenyl)methanone | 478 | 116 |
| 126 | 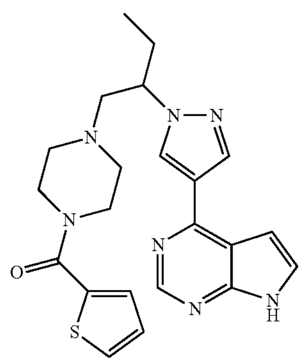 [SMILES: CCC(CN1CCN(C(=O)c2cccs2)CC1)n1cc(-c2ncnc3[nH]ccc23)cn1] | (4-(2-(4-(7H-pyrrolo[2,3-d]pyrimidin-4-yl)-1H-pyrazol-1-yl)butyl)piperazin-1-yl)(thiophen-2-yl)methanone | 436 | 116 |
| 127 | 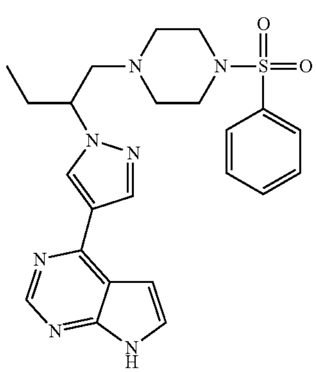 [SMILES: CCC(CN1CCN(S(=O)(=O)c2ccccc2)CC1)n1cc(-c2ncnc3[nH]ccc23)cn1] | 4-(1-(1-(4-(phenylsulfonyl)piperazin-1-yl)butan-2-yl)-1H-pyrazol-4-yl)-7H-pyrrolo[2,3-d]pyrimidine | 466 | 115 |

| Ex. No. | Structure | Name | MS (M + H) | Prep. Ex. No. |
|---|---|---|---|---|
| 128 | 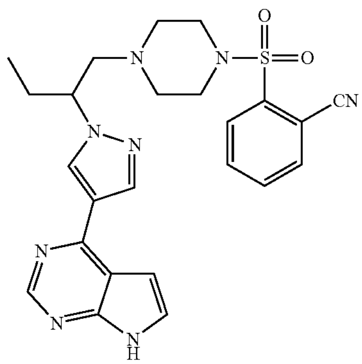 [SMILES: CCC(CN1CCN(S(=O)(=O)c2ccccc2C#N)CC1)n1cc(-c2ncnc3[nH]ccc23)cn1] | 2-(4-(2-(4-(7H-pyrrolo[2,3-d]pyrimidin-4-yl)-1H-pyrazol-1-yl)butyl)piperazin-1-ylsulfonyl)benzonitrile | 491 | 115 |
| 129 | 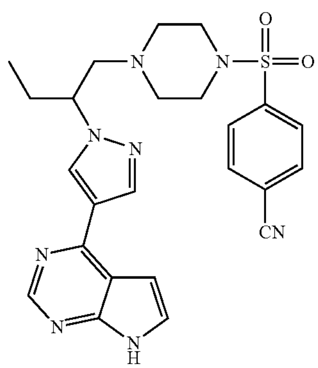 | 4-(4-(2-(4-(7H-pyrrolo[2,3-d]pyrimidin-4-yl)-1H-pyrazol-1-yl)butyl)piperazin-1-ylsulfonyl)benzonitrile | 491 | 115 |
| 130 | 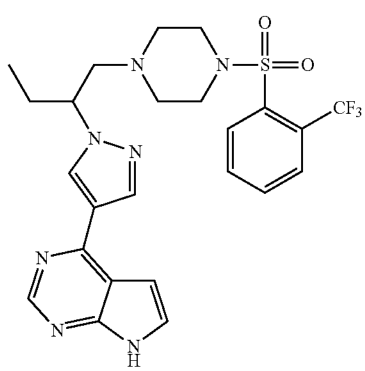 [SMILES: CCC(CN1CCN(S(=O)(=O)c2ccccc2C(F)(F)F)CC1)n1cc(-c2ncnc3[nH]ccc23)cn1] | 4-(1-(1-(4-(2-(trifluoromethyl)phenylsulfonyl)piperazin-1-yl)butan-2-yl)-1H-pyrazol-4-yl)-7H-pyrrolo[2,3-d]pyrimidine | 534 | 115 |
| 131 | 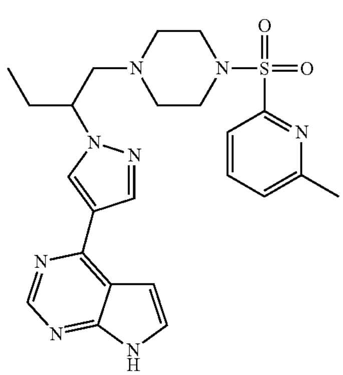 [SMILES: CCC(CN1CCN(S(=O)(=O)c2cccc(C)n2)CC1)n1cc(-c2ncnc3[nH]ccc23)cn1] | 4-(1-(1-(4-(6-methylpyridin-2-ylsulfonyl)piperazin-1-yl)butan-2-yl)-1H-pyrazol-4-yl)-7H-pyrrolo[2,3-d]pyrimidine | 481 | 115 |

-continued

| Ex. No. | Structure | Name | MS (M + H) | Prep. Ex. No. |
|---|---|---|---|---|
| 132 | 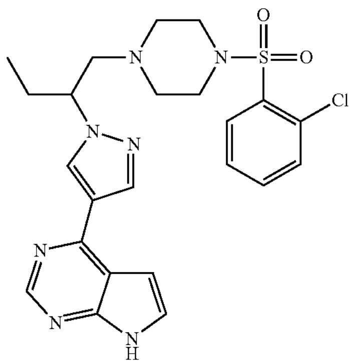 [SMILES: CCC(CN1CCN(S(=O)(=O)c2ccccc2Cl)CC1)n1cc(-c2ncnc3[nH]ccc23)cn1] | 4-(1-(1-(4-(2-chlorophenylsulfonyl)piperazin-1-yl)butan-2-yl)-1H-pyrazol-4-yl)-7H-pyrrolo[2,3-d]pyrimidine | 500 | 115 |
| 133 | 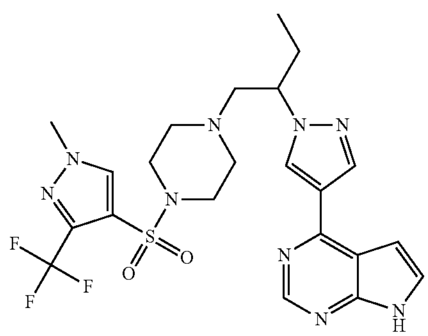 [SMILES: CCC(CN1CCN(S(=O)(=O)c2cn(C)nc2C(F)(F)F)CC1)n1cc(-c2ncnc3[nH]ccc23)cn1] | 4-(1-(1-(4-(1-methyl-3-(trifluoromethyl)-1H-pyrazol-4-ylsulfonyl)piperazin-1-yl)butan-2-yl)-1H-pyrazol-4-yl)-7H-pyrrolo[2,3-d]pyrimidine | 538 | 115 |
| 134 | 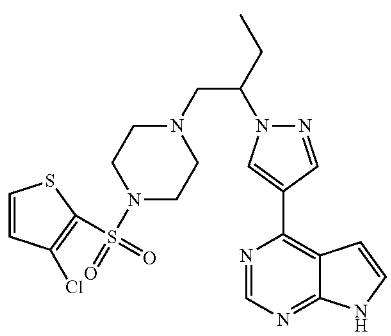 [SMILES: CCC(CN1CCN(S(=O)(=O)c2sccc2Cl)CC1)n1cc(-c2ncnc3[nH]ccc23)cn1] | 4-(1-(1-(4-(thiophen-2-ylsulfonyl)piperazin-1-yl)butan-2-yl)-1H-pyrazol-4-yl)-7H-pyrrolo[2,3-d]pyrimidine | 472 | 115 |
| 135 | 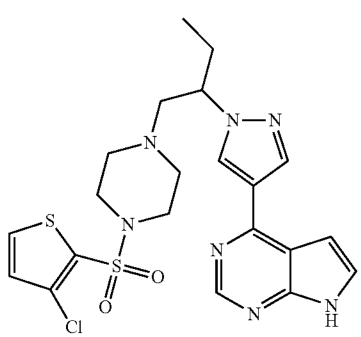 [SMILES: CCC(CN1CCN(S(=O)(=O)c2sccc2Cl)CC1)n1cc(-c2ncnc3[nH]ccc23)cn1] | 4-(1-(1-(4-(3-chlorothiophen-2-ylsulfonyl)piperazin-1-yl)butan-2-yl)-1H-pyrazol-4-yl)-7H-pyrrolo[2,3-d]pyrimidine | 506 | 115 |

-continued

| Ex. No. | Structure | Name | MS (M + H) | Prep. Ex. No. |
|---|---|---|---|---|
| 136 | 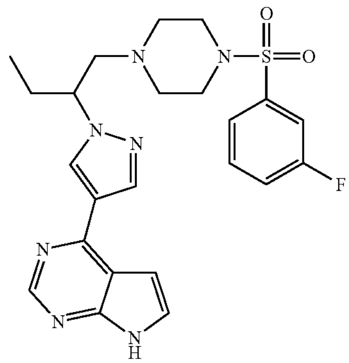 [SMILES: CCC(CN1CCN(S(=O)(=O)c2cccc(F)c2)CC1)n1cc(-c2ncnc3[nH]ccc23)cn1] | 4-(1-(1-(4-(3-fluorophenylsulfonyl)piperazin-1-yl)butan-2-yl)-1H-pyrazol-4-yl)-7H-pyrrolo[2,3-d]pyrimidine | 484 | 115 |
| 137 | 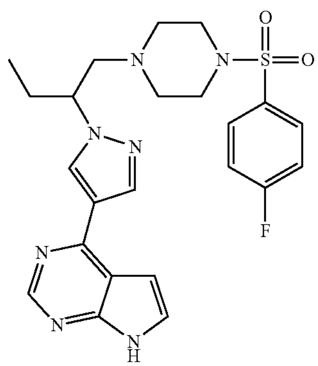 [SMILES: CCC(CN1CCN(S(=O)(=O)c2ccc(F)cc2)CC1)n1cc(-c2ncnc3[nH]ccc23)cn1] | 4-(1-(1-(4-(4-fluorophenylsulfonyl)piperazin-1-yl)butan-2-yl)-1H-pyrazol-4-yl)-7H-pyrrolo[2,3-d]pyrimidine | 484 | 115 |
| 138 | 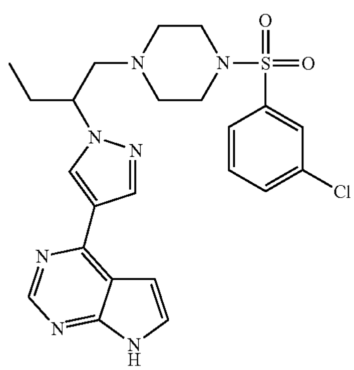 [SMILES: CCC(CN1CCN(S(=O)(=O)c2cccc(Cl)c2)CC1)n1cc(-c2ncnc3[nH]ccc23)cn1] | 4-(1-(1-(4-(2-chlorophenylsulfonyl)piperazin-1-yl)butan-2-yl)-1H-pyrazol-4-yl)-7H-pyrrolo[2,3-d]pyrimidine | 500 | 115 |
| 139 | 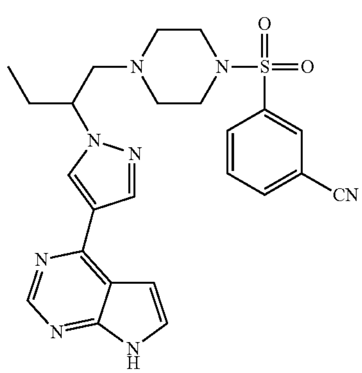 [SMILES: CCC(CN1CCN(S(=O)(=O)c2cccc(C#N)c2)CC1)n1cc(-c2ncnc3[nH]ccc23)cn1] | 3-(4-(2-(4-(7H-pyrrolo[2,3-d]pyrimidin-4-yl)-1H-pyrazol-1-yl)butyl)piperazin-1-ylsulfonyl)benzonitrile | 491 | 115 |

-continued

| Ex. No. | Structure | Name | MS (M + H) | Prep. Ex. No. |
|---|---|---|---|---|
| 140 | 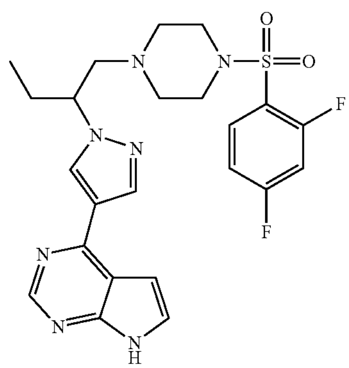 [SMILES: CCC(CN1CCN(S(=O)(=O)c2ccc(F)cc2F)CC1)n1cc(-c2ncnc3[nH]ccc23)cn1] | 4-(1-(1-(4-(2,4-difluorophenylsulfonyl)piperazin-1-yl)butan-2-yl)-1H-pyrazol-4-yl)-7H-pyrrolo[2,3-d]pyrimidine | 502 | 115 |
| 141 | 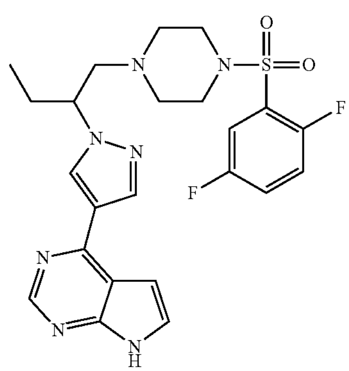 [SMILES: CCC(CN1CCN(S(=O)(=O)c2cc(F)ccc2F)CC1)n1cc(-c2ncnc3[nH]ccc23)cn1] | 4-(1-(1-(4-(2,5-difluorophenylsulfonyl)piperazin-1-yl)butan-2-yl)-1H-pyrazol-4-yl)-7H-pyrrolo[2,3-d]pyrimidine | 502 | 115 |
| 142 | 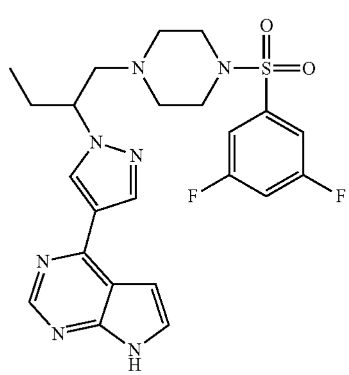 [SMILES: CCC(CN1CCN(S(=O)(=O)c2cc(F)cc(F)c2)CC1)n1cc(-c2ncnc3[nH]ccc23)cn1] | 4-(1-(1-(4-(3,5-difluorophenylsulfonyl)piperazin-1-yl)butan-2-yl)-1H-pyrazol-4-yl)-7H-pyrrolo[2,3-d]pyrimidine | 502 | 115 |
| 143 | 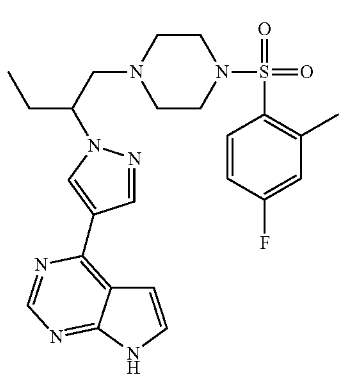 [SMILES: CCC(CN1CCN(S(=O)(=O)c2ccc(F)cc2C)CC1)n1cc(-c2ncnc3[nH]ccc23)cn1] | 4-(1-(1-(4-(4-floro-2-methylphenylsulfonyl)piperazin-1-yl)butan-2-yl)-1H-pyrazol-4-yl)-7H-pyrrolo[2,3-d]pyrimidine | 498 | 115 |

| Ex. No. | Structure | Name | MS (M + H) | Prep. Ex. No. |
|---|---|---|---|---|
| 144 | 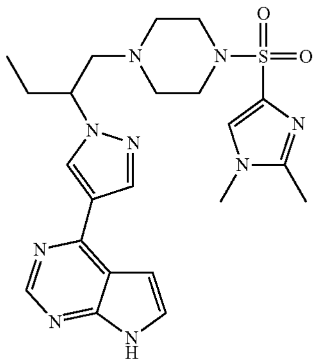 [SMILES: CCC(CN1CCN(S(=O)(=O)c2cn(C)c(C)n2)CC1)n1cc(-c2ncnc3[nH]ccc23)cn1] | 4-(1-(1-(4-(1,2-dimethyl-1H-imidazol-4-ylsulfonyl)piperazin-1-yl)butan-2-yl)-1H-pyrazol-4-yl)-7H-pyrrolo[2,3-d]pyrimidine | 484 | 115 |
| 145 | 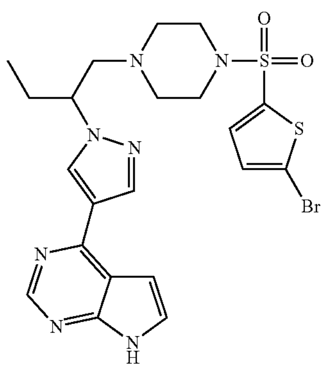 [SMILES: CCC(CN1CCN(S(=O)(=O)c2ccc(Br)s2)CC1)n1cc(-c2ncnc3[nH]ccc23)cn1] | 4-(1-(1-(4-(5-bromothiophen-2-ylsulfonyl)piperazin-1-yl)butan-2-yl)-1H-pyrazol-4-yl)-7H-pyrrolo[2,3-d]pyrimidine | 550 | 115 |
| 148 | 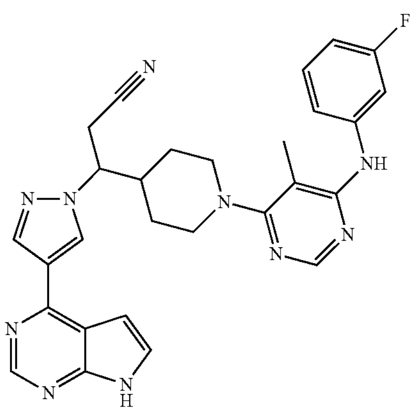 [SMILES: Cc1c(Nc2cccc(F)c2)ncnc1N1CCC(C(CC#N)n2cc(-c3ncnc4[nH]ccc34)cn2)CC1] | 3-(4-(7H-pyrrolo[2,3-d]pyrimidin-4-yl)-1H-pyrazol-1-yl)-3-(1-(6-(3-fluorophenylamino)-5-methylpyrimidin-4-yl)piperidin-4-yl)propanenitrile | 523 | 146 |
| 149 | 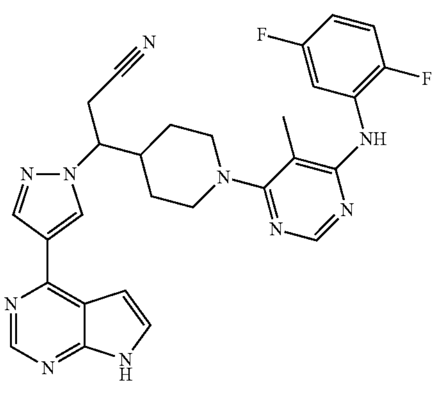 [SMILES: Cc1c(Nc2cc(F)ccc2F)ncnc1N1CCC(C(CC#N)n2cc(-c3ncnc4[nH]ccc34)cn2)CC1] | 3-(4-(7H-pyrrolo[2,3-d]pyrimidin-4-yl)-1H-pyrazol-1-yl)-3-(1-(6-(2,5-difluorophenylamino)-5-methylpyrimidin-4-yl)piperidin-4-yl)propanenitrile | 541 | 146 |

| Ex. No. | Structure | Name | MS (M + H) | Prep. Ex. No. |
|---|---|---|---|---|
| 150 | 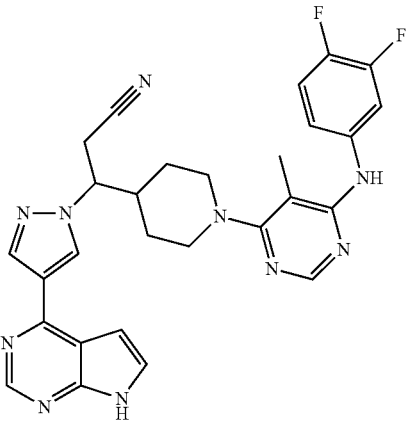 [SMILES: Cc1c(Nc2ccc(F)c(F)c2)ncnc1N1CCC(C(CC#N)n2cc(-c3ncnc4[nH]ccc34)cn2)CC1] | 3-(4-(7H-pyrrolo[2,3-d]pyrimidin-4-yl)-1H-pyrazol-1-yl)-3-(1-(6-(3,4-difluorophenylamino)-5-methylpyrimidin-4-yl)piperidin-4-yl)propanenitrile | 541 | 146 |
| 151 | 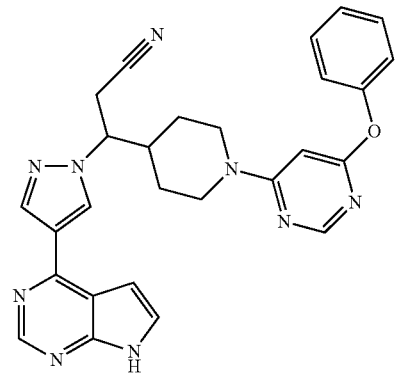 [SMILES: N#CCC(C1CCN(c2cc(Oc3ccccc3)ncn2)CC1)n1cc(-c2ncnc3[nH]ccc23)cn1] | 3-(4-(7H-pyrrolo[2,3-d]pyrimidin-4-yl)-1H-pyrazol-1-yl)-3-(1-(6-phenoxypyrimidin-4-yl)piperidin-4-yl)propanenitrile | 492 | 146 |
| 152 | 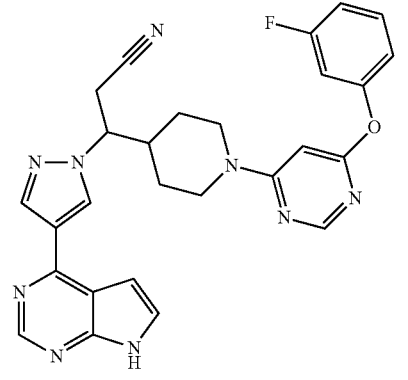 [SMILES: N#CCC(C1CCN(c2cc(Oc3cccc(F)c3)ncn2)CC1)n1cc(-c2ncnc3[nH]ccc23)cn1] | 3-(4-(7H-pyrrolo[2,3-d]pyrimidin-4-yl)-1H-pyrazol-1-yl)-3-(1-(6-(3-fluorophenoxy)pyrimidin-4-yl)piperidin-4-yl)propanenitrile | 510 | 146 |

| Ex. No. | Structure | Name | MS (M + H) | Prep. Ex. No. |
|---|---|---|---|---|
| 153 | 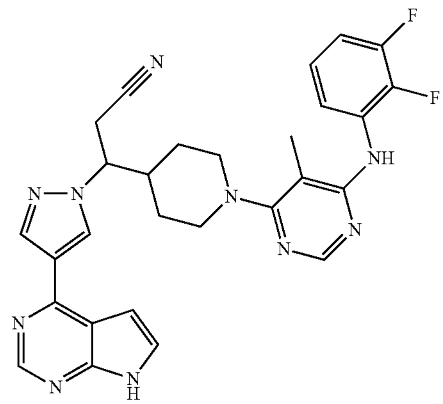 [SMILES: Cc1c(Nc2cccc(F)c2F)ncnc1N1CCC(C(CC#N)n2cc(-c3ncnc4[nH]ccc34)cn2)CC1] | 3-(4-(7H-pyrrolo[2,3-d]pyrimidin-4-yl)-1H-pyrazol-1-yl)-3-(1-(6-(2,3-difluorophenylamino)-5-methylpyrimidin-4-yl)piperidin-4-yl)propanenitrile | 541 | 146 |
| 154 | 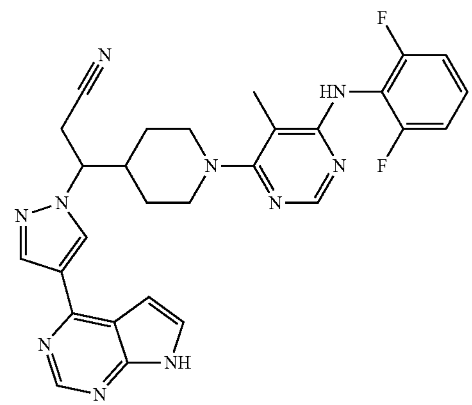 [SMILES: Cc1c(Nc2c(F)cccc2F)ncnc1N1CCC(C(CC#N)n2cc(-c3ncnc4[nH]ccc34)cn2)CC1] | 3-(4-(7H-pyrrolo[2,3-d]pyrimidin-4-yl)-1H-pyrazol-1-yl)-3-(1-(6-(2,6-difluorophenylamino)-5-methylpyrimidin-4-yl)piperidin-4-yl)propanenitrile | 541 | 147 |
| 155 | 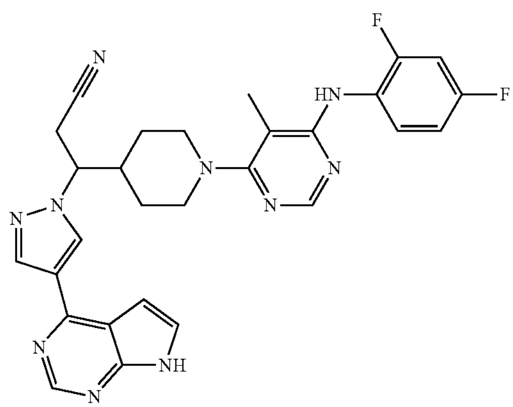 [SMILES: Cc1c(Nc2ccc(F)cc2F)ncnc1N1CCC(C(CC#N)n2cc(-c3ncnc4[nH]ccc34)cn2)CC1] | 3-(4-(7H-pyrrolo[2,3-d]pyrimidin-4-yl)-1H-pyrazol-1-yl)-3-(1-(6-(2,4-difluorophenylamino)-5-methylpyrimidin-4-yl)piperidin-4-yl)propanenitrile | 541 | 146 |

| Ex. No. | ¹H NMR (DMSO) |
|---|---|
| 118 | δ 12.05 (1H, br); 8.72 (1H, s); 8.68 (1H, s); 8.28 (1H, s); 7.57 (1H, d); 7.4 (1H, q); 7.35 (1H, t); 7.14 (1H, t); 6.96 (1H, d); 4.45 (1H, m); 3.53 (2H, br); 3.09 (2H, br); 2.87 (1H, m); 2.65 (1H, m); 2.58 (1H, br); 2.4 (1H, br); 2.35 (1H, br); 2.22 (1H, m); 1.82 (2H, m); 0.67 (3H, m) |
| 119 | δ 12.05 (1H, br); 8.7 (1H, s); 8.65 (1H, s); 8.28 (1H, s); 7.58 (1H, d); 7.35 (2H, m); 7.15 (1H, m); 6.98 (1H, d); 4.42 (1H, m); 3.53 (2H, br); 3.1 (2H, br); 2.87 (1H, m); 2.7 (1H, m); 2.58 (1H, br); 2.42 (1H, br); 2.35 (1H, br); 2.22 (1H, m); 1.82 (2H, m); 0.70 (3H, m) |

| Ex. No. | ¹H NMR (DMSO) |
|---|---|
| 120 | δ 8.62 (1H, s); 8.6 (1H, s); 8.21 (1H, s); 7.54 (1H, d); 7.45 (1H, m); 7.2 (1H, m) 7.08 (1H, m); 6.94 (1H, d); 4.4 (1H, m); 3.5 (2H, br); 3.05 (2H, br); 2.83 (1H, m); 2.63 (1H, m); 2.56 (1H, br); 2.38 (1H, br); 2.33 (1H, br); 2.19 (1H, m); 1.79 (2H, m); 0.63 (3H, m) |
| 121 | δ 8.68 (1H, s); 8.65 (1H, s); 8.3 (1H, s); 7.57 (1H, d); 7.33 (1H, m); 7.1 (2H, m); 6.97 (1H, d); 4.42 (1H, m); 3.5 (2H, br); 3.18 (2H, br); 2.9 (1H, m); 2.65 (1H, m); 2.58 (1H, br); 2.42 (1H, br); 2.35 (1H, br); 2.22 (1H, m); 1.82 (2H, m); 0.68 (3H, m) |
| 122 | δ 12.07 (1H, br); 8.66 (1H, s); 8.63 (1H, s); 8.29 (1H, s); 7.58 (1H, d); 6.99 (1H, m); 6.97 (1H, d); 6.74 (1H, m); 663 (1H, m); 4.42 (1H, m); 3.45 (2H, br); 3.12 (2H, br); 2.83 (1H, m); 2.64 (1H, m); 2.48 (2H, br); 2.3 (2H, m); (1.82) (2H, m); 0.69 (3H, t) |
| 123 | δ 8.68 (1H, s); 8.63 (1H, s); 8.29 (1H, s); 7.58 (1H, d); 7.15 (1H, m); 6.97 (1H, d); 6.74 (1H, m); 663 (1H, m); 4.42 (1H, m); 3.3 (4H, br); 2.85 (1H, m); 2.65 (1H, m); 2.48 (2H, br); 2.35 (2H, br); (1.82) (2H, m); 0.68 (3H, t) |
| 124 | δ 12.05 (1H, br); 8.67 (1H, s); 8.64 (1H, s); 8.27 (1H, s); 7.58 (1H, d); 7.55 (1H, m); 7.16 (2H, m); 6.97 (1H, d); 4.42 (1H, m); 3.5 5 (2H, br); 3.1 (2H, m); 2.91 (1H, m); 2.7 (1H, m); 2.59 (1H, br); 2.42 (1H, br); 2.35 (1H, br); 2.22 (1H, m); 1.82 (2H, m); 0.70 (3H, m) |
| 125 | δ 12.05 (1H, br); 8.67 (1H, s); 8.64 (1H, s); 8.28 (1H, s); 7.58 (1H, d); 7.16 (1H, m); 6.98 (2H, m); 6.75 (1H, m); 4.42 (1H, m); 3.73 (3H, d); 3.47 (2H, br); 2.99 (2H, m); 2.89 (1H, m); 2.68 (1H, m); 2.4-2.1 (4H, br); 1.82 (2H, m); 0.70 (3H, m) |
| 126 | δ 8.63 (1H, s); 8.6 (1H, s); 8.23 (1H, s); 7.65 (1H, m); 7.5 (1H, d); 7.28 (1H, m); 7.01 (1H, m); 6.93 (1H, d); 4.0 (1H, m); 3.49 (4H, m); 2.84 (1H, m); 2.62 (1H, m); 2.45 (2H, m); 2.25 (2H, m); 1.8 (2H, m); 0.65 (3H, m) |
| 127 | δ 12.05 (1H, br); 8.62 (1H, s); 8.58 (1H, s); 8.22 (1H, s); 7.65 (3H, m); 7.58 (3H, m); 6.89 (1H, d); 4.38 (1H, m); 2.81 (1H, m); 2.75 (4H, m); 2.62 (1H, m); 2.57 (2H, m); 2.35 (2H, m); 1.78 (2H, m); 0.63 (3H, m) |
| 128 | δ 12.05 (1H, br); 8.62 (1H, s); 8.59 (1H, s); 8.22 (1H, s); 8.03 (2H, m); 7.83 (2H, m); 7.55 (1H, d); 6.9 (1H, d); 4.38 (1H, m); 2.82 (5H, m); 2.62 (1H, m); 2.57 (2H, m); 2.35 (2H, m); 1.78 (2H, m); 0.63 (3H, m) |
| 129 | δ 8.59 (1H, s); 8.58 (1H, s); 8.2 (1H, s); 8.-7.75 (4H, m); 7.5 (1H, d); 6.85 (1H, d); 4.38 (1H, m); 2.92 (4H, m); 2.78 (1H, m); 2.58 (1H, m); 2.55 (2H, m); 2.32 (2H, m); 1.75 (2H, m); 0.61 (3H, m) |
| 130 | δ 12.0 (1H, br); 8.58 (2H, s); 8.21 (1H, s); 7.92 (2H, m); 7.78 (2H, m); 7.5 (1H, d); 6.85 (1H, d); 4.38 (1H, m); 2.99 (4H, m); 2.82 (1H, m); 2.62 (1H, m); 2.55 (2H, m); 2.34 (2H, m); 1.78 (2H, m); 0.63 (3H, m) |
| 131 | δ 12.0 (1H, br); 8.59 (1H, s); 5.58 (1H, s); 8.2 (1H, s); 7.85 1 (H, t); 7.6 (1H, m); 7.5 (1H, d); 7.4 (1H, m); 6.9 (1H, d); 4.38 (1H, m); 2.98 (4H, m); 2.77 (1H, m); 2.58 (1H, m); 2.53 (2H, m); 2.34 (3H, s); 2.25 (2H, m); 1.78 (2H, m); 0.63 (3H, m) |
| 132 | δ 12.0 (1H, br); 8.59 (2H, s); 8.2 (1H, s); 7.83 (1H, m); 7.57 (1H, m); 7.53 (1H, d); 7.45 (1H, m); 6.85 (1H, d); 4.38 (1H, m); 2.98 (4H, m); 2.79 (1H, m); 2.6 (1H, m); 2.45 (2H, m); 2.25; (2H, m); 1.75 (2H, m); 0.63 (3H, m) |
| 133 | δ 12.05 (1H, br); 8.63 (2H, s); 8.54 (1H, s); 8.25 (1H, s); 7.55 (1H, d); 6.85 (1H, d); 4.4 (1H, m); 3.88 (3H, s); 2.95 (5H, m); 2.6 (3H, m); 2.39 (2H, m); 1.8 (2H, m); 0.65 (3H, m) |
| 134 | δ 8.58 (1H, s); 8.57 (1H, s); 8.2 (1H, s); 7.9 (1H, m); 7.5 (2H, m); 7.15 (1H, m); 6.83 (1H, d); 4.35 (1H, m); 2.87 (5H, m); 2.57 (3H, m); 2.35 (2H, m); 1.75 (2H, m); 0.62 (3H, m) |
| 135 | δ 8.59 (1H, s); 8.2 (1H, s); 7.5 (1H, d); 7.44 (1H, m); 7.21 (1H, d); 6.83 (1H, d); 4.35 (1H, m); 2.8 (5H, m); 2.61 (1H, m); 2.55 (2H, m); 2.35 (2H, m); 1.75 (2H, m); 0.62 (3H, m) |
| 136 | δ 8.61 (1H, s); 8.59 (1H, s); 8.21 (1H, s); 7.62 (1H, m); 7.5 (4H, m); 6.88 (1H, d); 4.38 (1H, m); 2.8 (5H, m); 2.63 (1H, m); 2.45 (2H, m); 2.25; (2H, m); 1.78 (2H, m); 0.64 (3H, m) |
| 137 | δ 8.58 (1H, s); 8.56 (1H, s); 8.19 (1H, s); 7.65 (2H, m); 7.5 (1H, s); 7.35 (2H, m); 6.82 (1H, d); 4.35 (1H, m); 2.75 (1H, m); 2.7 (4H, m); 2.58 (1H, m); 2.51 (2H, m); 2.29; (2H, m); 1.73 (2H, m); 0.61 (3H, m) |
| 138 | δ 8.59 (1H, s); 8.57 (1H, s); 8.2 (1H, s); 7.7-7.52 (4H, m); 7.5 (1H, d); 6.88 (1H, d); 4.33 (1H, m); 2.76 (5H, m); 2.6 (1H, m); 2.48 (2H, m); 2.28 (1H, m); 1.73 (2H, m); 0.61 (3H, m) |
| 139 | δ 8.59 (1H, s); 8.57 (1H, s); 8.2 (1H, s); 8.15 (2H, m); 7.95 (1H, m); 7.62 (1H, m); 7.5 (1H, d); 6.82 (1H, d); 4.35 (1H, m); 2.78 (5H, m); 2.6 (1H, m); 2.55 (2H, m); 2.3; (2H, m); 1.73 (2H, m); 0.60 (3H, m) |

-continued

| Ex. No. | $^1$H NMR (DMSO) |
|---|---|
| 140 | δ 8.62 (1H, s); 8.61 (1H, s); 8.23 (1H, s); 7.78 (1H, m); 7.57 (1H, d); 7.53 (1H, m); 7.24 (1H, m); 6.9 (1H, d); 4.38 (1H, m); 2.95 (4H, m); 2.85 (1H, m); 2.63 (1H, m); 2.58 (2H, m); 2.37; (2H, m); 1.79 (2H, m); 0.64 (3H, m) |
| 141 | δ 12.05 (1H, br); 8.62 (1H, s); 8.61 (1H, s); 8.23 (1H, s); 7.75 (4H, m); 6.9 (1H, d); 4.39 (1H, m); 2.98 (4H, m); 2.85 (1H, m); 2.64 (1H, m); 2.58 (2H, m); 2.37; (2H, m); 1.79 (2H, m); 0.65 (3H, m) |
| 142 | δ 8.62 (1H, s); 8.6 (1H, s); 8.23 (1H, s); 7.62 (1H, m); 7.54 (1H, d); 7.4 (1H, m); 6.9 (1H, d); 4.38 (1H, m); 2.85 (1H, m); 2.63 (1H, m); 2.58 (2H, m); 2.37; (2H, m); 1.78 (2H, m); 0.64 (3H, m) |
| 143 | δ 8.62 (2H, s); 8.23 (1H, s); 7.78 (1H, m); 7.55 (1H, d); 7.28 (1H, m); 7.19 (1H, m); 6.92 (1H, d); 4.38 (1H, m); 2.9 (4H, m); 2.85 (1H, m); 2.63 (1H, m); 2.58 (2H, m); 2.42 (3H, s); 2.33; (2H, m); 1.79 (2H, m); 0.64 (3H, m) |
| 144 | δ 8.62 (1H, s); 8.61 (1H, s); 7.63 (1H, s); 7.57 (1H, d); 6.95 (1H, d); 4.4 (1H, m); 3.51 (3H, s); 2.85 (5H, m); 2.58 (3H, m); 2.35; (2H, m); 2.19 (3H, s); 1.79 (2H, m); 0.64 (3H, m) |
| 145 | δ 12.05 (1H, br); 8.62 (2H, s); 8.23 (1H, s); 7.55 (1H, d); 7.42 (1H, d); 7.38 (1H, d); 6.9 (1H, d); 4.39 (1H, m); 2.83 (5H, m); 2.65 (1H, m); 2.6 (2H, m); 2.38; (2H, m); 1.79 (2H, m); 0.64 (3H, m) |
| 149 | 8.87 (1H, σ); 8.81 (1H, σ); 8.76 (1H, σ); 8.21 (1H, σ); 8.1 (1H, σ); 7.6 (1H, δ); 7.42 (1H, μ); 7.24 (1H, μ); 6.99 (1H, σ); 6.97 (1H, μ); 4.6 (1H, μ); 3.61 (1H, μ); 3.45 (1H, μ); 3.27 (2H, μ); 2.7 (1H, μ); 2.58 (1H, μ); 2.02 (1H, μ); 1.98 (3H, σ); 1.82 (1H, μ); 1.3 (2H, μ); 1.01 (1H, μ) |
| 151 | δ 12.05 (1H, βρ); 8.75 (1H, σ); 8.62 (1H, σ); 8.35 (1H, σ); 8.07 (1H, σ); 7.55 (1H, δ); 7.35 (2H, μ); 7.13 (1H, μ); 7.04 (2H, μ); 6.92 (1H, δ); 6.24 (1H, σ); 4.57 (1H, μ); 4.37 (1H, μ); 4.24 (1H, μ); 3.22 (2H, μ); 2.82 (1H, μ); 2.78 (1H, μ); 2.15 (1H, μ); 1.81 (1H, μ); 1.05 (3H, μ) |
| 152 | δ 12.05 (1H, σ); 8.78 (1H, σ); 8.66 (1H, σ); 8.4 (1H, σ); 8.17 (1H, σ); 7.6 (1H, δ); 7.4 (1H, μ); 7.13 (2H, μ); 6.97 (2H, μ); 6.37 (1H, σ); 4.57 (1H, μ); 4.45 (1H, μ); 4.31 (1H, μ); 3.29 (2H, μ); 2.9 (1H, μ); 2.78 (1H, μ); 2.2 (1H, μ); 1.85 (1H, μ); 1.1 (3H, μ) |
| 153 | δ 12.11 (1H, σ); 8.82 (1H, σ); 8.67 (1H, σ); 8.4 (1H, σ); 8.32 (1H, σ); 8.05 (1H, σ); 7.6 (1H, δ); 7.15 (3H, μ); 6.99 (1H, σ); 4.6 (1H, μ); 3.66 (1H, μ); 3.55 (1H, μ); 3.3 (2H, μ); 2.78 (1H, μ); 2.62 (1H, μ); 2.05 (1H, μ); 2.01 (3H, σ); 1.85 (1H, μ); 1.35 (2H, μ); 1.05 (1H, μ) |

Example 156

4-{[4-{3-cyano-2-[4-(7H-pyrrolo[2,3-d]pyrimidin-4-yl)-1H-pyrazol-1-yl]propyl}-3-(hydroxymethyl)piperazin-1-yl]carbonyl}-3-fluorobenzonitrile trifluoroacetate Salt (Single Isomer Isolated)

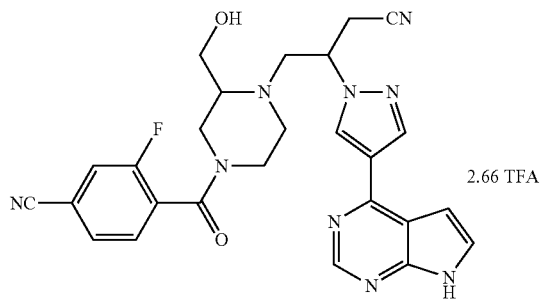 [SMILES: N#CCC(CN1CCN(C(=O)c2ccc(C#N)cc2F)CC1CO)n1cc(-c2ncnc3[nH]ccc23)cn1]

Step 1. tert-butyl 3-({[tert-butyl(dimethyl)silyl]oxy}methyl)piperazine-1-carboxylate (Racemic)

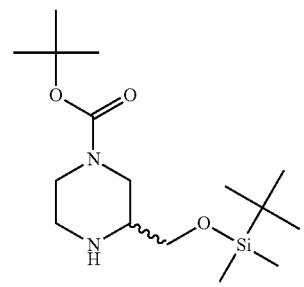 [SMILES: CC(C)(C)OC(=O)N1CCNC(CO[Si](C)(C)C(C)(C)C)C1]

To a solution of racemic tert-butyl 3-(hydroxymethyl)piperazine-1-carboxylate (1.5 g, 6.9 mmol, AstaTech) and 1H-imidazole (1.4 g, 21 mmol) in DMF (20 mL) cooled to 0° C. was added tert-butyldimethylsilyl chloride (2.1 g, 14 mmol). The mixture was then allowed to reach RT and stir for 20 h. The mixture was quenched by the addition of saturated ammonium chloride. The product was extracted with two portions of ethyl acetate. The organic extract was washed with water, brine, dried over sodium sulfate and concentrated to afford a clear oil. Flash chromatography on a 120 g silica gel cartridge, eluting with a slow gradient from 0-6% MeOH in DCM afforded purified product (1.15 g, 50%). ¹H NMR (400 MHz, CDCl₃): δ 4.00-1.63 (m, 9H), 1.45 (s, 9H), 0.89 (s, 9H), 0.05 (s, 6H); LCMS (M+H)⁺: 331.2.

Step 2. E- and Z-tert-butyl 3-({[tert-butyl(dimethyl)silyl]oxy}methyl)-4-[3-cyanoprop-2-en-1-yl]piperazine-1-carboxylate (Racemic)

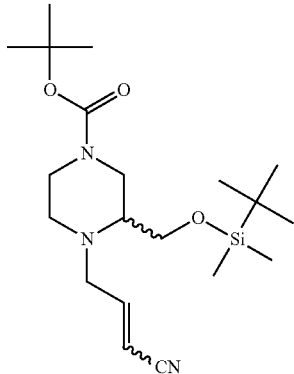 [SMILES: CC(C)(C)OC(=O)N1CCN(CC=CC#N)C(CO[Si](C)(C)C(C)(C)C)C1]

Racemic tert-butyl 3-({[tert-butyl(dimethyl)silyl]oxy}methyl)piperazine-1-carboxylate (0.55 g, 1.7 mmol) was dissolved in acetonitrile (2.2 mL), and 4-bromobut-2-enenitrile (0.267 g, 1.83 mmol as a mixture of E- and Z-isomers, prepared as described in *J. Am. Chem. Soc.* (1940), 62; pp 974-7) was added. Sodium bicarbonate (0.280 g, 3.33 mmol) was then added. After stirring overnight, additional 4-bromobut-2-enenitrile (73 mg, 0.5 mmol) was added. After stirring for 24 h, the reaction was considered complete. The mixture was filtered and concentrated. Flash chromatography, using a 40 g silica gel cartridge and eluting with 0-35% EtOAc:Hexanes afforded product as a mixture of E- and Z-isomers. (400 mg, 60%). ¹H NMR (400 MHz, CDCl₃): δ 6.74 (dt, 1H, trans), 6.66-6.56 (m, 1H, cis), 5.65 (dt, 1H, trans), 5.46 (dt, 1H, cis), 3.86-2.83 (m, 16H), 2.77-2.60 (m, 2H), 2.54-2.43 (m, 2H), 2.41-2.23 (m, 2H), 1.45 (s, 18H), 0.89 (s, 9H), 0.87 (s, 9H), 0.05 (s, 6H), 0.04 (s, 3H), 0.03 (s, 3H); LCMS (M+H)⁺: 396.2.

Step 3. tert-butyl 3-({[tert-butyl(dimethyl)silyl]oxy}methyl)-4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate (Mixture of Diastereomers)

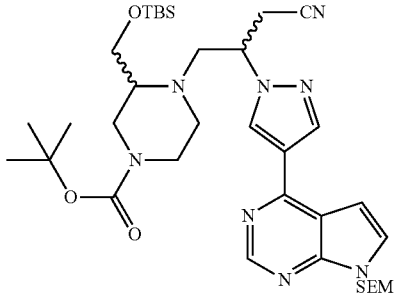

To a mixture of tert-butyl 3-({[tert-butyl(dimethyl)silyl]oxy}methyl)-4-[3-cyanoprop-2-en-1-yl]piperazine-1-car-
boxylate (0.31 g, 0.78 mmol, as a mixture of E- and Z-isomers from Step 2) and 4-(1H-pyrazol-4-yl)-7-{[2-(trimethylsilyl)ethoxy]methyl}-7H-pyrrolo[2,3-d]pyrimidine (0.18 g, 0.56 mmol, prepared as described in WO 2007/070514 Example 65) in DMF (0.50 mL) was added potassium carbonate (0.23 g, 1.7 mmol). The mixture was stirred at ambient temperature overnight. The mixture was filtered, diluted with EtOAc, washed with water three times, and washed once with brine, dried over sodium sulfate, decanted and concentrated in vacuo. Flash chromatography, on a 40 g silica gel cartridge, eluting with a gradient from 0-70% EtOAc in hexanes afforded product as a mixture of diastereomers (330 mg, 83%). ¹H NMR (400 MHz, CDCl₃): δ 8.84 (s, 2H), 8.33-8.29 (m, 4H), 7.40 (d, 2H), 6.78 (d, 2H), 5.68 (s, 4H), 4.66-4.52 (m, 2H), 3.81-2.29 (m, 30H), 1.43 (s, 9H), 1.43 (s, 9H), 0.92 (dd, 4H), 0.91 (s, 9H), 0.87 (s, 9H), 0.09 (s, 6H), 0.04 (s, 6H), −0.06 (s, 18H); LCMS (M+H)⁺: 711.5.

Step 4. 4-[2-(hydroxymethyl)piperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloric acid Salt (Mixture of Diastereomers)

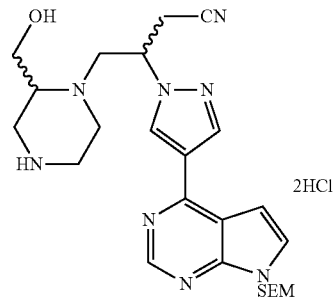 [SMILES: C[Si](C)(C)CCOCn1ccc2c(-c3cnn(C(CC#N)CN4CCNCC4CO)c3)ncnc21]

4.0 M of hydrogen chloride in p-dioxane (1.6 mL, 6.4 mmol) was added to a solution of tert-butyl 3-({[tert-butyl(dimethyl)silyl]oxy}methyl)-4-{3-cyano-2-[4-(7-{[2-(trimethylsilyl)ethoxy]methyl}-7H-pyrrolo[2,3-d]pyrimidin-4-yl)-1H-pyrazol-1-yl]propyl}piperazine-1-carboxylate (0.32 g, 0.45 mmol, a mixture of diastereomers from Step 3) in 1,4-dioxane (2 mL). After stirring for 80 min, solvent was removed from the mixture in vacuo to afford the product as a light yellow solid, which was used without further purification (270 mg). LCMS (M+H)⁺: 497.2.

Step 5. 4-{[4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(hydroxymethyl)piperazin-1-yl]carbonyl}-3-fluorobenzonitrile (Four Isomers Isolated)

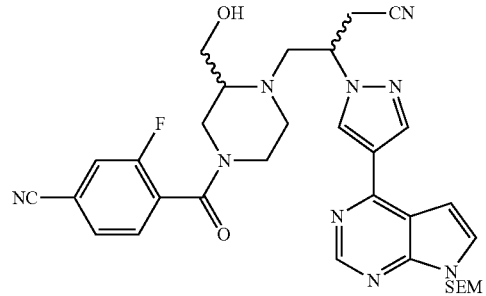 [SMILES: C[Si](C)(C)CCOCn1ccc2c(-c3cnn(C(CC#N)CN4CCN(C(=O)c5ccc(C#N)cc5F)CC4CO)c3)ncnc21]

4-[2-(hydroxymethyl)piperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloric acid salt (0.26 g, 0.46 mmol, prepared as in Step 4) was added to a mixture of 4-cyano-2-fluorobenzoic acid (106 mg, 0.639 mmol, Alfa Aesar), N,N,N',N'-tetramethyl-O-(7-azabenzotriazol-1-yl)uronium hexafluorophosphate (208 mg, 0.548 mmol) and triethylamine (382 µL, 2.74 mmol) in THF (5.4 mL) that was pre-stirred at RT for 15 min. After addition, the mixture was stirred for 1 h. Ethyl acetate and water were added. The organic layer was washed with water, 0.1N NaOH and brine, dried over sodium sulfate and concentrated. Flash chromatography, using a 40 g silica gel cartridge and eluting with 0-5% MeOH in EtOAc afforded a viscous oil (200 mg, 68%). Chiral HPLC (Chiral Technologies ChiralPak IA-H column, 20×250 mm, 5 micron particle size, eluting with 45% ethanol in hexanes at a flow rate of 8 mL/minute) afforded separation of individual isomers. Retention times: peak 1: 2.148 min, peak 2: 6.074 min, peak 3: 9.283 min, peak 4: 16.879 min. Peak 1: (41 mg), $^1$H NMR (400 MHz, CDCl$_3$, rotamers): δ 8.84 (s, 0.4H), 8.83 (s, 0.6H), 8.36 (s, 0.4H), 8.35 (s, 0.6H), 8.31 (s, 0.4H), 8.29 (s, 0.6H), 7.54-7.37 (m, 4H), 6.78 (d, 0.4H), 6.77 (d, 0.6H), 5.68, 5.67 (2s, 2H), 4.68 (dddd, 1H), 3.96-0.78 (m, 17H), −0.07 (s, 9H); LCMS (M+H)$^+$: 644.3. Peak 2: (25 mg), $^1$H NMR (400 MHz, CDCl$_3$, rotamers): δ 8.84 (s, 0.4H), 8.83 (s, 0.6H), 8.36 (s, 0.4H), 8.35 (s, 0.6H), 8.31 (s, 0.4H), 8.29 (s, 0.6H), 7.54-7.37 (m, 4H), 6.78 (d, 0.4H), 6.77 (d, 0.6H), 5.68, 5.67 (2s, 2H), 4.68 (dddd, 1H), 3.96-0.78 (m, 17H), −0.07 (s, 9H); LCMS (M+H)$^+$: 644.1. Peak 3: (25 mg), $^1$H NMR (400 MHz, CDCl$_3$, rotamers): δ 8.85 (s, 0.5H), 8.83 (s, 0.5H), 8.37-8.32 (m, 2H), 7.54-7.38 (m, 4H), 6.79 (d, 1H), 5.68 (s, 2H), 4.77-4.60 (m, 1H), 4.22-0.81 (m, 17H), −0.07 (s, 9H); LCMS (M+H)$^+$: 644.2. Peak 4: (46 mg), $^1$H NMR (400 MHz, CDCl$_3$, rotamers): δ 8.85 (s, 0.5H), 8.83 (s, 0.5H), 8.37-8.32 (m, 2H), 7.54-7.38 (m, 4H), 6.79 (d, 1H), 5.68 (s, 2H), 4.77-4.60 (m, 1H), 4.22-0.81 (m, 17H), −0.07 (s, 9H); LCMS (M+H)$^+$: 644.3.

Step 6. 4-{[4-{3-cyano-2-[4-(7H-pyrrolo[2,3-d]pyrimidin-4-yl)-1H-pyrazol-1-yl]propyl}-3-(hydroxymethyl)piperazin-1-yl]carbonyl}-3-fluorobenzonitrile trifluoroacetate Salt (Single Isomer)

4-{[4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(hydroxymethyl)piperazin-1-yl]carbonyl}-3-fluorobenzonitrile (9 mg, 0.01 mmol; peak 1 from Step 5) was stirred in a solution of 1:1 TFA:DCM (2 mL) for 1 h. Solvents were removed in vacuo. The residue was dissolved in methanol (1.0 mL), and ethylenediamine (0.050 mL, 0.75 mmol) was added. After 30 min, the product was purified via preparative HPLC-MS (C18, eluting first with a gradient of H$_2$O/MeCN containing 0.15% NH$_4$OH, then repurified eluting with a gradient of H$_2$O/MeCN containing 0.1% TFA) and lyophilized to afford product as the (2.66×) trifluoroacetate salt (6.3 mg, 60%). $^1$H NMR (500 MHz, DMSO-d$_6$, 90° C.): δ 12.11 (br s, 1H), 8.77 (s, 1H), 8.74 (s, 1H), 8.38 (s, 1H), 7.84 (d, 1H), 7.71 (d, 1H), 7.63-7.60 (m, 1H), 7.55 (t, 1H), 6.99 (br d, 1H), 4.92-4.85 (m, 1H), 3.85-2.35 (m, 13H); $^{19}$F NMR (400 MHz, DMSO-d$_6$): δ −74.94 (s, 8F), −114.23 to −114.96 (m, 1F); LCMS (M+H)$^+$: 514.2.

Peak 2 from Step 5 was deprotected and purified in the same manner as in Step 6 and peaks 3 and 4 were deprotected in the same manner but purified using only acidic conditions (C18 eluting with a gradient of H$_2$O/MeCN containing 0.1% TFA) to provide the deprotected compounds as the trifluoroacetate salts (for comparison):

Peak 2: $^1$H NMR (500 MHz, DMSO-d$_6$, 90° C.): δ 12.06 (br s, 1H), 8.76 (s, 1H), 8.72 (s, 1H), 8.36 (s, 1H), 7.84 (dd, 1H), 7.71 (d, 1H), 7.60 (dd, 1H), 7.55 (t, 1H), 6.98 (d, 1H), 4.92-4.84 (m, 1H), 3.97-2.33 (m, 13H); $^{19}$F NMR (400 MHz, DMSO-d$_6$): δ −74.87 (s, 9F), −114.31 to −114.83 (m, 1F); LCMS (M+H)$^+$: 514.2.

Peak 3: $^1$H NMR (400 MHz, CD$_3$OD, rotamers): δ 8.96, 8.95 (2s, 1H), 8.88 (s, 1H), 8.52, 8.51 (2s, 1H), 7.86 (2d, 1H), 7.70-7.62 (m, 2H), 7.57-7.50 (m, 1H), 7.29, 7.28 (2d, 1H), 5.03-4.93 (m, 1H), 4.00-2.34 (m, 13H); $^{19}$F NMR (400 MHz, CD$_3$OD): δ −77.67 (s, 9F), −115.18 to −115.62 (m, 1F); LCMS (M+H)$^+$: 514.2.

Peak 4: $^1$H NMR (500 MHz, DMSO-d$_6$, 90° C.): δ 12.10 (br s, 1H), 8.77 (s, 1H), 8.73 (s, 1H), 8.37 (s, 1H), 7.84 (d, 1H), 7.70 (d, 1H), 7.61 (d, 1H), 7.55 (t, 1H), 6.99 (d, 1H), 4.91 (tt, 1H), 3.90-2.26 (m, 13H); $^{19}$F NMR (400 MHz, DMSO-d$_6$): δ −74.89 (s, 9F), −114.30 to −114.70 (m, 1F); LCMS (M+H)$^+$: 514.2.

Example 157

4-{[4-{3-cyano-2-[4-(7H-pyrrolo[2,3-d]pyrimidin-4-yl)-1H-pyrazol-1-yl]propyl}-3-(methoxymethyl)piperazin-1-yl]carbonyl}-3-fluorobenzonitrile (Single Isomer Isolated)

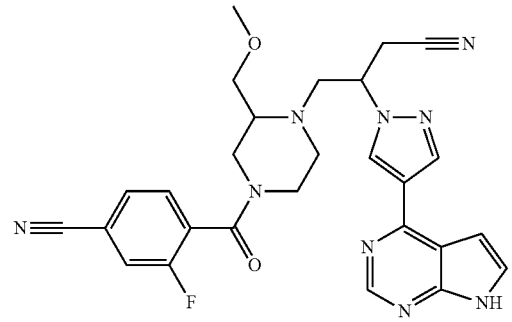 [SMILES: COCC1CN(C(=O)c2ccc(C#N)cc2F)CCN1CC(CC#N)n1cc(-c2ncnc3[nH]ccc23)cn1]

Step 1. tert-butyl 3-(methoxymethyl)piperazine-1-carboxylate (Racemic)

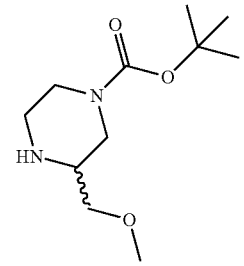 [SMILES: COCC1CN(C(=O)OC(C)(C)C)CCN1]

A suspension of sodium hydride (0.10 g, 2.6 mmol, 60% in mineral oil) in THF (6.0 mL) at 0° C., was treated with a solution of tert-butyl 3-(hydroxymethyl)piperazine-1-carboxylate (0.56 g, 2.6 mmol, racemic, AstaTech) in THF (6.0 mL). After 15 min, methyl iodide (0.16 mL, 2.6 mmol) was added. The mixture was allowed to warm to RT and stir for 1.5 h. The reaction was then quenched with water, and extracted with four portions of DCM. The combined extracts were dried over sodium sulfate, decanted and concentrated. Flash chromatography using a 40 g silica gel cartridge, eluting with a gradient from 0-15% MeOH in DCM afforded the purified desired product, as the second product to elute (60 mg, 10%). $^1$H NMR (500 MHz, CDCl$_3$): δ 3.90 (br s, 2H), 3.37 (dd, 1H), 3.34 (s, 3H), 3.25 (dd, 1H), 2.99-2.92 (m, 1H), 2.90-2.79 (m, 2H), 2.72 (td, 1H), 2.57 (br s, 1H), 2.15 (br s, 1H), 1.45 (s, 9H); LCMS (M+H)$^+$: 231.2.

Step 2. E- and Z-tert-butyl 4-[3-cyanoprop-2-en-1-yl]-3-(methoxymethyl)piperazine-1-carboxylate (Racemic)

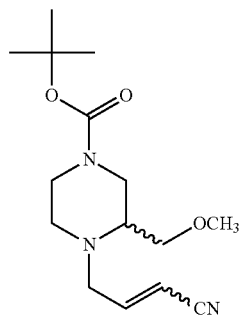 [SMILES: COCC1CN(C(=O)OC(C)(C)C)CCN1CC=CC#N]

Racemic tert-butyl 3-(methoxymethyl)piperazine-1-carboxylate (54 mg, 0.23 mmol; from Step 1) was dissolved in acetonitrile (0.31 mL), and into the mixture was added 4-bromobut-2-enenitrile (51 mg, 0.35 mmol, as a mixture of E- and Z-isomers prepared as described in *J. Am. Chem. Soc.* (1940), 62; 974-7) followed by sodium bicarbonate (39 mg, 0.47 mmol). After 4 days, the mixture was filtered and solvent removed in vacuo. The residue was treated with 1N HCl to pH 1, the aqueous solution was extracted with EtOAc, the extract was then discarded. The aqueous phase was then made basic by the addition of solid sodium bicarbonate, and the product was extracted with two portions of EtOAc. The extracts were washed with brine, dried over sodium sulfate, decanted and concentrated to afford product as a mixture of E- and Z-olefin isomers, which was used without further purification (54 mg, 78%). $^1$H NMR (400 MHz, CDCl$_3$): δ 6.74 (dt, 1H, trans), 6.63 (ddd, 1H, cis), 5.63 (dt, 1H, trans), 5.47 (dt, 1H, cis), 3.82-2.93 (m, 16H), 3.34 (s, 3H), 3.32 (s, 3H), 2.74 (dt, 1H), 2.68 (ddd, 1H), 2.57-2.48 (m, 2H), 2.40-2.21 (m, 2H), 1.45 (s, 18%); LCMS (M-tBu+2H)$^+$: 240.1.

Step 3. tert-butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(methoxymethyl) piperazine-1-carboxylate (Mixture of Diastereomers)

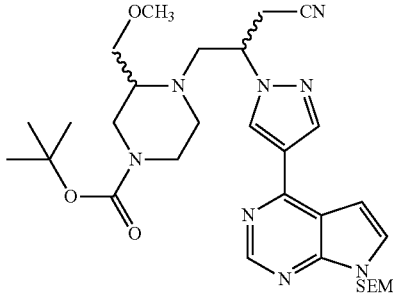 [SMILES: COCC1CN(C(=O)OC(C)(C)C)CCN1CC(CC#N)n1cc(-c2ncnc3c2ccn3COCC[Si](C)(C)C)cn1]

A mixture of tert-butyl 4-[3-cyanoprop-2-en-1-yl]-3-(methoxymethyl)piperazine-1-carboxylate (54 mg, 0.18 mmol; as a mixture of E- and Z-olefin isomers from Step 2) and 4-(1H-pyrazol-4-yl)-7-{[2-(trimethylsilyl)ethoxy]methyl}-7H-pyrrolo[2,3-d]pyrimidine (58 mg, 0.18 mmol, prepared as described in WO 2007/070514 Example 65) in DMF (0.28 mL, 3.6 mmol) was treated with potassium carbonate (0.081 g, 0.58 mmol) and stirred for 5 h. The mixture was filtered and the filtrate was diluted with EtOAc, which was then washed with water (3 times), brine (once), dried over sodium sulfate, decanted and concentrated. Flash chromatography, using a 12 g silica gel cartridge and eluting with a gradient of 0-100% EtOAc in hexanes afforded an impure mixture of diastereomers which was used without further purification in the next step (91 mg, 57%). LCMS (M+H)$^+$: 611.3.

Step 4. 4-[2-(methoxymethyl)piperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloric acid Salt (Mixture of Diastereomers)

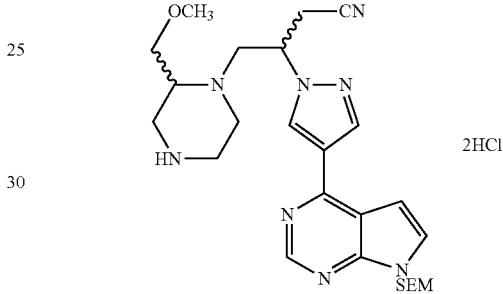

A solution of tert-butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(methoxymethyl)piperazine-1-carboxylate (91 mg, 0.10 mmol, as a mixture of diastereomers from Step 3) in 1,4-dioxane (0.6 mL) was treated with 4.0 M of hydrogen chloride in p-dioxane (0.50 mL, 2.0 mmol). After the mixture was stirred at RT for 80 min, solvent was removed in vacuo to afford product which was used without purification in Step 5. LCMS (M+H)$^+$: 511.2.

Step 5. 4-{[4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(methoxymethyl)piperazin-1-yl]carbonyl}-3-fluorobenzonitrile (Two Individual Isomers Isolated and One Mixture of Two Isomers Isolated)

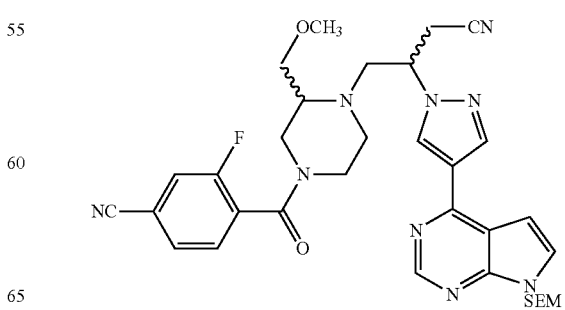

4-cyano-2-fluorobenzoic acid (24.2 mg, 0.146 mmol, Alfa Aesar), N,N,N',N'-tetramethyl-O-(7-azabenzotriazol-1-yl) uronium Hexafluorophosphate (51.7 mg, 0.136 mmol) and triethylamine (87.4 µL, 0.627 mmol) in THF (1.3 mL, 16 mmol) was stirred at RT for 15 min. Following this, 4-[2-(methoxymethyl)piperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloric acid salt (0.061 g, 0.10 mmol, as a mixture of diastereomers from Step 4) was added. After 1 h, the reaction mixture was partitioned between ethyl acetate and water. The organic layer was washed with water, 0.1N NaOH and brine, dried over sodium sulfate, decanted and concentrated. The product was purified by preparative HPLC-MS, (C18 eluting with a gradient of $H_2O$/MeCN/0.1% TFA. After removing solvent in vacuo, the residue was dissolved in saturated sodium bicarbonate and DCM. The aqueous phase was extracted with a further portion of DCM. The combined extracts were dried over sodium sulfate, decanted and concentrated under high vacuum to afford product as a mixture of diastereomers (55 mg, 80%). The diastereomers were partially separated using chiral HPLC (Phenomenex Lux Cellulose-1, 20×250 mm, 5 micron particle size, 30% ethanol in hexane, 20 mL/min, 8 mg/injection). Retention time of Peak 1: 32.84 min, retention time of peak 2: 37.30 min, retention time of peak 3: 45.74 min (contains two isomers).

Peak 1: $^1$H NMR (400 MHz, CDCl$_3$, rotamers): δ 8.85 (s, 0.5H), 8.84 (s, 0.5H), 8.32 (s, 1H), 8.31 (s, 0.5H), 8.30 (s, 0.5H), 7.55-7.35 (m, 4H), 6.79 (d, 0.5H), 6.79 (d, 0.5H), 5.68 (s, 2H), 4.70-4.56 (m, 1H), 3.97-0.66 (m, 20H) −0.07 (s, 9H); LCMS (M+H)$^+$: 658.3.

Peak 2: $^1$H NMR (400 MHz, CDCl$_3$, rotamers): δ 8.85 (s, 0.5H), 8.84 (s, 0.5H), 8.33 (s, 1H), 8.31 (s, 0.5H), 8.29 (s, 0.5H), 7.53-7.36 (m, 4H), 6.78 (d, 0.5H), 6.77 (d, 0.5H), 5.68 (s, 1H), 5.67 (s, 1H), 4.63-4.54 (m, 1H), 4.09-0.63 (m, 20H), −0.07 (s, 9H); LCMS (M+H)$^+$: 658.3.

Peak 3: $^1$H NMR (400 MHz, CDCl$_3$, two isomers): δ 8.86-8.82 (m, 2H), 8.36-8.27 (m, 4H), 7.45-7.29 (m, 8H), 6.81-6.75 (m, 2H), 5.68 (s, 4H), 4.71-4.51 (m, 2H), 4.11-0.66 (m, 40H), −0.07 (s, 18H); LCMS (M+H)$^+$: 658.3.

Step 6. 4-{[4-{3-cyano-2-[4-(7H-pyrrolo[2,3-d]pyrimidin-4-yl)-1H-pyrazol-1-yl]propyl}-3-(methoxymethyl)piperazin-1-yl]carbonyl}-3-fluorobenzonitrile (Single Isomer Prepared)

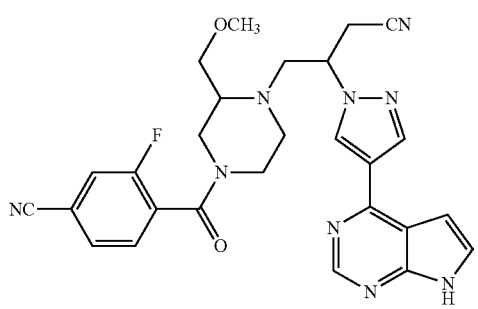 [SMILES: COCC1CN(C(=O)c2ccc(C#N)cc2F)CCN1CC(CC#N)n1cc(-c2ncnc3[nH]ccc23)cn1]

4-{[4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(methoxymethyl)piperazin-1-yl]carbonyl}-3-fluorobenzonitrile (12 mg, 0.018 mmol; Peak 2 from Step 5) was dissolved in a 1:1 mixture of TFA:DCM (3 mL) and was stirred for 1 h. Solvent was removed in vacuo. The residue was then stirred in a solution of methanol (1.5 mL), containing ammonium hydroxide solution (0.15 mL). Purification via preparative HPLC-MS (C18 eluting with a gradient of $H_2O$/MeCN containing 0.15% NH$_4$OH) afforded product (6.5 mg, 67%). $^1$H NMR (400 MHz, DMSO-d$_6$): δ 12.12 (br s, 1H), 8.81 (s, 0.6H), 8.79 (s, 0.4H), 8.68 (s, 0.6H), 8.67 (s, 0.4H), 8.37 (s, 1H), 8.00-7.94 (m, 1H), 7.80-7.73 (m, 1H), 7.63-7.55 (m, 2H), 6.98 (d, 0.6H), 6.97 (d, 0.4H), 4.90-4.76 (tt, 1H), 3.71-2.12 (m, 16H); $^{19}$F NMR (400 MHz, DMSO-d$_6$): δ −114.74 (s, 1F), LCMS (M+H)$^+$: 528.0.

Peaks 1 and 3 from Step 5 were deprotected and purified in the same manner as described in Step 6 to afford the isomers for comparison:

Peak 1: $^1$H NMR (500 MHz, DMSO-d$_6$, 90° C.): δ 11.85 (br s, 1H), 8.70 (s, 1H), 8.68 (s, 1H), 8.32 (s, 1H), 7.85 (d, 1H), 7.71 (br s, 1H), 7.55 (t, 1H), 7.53 (d, 1H), 6.92 (d, 1H), 4.85 (tt, 1H), 3.73-2.26 (m, 16H); $^{19}$F NMR (400 MHz, DMSO-d$_6$): −114.73 (s, 1F); LCMS (M+H)$^+$: 528.0.

Peak 3 (mixture of two isomers): $^1$H NMR (500 MHz, DMSO-d$_6$, 90° C.): δ 11.85 (br s, 1H), 8.71-8.69 (s, 1H), 8.68 (s, 1H), 8.32 (s, 1H), 7.85 (dd, 1H), 7.71 (dd, 1H), 7.56 (t, 1H), 7.53 (d, 1H), 6.92, 6.91 (2d, 1H), 4.89-4.79 (m, 1H), 3.72-2.23 (m, 16H); $^{19}$F NMR (400 MHz, DMSO-d$_6$): −114.72 (s, 1F); LCMS (M+H)$^+$: 528.0.

Example 158

4-[(4-{3-cyano-2-[4-(7H-pyrrolo[2,3-d]pyrimidin-4-yl)-1H-pyrazol-1-yl]propyl}-3-fluoromethylpiperazin-1-yl)carbonyl]-3-fluorobenzonitrile (Single Isomer Prepared)

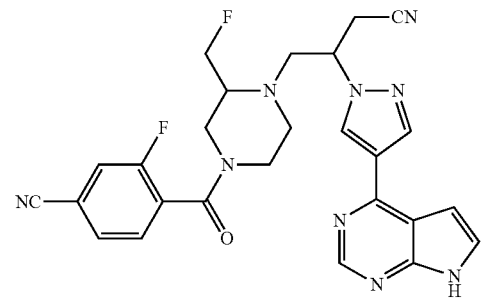 [SMILES: N#CCC(CN1CCN(C(=O)c2ccc(C#N)cc2F)CC1CF)n1cc(-c2ncnc3[nH]ccc23)cn1]

A solution of 4-{[4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(hydroxymethyl)piperazin-1-yl]carbonyl}-3-fluorobenzonitrile (13 mg, 0.020 mmol; Peak 1 from Example 156, Step 5) in methylene chloride (0.87 mL, 14 mmol) was cooled to 0° C., then 2-methoxy-N-(2-methoxyethyl)-N-(trifluoro-λ(4)-sulfanyl)ethanamine (11 µL, 0.060 mmol, Aldrich) was added, followed by ethanol (0.24 µL, 0.0040 mmol). The mixture was stirred at 0° C. for 70 min, then at RT for 20 min, and quenched by the addition of 5% sodium bicarbonate. The mixture was then extracted with EtOAc. The extract was washed with water (2×), brine, dried over sodium sulfate, decanted and concentrated. The yellow solid obtained was then dissolved and stirred for 1 h in a 1:1 mixture of TFA:DCM (1.74 mL). Solvent was removed in vacuo and the residue was stirred in a solution of methanol (0.43 mL) containing aqueous ammonium hydroxide (0.13 mL). After reaction was complete as determined by LCMS, solvent was removed in vacuo. Purification via preparative HPLC-MS (C18, eluting with a gradient of $H_2O$/MeCN containing 0.15% NH₄OH) afforded two regioisomeric products, the second peak to elute was the desired piperazine product (2 mg, 19%). ¹H NMR (500 MHz, CD₃OD, rotamers): δ 8.66 (s, 0.45H), 8.65 (s, 0.55H), 8.62 (s, 0.45H), 8.60 (s, 0.55H), 8.37 (s, 0.45H), 8.37 (s, 0.55H), 7.68-7.58 (m, 2H), 7.55-7.48 (m, 2H), 6.94 (d, 0.45H), 6.93 (d, 0.55H), 4.90-4.43 (m, 3H), 3.81-3.60 (m, 2H), 3.33-3.05 (m, 6H), 2.90-2.50 (m, 3H); ¹⁹F NMR (400 MHz, CD₃OD): −230.21 (t, 1F), −115.45 (br s, 1F); LCMS (M+H)⁺: 516.3.

Example 159

4-{[4-{3-cyano-2-[4-(7H-pyrrolo[2,3-d]pyrimidin-4-yl)-1H-pyrazol-1-yl]propyl}-3-(difluoromethyl)piperazin-1-yl]carbonyl}-3-fluorobenzonitrile (Single Isomer Isolated)

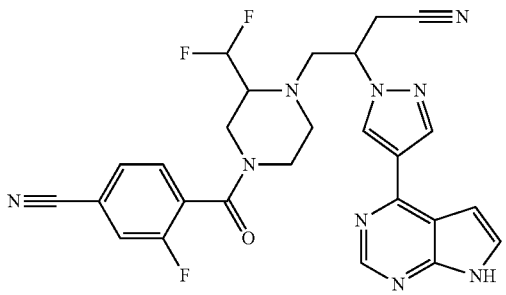 [SMILES: N#CCC(CN1CCN(C(=O)c2ccc(C#N)cc2F)CC1C(F)F)n1cc(-c2ncnc3[nH]ccc23)cn1]

Step 1. tert-butyl 4-benzyl-3-(hydroxymethyl)piperazine-1-carboxylate (Racemic)

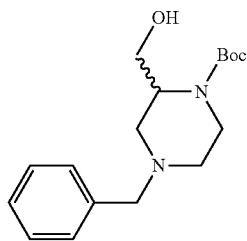 [SMILES: CC(C)(C)OC(=O)N1CCN(Cc2ccccc2)CC1CO]

Triethylamine (0.58 mL, 4.2 mmol) was added to a mixture of racemic tert-butyl 3-(hydroxymethyl)piperazine-1-carboxylate (0.60 g, 2.8 mmol, racemic, AstaTech) and benzyl bromide (0.36 mL, 3.0 mmol) in acetonitrile (5.0 mL). The mixture was heated to 80° C. in an oil bath for 4 h, then allowed to cool and stir at ambient temperature overnight. Solvent was removed in vacuo and the residue was dissolved in methylene chloride. The solution was washed with 0.1N NaOH, dried over sodium sulfate and concentrated. Flash chromatography, using a 40 g silica gel cartridge and eluting with a gradient from 0-60% EtOAc in hexanes afforded product as a viscous oil (630 mg, 71%). ¹H NMR (300 MHz, CDCl₃): δ 7.37-7.22 (m, 5H), 4.02 (d, 1H), 3.87 (dd, 1H), 3.69 (dd, 1H), 3.63-3.50 (m, 2H), 3.41 (d, 1H), 3.41-3.27 (br m, 1H), 3.22-3.06 (br m, 1H), 2.84-2.71 (br m, 1H), 2.64-2.50 (br m, 1H), 2.27 (ddd, 1H), 1.45 (s, 9H); LCMS (M+H)⁺: 307.2.

Step 2. tert-butyl 4-benzyl-3-formylpiperazine-1-carboxylate (Racemic)

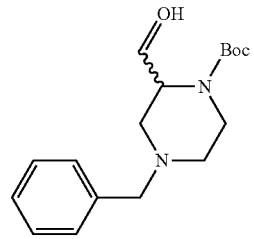 [SMILES: CC(C)(C)OC(=O)N1CCN(Cc2ccccc2)CC1C=O]

Dimethyl sulfoxide (0.252 mL, 3.55 mmol) was added to a to −78° C. solution of oxalyl chloride (0.200 mL, 2.37 mmol) in methylene chloride (5.4 mL). After 10 min, a solution of tert-butyl 4-benzyl-3-(hydroxymethyl)piperazine-1-carboxylate (0.63 g, 2.0 mmol from Step 1) in methylene chloride (2.8 mL) was slowly introduced over 15 min. After stirring at −78° C. for 1 h, triethylamine (1.38 mL, 9.87 mmol) was added. The mixture was warmed to RT over 30 min and then stirred for another 30 min at that temperature. The reaction mixture was diluted with DCM, washed with water (twice) and brine (once), dried over sodium sulfate, decanted and concentrated to give product as a light yellow oil (570 mg, 95%). ¹H NMR (300 MHz, CDCl₃): δ 9.67 (d, 1H), 7.36-7.24 (m, 5H), 3.89 (d, 1H), 3.65 (dd, 1H), 3.57 (d, 1H), 3.57-3.45 (br m, 2H), 3.36-3.22 (br m, 1H), 3.10-2.98 (br m, 1H), 2.93 (ddd, 1H), 2.30 (ddd, 1H), 1.45 (s, 9H); LCMS (M+H)⁺: 305.0.

Step 3. tert-butyl 4-benzyl-3-(difluoromethyl)piperazine-1-carboxylate (Racemic)

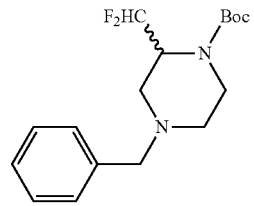 [SMILES: CC(C)(C)OC(=O)N1CCN(Cc2ccccc2)CC1C(F)F]

tert-butyl 4-benzyl-3-formylpiperazine-1-carboxylate (0.38 g, 1.2 mmol, from Step 2) in methylene chloride (8.0 mL) was cooled to 0° C. and 2-methoxy-N-(2-methoxyethyl)-N-(trifluoro-λ(4)-sulfanyl)ethanamine (0.921 mL, 4.99 mmol) was added, followed by ethanol (5.8 µL). The mixture was stirred at 0° C. for 2 h, then slowly warmed to RT over 30 min. The reaction was quenched by the addition of 5% sodium bicarbonate, and the product was extracted with EtOAc. The extracts were washed with water (twice), brine (once), dried over sodium sulfate, decanted and concentrated. Flash chromatography, using a 40 g silica gel cartridge and eluting with a gradient from 0-20% EtOAc in hexanes afforded product M+H 327.2 (92 mg, 22%). ¹H NMR (400 MHz, CDCl₃): δ 7.35-7.23 (m, 5H), 6.01 (td, 1H), 4.01-3.58 (br m, 4H), 3.56-3.34 (br m, 1H), 3.34-3.10 (br m, 1H), 2.93-2.83 (m, 1H), 2.80 (ddd, 1H), 2.55-2.32 (br m, 1H), 1.46 (s, 9H); ¹⁹F NMR (400 MHz, CDCl₃): −122.1 to −124.6 (m, 2F); LCMS (M+H)⁺: 327.2.

Step 4. tert-butyl 3-(difluoromethyl)piperazine-1-carboxylate (Racemic)

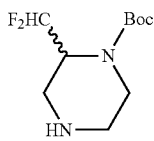

10% Palladium on carbon (65 mg, 0.061 mmol) was added to a solution of tert-butyl 4-benzyl-3-(difluoromethyl)piperazine-1-carboxylate (0.20 g, 0.61 mmol, racemic from Step 3) in methanol (15 mL). The suspension was stirred under an atmosphere of hydrogen provided by a balloon. When the reaction showed no progress, 20% Pd(OH)₂ on charcoal (47 mg, 0.061 mmol) was added and the suspension was shaken under 50-55 psi hydrogen for 2 h. The mixture was filtered and solvent removed in vacuo to afford product as a viscous oil (140 mg, 97%). ¹H NMR (300 MHz, CDCl₃): δ 5.90 (td, 0.1H), 5.52-5.12 (br s, 2H), 4.25-3.96 (br s, 1H), 3.94 (d, 1H), 3.27-2.77 (m, 4H), 1.45 (s, 9H); LCMS (M-tBu+2H)⁺: 181.0.

Step 5. E- and Z-tert-butyl 4-[3-cyanoprop-2-en-1-yl]-3-(difluoromethyl)piperazine-1-carboxylate (Racemic)

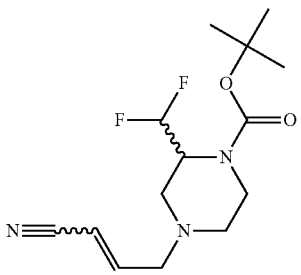 [SMILES: CC(C)(C)OC(=O)N1CCN(CC=CC#N)CC1C(F)F]

tert-butyl 3-(difluoromethyl)piperazine-1-carboxylate (0.14 g, 0.59 mmol, racemic, from Step 4) was dissolved in acetonitrile (1.0 mL), and 4-bromobut-2-enenitrile (0.112 g, 0.770 mmol, a mixture of E- and Z-isomers prepared as described in *J. Am. Chem. Soc.* (1940), 62; 974-7) was added. Following this, sodium bicarbonate (149 mg, 1.78 mmol) was added. The mixture was stirred at RT overnight. To complete the reaction, additional 4-bromobut-2-enenitrile (0.10 g, 0.68 mmol) was added and the mixture stirred for an additional 4 h. The mixture was then filtered and solvent removed in vacuo. Flash chromatography on a 40 g silica gel cartridge, eluting with a gradient from 0-40% EtOAc in hexanes afforded the racemic product as a mixture of E- and Z-isomers (120 mg, 67%). ¹H NMR (400 MHz, CDCl₃): δ 6.67 (dt, 1H, trans), 6.52 (dt, 1H, cis), 6.07-5.73 (2td, 2H), 5.64 (dt, 1H, trans), 5.49 (dt, 1H, cis), 3.94-3.05 (m, 12H), 2.90-2.69 (m, 4H), 2.60-2.42 (br m, 2H), 1.45 (s, 18H); LCMS (M-Boc+H)⁺: 202.1.

Step 6. tert-butyl 4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(difluoromethyl)piperazine-1-carboxylate (Mixture of Diastereomers)

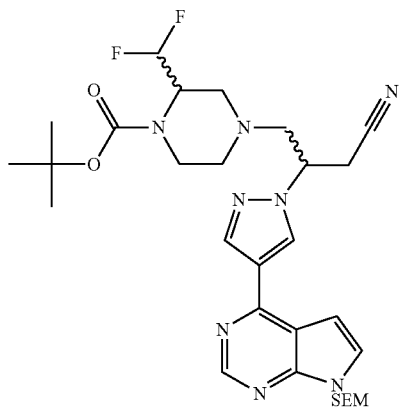 [SMILES: CC(C)(C)OC(=O)N1CCN(CC(CC#N)n2cc(-c3ncnc4c3ccn4COCC[Si](C)(C)C)cn2)CC1C(F)F]

A mixture of tert-butyl 4-[3-cyanoprop-2-en-1-yl]-3-(difluoromethyl)piperazine-1-carboxylate (0.12 g, 0.40 mmol from Step 5) and 4-(1H-pyrazol-4-yl)-7-{[2-(trimethylsilyl)ethoxy]methyl}-7H-pyrrolo[2,3-d]pyrimidine (0.12 g, 0.40 mmol, prepared as described in WO 2007/070514, Example 65) and potassium carbonate (0.16 g, 1.2 mmol) in DMF (0.36 mL) was stirred for 4.5 h. The mixture was then filtered, the filtrate was diluted with EtOAc, washed with water (thrice), brine, dried over sodium sulfate, decanted and concentrated. Flash chromatography on a 40 g silica gel cartridge eluting with a gradient of 0-80% solvent mixture [A] in hexanes ([A]=10% IPA: 50% EtOAc: 40% Hexanes) afforded a purified product (130 mg, 53%). ¹H NMR (300 MHz, CDCl₃): δ 8.83 (s, 2H), 8.33-8.28 (m, 4H), 7.42-7.38 (d, 2H), 6.79-6.76 (d, 2H), 5.89 (td, 1H), 5.63 (td, 1H), 5.67 (s, 4H), 4.57 (tt, 2H), 4.18-1.10 (m, 26H), 1.45, 1.43, 1.40 (3s, together 18H), 0.92 (dd, 4H), −0.08 (s, 18H); LCMS (M+H)⁺: 617.3.

Step 7. 4-[2-(difluoromethyl)piperazin-1-yl]-3-[4-(7-{[(2-(trimethylsilyl)ethoxy]methyl}-7H-pyrrolo[2,3-d]pyrimidin-4-yl)-1H-pyrazol-1-yl]butanenitrile hydrochloric acid Salt (Mixture of Diastereomers)

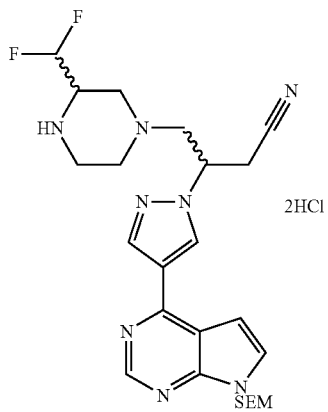 [SMILES: C[Si](C)(C)CCOCn1ccc2c(-c3cnn(C(CC#N)CN4CCNC(C(F)F)C4)c3)ncnc21]

A solution of tert-butyl 4-{3-cyano-2-[4-(7-{[2-(trimethylsilyl)ethoxy]methyl}-7H-pyrrolo[2,3-d]pyrimidin-4-yl)-

1H-pyrazol-1-yl]propyl}-3-(difluoromethyl)piperazine-1-carboxylate (0.13 g, 0.21 mmol, a mixture of diastereomers from Step 6) in 1,4-dioxane (1 mL) was treated with 4.0 M of hydrogen chloride in p-dioxane (0.75 mL, 3.0 mmol) and the mixture was stirred at RT for 80 min. Solvent was removed in vacuo to afford product as a light yellow solid (120 mg, 96%). LCMS (M+H)+: 517.1.

Step 8. 4-{[4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(difluoromethyl)piperazin-1-yl]carbonyl}-3-fluorobenzonitrile (Mixture of Diastereomers, Separated into Two Single Isomers and a Mixture of Two Isomers)

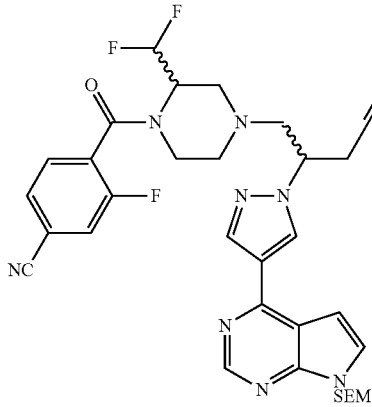

A mixture of 4-cyano-2-fluorobenzoic acid (47.0 mg, 0.285 mmol, Alfa Aesar), N,N,N',N'-Tetramethyl-O-(7-azabenzotriazol-1-yl)uronium hexafluorophosphate (101 mg, 0.264 mmol) and triethylamine (0.170 mL, 1.22 mmol) in THF (2.5 mL) was stirred at RT for 15 min, and then 4-[2-(difluoromethyl)piperazin-1-yl]-3-[4-(7-{[2-(trimethylsilyl)ethoxy]methyl}-7H-pyrrolo[2,3-d]pyrimidin-4-yl)-1H-pyrazol-1-yl]butanenitrile hydrochloric acid salt (0.12 g, 0.20 mmol; a mixture of diastereomers from Step 7) was added. The mixture was stirred at RT for 1 h. The reaction was partitioned between ethyl acetate and water. The layers were separated, and the organic layer was washed with water, 0.1N NaOH, and brine; dried over sodium sulfate, decanted and concentrated. Flash chromatography on a 12 g silica gel cartridge, eluting with 0-80% solvent mixture [A] in hexanes ([A]=10% IPA: 50% EtOAc: 40% Hexanes); afforded desired product as a mixture of diastereomers (110 mg, 81%). The isomers were separated by chiral HPLC (Chiral Technologies Chiralcel OD-H, 20×250 mm, eluting with 30% EtOH/Hexanes at a flow rate of 10 mL/min and a loading of 20 mg/injection). Three peaks were obtained: Peak 1 retention time: 26.30 min, 19 mg; Peak 2 retention time: 33.82 min, 49 mg, mixture of 2 isomers; Peak 3 retention time 44.26 min, 29 mg. Peak 1: $^1$H NMR (300 MHz, CDCl$_3$, rotamers): δ 8.84 (s, 0.4H), 8.83 (s, 0.6H), 8.32 (s, 1H), 8.31 (s, 0.4H), 8.30 (s, 0.6H), 7.79-7.32 (m, 4H), 6.79-6.76 (2d, 1H), 5.96 (td, 0.6H), 5.84 (br t, 0.4H), 5.67 (s, 2H), 4.68-4.55 (m, 1H), 4.51-4.21 (m, 1H), 3.61-0.75 (m, 14H), −0.07 (s, 9H); LCMS (M+H)+: 663.8. Peak 2 (mixture of two isomers and rotamers observed): $^1$H NMR (300 MHz, CDCl$_3$): δ 8.84 (s, 0.814), 8.83 (s, 1.2H), 8.33 (s, 0.8H), 8.32 (s, 1.2H), 8.30 (s, 2H), 7.54-7.35 (m, 8H), 6.78 (d, 2H), 5.97 (td, 1.2H), 5.91 (td, 0.8H), 5.68 (s, 4H), 4.65-4.51 (m, 2H), 4.24-4.08 (m, 2H), 3.56 (dd, 4H), 3.47-0.80 (m, 24H), −0.07 (s, 18H); LCMS (M+H)+: 663.8. Peak 3: $^1$H NMR (300 MHz, CDCl$_3$, rotamers): δ 8.84 (s, 0.4H), 8.83 (s, 0.6H), 8.32 (s, 1H), 8.31 (s, 0.4H), 8.30 (s, 0.6H), 7.79-7.32 (m, 4H), 6.79-6.76 (2d, 1H), 5.96 (td, 0.6H), 5.84 (br t, 0.4H), 5.67 (s, 2H), 4.68-4.55 (m, 1H), 4.51-4.21 (m, 1H), 3.61-0.75 (m, 14H), −0.07 (s, 9H); LCMS (M+H)+: 663.8.

Step 9. 4-{[4-{3-cyano-2-[4-(7H-pyrrolo[2,3-d]pyrimidin-4-yl)-1H-pyrazol-1-yl]propyl}-3-(difluoromethyl)piperazin-1-yl]carbonyl}-3-fluorobenzonitrile (Single Isomer Prepared)

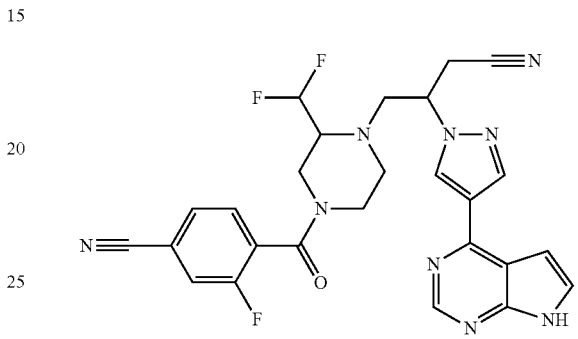

4-{[4-{3-cyano-2-[4-(7-{[2-(trimethylsilyl)ethoxy]methyl}-7H-pyrrolo[2,3-d]pyrimidin-4-yl)-1H-pyrazol-1-yl]propyl}-3-(difluoromethyl)piperazin-1-yl]carbonyl}-3-fluorobenzonitrile (27 mg, 0.041 mmol; Peak 3 from Step 8) was stirred in a 1:1 mixture of TFA:DCM (4 mL) for 1 h. Solvent was removed in vacuo. The residue was dissolved in methanol (1.9 mL), and 0.2 mL of ammonium hydroxide aqueous solution was added. Preparative HPLC-MS (C18, eluting with a gradient of H$_2$O/MeCN containing 0.15% NH$_4$OH) afforded purified product (7.7 mg, 35%). $^1$H NMR (400 MHz, DMSO-d$_6$, rotamers): δ 12.13 (br s, 1H), 8.82 (s, 0.55H), 8.81 (s, 0.45H), 8.68 (s, 0.45H), 8.68 (s, 0.55H), 8.38 (s, 0.45H), 8.37 (s, 0.55H), 8.01 (dd, 0.45H), 7.96 (dd, 0.55H), 7.81 (dd, 0.45H), 7.76 (br d, 0.55H), 7.65-7.57 (m, 2H), 6.97 (d, 1H), 6.24 (br t, 1H), 4.91 (ddd, 1H), 4.25 (d, 0.55H), 4.05 (br m, 0.45H), 3.53-2.33 (m, 10H); $^{19}$F NMR (400 MHz, DMSO-d$_6$): −114.10 to −115.21 (m, 1F), −123.22 to −125.01 (m, 2F); LCMS (M+H)+: 534.2.

Peaks 1 and 2 from Step 8 were also deprotected according to the method of Step 9 to provide the isomers for comparison:

Peak 1: $^1$H NMR (400 MHz, DMSO-d$_6$, rotamers): δ 12.12 (br s, 1H), 8.82 (s, 0.55H), 8.81 (s, 0.45H), 8.68 (s, 0.45H), 8.68 (s, 0.55H), 8.38 (s, 0.45H), 8.37 (s, 0.55H), 8.01 (dd, 0.45H), 7.96 (dd, 0.55H), 7.82 (dd, 0.45H), 7.76 (d, 0.55H), 7.64-7.58 (m, 2H), 6.97 (d, 1H), 6.24 (br t, 1H), 4.96-4.85 (m, 1H), 4.29-4.21 (m, 0.55H), 4.10-3.98 (br m, 0.45H), 3.51-2.32 (m, 10H); $^{19}$F NMR (400 MHz, DMSO-d$_6$): −114.14 to −115.13 (m, 1F), −122.98 to −125.10 (m, 2F); LCMS (M+H)+: 533.8.

Peak 2 (mixture of two isomers, rotamers): $^1$H NMR (400 MHz, DMSO-d$_6$): δ 12.12 (br s, 1H), 8.81 (s, 0.45H), 8.79 (s, 0.55H), 8.68 (s, 0.45H), 8.68 (s, 0.55H), 8.38 (s, 1H), 7.98 (dd, 0.55H), 7.97 (d, 0.45H), 7.79 (dd, 0.55H), 7.80-7.85 (br m, 0.45H), 7.65-7.55 (m, 2H), 6.98 (d, 0.45H), 6.97 (d, 0.55H), 6.26 (br t, 1H), 4.93-4.81 (m, 1H), 4.15 (dd, 0.55H), 4.09-3.99 (br, 0.45H), 3.37-2.43 (m, 10H); $^{19}$F NMR (400

MHz, DMSO-d$_6$): −114.24 to −115.10 (m, 1F), −123.51 to −124.77 (m, 2F); LCMS (M+H)$^+$: 533.8.

Example 160

4-{[4-{3-cyano-2-[4-(7H-pyrrolo[2,3-d]pyrimidin-4-yl)-1H-pyrazol-1-yl]propyl}-2-(hydroxymethyl)piperazin-1-yl]carbonyl}-3-fluorobenzonitrile (Mixture of Diastereomers)

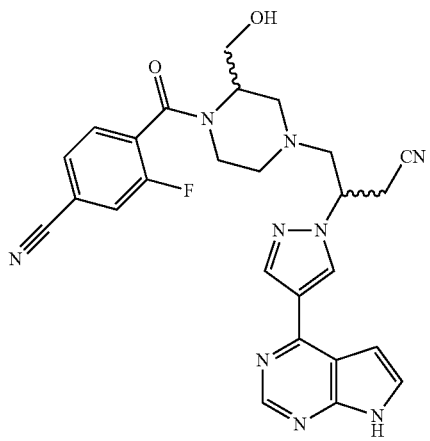 [SMILES: N#CCC(CN1CCN(C(=O)c2ccc(C#N)cc2F)C(CO)C1)n1cc(-c2ncnc3[nH]ccc23)cn1]

Step 1. tert-butyl 4-(4-cyano-2-fluorobenzoyl)-3-(hydroxymethyl)piperazine-1-carboxylate (Racemic)

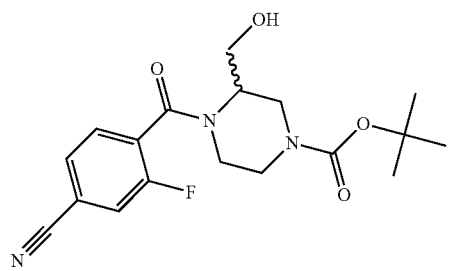 [SMILES: CC(C)(C)OC(=O)N1CCN(C(=O)c2ccc(C#N)cc2F)C(CO)C1]

Triethylamine (892 μL, 6.40 mmol) was added to a mixture of 4-cyano-2-fluorobenzoic acid (275 mg, 1.66 mmol, Alfa Aesar) and N,N,N',N'-tetramethyl-O-(7-azabenzotriazol-1-yl)uronium hexafluorophosphate (580 mg, 1.52 mmol) in THF (13 mL). After stirring for 15 min, tert-butyl 3-(hydroxymethyl)piperazine-1-carboxylate (0.30 g, 1.4 mmol, racemic, AstaTech) was added. The reaction was stirred overnight. Ethyl acetate and water were added, the mixture shaken, and layers separated. The organic layer was washed with water, 0.1 N NaOH, and brine; dried over sodium sulfate, decanted and concentrated. Flash chromatography on a 40 g silica gel cartridge, eluting with a gradient from 0-100% EtOAc in hexanes afforded the racemic product as a white solid (400 mg, 71%). $^1$H NMR (300 MHz, CDCl$_3$): δ 7.61-7.38 (m, 3H), 4.90-2.51 (m, 9H), 1.47 (s, 9H); LCMS (M-tBu+2H)$^+$: 308.1.

Step 2

E- and Z-4-{[4-[3-cyanoprop-2-en-1-yl]-2-(hydroxymethyl)piperazin-1-yl]carbonyl}-3-fluorobenzonitrile (Racemic)

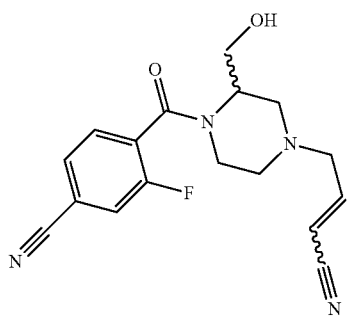 [SMILES: N#CC=CCN1CCN(C(=O)c2ccc(C#N)cc2F)C(CO)C1]

To a solution of tert-butyl 4-(4-cyano-2-fluorobenzoyl)-3-(hydroxymethyl)piperazine-1-carboxylate (0.20 g, 0.55 mmol) in 1,4-dioxane (3 mL), was added 4.0 M of Hydrogen chloride in p-dioxane (1.9 mL, 7.8 mmol). The mixture was stirred for 1 h. The solvent was removed in vacuo to afford a white solid. The solid was mixed with acetonitrile (1.0 mL), then sodium bicarbonate (140 mg, 1.6 mmol), followed by 4-bromobut-2-enenitrile (0.080 g, 0.55 mmol, as a mixture of E- and Z-isomers prepared in Step 1) were added. The mixture was stirred for two days, then was filtered and concentrated. The crude residue was treated with 1N HCl to pH 1, then extracted with EtOAc, and the organic layer was discarded. The aqueous layer was treated with solid sodium bicarbonate to make the pH basic, then was extracted with two portions of ethyl acetate. The combined organic extract was washed with brine, dried over sodium sulfate, decanted and concentrated to afford product which was used without further purification (100 mg, 50%). LCMS (M+H)$^+$: 329.1.

Step 3. 4-{[4-{3-cyano-2-[4-(7H-pyrrolo[2,3-d]pyrimidin-4-yl)-1H-pyrazol-1-yl]propyl}-2-(hydroxymethyl)piperazin-1-yl]carbonyl}-3-fluorobenzonitrile (Mixture of Diastereomers)

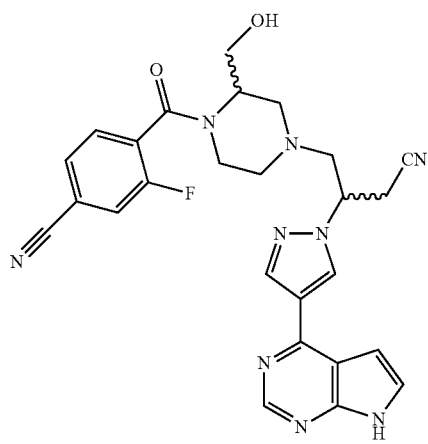 [SMILES: N#CCC(CN1CCN(C(=O)c2ccc(C#N)cc2F)C(CO)C1)n1cc(-c2ncnc3[nH]ccc23)cn1]

4-{[4-[3-cyanoprop-2-en-1-yl]-2-(hydroxymethyl)piperazin-1-yl]carbonyl}-3-fluorobenzonitrile (46 mg, 0.14 mmol, as a mixture of E- and Z-mixtures from Step 2) was combined with 4-(1H-pyrazol-4-yl)-7-{[2-(trimethylsilyl)ethoxy]methyl}-7H-pyrrolo[2,3-d]pyrimidine (29 mg, 0.093 mmol, prepared as described in WO 2007/070514 Example 65) in DMF (0.14 mL) and potassium carbonate (0.0414 g, 0.299 mmol) was added. The reaction mixture was stirred overnight. The mixture was then filtered and the filtrate was diluted with EtOAc. This solution was washed with water (thrice), brine; dried over sodium sulfate, decanted and concentrated. The crude was then stirred in 1:1 DCM:TFA (4 mL) for 1 h and the solvent removed in vacuo. The residue was then stirred with 0.2 mL ethylenediamine in 1.5 mL MeOH for 30 min. Preparative HPLC-MS (C18, eluting with a gradient of $H_2O$/MeCN containing 0.15% $NH_4OH$) was used to purify product—a mixture of diastereomers (24 mg, 50%). $^1$H NMR (400 MHz, DMSO-$d_6$, mixture of diastereomers and rotamers): δ 12.12 (br s, 2H), 8.81, 8.80, 8.78, 8.78 (4s, 2H), 8.68, 8.67 (2s, 2H), 8.37, 8.37, 8.36 (3s, 2H), 7.99-7.91 (m, 2H), 7.80-7.72 (m, 2H), 7.63-7.50 (m, 4H), 6.99-6.95 (m, 2H), 5.07-1.84 (m, 28H); LCMS (M+H)$^+$: 514.2.

Example 161

4-[((2R)-4-{3-cyano-2-[4-(7H-pyrrolo[2,3-d]pyrimidin-4-yl)-1H-pyrazol-1-yl]propyl}-2-methylpiperazin-1-yl)carbonyl]-3-fluorobenzonitrile (Mixture of Diastereomers)

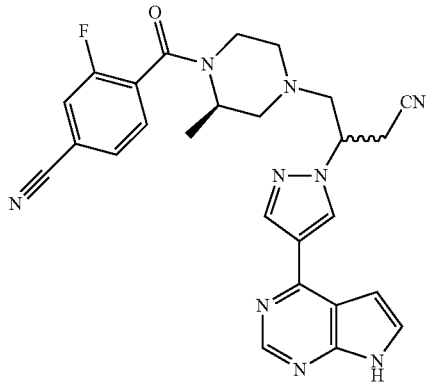 [SMILES: C[C@@H]1CN(CC(CC#N)n2cc(-c3ncnc4[nH]ccc34)cn2)CCN1C(=O)c1ccc(C#N)cc1F]

Step 1. tert-butyl (3R)-4-(4-cyano-2-fluorobenzoyl)-3-methylpiperazine-1-carboxylate

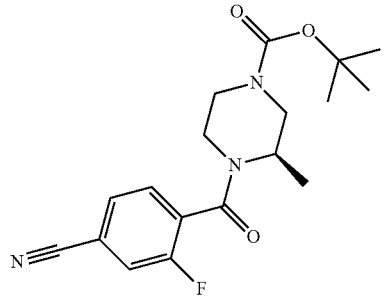 [SMILES: C[C@@H]1CN(C(=O)OC(C)(C)C)CCN1C(=O)c1ccc(C#N)cc1F]

Triethylamine (803 µL, 5.76 mmol) was added to a mixture of 4-cyano-2-fluorobenzoic acid (247 mg, 1.50 mmol, Alfa Aesar) and N,N,N',N'-tetramethyl-O-(7-azabenzotriazol-1-yl)uronium hexafluorophosphate (522 mg, 1.37 mmol) in THF (11 mL). After stirring for 15 min, tert-butyl (3R)-3-methylpiperazine-1-carboxylate (0.25 g, 1.2 mmol, Aldrich) was added. The mixture was stirred for 3 h. Ethyl acetate and water were added, shaken and the layers separated. The organic layer was washed with water, 0.1N NaOH, and brine;

dried over sodium sulfate, decanted and concentrated to afford product which was used without further purification (450 mg, 100%). $^1$H NMR (400 MHz, CDCl$_3$, rotamers): δ 7.57-7.40 (m, 3H), 4.98-2.63 (m, 7H), 1.47 (s, 9H), 1.28 (d, 1.8H), 1.19 (br s, 1.2H); LCMS (M-tBu+2H)$^+$: 292.1.

Step 2. E- and Z-4-({(2R)-4-[3-cyanoprop-2-en-1-yl]-2-methylpiperazin-1-yl}carbonyl)-3-fluorobenzonitrile

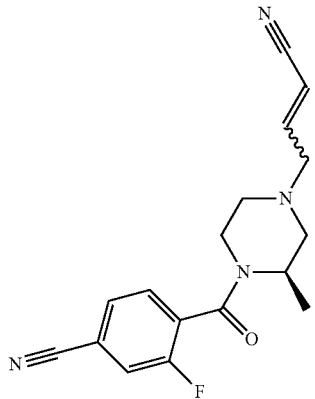 [SMILES: C[C@@H]1CN(CC=CC#N)CCN1C(=O)c1ccc(C#N)cc1F]

tert-Butyl (3R)-4-(4-cyano-2-fluorobenzoyl)-3-methylpiperazine-1-carboxylate (0.45 g, 1.3 mmol, from Step 1) in 1,4-dioxane (7 mL) was treated with 4.0 M of hydrogen chloride in p-dioxane (4.6 mL, 0.018 mol). After stirring for 6.5 h, solvent was removed in vacuo to afford a light yellow solid. The solid was mixed with acetonitrile (3.0 mL) and sodium bicarbonate (0.44 g, 5.2 mmol), followed by 4-bromobut-2-enenitrile (0.23 g, 1.6 mmol, prepared as described in J. Am. Chem. Soc. (1940), 62; 974-7) were added. The mixture was stirred for 24 h. The mixture was then filtered and concentrated. Flash chromatography on a 40 g silica gel cartridge eluting with a gradient from 0-100% EtOAc:hexanes afforded product as a viscous oil (120 mg, 30%). $^1$H NMR (300 MHz, CD$_3$OD, rotamers): δ 7.77-7.51 (m, 6H), 6.79 (dt, 1H, trans), 6.65 (dt, 1H, cis), 5.80 (dt, 1H, trans), 5.67 (dt, 1H, cis) 4.93-4.77 (m, 1H), 4.50-4.40 (m, 1H), 3.77-1.98 (m, 16H), 1.41 (d, 2H), 1.39 (d, 1.3H), 1.36-1.27 (m, 2.7H); LCMS (M+H)$^+$: 313.0.

Step 3. 4-[((2R)-4-{3-cyano-2-[4-(7H-pyrrolo[2,3-d]pyrimidin-4-yl)-1H-pyrazol-1-yl]propyl}-2-methylpiperazin-1-yl)carbonyl]-3-fluorobenzonitrile (Mixture of Diastereomers)

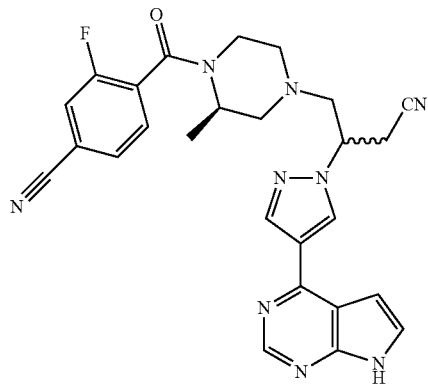 [SMILES: C[C@@H]1CN(CC(CC#N)n2cc(-c3ncnc4[nH]ccc34)cn2)CCN1C(=O)c1ccc(C#N)cc1F]

Potassium carbonate (0.170 g, 1.23 mmol) was added to a mixture of 4-({(2R)-4-[3-cyanoprop-2-en-1-yl]-2-methylpiperazin-1-yl}carbonyl)-3-fluorobenzonitrile (0.12 g, 0.38 mmol, mixture of E- and Z-isomers from Step 2) and 4-(1H-pyrazol-4-yl)-7-{[2-(trimethylsilyl)ethoxy]methyl}-7H-pyrrolo[2,3-d]pyrimidine (0.12 g, 0.38 mmol, prepared as described in WO 2007/070514 Example 65) in DMF (0.59 mL) and the mixture was stirred overnight. The reaction mixture was then filtered and the filtrate was diluted with EtOAc. The filtrate was then washed with water (thrice), followed by brine, dried over sodium sulfate, decanted and concentrated. A portion of the crude product was dissolved in a 1:1 mixture of DCM:TFA, stirred at RT for 1 h, and concentrated. The residue was dissolved in methanol (1 mL) and 0.2 mL of aqueous ammonium hydroxide was added. After stirring for 2 h, the reaction mixture was concentrated. Preparative HPLC-MS (C18, eluting with a gradient of $H_2O$/MeCN containing 0.15% $NH_4OH$) afforded product as a mixture of two diastereomers. $^1H$ NMR (300 MHz, DMSO-$d_6$, diastereomers, rotamers): δ 12.11 (br s, 2H), 8.84-8.79 (m, 2H), 8.68-8.66 (m, 2H), 8.37-8.35 (m, 2H), 8.02-7.93 (m, 2H), 7.80-7.73 (m, 2H), 7.64-7.53 (m, 4H), 6.99-6.94 (m, 2H), 5.07-4.85 (m, 2H), 4.71-4.51 (m, 1H), 4.34 (t, 1H), 3.58-1.94 (m, 20H), 1.19 (d, 1.5H), 1.12 (d, 1.5H), 1.05 (d, 1.5H), 0.94 (d, 1.5H); $^{19}F$ NMR (300 MHz, DMSO-$D_6$): −114.54 to −115.75 (m, 2F); LCMS (M+H)$^+$: 498.2.

Example 162

4-[((2S)-4-{3-cyano-2-[4-(7H-pyrrolo[2,3-d]pyrimidin-4-yl)-1H-pyrazol-1-yl]propyl}-2-methylpiperazin-1-yl)carbonyl]-3-fluorobenzonitrile (Mixture of Diastereomers)

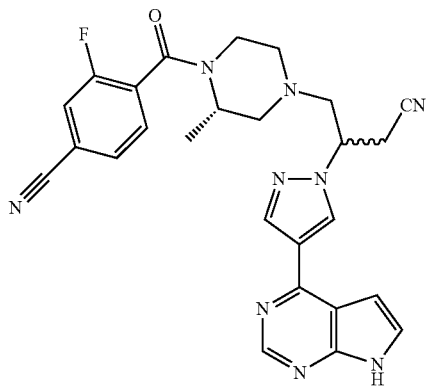 [SMILES: C[C@H]1CN(CC(CC#N)n2cc(-c3ncnc4[nH]ccc34)cn2)CCN1C(=O)c1ccc(C#N)cc1F]

Prepared in the manner described for Example 161, starting with tert-butyl (3S)-3-methylpiperazine-1-carboxylate (Aldrich). $^1H$ NMR (300 MHz, DMSO-$d_6$, diastereomers, rotamers): δ 12.11 (br s, 2H), 8.83-8.79 (m, 2H), 8.68-8.66 (m, 2H), 8.37, 8.35 (2s, 2H), 8.02-7.93 (m, 2H), 7.81-7.72 (m, 2H), 7.64-7.52 (m, 4H), 6.99-6.94 (m, 2H), 5.05-4.87 (m, 2H), 4.70-4.52 (m, 1H), 4.32-4.17 (m, 1H), 3.53-1.95 (m, 20H), 1.19 (d, 1.5H), 1.12 (d, 1.5H), 1.05 (d, 1.5H), 0.94 (d, 1.5H); $^{19}F$ NMR (300 MHz, DMSO-$d_6$): −114.44 to −115.77 (m, 2F); LCMS (M+H)$^+$: 498.2.

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 μM for Jak1, 30 μM for Jak2 and 3 μM for Jak3 for Km conditions. For the 1 mM $IC_{50}$ measurements, ATP concentration in the reactions was 1 mM. Reactions were carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). See Tables 1, 2, 3, and 4 for data related to compounds of the invention.

TABLE 1

$IC_{50}$ data for JAK enzyme assay*

| Example | $IC_{50}$ (nM) @ Km ATP | | $IC_{50}$ (nM) @ 1 mM ATP | |
| --- | --- | --- | --- | --- |
| | JAK1 | JAK2 | JAK1 | JAK2 |
| 1 | + | + | + | ++ |
| 2 | + | ++ | + | +++ |
| 3 | + | + | ++ | + |
| 4 | + | + | + | + |
| 5 | + | + | | + |
| 6 | + | + | | |
| 7 | + | + | + | + |
| 8 | + | + | | + |
| 9 | | | + | +++ |
| 10 | | | + | +++ |
| 11 | | | + | +++ |

*"+" = <10 nM; "++" = 10-20 nM; "+++" = >20 nM

| Ex No. | JAK1 $IC_{50}$ (nM) @ 1 mM ATP | JAK2 $IC_{50}$ (nM) @ 1 mM ATP |
| --- | --- | --- |
| 12 | + | +++ |
| 13 | + | +++ |
| 14 | + | ++ |
| 15 | + | +++ |
| 16 | + | + |
| 17 | ++ | ++++ |
| 18 | ++ | +++ |
| 19 | ++ | ++++ |
| 20 | ++ | ++++ |
| 21 | ++ | +++ |
| 22 | + | + |
| 23 | ++ | ++++ |
| 24, R-1 | + | ++++ |
| 24, R-2 | ++++ | ++++ |
| 25, S-1 | ++++ | ++++ |
| 25, S-2 | + | ++++ |
| 26 | + | + |
| 27 | + | + |
| 28 | + | + |
| 29 | + | + |
| 30 | + | + |
| 31 | + | ++ |
| 32 | + | + |
| 33 | + | + |
| 34 | + | ++ |
| 35 | + | + |
| 36 | + | ++ |
| 37 | + | ++ |
| 38 | + | ++ |

TABLE 1-continued

| Example No. | Salt Form | JAK1 IC₅₀ | JAK2 IC₅₀ |
|---|---|---|---|
| 39 | | + | ++ |
| 40 | | + | ++ |
| 41 | | + | ++ |
| 42 | | + | ++ |
| 43 | | + | ++ |
| 44 | | + | ++ |
| 45 | | + | ++ |
| 46 | | + | ++ |
| 47 | | + | ++ |
| 48 | | + | ++ |
| 49 | | ++ | ++++ |
| 50 | | ++ | ++ |
| 51 | | ++ | ++ |
| 52 | | ++ | +++ |
| 53 | | ++ | +++ |
| 54 | | ++ | +++ |
| 55 | | ++ | +++ |
| 56 | | ++ | ++++ |
| 57 | | ++ | ++++ |
| 58 | | ++ | ++++ |
| 59 | | ++ | ++++ |
| 60 | | + | + |
| 61 | | + | + |
| 62 | | + | + |
| 63 | | + | + |
| 64 | | + | + |
| 65 | | + | ++ |
| 66 | | + | + |
| 67 | | + | + |
| 68 | | + | + |
| 69 | | + | ++ |
| 70 | | ++ | +++ |
| 71 | | ++ | ++ |
| 72 | | ++ | +++ |
| 73 | | ++ | ++++ |
| 74 | | ++ | +++ |
| 75 | | ++ | +++ |
| 76 | | ++ | ++++ |
| 77 | | + | ++ |
| 78 | | + | ++ |
| 79 | | + | +++ |
| 80 | | + | ++ |
| 81 | | + | +++ |
| 82 | | + | ++ |
| 83 | | + | ++ |
| 84 | | ++ | ++ |
| 85 | | ++ | ++++ |
| 86 | | ++ | ++++ |
| 87 | | ++ | ++++ |
| 88 | | ++ | ++++ |
| 89 | | ++ | ++++ |
| 90 | | + | + |
| 91 | | + | ++ |

"+" is <10 nM;
"++" is 10-50 nM;
"+++" is >50 to 100 nM;
"++++" is >100 nM

| Example No. | Salt Form | JAK1 IC₅₀ (nM) @ 1 mM ATP | JAK2 IC₅₀ (nM) @ 1 mM ATP |
|---|---|---|---|
| 92 | — | ++ | ++++ |
| 93 | — | ++ | ++++ |
| 94 | — | ++ | ++++ |
| 95 | 2 TFA | ++ | ++++ |
| 96 | 2 TFA | ++ | ++++ |
| 97 | — | ++ | ++++ |
| 98 | — | ++ | ++++ |
| 99 | — | ++ | +++ |
| 100 | — | + | ++ |
| 101 | — | ++ | ++++ |
| 102 | — | ++ | +++ |
| 103 | — | ++ | ++++ |
| 104 | — | ++ | ++++ |
| 105 | — | ++ | ++++ |
| 106 | — | + | +++ |
| 107 | — | ++ | ++++ |
| 108 | — | + | +++ |
| 109 | — | ++ | ++++ |
| 110 | — | ++ | ++++ |
| 111 | — | ++ | +++ |
| 112 | — | + | ++ |
| 113 | — | ++ | ++++ |
| 114 | — | ++ | +++ |
| 115 | — | + | ++ |
| 116 | — | ++ | ++++ |
| 117 | — | ++ | +++ |
| 118 | — | + | ++ |
| 119 | — | ++ | +++ |
| 120 | — | ++ | +++ |
| 121 | — | ++ | ++++ |
| 122 | — | + | +++ |
| 123 | — | + | + |
| 124 | — | + | ++ |
| 125 | — | ++ | ++++ |
| 126 | — | ++ | ++++ |
| 127 | — | + | ++ |
| 128 | — | + | +++ |
| 129 | — | ++ | +++ |
| 130 | — | + | +++ |
| 131 | — | + | ++ |
| 132 | — | + | ++ |
| 133 | — | ++ | ++++ |
| 134 | — | + | ++ |
| 135 | — | + | ++ |
| 136 | — | + | ++ |
| 137 | — | + | +++ |
| 138 | — | + | +++ |
| 139 | — | ++ | ++++ |
| 140 | — | + | +++ |
| 141 | — | + | +++ |
| 142 | — | + | +++ |
| 143 | — | + | ++++ |
| 144 | — | ++ | +++ |
| 145 | — | + | ++ |
| 146 | — | ++ | ++++ |
| 147 | — | + | ++++ |
| 148 | — | + | +++ |
| 149 | — | + | ++++ |
| 150 | — | + | + |
| 151 | | + | +++ |
| 152 | — | ++ | + |
| 153 | — | ++ | ++++ |
| 154 | | + | +++ |
| 155 | — | + | ++++ |
| 156—peak 1 | 2.66 TFA | + | ++++ |
| 156—peak 2 | 3 TFA | ++++ | ++++ |
| 156—peak 3 | 3 TFA | +++ | ++++ |
| 156—peak 4 | 3 TFA | ++++ | ++++ |
| 157—peak 1 | — | ++++ | ++++ |
| 157—peak 2 | — | + | ++++ |
| 157—peak 3 | — | ++++ | ++++ |
| 158 | — | + | ++++ |
| 159—peak 1 | — | ++++ | ++++ |
| 159—peak 2 | — | +++ | +++ |
| 159—peak 3 | — | + | ++ |
| 160 | — | ++ | ++++ |
| 161 | — | +++ | ++++ |
| 162 | — | ++ | ++++ |

"+" is <20 nM;
"++" is 20-50 nM;
"+++" is >50 to 100 nM;
"++++" is >100 nM

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega)

followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. *JBC* 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of $2\times10^6$ cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (*Agents Actions.* 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL, (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press; *Methods in Molecular Biology*: Vol. 225, Inflammation Protocols., Winyard, P. G. and Willoughby, D. A., Humana Press, 2003).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent auto-immune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

$$\text{Formula I}$$

(structure showing A—L—N in a ring with (R$^6$)$_n$, Z, )$_m$, R$^5$, R$^4$, Y, N—X, and a pyrrolopyrimidine bearing R$^1$, R$^2$, R$^3$)

or a pharmaceutically acceptable salt thereof; wherein:

A is C$_{3-14}$ cycloalkyl, C$_{2-13}$ heterocycloalkyl, C$_{6-14}$ aryl, or C$_{1-14}$ heteroaryl, wherein said C$_{3-14}$ cycloalkyl, C$_{2-13}$ heterocycloalkyl, C$_{6-14}$ aryl, and C$_{1-14}$ heteroaryl are each optionally substituted with 1, 2, 3, 4, 5, or 6 independently selected R$^8$ substituents;

each R$^8$ is independently selected from halo, cyano, nitro, C$_{1-6}$ alkyl, C$_{1-6}$ haloalkyl, C$_{2-6}$ alkenyl, C$_{2-6}$ alkynyl, C$_{3-14}$ cycloalkyl, C$_{3-14}$ cycloalkyl-C$_{1-4}$-alkyl, C$_{2-14}$ heterocycloalkyl, C$_{2-14}$ heterocycloalkyl-C$_{1-4}$-alkyl, C$_{6-14}$ aryl, C$_{6-14}$ aryl-C$_{1-4}$-alkyl, C$_{1-13}$ heteroaryl, C$_{1-13}$ heteroaryl-C$_{1-4}$-alkyl, —OR$^a$, —SR$^a$, —S(=O)R$^b$, —S(=O)$_2$R$^b$, —S(=O)NR$^e$R$^f$, —C(=O)R$^b$, —C(=O)OR$^b$, —C(=O)NR$^e$R$^f$, —OC(=O)R$^b$, —OC(=O)NR$^e$R$^f$, —NR$^e$R$^f$, —NR$^c$C(=O)R$^d$, —NR$^c$C(=O)OR$^d$, —NR$^c$S(=O)$_2$R$^d$, and —NR$^b$S(=O)$_2$NR$^e$R$^f$;

L is absent, C(=O), C(=O)NH, S(=O), or S(=O)$_2$;

X is CH or N;

Y is H, cyano, halo, C$_{1-4}$ alkyl, or C$_{1-4}$ haloalkyl;

Z is CR$^7$ or N;

R$^1$, R$^2$, and R$^3$ are each independently H, hydroxyl, halo, C$_{1-3}$ alkyl, or C$_{1-3}$ haloalkyl;

R$^4$ and R$^5$ are each independently H, C$_{1-3}$ alkyl, or C$_{1-3}$ haloalkyl;

or R$^4$ and R$^5$ together with the carbon atom to which they are attached can form a 3-, 4-, 5-, 6- or 7-membered cycloalkyl ring;

each R$^6$ is independently hydroxyl, fluorine, C$_{1-4}$ alkyl, hydroxy-C$_{1-4}$-alkyl, C$_{1-4}$ alkoxy-C$_{1-4}$-alkyl, or C$_{1-4}$ fluoroalkyl;

R$^7$ is H, fluorine, C$_{1-4}$ alkyl, or C$_{1-4}$ fluoroalkyl;

each R$^a$, R$^b$, R$^c$, R$^d$, R$^e$, and R$^f$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-4}$-alkyl, C$_{2-7}$ heterocycloalkyl, C$_{2-7}$ heterocycloalkyl-C$_{1-4}$-alkyl, C$_{6-14}$ aryl, C$_{6-14}$ aryl-C$_{1-4}$-alkyl, C$_{1-7}$ heteroaryl, and C$_{1-7}$ heteroaryl-C$_{1-4}$-alkyl; wherein said C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-4}$-alkyl, C$_{2-7}$ heterocycloalkyl, C$_{2-7}$ heterocycloalkyl-C$_{1-4}$-alkyl, C$_{6-14}$ aryl, C$_{6-14}$ aryl-C$_{1-4}$-alkyl, C$_{1-7}$ heteroaryl, and C$_{1-7}$ heteroaryl-C$_{1-4}$-alkyl are each optionally substituted by 1, 2, 3, or 4 groups independently selected from hydroxyl, halo, cyano, nitro, C$_{1-4}$ alkyl, C$_{1-4}$ haloalkyl, C$_{1-4}$ alkoxy, C$_{1-4}$ haloalkoxy, amino, C$_{1-4}$ alkylamino, and di-C$_{1-4}$-alkylamino;

or any R$^c$ and R$^d$, together with the moiety to which they are attached, can form a 3-, 4-, 5-, 6-, or 7-membered heterocycloalkyl ring optionally substituted with 1, 2, 3, or 4 groups independently selected from hydroxyl, C$_{1-4}$ alkyl, C$_{1-4}$ haloalkyl, C$_{1-4}$ alkoxy, C$_{1-4}$ haloalkoxy, amino, C$_{1-4}$ alkylamino, and di-C$_{1-4}$-alkylamino;

or any R$^e$ and R$^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, C$_{1-4}$ alkyl, C$_{1-4}$ haloalkyl, C$_{1-4}$ alkoxy, C$_{1-4}$ haloalkoxy, amino, C$_{1-4}$ alkylamino, and di-C$_{1-4}$-alkylamino;

m is 0 or 1; and n is 0, 1, 2, 3, 4, 5, 6, 7, 8, 9, or 10;

provided that the valency of each atom in the optionally substituted moieties is not exceeded.

2. The compound according to claim 1, or a pharmaceutically acceptable salt thereof; wherein:

L is absent, C(=O), S(=O) or S(=O)$_2$;

R$^1$, R$^2$, and R$^3$ are each independently H, halo, C$_{1-3}$ alkyl, or C$_{1-3}$ haloalkyl; and each R$^6$ is independently fluorine, C$_{1-4}$ alkyl, or C$_{1-4}$ fluoroalkyl.

3. The compound according to claim 2, or a pharmaceutically acceptable salt thereof, wherein A is C$_{3-14}$ cycloalkyl.

4. The compound according to claim 2, or a pharmaceutically acceptable salt thereof, wherein A is C$_{6-14}$ aryl.

5. The compound according to claim 2, or a pharmaceutically acceptable salt thereof, wherein A is phenyl.

6. The compound according to claim 2, or a pharmaceutically acceptable salt thereof, wherein A is C$_{1-14}$ heteroaryl, which is optionally substituted with 1 or 2 substituents independently selected from C$_{1-6}$ alkyl.

7. The compound according to claim 2, or a pharmaceutically acceptable salt thereof, wherein A is C$_{3-14}$ cycloalkyl, C$_{6-14}$ aryl, or C$_{1-14}$ heteroaryl, each of which is optionally substituted by 1, 2, 3, or 4 independently selected R$^8$ substituents.

8. The compound according to claim 2, or a pharmaceutically acceptable salt thereof, wherein A is C$_{3-14}$ cycloalkyl, C$_{6-14}$ aryl, or C$_{1-14}$ heteroaryl, wherein said C$_{3-14}$ cycloalkyl, C$_{6-14}$ aryl, and C$_{1-14}$ heteroaryl are each optionally substituted with 1 or 2 substituents independently selected from halo, cyano, C$_{1-6}$ alkyl, C$_{1-6}$ haloalkyl, —OR$^a$, and —NR$^e$R$^f$.

9. The compound according to claim 2, or a pharmaceutically acceptable salt thereof, wherein A is cyclopropyl, phenyl, a pyrazole ring, a pyridine ring, an indazole ring, a thiophene ring, a furan ring, a pyrimidine ring, or an imidazole ring; wherein said phenyl, pyrazole ring, pyridine ring, indazole ring, thiophene ring, furan ring, pyrimidine ring, and imidazole ring are each optionally substituted with 1, 2, or 3 substituents independently selected from halo, cyano, C$_{1-6}$ alkyl, C$_{1-6}$ haloalkyl, —OR$^a$, and —NR$^e$R$^f$.

10. The compound according to claim 2, or a pharmaceutically acceptable salt thereof, wherein each R$^8$ is independently selected from halo, cyano, nitro, C$_{1-6}$ alkyl, C$_{1-6}$ haloalkyl, C$_{2-6}$ alkenyl, C$_{2-6}$ alkynyl, C$_{3-7}$ cycloalkyl, C$_{2-9}$ heterocycloalkyl, C$_{6-10}$ aryl, C$_{1-9}$ heteroaryl, —OR$^a$, —SR$^a$, —S(=O)R$^b$, —S(=O)$_2$R$^b$, —S(=O)NR$^e$R$^f$, —C(=O)R$^b$, —C(=O)OR$^b$, —C(=O)NR$^e$R$^f$, —OC(=O)R$^b$, —OC(=O)NR$^e$R$^f$, —NR$^e$R$^f$, —NR$^c$C(=O)R$^d$, —NR$^c$C(=O)OR$^d$, —NR$^c$S(=O)$_2$R$^d$, and —NR$^b$S(=O)$_2$NR$^e$R$^f$.

11. The compound according to claim 2, or a pharmaceutically acceptable salt thereof, wherein each R$^8$ is independently selected from halo, cyano, nitro, C$_{1-6}$ alkyl, C$_{1-6}$ haloalkyl, —OR$^a$, —S(=O)$_2$R$^b$, —C(=O)OR$^b$, —C(=O)NR$^e$R$^f$, —NR$^e$R$^f$, and —NR$^c$C(=O)R$^d$.

12. The compound according to claim 2, or a pharmaceutically acceptable salt thereof, wherein each R$^8$ is independently selected from halo, cyano, C$_{1-6}$ alkyl, C$_{1-6}$ haloalkyl, —OR$^a$, and —NR$^e$R$^f$.

13. The compound according to claim 2, or a pharmaceutically acceptable salt thereof, wherein L is absent.

14. The compound according to claim 2, or a pharmaceutically acceptable salt thereof, wherein L is C(=O).

15. The compound according to claim 2, or a pharmaceutically acceptable salt thereof, wherein L is S(=O)$_2$.

16. The compound according to claim 1, or a pharmaceutically acceptable salt thereof, wherein L is C(=O)NH.

17. The compound according to claim 2, or a pharmaceutically acceptable salt thereof, wherein X is CH.

18. The compound according to claim 2, or a pharmaceutically acceptable salt thereof, wherein X is N.

19. The compound according to claim 2, or a pharmaceutically acceptable salt thereof, wherein Y is H, cyano, or halo.

20. The compound according to claim 2, or a pharmaceutically acceptable salt thereof, wherein Y is H, cyano, methyl or fluoro.

21. The compound according to claim 2, or a pharmaceutically acceptable salt thereof, wherein Z is CR$^7$.

22. The compound according to claim 2, or a pharmaceutically acceptable salt thereof, wherein Z is CH.

23. The compound according to claim 2, or a pharmaceutically acceptable salt thereof, wherein Z is N.

24. The compound according to claim 2, or a pharmaceutically acceptable salt thereof, wherein R$^1$, R$^2$, and R$^3$ are each H.

25. The compound according to claim 2, or a pharmaceutically acceptable salt thereof, wherein R$^4$ and R$^5$ are each H.

26. The compound according to claim 2, or a pharmaceutically acceptable salt thereof, wherein each R$^6$ is C$_{1-4}$ alkyl.

27. The compound according to claim 2, or a pharmaceutically acceptable salt thereof, wherein m is 1.

28. The compound according to claim 2, or a pharmaceutically acceptable salt thereof, wherein n is 0.

29. A compound according to claim 2, having formula II:

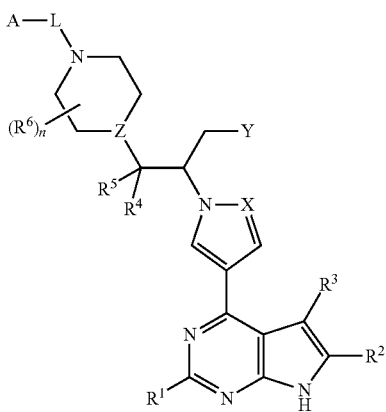

or a pharmaceutically acceptable salt thereof.

30. A compound according to claim 2, having formula IIa:

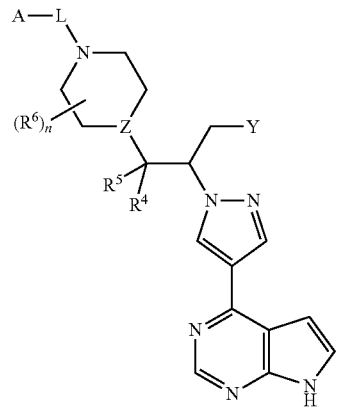

or a pharmaceutically acceptable salt thereof.

31. A compound according to claim 2, having formula IIb:

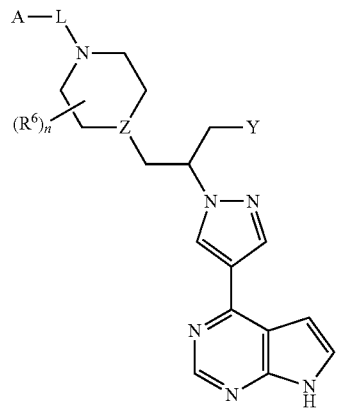

or a pharmaceutically acceptable salt thereof.

32. The compound according to claim 2, or a pharmaceutically acceptable salt thereof, wherein:
A is C$_{3-14}$ cycloalkyl, C$_{6-14}$ aryl, or C$_{1-14}$ heteroaryl, each optionally substituted with 1, 2, 3, 4, 5, or 6 independently selected R$^8$ substituents;
each R$^8$ is independently selected from halo, cyano, nitro, C$_{1-6}$ alkyl, C$_{1-6}$ haloalkyl, C$_{2-6}$ alkenyl, C$_{2-6}$ alkynyl, C$_{3-14}$ cycloalkyl, C$_{3-14}$ cycloalkyl-C$_{1-4}$-alkyl, C$_{2-14}$ heterocycloalkyl, C$_{2-14}$ heterocycloalkyl-C$_{1-4}$-alkyl, C$_{6-14}$ aryl, C$_{6-14}$ aryl-C$_{1-4}$-alkyl, C$_{1-13}$ heteroaryl, C$_{1-13}$ heteroaryl-C$_{1-4}$-alkyl, —OR$^a$, —SR$^a$, —S(=O)R$^b$, —S(=O)$_2$R$^b$, —S(=O)NR$^e$R$^f$, —C(=O)R$^b$, —C(=O)OR$^b$, —C(=O)NR$^e$R$^f$, —OC(=O)R$^b$, —OC(=O)NR$^e$R$^f$, —NR$^e$R$^f$, —NR$^c$C(=O)R$^d$, —NR$^c$C(=O)OR$^d$, —NR$^c$S(=O)$_2$R$^d$, and —NR$^b$S(=O)$_2$NR$^e$R$^f$;
L is C(=O) or S(=O)$_2$;
X is N;
Y is H, cyano, or halo;
Z is CH or N;
R$^1$, R$^2$, R$^3$, R$^4$, and R$^5$ are each H;
m is 0;
n is 0; and
each R$^a$, R$^b$, R$^c$, R$^d$, R$^e$, and R$^f$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-4}$-alkyl, C$_{2-7}$ heterocycloalkyl, C$_{2-7}$ heterocycloalkyl-C$_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^c$ and $R^d$, together with the moiety to which they are attached, can form a 3-, 4-, 5-, 6-, or 7-membered heterocycloalkyl ring optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

33. The compound according to claim 2, or a pharmaceutically acceptable salt thereof, wherein:

A is $C_{3-14}$ cycloalkyl, $C_{6-14}$ aryl, or $C_{1-14}$ heteroaryl, each optionally substituted with 1, 2, 3, 4, 5, or 6 independently selected $R^8$ substituents;

each $R^8$ is independently selected from halo, cyano, nitro, $C_{1-6}$ alkyl, $C_{1-6}$ haloalkyl, $-OR^a$, $-S(=O)_2R^b$, $-C(=O)OR^b$, $-C(=O)NR^eR^f$, $-NR^eR^f$, and $-NR^cC(=O)R^d$;

L is $C(=O)$ or $S(=O)_2$;

X is N;

Y is H, cyano, or halo;

Z is CH or N;

$R^1$, $R^2$, $R^3$, $R^4$, and $R^5$ are each H;

m is 0;

n is 0; and each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^c$ and $R^d$, together with the moiety to which they are attached, can form a 3-, 4-, 5-, 6-, or 7-membered heterocycloalkyl ring optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

34. The compound according to claim 1, or a pharmaceutically acceptable salt thereof, wherein:

A is $C_{3-14}$ cycloalkyl, $C_{6-14}$ aryl, or $C_{1-14}$ heteroaryl, wherein said $C_{3-14}$ cycloalkyl, $C_{6-14}$ aryl, and $C_{1-14}$ heteroaryl are each optionally substituted with 1, 2, or 3 independently selected $R^8$ substituents;

each $R^8$ is independently selected from halo, cyano, $C_{1-6}$ alkyl, $C_{1-6}$ haloalkyl, $-OR^a$, and $-NR^eR^f$;

L is absent, $C(=O)$, $C(=O)NH$, or $S(=O)_2$;

X is N or CH;

Y is H, cyano, methyl, or fluoro;

Z is CH or N;

$R^1$, $R^2$, $R^3$, $R^4$, and $R^5$ are each H;

each $R^6$ is $C_{1-4}$ alkyl;

m is 0 or 1;

n is 0 or 1;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, $C_{6-14}$ aryl, $C_{6-14}$ aryl-$C_{1-4}$-alkyl, $C_{1-7}$ heteroaryl, and $C_{1-7}$ heteroaryl-$C_{1-4}$-alkyl are each optionally substituted by 1, 2, 3, or 4 groups independently selected from hydroxyl, halo, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

35. The compound according to claim 2, or a pharmaceutically acceptable salt thereof, wherein:

A is $C_{3-14}$ cycloalkyl, $C_{6-14}$ aryl, or $C_{1-14}$ heteroaryl, each optionally substituted with 1, 2, 3, 4, 5, or 6 independently selected $R^8$ substituents;

each $R^8$ is independently selected from halo, cyano, and $C_{1-6}$ alkyl;

L is $C(=O)$ or $S(=O)_2$;

X is N;

Y is H, cyano, or fluoro;

Z is CH or N;

$R^1$, $R^2$, $R^3$, $R^4$, and $R^5$ are each H;

m is 0; and n is 0.

36. A compound according to claim 2, having a formula selected from:

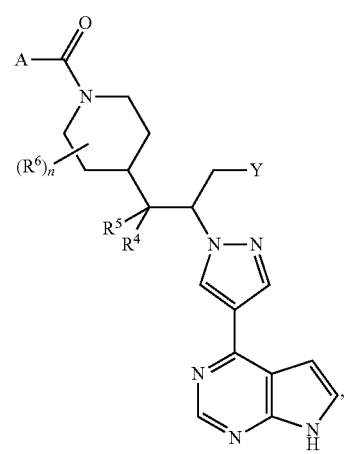

-continued
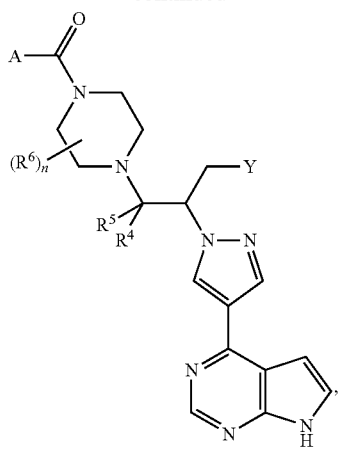
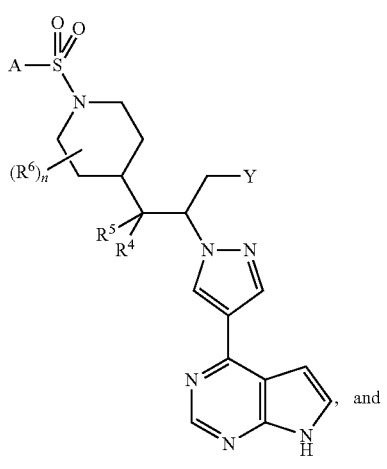
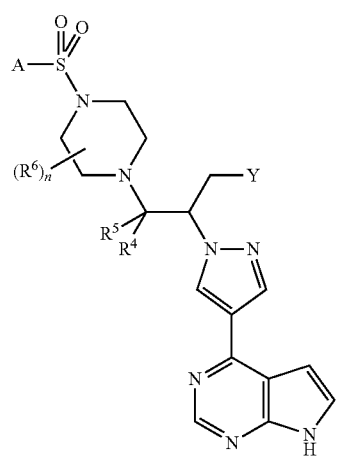
or a pharmaceutically acceptable salt thereof.
37. A compound according to claim 2, having a formula selected from:
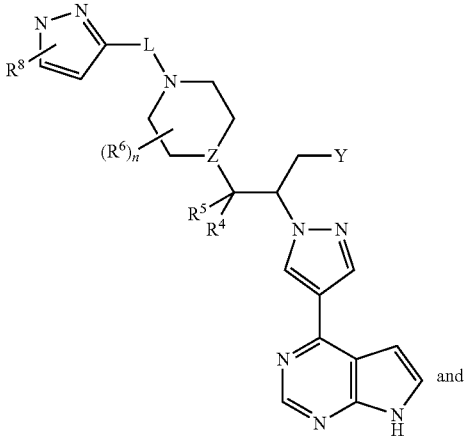
and
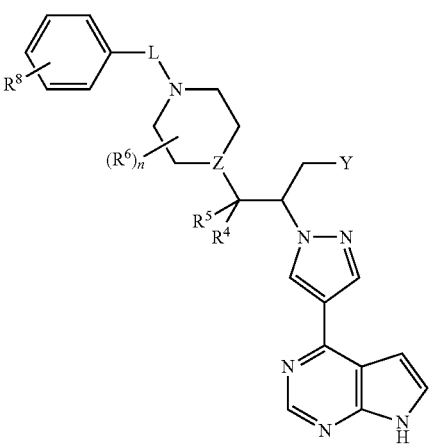
or a pharmaceutically acceptable salt thereof.
38. A compound according to claim 2, having a formula selected from:
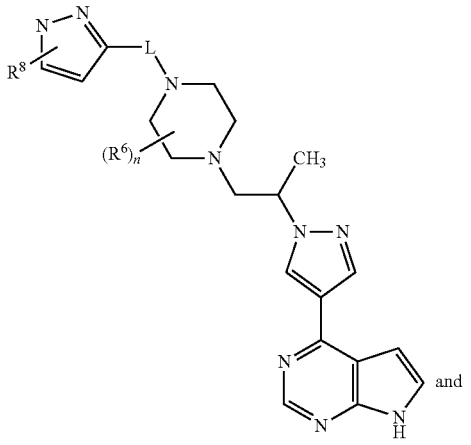
and -continued

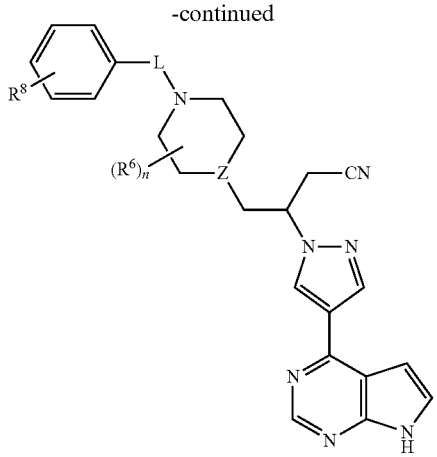

or a pharmaceutically acceptable salt thereof.

39. A compound according to claim 1, wherein said compound is selected from:
    4-[(4-{3-cyano-2-[4-(7H-pyrrolo[2,3-d]pyrimidin-4-yl)-1H-pyrazol-1-yl]propyl}piperazin-1-yl)carbonyl]benzonitrile;
    4-[4-(3,5-difluorobenzoyl)piperazin-1-yl]-3-[4-(7H-pyrrolo[2,3-d]pyrimidin-4-yl)-1H-pyrazol-1-yl]butanenitrile;
    4-{4-[(1-methyl-1H-pyrazol-3-yl)sulfonyl]piperazin-1-yl}-3-[4-(7H-pyrrolo[2,3-d]pyrimidin-4-yl)-1H-pyrazol-1-yl]butanenitrile;
    4-[1-(cyclopropylsulfonyl)piperidin-4-yl]-3-[4-(7H-pyrrolo[2,3-d]pyrimidin-4-yl)-1H-pyrazol-1-yl]butanenitrile;
    4-[1-(2,4-difluorobenzoyl)piperidin-4-yl]-3-[4-(7H-pyrrolo[2,3-d]pyrimidin-4-yl)-1H-pyrazol-1-yl]butanenitrile;
    4-{1-[(1-methyl-1H-pyrazol-3-yl)sulfonyl]piperidin-4-yl}-3-[4-(7H-pyrrolo[2,3-d]pyrimidin-4-yl)-1H-pyrazol-1-yl]butanenitrile;
    4-[1-(4-fluorobenzoyl)piperidin-4-yl]-3-[4-(7H-pyrrolo[2,3-d]pyrimidin-4-yl)-1H-pyrazol-1-yl]butanenitrile;
    4-[1-(1-methyl-2-{4-[(1-methyl-1H-pyrazol-3-yl)sulfonyl]piperazin-1-yl}ethyl)-1H-pyrazol-4-yl]-7H-pyrrolo[2,3-d]pyrimidine; and
    4-(1-(1-fluoro-3-(4-(1-methyl-1H-pyrazol-3-ylsulfonyl)piperazin-1-yl)propan-2-yl)-1H-pyrazol-4-yl)-7H-pyrrolo[2,3-d]pyrimidine;
    or a pharmaceutically acceptable salt thereof.

40. A compound according to claim 1, wherein said compound is selected from:
    4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile;
    4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile;
    4-{4-[4-(difluoromethyl)-2-fluorobenzoyl]piperazin-1-yl}-3-[4-(7H-pyrrolo[2,3-d]pyrimidin-4-yl)-1H-pyrazol-1-yl]butanenitrile;
    4-[(4-{3-cyano-2-[4-(7H-pyrrolo[2,3-d]pyrimidin-4-yl)-1H-pyrazol-1-yl]propyl}piperazin-1-yl)carbonyl]-3,5-difluorobenzonitrile;
    4-{4-[(5-chloro-3-fluoropyridin-2-yl)carbonyl]piperazin-1-yl}-3-[4-(7H-pyrrolo[2,3-d]pyrimidin-4-yl)-1H-pyrazol-1-yl]butanenitrile;
    6-[(4-{3-cyano-2-[4-(7H-pyrrolo[2,3-d]pyrimidin-4-yl)-1H-pyrazol-1-yl]propyl}piperazin-1-yl)carbonyl]-5-fluoronicotinonitrile;
    4-[4-(3-fluoro-4-methoxybenzoyl)piperazin-1-yl]-3-[4-(7H-pyrrolo[2,3-d]pyrimidin-4-yl)-1H-pyrazol-1-yl]butanenitrile;
    4-(4-{[3-fluoro-5-(trifluoromethyl)pyridin-2-yl]carbonyl}piperazin-1-yl)-3-[4-(7H-pyrrolo[2,3-d]pyrimidin-4-yl)-1H-pyrazol-1-yl]butanenitrile;
    6-[(4-{3-cyano-2-[4-(7H-pyrrolo[2,3-d]pyrimidin-4-yl)-1H-pyrazol-1-yl]propyl}piperazin-1-yl)carbonyl]nicotinonitrile;
    4-{4-[(5-fluoropyridin-2-yl)carbonyl]piperazin-1-yl}-3-[4-(7H-pyrrolo[2,3-d]pyrimidin-4-yl)-1H-pyrazol-1-yl]butanenitrile;
    4-[4-(1H-indazol-5-ylsulfonyl)piperazin-1-yl]-3-[4-(7H-pyrrolo[2,3-d]pyrimidin-4-yl)-1H-pyrazol-1-yl]butanenitrile;
    4-(2-(4-(7H-pyrrolo[2,3-d]pyrimidin-4-yl)-1H-pyrazol-1-yl)-3-cyanopropyl)-N-(4-fluoro-2-methylphenyl)piperazine-1-carboxamide;
    4-[((3R)-4-{3-cyano-2-[4-(7H-pyrrolo[2,3-d]pyrimidin-4-yl)-1H-pyrazol-1-yl]propyl}-3-methylpiperazin-1-yl)carbonyl]-3-fluorobenzonitrile;
    4-[((3 S)-4-{3-cyano-2-[4-(7H-pyrrolo[2,3-d]pyrimidin-4-yl)-1H-pyrazol-1-yl]propyl}-3-methylpiperazin-1-yl)carbonyl]-3-fluorobenzonitrile;
    3-(4-(7H-pyrrolo[2,3-d]pyrimidin-4-yl)-1H-pyrazol-1-yl)-4-(4-(4-chloro-2-fluorobenzoyl)piperazin-1-yl)butanenitrile;
    3-(4-(7H-pyrrolo[2,3-d]pyrimidin-4-yl)-1H-pyrazol-1-yl)-4-(4-(4-chloro-2,6-difluorobenzoyl)piperazin-1-yl)butanenitrile;
    3-(4-(7H-pyrrolo[2,3-d]pyrimidin-4-yl)-1H-pyrazol-1-yl)-4-(4-(2-fluoro-4-methylbenzoyl)piperazin-1-yl)butanenitrile;
    3-(4-(7H-pyrrolo[2,3-d]pyrimidin-4-yl)-1H-pyrazol-1-yl)-4-(4-(2,4,6-trifluorobenzoyl)piperazin-1-yl)butanenitrile;
    3-(4-(7H-pyrrolo[2,3-d]pyrimidin-4-yl)-1H-pyrazol-1-yl)-4-(4-(2,4-difluorobenzoyl)piperazin-1-yl)butanenitrile;
    3-(4-(7H-pyrrolo[2,3-d]pyrimidin-4-yl)-1H-pyrazol-1-yl)-4-(4-(2-fluoro-4-hydroxybenzoyl)piperazin-1-yl)butanenitrile;
    3-(4-(7H-pyrrolo[2,3-d]pyrimidin-4-yl)-1H-pyrazol-1-yl)-4-(4-(2-fluoro-5-(trifluoromethyl)benzoyl)piperazin-1-yl)butanenitrile;
    3-(4-(7H-pyrrolo[2,3-d]pyrimidin-4-yl)-1H-pyrazol-1-yl)-4-(4-(2,3-difluorobenzoyl)piperazin-1-yl)butanenitrile;
    3-(4-(7H-pyrrolo[2,3-d]pyrimidin-4-yl)-1H-pyrazol-1-yl)-4-(4-(2,3-difluoro-4-methoxybenzoyl)piperazin-1-yl)butanenitrile;
    3-(4-(7H-pyrrolo[2,3-d]pyrimidin-4-yl)-1H-pyrazol-1-yl)-4-(4-(2-fluoro-6-hydroxybenzoyl)piperazin-1-yl)butanenitrile;
    3-(4-(7H-pyrrolo[2,3-d]pyrimidin-4-yl)-1H-pyrazol-1-yl)-4-(4-(4-fluorobenzoyl)piperazin-1-yl)butanenitrile;
    3-(4-(7H-pyrrolo[2,3-d]pyrimidin-4-yl)-1H-pyrazol-1-yl)-4-(4-(4-fluoro-3-methylbenzoyl)piperazin-1-yl)butanenitrile;
    3-(4-(7H-pyrrolo[2,3-d]pyrimidin-4-yl)-1H-pyrazol-1-yl)-4-(4-(5-chloropicolinoyl)piperazin-1-yl)butanenitrile;

3-(4-(7H-pyrrolo[2,3-d]pyrimidin-4-yl)-1H-pyrazol-1-yl)-4-(4-(2-chloro-4-fluorobenzoyl)piperazin-1-yl)butanenitrile;
3-(4-(7H-pyrrolo[2,3-d]pyrimidin-4-yl)-1H-pyrazol-1-yl)-4-(4-(3,5-difluoropicolinoyl)piperazin-1-yl)butanenitrile;
3-(4-(7H-pyrrolo[2,3-d]pyrimidin-4-yl)-1H-pyrazol-1-yl)-4-(4-(2-fluoro-5-(trifluoromethoxy)benzoyl)piperazin-1-yl)butanenitrile;
3-(4-(7H-pyrrolo[2,3-d]pyrimidin-4-yl)-1H-pyrazol-1-yl)-4-(4-(thiophene-2-carbonyl)piperazin-1-yl)butanenitrile;
3-(4-(7H-pyrrolo[2,3-d]pyrimidin-4-yl)-1H-pyrazol-1-yl)-4-(4-(4-fluoro-3-methoxybenzoyl)piperazin-1-yl)butanenitrile;
3-(4-(7H-pyrrolo[2,3-d]pyrimidin-4-yl)-1H-pyrazol-1-yl)-4-(4-(3-chloro-4-methoxybenzoyl)piperazin-1-yl)butanenitrile;
3-(4-(7H-pyrrolo[2,3-d]pyrimidin-4-yl)-1H-pyrazol-1-yl)-4-(4-(2-fluoro-4-(trifluoromethyl)benzoyl)piperazin-1-yl)butanenitrile;
3-(4-(7H-pyrrolo[2,3-d]pyrimidin-4-yl)-1H-pyrazol-1-yl)-4-(4-(3-chloro-5-fluorobenzoyl)piperazin-1-yl)butanenitrile;
3-(4-(7H-pyrrolo[2,3-d]pyrimidin-4-yl)-1H-pyrazol-1-yl)-4-(4-(4-fluoro-2-methylbenzoyl)piperazin-1-yl)butanenitrile;
3-(4-(7H-pyrrolo[2,3-d]pyrimidin-4-yl)-1H-pyrazol-1-yl)-4-(4-(2,3,4-trifluorobenzoyl)piperazin-1-yl)butanenitrile;
3-(4-(7H-pyrrolo[2,3-d]pyrimidin-4-yl)-1H-pyrazol-1-yl)-4-(4-(4-fluoro-3-(trifluoromethoxy)benzoyl)piperazin-1-yl)butanenitrile;
3-(4-(7H-pyrrolo[2,3-d]pyrimidin-4-yl)-1H-pyrazol-1-yl)-4-(4-(3,4-difluorobenzoyl)piperazin-1-yl)butanenitrile;
3-(4-(7H-pyrrolo[2,3-d]pyrimidin-4-yl)-1H-pyrazol-1-yl)-4-(4-(2-fluoro-3-(trifluoromethoxy)benzoyl)piperazin-1-yl)butanenitrile;
3-(4-(7H-pyrrolo[2,3-d]pyrimidin-4-yl)-1H-pyrazol-1-yl)-4-(4-(4-methoxythiophene-3-carbonyl)piperazin-1-yl)butanenitrile;
3-(4-(7H-pyrrolo[2,3-d]pyrimidin-4-yl)-1H-pyrazol-1-yl)-4-(4-(3-chloro-5-(trifluoromethoxy)benzoyl)piperazin-1-yl)butanenitrile;
3-(4-(7H-pyrrolo[2,3-d]pyrimidin-4-yl)-1H-pyrazol-1-yl)-4-(4-(3-chloro-4-hydroxybenzoyl)piperazin-1-yl)butanenitrile;
3-(4-(7H-pyrrolo[2,3-d]pyrimidin-4-yl)-1H-pyrazol-1-yl)-4-(4-(3,5-difluoro-4-methoxybenzoyl)piperazin-1-yl)butanenitrile;
3-(4-(7H-pyrrolo[2,3-d]pyrimidin-4-yl)-1H-pyrazol-1-yl)-4-(4-(3-fluoro-4-(trifluoromethyl)benzoyl)piperazin-1-yl)butanenitrile;
3-(4-(7H-pyrrolo[2,3-d]pyrimidin-4-yl)-1H-pyrazol-1-yl)-4-(4-(4-fluoro-3-(trifluoromethyl)benzoyl)piperazin-1-yl)butanenitrile;
3-(4-(7H-pyrrolo[2,3-d]pyrimidin-4-yl)-1H-pyrazol-1-yl)-4-(4-picolinoylpiperazin-1-yl)butanenitrile;
6-(4-(2-(4-(7H-pyrrolo[2,3-d]pyrimidin-4-yl)-1H-pyrazol-1-yl)-3-cyanopropyl)piperazine-1-carbonyl)nicotinonitrile;
3-(4-(7H-pyrrolo[2,3-d]pyrimidin-4-yl)-1H-pyrazol-1-yl)-4-(4-(4-fluoro-2-(trifluoromethyl)benzoyl)piperazin-1-yl)butanenitrile;
2-(4-(2-(4-(7H-pyrrolo[2,3-d]pyrimidin-4-yl)-1H-pyrazol-1-yl)-3-cyanopropyl)piperazin-1-ylsulfonyl)benzonitrile;
3-(4-(7H-pyrrolo[2,3-d]pyrimidin-4-yl)-1H-pyrazol-1-yl)-4-(4-(3,5-difluorophenylsulfonyl)piperazin-1-yl)butanenitrile;
3-(4-(7H-pyrrolo[2,3-d]pyrimidin-4-yl)-1H-pyrazol-1-yl)-4-(4-(2,5-difluorophenylsulfonyl)piperazin-1-yl)butanenitrile;
3-(4-(7H-pyrrolo[2,3-d]pyrimidin-4-yl)-1H-pyrazol-1-yl)-4-(4-(5-methylpyridin-2-ylsulfonyl)piperazin-1-yl)butanenitrile;
3-(4-(7H-pyrrolo[2,3-d]pyrimidin-4-yl)-1H-pyrazol-1-yl)-4-(4-(6-methylpyridin-2-ylsulfonyl)piperazin-1-yl)butanenitrile;
3-(4-(7H-pyrrolo[2,3-d]pyrimidin-4-yl)-1H-pyrazol-1-yl)-4-(4-(pyridin-3-ylsulfonyl)piperazin-1-yl)butanenitrile;
3-(4-(7H-pyrrolo[2,3-d]pyrimidin-4-yl)-1H-pyrazol-1-yl)-4-(4-(2-(trifluoromethyl)phenylsulfonyl)piperazin-1-yl)butanenitrile;
3-(4-(7H-pyrrolo[2,3-d]pyrimidin-4-yl)-1H-pyrazol-1-yl)-4-(4-(thiophen-2-ylsulfonyl)piperazin-1-yl)butanenitrile;
3-(4-(7H-pyrrolo[2,3-d]pyrimidin-4-yl)-1H-pyrazol-1-yl)-4-(4-(5-chlorothiophen-2-ylsulfonyl)piperazin-1-yl)butanenitrile;
4-(2-(4-(7H-pyrrolo[2,3-d]pyrimidin-4-yl)-1H-pyrazol-1-yl)-3-cyanopropyl)-N-(2,6-difluorophenyl)piperazine-1-carboxamide;
4-(2-(4-(7H-pyrrolo[2,3-d]pyrimidin-4-yl)-1H-pyrazol-1-yl)-3-cyanopropyl)-N-(2,6-dichlorophenyl)piperazine-1-carboxamide;
4-(2-(4-(7H-pyrrolo[2,3-d]pyrimidin-4-yl)-1H-pyrazol-1-yl)-3-cyanopropyl)-N-(2-chloro-6-methylphenyl)piperazine-1-carboxamide;
4-(2-(4-(7H-pyrrolo[2,3-d]pyrimidin-4-yl)-1H-pyrazol-1-yl)-3-cyanopropyl)-N-(2,4-difluorophenyl)piperazine-1-carboxamide;
4-(2-(4-(7H-pyrrolo[2,3-d]pyrimidin-4-yl)-1H-pyrazol-1-yl)-3-cyanopropyl)-N-(2-fluoro-3-(trifluoromethyl)phenyl)piperazine-1-carboxamide;
4-(2-(4-(7H-pyrrolo[2,3-d]pyrimidin-4-yl)-1H-pyrazol-1-yl)-3-cyanopropyl)-N-(2-(difluoromethoxy)phenyl)piperazine-1-carboxamide;
4-(2-(4-(7H-pyrrolo[2,3-d]pyrimidin-4-yl)-1H-pyrazol-1-yl)-3-cyanopropyl)-N-(2-(trifluoromethoxy)phenyl)piperazine-1-carboxamide;
4-(2-(4-(7H-pyrrolo[2,3-d]pyrimidin-4-yl)-1H-pyrazol-1-yl)-3-cyanopropyl)-N-(2-(trifluoromethyl)phenyl)piperazine-1-carboxamide;
4-(4-(2-(4-(7H-pyrrolo[2,3-d]pyrimidin-4-yl)-1H-pyrazol-1-yl)-3-cyanopropyl)piperazine-1-carbonyl)-3-hydroxybenzonitrile;
3-(3-(7H-pyrrolo[2,3-d]pyrimidin-4-yl)-1H-pyrrol-1-yl)-4-(4-(2-fluoro-4-(trifluoromethyl)benzoyl)piperazin-1-yl)butanenitrile;
4-(4-(2-(3-(7H-pyrrolo[2,3-d]pyrimidin-4-yl)-1H-pyrrol-1-yl)-3-cyanopropyl)piperazine-1-carbonyl)-3,5-difluorobenzonitrile;
3-(3-(7H-pyrrolo[2,3-d]pyrimidin-4-yl)-1H-pyrrol-1-yl)-4-(4-(3,5-difluoropicolinoyl)piperazin-1-yl)butanenitrile;
3-(3-(7H-pyrrolo[2,3-d]pyrimidin-4-yl)-1H-pyrrol-1-yl)-4-(4-(3,5-difluorobenzoyl)piperazin-1-yl)butanenitrile;

3-(3-(7H-pyrrolo[2,3-d]pyrimidin-4-yl)-1H-pyrrol-1-yl)-4-(4-(3-fluoro-4-methoxybenzoyl)piperazin-1-yl)butanenitrile;

3-(3-(7H-pyrrolo[2,3-d]pyrimidin-4-yl)-1H-pyrrol-1-yl)-4-(4-(5-fluoropicolinoyl)piperazin-1-yl)butanenitrile;

3-(3-(7H-pyrrolo[2,3-d]pyrimidin-4-yl)-1H-pyrrol-1-yl)-4-(4-(5-chloro-3-fluoropicolinoyl)piperazin-1-yl)butanenitrile;

3-(3-(7H-pyrrolo[2,3-d]pyrimidin-4-yl)-1H-pyrrol-1-yl)-4-(4-(4-fluoro-3-(trifluoromethoxy)benzoyl)piperazin-1-yl)butanenitrile;

3-(4-(2-(3-(7H-pyrrolo[2,3-d]pyrimidin-4-yl)-1H-pyrrol-1-yl)-3-cyanopropyl)piperazine-1-carbonyl)-5-fluorobenzonitrile;

6-(4-(2-(3-(7H-pyrrolo[2,3-d]pyrimidin-4-yl)-1H-pyrrol-1-yl)-3-cyanopropyl)piperazine-1-carbonyl)-5-fluoronicotinonitrile;

4-(4-(2-(3-(7H-pyrrolo[2,3-d]pyrimidin-4-yl)-1H-pyrrol-1-yl)-3-cyanopropyl)piperazine-1-carbonyl)benzonitrile;

3-(3-(7H-pyrrolo[2,3-d]pyrimidin-4-yl)-1H-pyrrol-1-yl)-4-(4-(3-fluoro-5-(trifluoromethyl)picolinoyl)piperazin-1-yl)butanenitrile;

3-(3-(7H-pyrrolo[2,3-d]pyrimidin-4-yl)-1H-pyrrol-1-yl)-4-(4-(2,4-difluorobenzoyl)piperazin-1-yl)butanenitrile;

3-(3-(7H-pyrrolo[2,3-d]pyrimidin-4-yl)-1H-pyrrol-1-yl)-4-(4-(4-(difluoromethyl)-2-fluorobenzoyl)piperazin-1-yl)butanenitrile;

4-{1-[1-methyl-2-(4-{[5-methyl-2-(trifluoromethyl)-3-furyl]sulfonyl}piperazin-1-yl)ethyl]-1H-pyrazol-4-yl}-7H-pyrrolo[2,3-d]pyrimidine;

4-[1-(2-{4-[(5-chloro-2-thienyl)sulfonyl]piperazin-1-yl}-1-methylethyl)-1H-pyrazol-4-yl]-7H-pyrrolo[2,3-d]pyrimidine;

2-[(4-{2-[4-(7H-pyrrolo[2,3-d]pyrimidin-4-yl)-1H-pyrazol-1-yl]propyl}piperazin-1-yl)sulfonyl]benzonitrile;

4-(1-{2-[4-(2,4-difluorobenzoyl)piperazin-1-yl]-1-methylethyl}-1H-pyrazol-4-yl)-7H-pyrrolo[2,3-d]pyrimidine;

4-[1-(2-{4-[(3-fluorophenyl)sulfonyl]piperazin-1-yl}-1-methylethyl)-1H-pyrazol-4-yl]-7H-pyrrolo[2,3-d]pyrimidine;

4-[4-(2-fluoro-4-hydroxybenzoyl)-1,4-diazepan-1-yl]-3-[4-(7H-pyrrolo[2,3-d]pyrimidin-4-yl)-1H-pyrazol-1-yl]butanenitrile;

4-[4-(4-fluorobenzoyl)-1,4-diazepan-1-yl]-3-[4-(7H-pyrrolo[2,3-d]pyrimidin-4-yl)-1H-pyrazol-1-yl]butanenitrile;

4-[4-(2,4-difluorobenzoyl)-1,4-diazepan-1-yl]-3-[4-(7H-pyrrolo[2,3-d]pyrimidin-4-yl)-1H-pyrazol-1-yl]butanenitrile;

4-[4-(4-chloro-2-fluorobenzoyl)-1,4-diazepan-1-yl]-3-[4-(7H-pyrrolo[2,3-d]pyrimidin-4-yl)-1H-pyrazol-1-yl]butanenitrile;

4-[4-(2-fluorobenzoyl)-1,4-diazepan-1-yl]-3-[4-(7H-pyrrolo[2,3-d]pyrimidin-4-yl)-1H-pyrazol-1-yl]butanenitrile;

2-[(4-{3-cyano-2-[4-(7H-pyrrolo[2,3-d]pyrimidin-4-yl)-1H-pyrazol-1-yl]propyl}-1,4-diazepan-1-yl)sulfonyl]benzonitrile;

4-[4-(2,4-dichlorobenzoyl)-1,4-diazepan-1-yl]-3-[4-(7H-pyrrolo[2,3-d]pyrimidin-4-yl)-1H-pyrazol-1-yl]butanenitrile;

4-[4-(4-amino-2-fluorobenzoyl)-1,4-diazepan-1-yl]-3-[4-(7H-pyrrolo[2,3-d]pyrimidin-4-yl)-1H-pyrazol-1-yl]butanenitrile;

4-[4-(4-chloro-2-methylbenzoyl)-1,4-diazepan-1-yl]-3-[4-(7H-pyrrolo[2,3-d]pyrimidin-4-yl)-1H-pyrazol-1-yl]butanenitrile;

4-[4-(4-chloro-2-methoxybenzoyl)-1,4-diazepan-1-yl]-3-[4-(7H-pyrrolo[2,3-d]pyrimidin-4-yl)-1H-pyrazol-1-yl]butanenitrile;

4-[4-(4-chlorobenzoyl)-1,4-diazepan-1-yl]-3-[4-(7H-pyrrolo[2,3-d]pyrimidin-4-yl)-1H-pyrazol-1-yl]butanenitrile;

4-{4-[(2-methylphenyl)sulfonyl]-1,4-diazepan-1-yl}-3-[4-(7H-pyrrolo[2,3-d]pyrimidin-4-yl)-1H-pyrazol-1-yl]butanenitrile;

3-[4-(7H-pyrrolo[2,3-d]pyrimidin-4-yl)-1H-pyrazol-1-yl]-4-(4-{[2-(trifluoromethyl)phenyl]sulfonyl}-1,4-diazepan-1-yl)butanenitrile;

3-[4-(7H-pyrrolo[2,3-d]pyrimidin-4-yl)-1H-pyrazol-1-yl]-4-(4-{[2-(trifluoromethoxy)phenyl]sulfonyl}-1,4-diazepan-1-yl)butanenitrile;

4-{4-[(2,5-dimethoxyphenyl)sulfonyl]-1,4-diazepan-1-yl}-3-[4-(7H-pyrrolo[2,3-d]pyrimidin-4-yl)-1H-pyrazol-1-yl]butanenitrile;

4-{4-[(5-chloro-2-methoxyphenyl)sulfonyl]-1,4-diazepan-1-yl}-3-[4-(7H-pyrrolo[2,3-d]pyrimidin-4-yl)-1H-pyrazol-1-yl]butanenitrile;

4-{4-[(2-phenoxyphenyl)sulfonyl]-1,4-diazepan-1-yl}-3-[4-(7H-pyrrolo[2,3-d]pyrimidin-4-yl)-1H-pyrazol-1-yl]butanenitrile;

4-{4-[(5-bromo-2-methoxyphenyl)sulfonyl]-1,4-diazepan-1-yl}-3-[4-(7H-pyrrolo[2,3-d]pyrimidin-4-yl)-1H-pyrazol-1-yl]butanenitrile;

4-{1-[1-({4-[(1-methyl-1H-pyrazol-3-yl)sulfonyl]piperazin-1-yl}methyl)propyl]-1H-pyrazol-4-yl}-7H-pyrrolo[2,3-d]pyrimidine;

(4-(2-(4-(7H-pyrrolo[2,3-d]pyrimidin-4-yl)-1H-pyrazol-1-yl)butyl)piperazin-1-yl)(4-fluorophenyl)methanone;

2-[(4-{2-[4-(7H-pyrrolo[2,3-d]pyrimidin-4-yl)-1H-pyrazol-1-yl]butyl}piperazin-1-yl)carbonyl]phenol;

(4-(2-(4-(7H-pyrrolo[2,3-d]pyrimidin-4-yl)-1H-pyrazol-1-yl)butyl)piperazin-1-yl)(2,4-difluorophenyl)methanone;

(4-(2-(4-(7H-pyrrolo[2,3-d]pyrimidin-4-yl)-1H-pyrazol-1-yl)butyl)piperazin-1-yl)(2,5-difluorophenyl)methanone;

(4-(2-(4-(7H-pyrrolo[2,3-d]pyrimidin-4-yl)-1H-pyrazol-1-yl)butyl)piperazin-1-yl)(2,3-difluorophenyl)methanone;

(4-(2-(4-(7H-pyrrolo[2,3-d]pyrimidin-4-yl)-1H-pyrazol-1-yl)butyl)piperazin-1-yl)(3,5-difluorophenyl)methanone;

(4-(2-(4-(7H-pyrrolo[2,3-d]pyrimidin-4-yl)-1H-pyrazol-1-yl)butyl)piperazin-1-yl)(2-chloro-4-hydroxyphenyl)methanone;

(4-(2-(4-(7H-pyrrolo[2,3-d]pyrimidin-4-yl)-1H-pyrazol-1-yl)butyl)piperazin-1-yl)(2-fluoro-4-hydroxyphenyl)methanone;

(4-(2-(4-(7H-pyrrolo[2,3-d]pyrimidin-4-yl)-1H-pyrazol-1-yl)butyl)piperazin-1-yl)(4-chloro-2-fluorophenyl)methanone;

(4-(2-(4-(7H-pyrrolo[2,3-d]pyrimidin-4-yl)-1H-pyrazol-1-yl)butyl)piperazin-1-yl)(4-fluoro-2-methoxyphenyl)methanone;

(4-(2-(4-(7H-pyrrolo[2,3-d]pyrimidin-4-yl)-1H-pyrazol-1-yl)butyl)piperazin-1-yl)(thiophen-2-yl)methanone;

4-(1-(1-(4-(phenylsulfonyl)piperazin-1-yl)butan-2-yl)-1H-pyrazol-4-yl)-7H-pyrrolo[2,3-d]pyrimidine;

2-(4-(2-(4-(7H-pyrrolo[2,3-d]pyrimidin-4-yl)-1H-pyrazol-1-yl)butyl)piperazin-1-ylsulfonyl)benzonitrile;

4-(4-(2-(4-(7H-pyrrolo[2,3-d]pyrimidin-4-yl)-1H-pyrazol-1-yl)butyl)piperazin-1-ylsulfonyl)benzonitrile;
4-(1-(1-(4-(2-(trifluoromethyl)phenylsulfonyl)piperazin-1-yl)butan-2-yl)-1H-pyrazol-4-yl)-7H-pyrrolo[2,3-d]pyrimidine;
4-(1-(1-(4-(6-methylpyridin-2-ylsulfonyl)piperazin-1-yl)butan-2-yl)-1H-pyrazol-4-yl)-7H-pyrrolo[2,3-d]pyrimidine;
4-(1-(1-(4-(2-chlorophenylsulfonyl)piperazin-1-yl)butan-2-yl)-1H-pyrazol-4-yl)-7H-pyrrolo[2,3-d]pyrimidine;
4-(1-(1-(4-(1-methyl-3-(trifluoromethyl)-1H-pyrazol-4-ylsulfonyl)piperazin-1-yl)butan-2-yl)-1H-pyrazol-4-yl)-7H-pyrrolo[2,3-d]pyrimidine;
4-(1-(1-(4-(thiophen-2-ylsulfonyl)piperazin-1-yl)butan-2-yl)-1H-pyrazol-4-yl)-7H-pyrrolo[2,3-d]pyrimidine;
4-(1-(1-(4-(3-chlorothiophen-2-ylsulfonyl)piperazin-1-yl)butan-2-yl)-1H-pyrazol-4-yl)-7H-pyrrolo[2,3-d]pyrimidine;
4-(1-(1-(4-(3-fluorophenylsulfonyl)piperazin-1-yl)butan-2-yl)-1H-pyrazol-4-yl)-7H-pyrrolo[2,3-d]pyrimidine;
4-(1-(1-(4-(4-fluorophenylsulfonyl)piperazin-1-yl)butan-2-yl)-1H-pyrazol-4-yl)-7H-pyrrolo[2,3-d]pyrimidine;
4-(1-(1-(4-(2-chlorophenylsulfonyl)piperazin-1-yl)butan-2-yl)-1H-pyrazol-4-yl)-7H-pyrrolo[2,3-d]pyrimidine;
3-(4-(2-(4-(7H-pyrrolo[2,3-d]pyrimidin-4-yl)-1H-pyrazol-1-yl)butyl)piperazin-1-ylsulfonyl)benzonitrile;
4-(1-(1-(4-(2,4-difluorophenylsulfonyl)piperazin-1-yl)butan-2-yl)-1H-pyrazol-4-yl)-7H-pyrrolo[2,3-d]pyrimidine;
4-(1-(1-(4-(2,5-difluorophenylsulfonyl)piperazin-1-yl)butan-2-yl)-1H-pyrazol-4-yl)-7H-pyrrolo[2,3-d]pyrimidine;
4-(1-(1-(4-(3,5-difluorophenylsulfonyl)piperazin-1-yl)butan-2-yl)-1H-pyrazol-4-yl)-7H-pyrrolo[2,3-d]pyrimidine;
4-(1-(1-(4-(4-fluoro-2-methylphenylsulfonyl)piperazin-1-yl)butan-2-yl)-1H-pyrazol-4-yl)-7H-pyrrolo[2,3-d]pyrimidine;
4-(1-(1-(4-(1,2-dimethyl-1H-imidazol-4-ylsulfonyl)piperazin-1-yl)butan-2-yl)-1H-pyrazol-4-yl)-7H-pyrrolo[2,3-d]pyrimidine;
4-(1-(1-(4-(5-bromothiophen-2-ylsulfonyl)piperazin-1-yl)butan-2-yl)-1H-pyrazol-4-yl)-7H-pyrrolo[2,3-d]pyrimidine;
4-{[4-{3-cyano-2-[4-(7H-pyrrolo[2,3-d]pyrimidin-4-yl)-1H-pyrazol-1-yl]propyl}-3-(hydroxymethyl)piperazin-1-yl]carbonyl}-3-fluorobenzonitrile;
4-{[4-{3-cyano-2-[4-(7H-pyrrolo[2,3-d]pyrimidin-4-yl)-1H-pyrazol-1-yl]propyl}-3-(methoxymethyl)piperazin-1-yl]carbonyl}-3-fluorobenzonitrile;
4-[(4-{3-cyano-2-[4-(7H-pyrrolo[2,3-d]pyrimidin-4-yl)-1H-pyrazol-1-yl]propyl}-3-fluoromethylpiperazin-1-yl)carbonyl]-3-fluorobenzonitrile;
4-{[4-{3-cyano-2-[4-(7H-pyrrolo[2,3-d]pyrimidin-4-yl)-1H-pyrazol-1-yl]propyl}-3-(difluoromethyl)piperazin-1-yl]carbonyl}-3-fluorobenzonitrile;
4-{[4-{3-cyano-2-[4-(7H-pyrrolo[2,3-d]pyrimidin-4-yl)-1H-pyrazol-1-yl]propyl}-2-(hydroxymethyl)piperazin-1-yl]carbonyl}-3-fluorobenzonitrile;
4-[((2R)-4-{3-cyano-2-[4-(7H-pyrrolo[2,3-d]pyrimidin-4-yl)-1H-pyrazol-1-yl]propyl}-2-methylpiperazin-1-yl)carbonyl]-3-fluorobenzonitrile; and
4-[((2S)-4-{3-cyano-2-[4-(7H-pyrrolo[2,3-d]pyrimidin-4-yl)-1H-pyrazol-1-yl]propyl}-2-methylpiperazin-1-yl)carbonyl]-3-fluorobenzonitrile or a pharmaceutically acceptable salt thereof.

41. The compound according to claim 2, wherein the compound is the (R)-enantiomer, or a pharmaceutically acceptable salt thereof.

42. The compound according to claim 2, wherein the compound is the (S)-enantiomer, or a pharmaceutically acceptable salt thereof.

43. A composition comprising a compound according to claim 1, or a pharmaceutically acceptable salt thereof, and at least one pharmaceutically acceptable carrier.

44. A method of inhibiting an activity of JAK1 comprising contacting JAK1 with a compound according to claim 1, or a pharmaceutically acceptable salt thereof.

45. A method according to claim 44, wherein said compound, or pharmaceutically acceptable salt thereof, is selective for JAK1 over JAK2.

46. A method of treating a disease selected from multiple myeloma, rheumatoid arthritis, primary myelofibrosis (PMF), polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), idiopathic myelofibrosis (IMF), and systemic mast cell disease (SMCD) in a patient in need thereof, comprising administering to said patient a therapeutically effective amount of a compound of claim 1, or a pharmaceutically acceptable salt thereof, wherein treating refers to inhibiting or ameliorating the disease.

47. A composition comprising a compound according to claim 2, or a pharmaceutically acceptable salt thereof, and at least one pharmaceutically acceptable carrier.

48. A compound, which is 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, or a pharmaceutically acceptable salt thereof.

49. The compound of claim 48, which is (R)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, or a pharmaceutically acceptable salt thereof.

50. The compound of claim 48, which is (S)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, or a pharmaceutically acceptable salt thereof.

51. A compound, which is 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or a pharmaceutically acceptable salt thereof.

52. The compound of claim 51, which is (R)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or a pharmaceutically acceptable salt thereof.

53. The compound of claim 51, which is (S)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or a pharmaceutically acceptable salt thereof.

54. The method of claim 46, wherein the disease is primary myelofibrosis (PMF).

55. The method of claim 46, wherein the disease is polycythemia vera (PV).

56. The method of claim 46, wherein the disease is essential thrombocythemia (ET).

* * * * *